US012571049B2

(12) United States Patent
Chapuy et al.

(10) Patent No.: US 12,571,049 B2
(45) Date of Patent: Mar. 10, 2026

(54) THERAPEUTIC TREATMENT OF SELECT DIFFUSE LARGE B CELL LYMPHOMAS EXHIBITING DISTINCT PATHOGENIC MECHANISMS AND OUTCOMES

(71) Applicants: DANA-FARBER CANCER INSTITUTE, INC., Boston, MA (US); THE BROAD INSTITUTE, INC., Cambridge, MA (US); THE GENERAL HOSPITAL CORPORATION, Boston, MA (US)

(72) Inventors: Bjoern Chapuy, Boston, MA (US); Margaret Shipp, Boston, MA (US); Donald Stewart, Cambridge, MA (US); Andrew Dunford, Cambridge, MA (US); Gad Getz, Boston, MA (US)

(73) Assignees: DANA-FARBER CANCER INSTITUTE, INC., Boston, MA (US); THE BROAD INSTITUTE, INC., Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 1050 days.

(21) Appl. No.: 16/358,825

(22) Filed: Mar. 20, 2019

(65) Prior Publication Data

US 2019/0292602 A1 Sep. 26, 2019

Related U.S. Application Data

(60) Provisional application No. 62/646,214, filed on Mar. 21, 2018.

(51) Int. Cl.
| | |
|---|---|
| *C12Q 1/68* | (2018.01) |
| *C12P 19/34* | (2006.01) |
| *C12Q 1/686* | (2018.01) |
| *C12Q 1/6886* | (2018.01) |

(52) U.S. Cl.
CPC ........... *C12Q 1/6886* (2013.01); *C12Q 1/686* (2013.01); *C12Q 2600/106* (2013.01); *C12Q 2600/112* (2013.01); *C12Q 2600/118* (2013.01); *C12Q 2600/156* (2013.01)

(58) Field of Classification Search
CPC ...... C12Q 1/6886; C12Q 1/6869; C12Q 1/68; C12Q 1/686
See application file for complete search history.

(56) References Cited

PUBLICATIONS

McKinney et al. Machine Learning for Detecting Gene-Gene Interactions: A Review (2006) 5(2) 77-88. (Year: 2006).*

Lenz et al. Molecular subtypes of diffuse large B-cell lymphoma arise by distinct genetic pathways (2008) PNAS 105(36): 13520-13525. (Year: 2008).*
Purow Notch Inhibitors as a New Tool in the War on Cancer: A Pathway to Watch (2009) Curr Pharm Biotechnol (2009) 10(2) 154-160 (Year: 2009).*
Basso et al. Advances in Immunology (2010) Emery and Rimoin's Principles and Practice of Medical Genetics, 2 pages. (Year: 2010).*
Morin et al. Frequent mutation of histone-modifying genes in non-Hodgkin lymphoma (2011) Nature 476:298-303. (Year: 2011).*
Lohr et al. Discovery and prioritization of somatic mutations in diffuse large B-cell lymphoma (DLBCL) by whole-exome sequencing (2012) PNAS 109:10 3879-3884 (Year: 2012).*
Purrow NOTCH inhibition as a promising new approach to cancer therapy (2012) Adv Exp Med Biol 727:305-319. (Year: 2012).*
Espinoza et al Notch Inhibitors for Cancer Treatment (2013) Pharmacol Ther 139(2): 95-110. (Year: 2013).*
De Miranda et al. Exome sequencing reveals novel mutation targ4ets in diffuse large B-cell lymphomas derived from Chinese patients (2014) 124(16) 2544-2553. (Year: 2014).*
Feinberg et al. Epigenetic modulators, modifiers and mediators in cancer aetiology and progression (2016) Nat Rev Genet 17(5): 284-299. (Year: 2016).*
Rovira et al. MYD88 L265P Mutations, But No. Other Variants, Identify a Subpopulation of DLBCL Patients of Activated B-cell Origin , Extranodal Involvement, and Poor Outcome (2016) Clin Cancer Res 22(11) 2755-2764. (Year: 2016).*
Katz EZH2 Inhibitor Tested as Epigenetic Option in NHL Types (2017) Oncology Live 18:20, 2 pages. (Year: 2017).*
Amin et al. Diffuse large B-cell lymphoma: can genomics improve treatment options for a curable cancer? (2017) Cold Spring Harb Mol Case Stud 3:a001719 23 pages. (Year: 2017).*
Moore, et al. Top Notch Targeting Strategies in Cancer: A Detailed Overview of Recent Insights and Current Perspectives (2020) Cells 9:1503, 46 pages. (Year: 2020).*
Simen Myhre, et al. "Influence of DNA copy number and mRNA levels on the expression of breast cancer related proteins" Molecular Oncology (7), 704-718. (Year: 2013).*
Fabrice Jardin. "Next Generation Sequencing and the Management of Diffuse Large B-cell Lymphoma: From Whole Exome Analysis to Targeted Therapy", Discovery Medicine, vol. 18, No. 97, pp. 51-65. Published on Jul. 25, 2014. (Year: 2014).*

* cited by examiner

*Primary Examiner* — Stephen T Kapushoc
(74) *Attorney, Agent, or Firm* — Day Pitney LLP; Christopher R. Cowles; Richard B. Emmons

(57) ABSTRACT

The present disclosure relates to compositions and methods for the diagnosis and treatment or prevention of DLBCL. In particular, the instant disclosure provides a DLBCL classifier that has identified at least five distinct classes of DLBCL cancer, each of which possesses distinct pathogenic mechanisms and outcomes. The instant classifier identifies preferred therapeutic options (including combination therapies) for each such class of DLBCL cancer.

10 Claims, 80 Drawing Sheets

TP53

BRAF

GNAI2

† IgH translocation  † Igκ translocation  † Igλ translocation  ⸋ Non-Ig translocation  ▬ Super-enhancer  ▬ Protein coding exons  | First coding exon Index for mutation diagrams (lollipop figures)

| Gene | Longname | nnon | npat | nsite | q | Stickfig. at page |
|---|---|---|---|---|---|---|
| ACTB | actin, beta | 37 | 32 | 27 | 7.90E-08 | 21 |
| B2M | beta-2-microglobulin | 31 | 26 | 22 | 1.54E-12 | 17 |
| BCL10 | B-cell CLL/lymphoma 10 | 21 | 16 | 16 | 3.16E-05 | 24 |
| BCL11A | B-cell CLL/lymphoma 11A (zinc finger protein) | 11 | 10 | 10 | 8.00E-02 | 30 |
| BCL2 | B-cell CLL/lymphoma 2 | 111 | 53 | 76 | 8.41E-13 | 18 |
| BCL6 | B-cell CLL/lymphoma 6 (zinc finger protein 51) | 18 | 17 | 16 | 6.59E-08 | 21 |
| BRAF | v-raf murine sarcoma viral oncogene homolog B1 | 19 | 18 | 13 | 1.24E-08 | 20 |
| BTG1 | B-cell translocation gene 1, anti-proliferative | 68 | 43 | 55 | 3.67E-13 | 16 |
| CARD11 | caspase recruitment domain family, member 11 | 43 | 34 | 31 | 1.15E-12 | 17 |
| CCL4 | chemokine (C-C motif) ligand 4 | 5 | 4 | 4 | 3.78E-03 | 27 |
| CCND3 | cyclin D3 | 14 | 14 | 11 | 1.39E-12 | 17 |
| CD274 | CD274 molecule | 10 | 8 | 10 | 7.89E-04 | 26 |
| CD58 | CD58 molecule | 30 | 19 | 29 | 1.16E-11 | 18 |
| CD70 | CD70 molecule | 36 | 27 | 33 | 2.02E-13 | 15 |
| CD79B | CD79b molecule, immunoglobulin-associated beta | 50 | 44 | 23 | 2.02E-13 | 15 |
| CD83 | CD83 molecule | 24 | 18 | 18 | 3.23E-05 | 24 |
| CIITA | class II, major histocompatibility complex, transactivator | 11 | 9 | 10 | 5.49E-02 | 29 |
| COQ7 | coenzyme Q7 homolog, ubiquinone (yeast) | 4 | 4 | 3 | 9.50E-02 | 31 |
| CREBBP | CREB binding protein (Rubinstein-Taybi syndrome) | 64 | 51 | 54 | 2.02E-13 | 15 |
| CRIP1 | cysteine-rich protein 1 (intestinal) | 7 | 7 | 7 | 1.42E-05 | 23 |
| CXCR4 | chemokine (C-X-C motif) receptor 4 | 9 | 8 | 8 | 2.87E-06 | 22 |
| DTX1 | deltex homolog 1 (Drosophila) | 46 | 37 | 37 | 2.29E-03 | 26 |
| EBF1 | early B-cell factor 1 | 37 | 32 | 34 | 1.09E-11 | 18 |
| EEF1A1 | eukaryotic translation elongation factor 1 alpha 1 | 19 | 17 | 16 | 2.22E-10 | 19 |
| EP300 | E1A binding protein p300 | 26 | 25 | 22 | 5.34E-05 | 24 |
| ETS1 | v-ets erythroblastosis virus E26 oncogene homolog 1 (avian) | 17 | 15 | 14 | 3.09E-02 | 28 |
| ETV6 | ets variant gene 6 (TEL oncogene) | 24 | 21 | 13 | 9.48E-07 | 22 |
| EZH2 | enhancer of zeste homolog 2 (Drosophila) | 24 | 22 | 10 | 3.02E-10 | 20 |
| FAS | Fas (TNF receptor superfamily, member 6) | 27 | 24 | 18 | 2.02E-13 | 16 |
| FUT5 | fucosyltransferase 5 (alpha (1,3) fucosyltransferase) | 4 | 4 | 4 | 8.29E-02 | 30 |
| GNA13 | guanine nucleotide binding protein (G protein), alpha 13 | 48 | 33 | 45 | 6.47E-08 | 21 |
| GNAI2 | guanine nucleotide binding protein (G protein), alpha inhibiting activity polypeptide 2 | 11 | 10 | 11 | 8.14E-02 | 30 |
| GRB2 | growth factor receptor-bound protein 2 | 10 | 8 | 9 | 1.04E-04 | 25 |
| HIST1H1B | histone cluster 1, H1b | 30 | 26 | 23 | 7.17E-06 | 23 |
| HIST1H1C | histone cluster 1, H1c | 41 | 37 | 31 | 2.22E-13 | 18 |
| HIST1H1D | histone cluster 1, H1d | 25 | 20 | 22 | 8.34E-04 | 26 |
| HIST1H1E | histone cluster 1, H1e | 58 | 39 | 43 | 7.88E-09 | 20 |
| HIST1H2AC | histone cluster 1, H2ac | 19 | 17 | 16 | 1.95E-05 | 24 |
| HIST1H2AM | histone cluster 1, H2am | 18 | 17 | 13 | 3.80E-03 | 27 |
| HIST1H2BC | histone cluster 1, H2bc | 25 | 18 | 20 | 7.68E-06 | 23 |
| HIST1H2BK | histone cluster 1, H2bk | 27 | 24 | 27 | 1.71E-04 | 25 |
| HIST1H3B | histone cluster 1, H3b | 10 | 10 | 6 | 8.60E-02 | 30 |
| HIST2H2BE | histone cluster 2, H2be | 17 | 14 | 13 | 8.99E-02 | 30 |
| HLA-A | major histocompatibility complex, class I, A | 27 | 25 | 24 | 1.15E-12 | 17 |
| HLA-B | major histocompatibility complex, class I, B | 38 | 35 | 26 | 2.02E-13 | 15 |
| HLA-C | major histocompatibility complex, class I, C | 16 | 13 | 12 | 8.88E-11 | 19 |
| HLA-DMA | major histocompatibility complex, class II, DM alpha | 6 | 6 | 6 | 1.94E-02 | 28 |
| HVCN1 | hydrogen voltage-gated channel 1 | 11 | 10 | 10 | 8.95E-07 | 22 |
| IGLL5 | immunoglobulin lambda-like polypeptide 5 | 51 | 30 | 39 | 3.70E-06 | 21 |
| IKZF3 | IKAROS family zinc finger 3 (Aiolos) | 11 | 10 | 8 | 4.97E-06 | 23 |
| IL6 | interleukin 6 (interferon, beta 2) | 6 | 6 | 6 | 9.82E-02 | 31 |
| IRF8 | interferon regulatory factor 8 | 25 | 24 | 20 | 6.47E-04 | 25 |
| KLHL6 | kelch-like 6 (Drosophila) | 37 | 28 | 31 | 2.02E-13 | 18 |
| KMT2D | myeloid/lymphoid or mixed-lineage leukemia 2 | 96 | 75 | 95 | 2.07E-11 | 19 |
| KRAS | v-Ki-ras2 Kirsten rat sarcoma viral oncogene homolog | 8 | 8 | 3 | 4.97E-06 | 23 |
| LTB | lymphotoxin beta (TNF superfamily, member 3) | 29 | 20 | 23 | 5.48E-03 | 27 |
| LYN | v-yes-1 Yamaguchi sarcoma viral related oncogene homolog | 15 | 12 | 14 | 6.11E-07 | 22 |
| MEF2B | myocyte enhancer factor 2B | 20 | 20 | 19 | 2.99E-11 | 19 |
| MYD88 | myeloid differentiation primary response gene (88) | 57 | 55 | 10 | 2.02E-13 | 18 |
| NANOG | Nanog homeobox | 6 | 5 | 4 | 1.22E-02 | 28 |

FIG. 8

| | | | | | |
|---|---|---|---|---|---|
| NAV1 | neuron navigator 1 | 7 | 7 | 5 | 3.46E-03 | 27 |
| NFKBIA | nuclear factor of kappa light polypeptide gene enhancer in B-cells inhibitor, alpha | 22 | 15 | 22 | 5.22E-11 | 18 |
| NFKBIE | nuclear factor of kappa light polypeptide gene enhancer in B-cells inhibitor, epsilon | 12 | 10 | 9 | 1.43E-04 | 25 |
| NLRP8 | NLR family, pyrin domain containing 8 | 10 | 10 | 9 | 6.37E-02 | 29 |
| NOTCH2 | Notch homolog 2 (Drosophila) | 21 | 20 | 15 | 1.00E-06 | 22 |
| PDE4DIP | phosphodiesterase 4D interacting protein (myomegalin) | 27 | 24 | 24 | 3.49E-02 | 29 |
| PIM1 | pim-1 oncogene | 142 | 67 | 64 | 1.35E-12 | 17 |
| POU2AF1 | POU class 2 associating factor 1 | 12 | 12 | 8 | 4.01E-10 | 20 |
| POU2F2 | POU class 2 homeobox 2 | 17 | 17 | 9 | 8.54E-08 | 30 |
| PRDM1 | PR domain containing 1, with ZNF domain | 23 | 22 | 19 | 2.02E-13 | 16 |
| PRKCB | protein kinase C, beta | 12 | 11 | 10 | 3.14E-03 | 28 |
| PRPS1 | phosphoribosyl pyrophosphate synthetase 1 | 4 | 4 | 3 | 3.26E-02 | 28 |
| PTEN | phosphatase and tensin homolog (mutated in multiple advanced cancers 1) | 11 | 10 | 10 | 3.88E-05 | 24 |
| PTPN6 | protein tyrosine phosphatase, non-receptor type 6 | 21 | 13 | 20 | 2.17E-05 | 24 |
| RAD9A | RAD9 homolog A (S. pombe) | 5 | 5 | 3 | 2.08E-03 | 29 |
| RHOA | ras homolog gene family, member A | 19 | 16 | 15 | 1.03E-10 | 19 |
| SF3B1 | splicing factor 3b, subunit 1, 155kDa | 9 | 9 | 7 | 5.05E-02 | 29 |
| SGK1 | serum/glucocorticoid regulated kinase 1 | 118 | 43 | 73 | 3.13E-08 | 21 |
| SIN3A | SIN3 homolog A, transcription regulator (yeast) | 12 | 11 | 12 | 2.46E-02 | 26 |
| SMEK1 | SMEK homolog 1, suppressor of mek1 (Dictyostelium) | 8 | 8 | 8 | 6.80E-03 | 27 |
| SPEN | spen homolog, transcriptional regulator (Drosophila) | 29 | 27 | 26 | 6.87E-04 | 26 |
| STAT3 | signal transducer and activator of transcription 3 (acute-phase response factor) | 22 | 19 | 18 | 4.72E-08 | 21 |
| STAT6 | signal transducer and activator of transcription 6, interleukin-4 induced | 16 | 14 | 11 | 5.24E-07 | 22 |
| TBL1XR1 | transducin (beta)-like 1 X-linked receptor 1 | 23 | 22 | 18 | 2.02E-13 | 16 |
| TLR2 | toll-like receptor 2 | 9 | 9 | 7 | 3.96E-02 | 29 |
| TMEM30A | transmembrane protein 30A | 19 | 17 | 16 | 2.22E-12 | 18 |
| TMSB4X | thymosin beta 4, X-linked | 44 | 36 | 27 | 9.32E-12 | 18 |
| TNFAIP3 | tumor necrosis factor, alpha-induced protein 3 | 29 | 26 | 26 | 1.45E-11 | 18 |
| TNFRSF14 | tumor necrosis factor receptor superfamily, member 14 (herpesvirus entry mediator) | 43 | 42 | 39 | 2.22E-12 | 17 |
| TOX | thymocyte selection-associated high mobility group box | 13 | 12 | 9 | 6.83E-06 | 23 |
| TP53 | tumor protein p53 | 70 | 65 | 53 | 2.02E-13 | 15 |
| UBE2A | ubiquitin-conjugating enzyme E2A (RAD6 homolog) | 13 | 12 | 12 | 2.88E-10 | 20 |
| XPO1 | exportin 1 (CRM1 homolog, yeast) | 7 | 7 | 3 | 5.39E-04 | 26 |
| YY1 | YY1 transcription factor | 8 | 8 | 8 | 2.53E-03 | 27 |
| ZC3H12A | zinc finger CCCH-type containing 12A | 10 | 10 | 10 | 3.30E-04 | 26 |
| ZEB2 | zinc finger E-box binding homeobox 2 | 14 | 13 | 14 | 8.00E-02 | 30 |
| ZFP36L1 | zinc finger protein 36, C3H type-like 1 | 30 | 25 | 20 | 1.73E-03 | 26 |
| ZNF423 | zinc finger protein 423 | 5 | 5 | 5 | 4.80E-02 | 29 |

FIG. 8 (Continued)

MAP2K1

PTPN6

| Term | N | | HR | p-value |
|---|---|---|---|---|
| Low (0-1) | 88 | | Ref. | - |
| Low-int (2) | 56 | | 2.07 | 0.040 |
| High-int (3) | 75 | | 3.80 | < 0.001 |
| High (4-5) | 36 | | 4.84 | < 0.001 |
| MYC - 0 | 231 | | Ref. | - |
| MYC | 21 | | 2.58 | 0.002 |
| 13q31.3 - 0 | 232 | | Ref. | - |
| 13q31.3 | 27 | | 2.08 | 0.007 |
| 1q42.12 - 0 | 239 | | Ref. | - |
| 1q42.12 | 20 | | 2.30 | 0.009 |
| 18p - 0 | 198 | | Ref. | - |
| 18p | 61 | | 1.42 | 0.14 |

0  2  4  6  8  10
HR (95% conf. interval)

THERAPEUTIC TREATMENT OF SELECT DIFFUSE LARGE B CELL LYMPHOMAS EXHIBITING DISTINCT PATHOGENIC MECHANISMS AND OUTCOMES

CROSS-REFERENCE TO RELATED APPLICATION

The present application is related to and claims priority under 35 U.S.C. § 119(e) to U.S. provisional patent application No. 62/646,214, entitled "Therapeutic Treatment of Select Diffuse Large B Cell Lymphomas Exhibiting Distinct Pathogenic Mechanisms and Outcomes," filed Mar. 21, 2018. The entire content of the aforementioned patent application is incorporated herein by this reference.

STATEMENT REGARDING FEDERALLY SPONSORED RESEARCH

This invention was made with government support under Grant Nos. U54HG003067, P01CA163222, R01CA018246, U24CA143845, U24CA210999 and R01CA155010, awarded by the National Institutes of Health. The government has certain rights in the invention.

MEGA TABLE

The present application is being filed along with a mega table in electronic format. The mega table is submitted as three files, entitled "52199_510P01US_mega_table_part1", "52199_510P01US_mega_table_part2" and "52199_510P01US_mega_table_part3", which were created on Mar. 21, 2018 and are respectively 20.1, 15.4 and 19.4 MB in size. The instant mega table contains: Table S1; Tables S2a and S2b; Tables S3a to S3f; Tables S4a to S4f; Tables S5a to S5d; Tables S6a to S6h; Tables S7a and S7b; Tables S8a to S8c; Tables S9a and S9b; Tables S10a to S10c; and Tables S11a and S11b. The information in the electronic format of the mega table is part of the present application and is incorporated herein by reference in its entirety.

disease that is often fatal. To date, limited treatment options have been available for this remainder of patients having recurrent or progressive diffuse large B-cell lymphoma (DLBCL). A need exists for improved compositions and methods for treating DLBCL, as well as for treating other forms of cancer.

BRIEF SUMMARY OF THE INVENTION

The current disclosure relates, at least in part, to compositions and methods for the diagnosis and treatment of DLBCL. In particular, the instant disclosure has identified at least five distinct classes of DLBCL cancer, each of which possesses distinct pathogenic mechanisms and outcomes. This classification further identifies preferred therapeutic options for each such class of DLBCL cancer, in many cases distinct from those treatments previously appreciated for DLBCL treatment, particularly where such classification indicates use of a combination therapy.

In one aspect the instant disclosure provides a method for selecting a treatment for a subject having or at risk of developing DLBCL, the method involving (a) obtaining a sample from a subject having or at risk of DLBCL; (b) identifying the presence or absence in the sample of five or more sequence variants and/or sites of copy number variation from among the following: 1P13.1:DEL; 1P31.1:DEL; 1P36.11:DEL; 2P16.1:AMP; 3P:AMP; 3P21.31:DEL; 3Q:AMP; 4Q21.22:DEL; 4Q35.1:DEL; 5P:AMP; 9P21.3: DEL; 9Q21.13:DEL; 10Q23.31:DEL; 14Q32.31:DEL; 16Q12.1:DEL; 17P:DEL; 17Q25.1:DEL; 18P:AMP; 18Q: AMP; 19P13.2:DEL; 19Q:AMP; 19Q13.42:AMP; 21Q: AMP; a variant or copy number variation in B2M; a variant or copy number variation in BCL2; a variant or copy number variation in BCL10; a variant or copy number variation in BRAF; a variant or copy number variation in CD58; a variant or copy number variation in CD70; a variant or copy number variation in CD79B; a variant or copy number variation in CD83; a variant or copy number variation in CREBBP; a variant or copy number variation in ETV6; a

LENGTHY TABLES

The patent contains a lengthy table section. A copy of the table is available in electronic form from the USPTO web site (https://seqdata.uspto.gov/docdetail?docId=US12571049B2). An electronic copy of the table will also be available from the USPTO upon request and payment of the fee set forth in 37 CFR 1.19(b)(3).

FIELD OF THE INVENTION

The invention relates generally to methods and compositions for the treatment of select classes of diffuse large B-cell lymphoma (DLBCL).

BACKGROUND OF THE INVENTION

Diffuse large B-cell lymphoma (DLBCL), the most common lymphoid malignancy in adults (accounting for up to 35% of non-Hodgkin lymphomas), is a clinically and genetically heterogenous disease that is further classified into transcriptionally defined activated B-cell (ABC) and germinal center B-cell (GCB) subtypes. Although DLBCL is curable with combination therapy (R-CHOP) in over 60% of patients, the remainder develop recurrent or progressive variant or copy number variation in EZH2; a variant or copy number variation in FAS; a marker that indicates genome doubling; a variant or copy number variation in GNA13; a variant or copy number variation in GNAI2; a variant or copy number variation in GRHPR; a variant or copy number variation in HIST1H1B; a variant or copy number variation in HIST1H1C; a variant or copy number variation in HIST1H1D; a variant or copy number variation in HIST1H1E; a variant or copy number variation in HIST1H2BC; a variant or copy number variation in HLA-B; a variant or copy number variation in HVCN1; a variant or copy number variation in IRF8; a variant or copy number variation in KLHL6; a variant or copy number variation in KMT2D; a variant or copy number variation in MEF2B; MYD88:L265; a non-L265 variant in MYD88; a variant or copy number variation in NFKBIA; a variant or copy number variation in NFKBIE; a variant or copy number variation in NOTCH2; a variant or copy number variation in PIM1; a variant or copy number variation in POU2F2; a variant or copy number variation in PTEN; a variant or copy number variation in SGK1; a variant or copy number variation in SPEN; a variant or copy number variation in STAT3; a variant or copy number variation in SV:BCL2; a variant or copy number variation in SV:BCL6; a variant or copy number variation in SV:CD274/PDCD1LG2; a variant or copy number variation in SV:MYC; a variant or copy number variation in SV:TP63; a variant or copy number variation in TBL1XR1; a variant or copy number variation in TMEM30A; a variant or copy number variation in TNFAIP3; a variant or copy number variation in TNFRSFI4; a variant or copy number variation in TP53; a variant or copy number variation in UBE2A; a variant or copy number variation in ZC3H12A; a variant or copy number variation in ZEB2; and a variant or copy number variation in ZFP36L1; (c) analyzing the presence or absence of sequence variants of step (b) to assign the sample to a discrete class of activated B-cell DLBCL (ABC-DLBCL) or germinal center B-cell DLBCL (GCB-DLBCL); (d) if the sample is assigned to an ABC-DLBCL class, selecting either the treatment of (i) or the treatment of (ii) for administration to the subject: (i) a NOTCH inhibitor, a BCL6 inhibitor and/or an activator of immune evasion, optionally an oligonucleotide inhibitor of NOTCH and/or BCL6; or (ii) a BCR/TLR signaling inhibitor and/or a BCL2 inhibitor, optionally oblimersen, ABT-263, Venetoclax (ABT-199), an antibody or oligonucleotide inhibitor of BCR/TLR signaling and/or an oligonucleotide inhibitor of BCL2; or if the sample is assigned to a GBC-DLBCL class, selecting either the treatment of (iii) or the treatment of (iv) for administration to the subject: (iii) a BCL2 inhibitor, a PI3K inhibitor and/or an epigenetic modifier inhibitor, optionally oblimersen, ABT-263, Venetoclax (ABT-199), wortmannin, LY294002, an E2H2 inhibitor (optionally 3-deazaneplanocin A (DZNep), EPZ005687, EI1, GSK126, and/or UNC1999), a CREBBP inhibitor, an oligonucleotide inhibitor of BCL2, an oligonucleotide inhibitor of PI3K and/or an oligonucleotide inhibitor of an epigenetic modifier; or (iv) a JAK/STAT inhibitor and/or a BRAF/MEK1 inhibitor, optionally ruxolitinib, Vemurafenib, Cobimetinib, an oligonucleotide inhibitor of JAK/STAT and/or an oligonucleotide inhibitor of BRAF/MEK1, or if the sample is assigned to a DLBCL class that is characterized by frequent bi-allelic inactivation of TP53 by mutations and 17p copy loss, selecting (v) a treatment comprising a CDK inhibitor, thereby selecting a treatment for the subject having or at risk of developing DLBCL.

In one embodiment, the identifying step (b) involves whole exome sequencing (WES) of the sample. In other embodiments, the identifying step (b) involves sequencing of selected exomic regions of the sample, optionally involving sequencing of the five or more sequence variants and/or sites of copy number variation within a selection of no more than 300,000 probe sequence regions, optionally involving sequencing of the five or more sequence variants and/or sites of copy number variation within a selection of no more than 50,000 probe sequence regions, optionally involving sequencing of the five or more sequence variants and/or sites of copy number variation within a selection of no more than 30,000 probe sequence regions, optionally involving sequencing of the five or more sequence variants and/or sites of copy number variation within a selection of no more than 10,000 probe sequence regions, optionally involving sequencing of the five or more sequence variants and/or sites of copy number variation within a selection of no more than 3,000 probe sequence regions, optionally involving sequencing of the five or more sequence variants and/or sites of copy number variation within a selection of no more than 1,000 probe sequence regions, optionally involving sequencing of the five or more sequence variants and/or sites of copy number variation within a selection of no more than 500 probe sequence regions, optionally involving sequencing of the five or more sequence variants and/or sites of copy number variation within a selection of no more than 300 probe sequence regions, optionally involving sequencing of the five or more sequence variants and/or sites of copy number variation via PCR amplification and sequencing of the sample. Optionally, sequencing and classification of the sample is performed via use of targeted hybrid capture, an amplicon-based sequencing technology, and/or a non-targeted sequencing technology, optionally whole genome sequencing (WGS).

In one embodiment, the sample from the subject having or at risk of DLBCL is compared to a paired normal sample in performing analyzing step (c).

In certain embodiments, the method further involves administering one or more selected treatments to the subject having or at risk of developing DLBCL, in an amount sufficient to treat or prevent DLBCL in the subject. Optionally, a combination therapy is administered.

In another embodiment, step (b) involves identifying the presence or absence in the sample of all seventy-five sequence variants and/or sites of copy number variation.

In some embodiments, step (b) involves identifying the presence or absence in the sample of ten or more of the above-recited sequence variants and/or sites of copy number variation, optionally twenty or more of the above-recited sequence variants and/or sites of copy number variation, optionally thirty or more of the above-recited sequence variants and/or sites of copy number variation, optionally forty or more of the above-recited sequence variants and/or sites of copy number variation, optionally fifty or more of the above-recited sequence variants and/or sites of copy number variation, optionally sixty or more of the above-recited sequence variants and/or sites of copy number variation and optionally seventy or more of the above-recited sequence variants and/or sites of copy number variation.

In certain embodiments, analyzing step (c) involves use of a neural net classifier.

In one embodiment, the identifying step (b) involves use of a kit of the instant disclosure.

Another aspect of the instant disclosure provides a kit for identifying genetic variation (including sequence variants, copy number variation, etc.) in a sample, the kit containing fewer than 500,000 oligonucleotide probes, among which are five or more of the following oligonucleotide probes: an oligonucleotide probe for detecting the sequence or copy number of 1P13.1:DEL; an oligonucleotide probe for detecting the sequence or copy number of 1P31.1:DEL; an oligonucleotide probe for detecting the sequence or copy number of 1P36.11:DEL; an oligonucleotide probe for detecting the sequence or copy number of 2P16.1:AMP; an oligonucleotide probe for detecting the sequence or copy number of 3P:AMP; an oligonucleotide probe for detecting the sequence or copy number of 3P21.31:DEL; an oligonucleotide probe for detecting the sequence or copy number of 3Q:AMP; an oligonucleotide probe for detecting the sequence or copy number of 4Q21.22:DEL; an oligonucleotide probe for detecting the sequence or copy number of 4Q35.1:DEL; an oligonucleotide probe for detecting the sequence or copy number of 5P:AMP; an oligonucleotide probe for detecting the sequence or copy number of 9P21.3: DEL; an oligonucleotide probe for detecting the sequence or copy number of 9Q21.13:DEL; an oligonucleotide probe for detecting the sequence or copy number of 10Q23.31:DEL; an oligonucleotide probe for detecting the sequence or copy number of 14Q32.31:DEL; an oligonucleotide probe for detecting the sequence or copy number of 16Q12.1:DEL; an oligonucleotide probe for detecting the sequence or copy number of 17P:DEL; an oligonucleotide probe for detecting the sequence or copy number of 17Q25.1:DEL; an oligo-nucleotide probe for detecting the sequence or copy number of 18P:AMP; an oligonucleotide probe for detecting the sequence or copy number of 18Q:AMP; an oligonucleotide probe for detecting the sequence or copy number of 19P13.2:DEL; an oligonucleotide probe for detecting the sequence or copy number of 19Q:AMP; an oligonucleotide probe for detecting the sequence or copy number of 19Q13.42:AMP; an oligonucleotide probe for detecting the sequence or copy number of 21Q:AMP; an oligonucleotide probe for detecting the sequence or copy number of B2M; an oligonucleotide probe for detecting the sequence or copy number of BCL2; an oligonucleotide probe for detecting the sequence or copy number of BCL10; an oligonucleotide probe for detecting the sequence or copy number of BRAF; an oligonucleotide probe for detecting the sequence or copy number of CD58; an oligonucleotide probe for detecting the sequence or copy number of CD70; an oligonucleotide probe for detecting the sequence or copy number of CD79B; an oligonucleotide probe for detecting the sequence or copy number of CD83; an oligonucleotide probe for detecting the sequence or copy number of CREBBP; an oligonucleotide probe for detecting the sequence or copy number of ETV6; an oligonucleotide probe for detecting the sequence or copy number of EZH2; an oligonucleotide probe for detecting the sequence or copy number of FAS; an oligonucleotide probe for detecting genome doubling; an oligonucleotide probe for detecting the sequence or copy number of GNA13; an oligonucleotide probe for detecting the sequence or copy number of GNAI2; an oligonucleotide probe for detecting the sequence or copy number of GRHPR; an oligonucleotide probe for detecting the sequence or copy number of HIS-TIHIB; an oligonucleotide probe for detecting the sequence or copy number of HISTIHIC; an oligonucleotide probe for detecting the sequence or copy number of HISTIHID; an oligonucleotide probe for detecting the sequence or copy number of HIST1H1E; an oligonucleotide probe for detecting the sequence or copy number of HIST1H2BC; an oligonucleotide probe for detecting the sequence or copy number of HLA-B; an oligonucleotide probe for detecting the sequence or copy number of HVCN1; an oligonucleotide probe for detecting the sequence or copy number of IRF8; an oligonucleotide probe for detecting the sequence or copy number of KLHL6; an oligonucleotide probe for detecting the sequence or copy number of KMT2D; an oligonucle-otide probe for detecting the sequence or copy number of MEF2B; an oligonucleotide probe for detecting the sequence or copy number of MYD88:L265; an oligonucle-otide probe for detecting the sequence or copy number of MYD88:OTHER; an oligonucleotide probe for detecting the sequence or copy number of NFKBIA; an oligonucleotide probe for detecting the sequence or copy number of NFK-BIE; an oligonucleotide probe for detecting the sequence or copy number of NOTCH2; an oligonucleotide probe for detecting the sequence or copy number of PIM1; an oligo-nucleotide probe for detecting the sequence or copy number of POU2F2; an oligonucleotide probe for detecting the sequence or copy number of PTEN; an oligonucleotide probe for detecting the sequence or copy number of SGK1; an oligonucleotide probe for detecting the sequence or copy number of SPEN; an oligonucleotide probe for detecting the sequence or copy number of STAT3; an oligonucleotide probe for detecting the sequence or copy number of SV:BCL2; an oligonucleotide probe for detecting the sequence or copy number of SV:BCL6; an oligonucleotide probe for detecting the sequence or copy number of SV:CD274/PDCD1LG2; an oligonucleotide probe for detecting the sequence or copy number of SV:MYC; an oligonucleotide probe for detecting the sequence or copy number of SV:TP63; an oligonucleotide probe for detecting the sequence or copy number of TBL1XR1; an oligonucle-otide probe for detecting the sequence or copy number of TMEM30A; an oligonucleotide probe for detecting the sequence or copy number of TNFAIP3; an oligonucleotide probe for detecting the sequence or copy number of TNFRSFI4; an oligonucleotide probe for detecting the sequence or copy number of TP53; an oligonucleotide probe for detecting the sequence or copy number of UBE2A; an oligonucleotide probe for detecting the sequence or copy number of ZC3H12A; an oligonucleotide probe for detect-ing the sequence or copy number of ZEB2; and an oligo-nucleotide probe for detecting the sequence or copy number of ZFP36L1, and instructions for its use.

In one embodiment, the sample is a tumor sample. Optionally, the sample is a diffuse large B-cell lymphoma (DLBCL) tumor sample.

In another embodiment, the sample is a tissue sample of a subject having DLBCL. Optionally, the sample is a blood sample.

In certain embodiments, the kit contains ten or more of the above-recited oligonucleotide probes, optionally the kit con-tains twenty or more of the above-recited oligonucleotide probes, optionally the kit contains thirty or more of the above-recited oligonucleotide probes, optionally the kit con-tains forty or more of the above-recited oligonucleotide probes, optionally the kit contains fifty or more of the above-recited oligonucleotide probes, optionally the kit con-tains sixty or more of the above-recited oligonucleotide probes, optionally the kit contains seventy or more of the above-recited oligonucleotide probes, optionally the kit con-tains the seventy-five above-recited oligonucleotide probes.

In some embodiments, the kit includes fewer than 300,000 oligonucleotide probes, optionally fewer than 50,000 oligonucleotide probes, optionally fewer than 30,000 oligo-nucleotide probes, optionally fewer than 10,000 oligonucle-otide probes, optionally fewer than 5,000 oligonucleotide probes, optionally fewer than 1,000 oligonucleotide probes, optionally fewer than 500 oligonucleotide probes, optionally fewer than 400 oligonucleotide probes, optionally fewer than 300 oligonucleotide probes.

Another aspect of the instant disclosure provides a kit for identifying sequence variants and/or copy number variation in a sample, where the kit contains fewer than 500,000 oligonucleotide probes including a first oligonucleotide probe for detecting the sequence or copy number of 1P13.1: DEL; a second oligonucleotide probe for detecting the sequence or copy number of 1P31.1:DEL; a third oligo-nucleotide probe for detecting the sequence or copy number of 1P36.11:DEL; a fourth oligonucleotide probe for detect-ing the sequence or copy number of 2P16.1:AMP; a fifth oligonucleotide probe for detecting the sequence or copy number of 3P:AMP; a sixth oligonucleotide probe for detecting the sequence or copy number of 3P21.31:DEL; a seventh oligonucleotide probe for detecting the sequence or copy number of 3Q:AMP; an eighth oligonucleotide probe for detecting the sequence or copy number of 4Q21.22:DEL; a ninth oligonucleotide probe for detecting the sequence or copy number of 4Q35.1:DEL; a tenth oligonucleotide probe for detecting the sequence or copy number of 5P:AMP; an eleventh oligonucleotide probe for detecting the sequence or copy number of 9P21.3:DEL; a twelfth oligonucleotide probe for detecting the sequence or copy number of 9Q21.13:DEL; a thirteenth oligonucleotide probe for detecting the sequence or copy number of 10Q23.31:DEL; a fourteenth oligonucleotide probe for detecting the sequence or copy number of 14Q32.31:DEL; a fifteenth oligonucleotide probe for detecting the sequence or copy number of 16Q12.1:DEL; a sixteenth oligonucleotide probe for detecting the sequence or copy number of 17P:DEL; a seventeenth oligonucleotide probe for detecting the sequence or copy number of 17Q25.1:DEL; an eighteenth oligonucleotide probe for detecting the sequence or copy number of 18P: AMP; a nineteenth oligonucleotide probe for detecting the sequence or copy number of 18Q:AMP; a twentieth oligonucleotide probe for detecting the sequence or copy number of 19P13.2:DEL; a twenty-first oligonucleotide probe for detecting the sequence or copy number of 19Q:AMP; a twenty-second oligonucleotide probe for detecting the sequence or copy number of 19Q13.42:AMP; a twenty-third oligonucleotide probe for detecting the sequence or copy number of 21Q:AMP; a twenty-fourth oligonucleotide probe for detecting the sequence or copy number of B2M; a twenty-fifth oligonucleotide probe for detecting the sequence or copy number of BCL2; a twenty-sixth oligonucleotide probe for detecting the sequence or copy number of BCL10; a twenty-seventh oligonucleotide probe for detecting the sequence or copy number of BRAF; a twenty-eighth oligonucleotide probe for detecting the sequence or copy number of CD58; a twenty-ninth oligonucleotide probe for detecting the sequence or copy number of CD70; a thirtieth oligonucleotide probe for detecting the sequence or copy number of CD79B; a thirty-first oligonucleotide probe for detecting the sequence or copy number of CD83; a thirty-second oligonucleotide probe for detecting the sequence or copy number of CREBBP; a thirty-third oligonucleotide probe for detecting the sequence or copy number of ETV6; a thirty-fourth oligonucleotide probe for detecting the sequence or copy number of EZH2; a thirty-fifth oligonucleotide probe for detecting the sequence or copy number of FAS; a thirty-sixth oligonucleotide probe for detecting the presence of genome doubling; a thirty-seventh oligonucleotide probe for detecting the sequence or copy number of GNA13; a thirty-eighth oligonucleotide probe for detecting the sequence or copy number of GNAI2; a thirty-ninth oligonucleotide probe for detecting the sequence or copy number of GRHPR; a fortieth oligonucleotide probe for detecting the sequence or copy number of HIST1HIB; a forty-first oligonucleotide probe for detecting the sequence or copy number of HIST1HIC; a forty-second oligonucleotide probe for detecting the sequence or copy number of HIST1HID; a forty-third oligonucleotide probe for detecting the sequence or copy number of HIST1H1E; a forty-fourth oligonucleotide probe for detecting the sequence or copy number of HIST1H2BC; a forty-fifth oligonucleotide probe for detecting the sequence or copy number of HLA-B; a forty-sixth oligonucleotide probe for detecting the sequence or copy number of HVCN1; a forty-seventh oligonucleotide probe for detecting the sequence or copy number of IRF8; a forty-eighth oligonucleotide probe for detecting the sequence or copy number of KLHL6; a forty-ninth oligonucleotide probe for detecting the sequence or copy number of KMT2D; a fiftieth oligonucleotide probe for detecting the sequence or copy number of MEF2B; a fifty-first oligonucleotide probe for detecting the sequence or copy number of MYD88:L265; a fifty-second oligonucleotide probe for detecting the sequence or copy number of MYD88:OTHER; a fifty-third oligonucleotide probe for detecting the sequence or copy number of NFKBIA; a fifty-fourth oligonucleotide probe for detecting the sequence or copy number of NFK-BIE; a fifty-fifth oligonucleotide probe for detecting the sequence or copy number of NOTCH2; a fifty-sixth oligonucleotide probe for detecting the sequence or copy number of PIM1; a fifty-seventh oligonucleotide probe for detecting the sequence or copy number of POU2F2; a fifty-eighth oligonucleotide probe for detecting the sequence or copy number of PTEN; a fifty-ninth oligonucleotide probe for detecting the sequence or copy number of SGK1; a sixtieth oligonucleotide probe for detecting the sequence or copy number of SPEN; a sixty-first oligonucleotide probe for detecting the sequence or copy number of STAT3; a sixty-second oligonucleotide probe for detecting the sequence or copy number of SV:BCL2; a sixty-third oligonucleotide probe for detecting the sequence or copy number of SV:BCL6; a sixty-fourth oligonucleotide probe for detecting the sequence or copy number of SV:CD274/PDCD1LG2; a sixty-fifth oligonucleotide probe for detecting the sequence or copy number of SV:MYC; a sixty-sixth oligonucleotide probe for detecting the sequence or copy number of SV:TP63; a sixty-seventh oligonucleotide probe for detecting the sequence or copy number of TBL1XR1; a sixty-eighth oligonucleotide probe for detecting the sequence or copy number of TMEM30A; a sixty-ninth oligonucleotide probe for detecting the sequence or copy number of TNFAIP3; a seventieth oligonucleotide probe for detecting the sequence or copy number of TNFRSFI4; a seventy-first oligonucleotide probe for detecting the sequence or copy number of TP53; a seventy-second oligonucleotide probe for detecting the sequence or copy number of UBE2A; a seventy-third oligonucleotide probe for detecting the sequence or copy number of ZC3H12A; a seventy-fourth oligonucleotide probe for detecting the sequence or copy number of ZEB2; and a seventy-fifth oligonucleotide probe for detecting the sequence or copy number of ZFP36L1, and instructions for its use.

Optionally, the kit includes one or more oligonucleotides possessing a modification, optionally where the modification is a 5'-tail sequence, a barcode sequence and/or a labeled probe, optionally where the modification or label is a fluorescent label or a radiolabel.

Definitions

Unless specifically stated or obvious from context, as used herein, the term "about" is understood as within a range of normal tolerance in the art, for example within 2 standard deviations of the mean. "About" can be understood as within 10%, 9%, 8%, 7%, 6%, 5%, 4%, 3%, 2%, 1%, 0.5%, 0.1%, 0.05%, or 0.01% of the stated value.

In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Unless otherwise clear from context, all numerical values provided herein are modified by the term "about."

The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In some embodiments, administration is oral. Additionally or alternatively, in some embodiments, administration is parenteral. In some embodiments, administration is intravenous.

By "agent" is meant any small compound (e.g., small molecule), antibody, nucleic acid molecule, or polypeptide, or fragments thereof or cellular therapeutics such as allogeneic transplantation and/or CART-cell therapy.

The term "cancer" refers to a malignant neoplasm (Stedman's Medical Dictionary, 25th ed.; Hensyl ed.; Williams & Wilkins: Philadelphia, 1990). Exemplary cancers include, but are not limited to, diffuse large B-cell lymphoma (DLBCL), as well as the broader class of lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above, hematopoietic cancers (e.g., myeloid malignancies (e.g., acute myeloid leukemia (AML) (e.g., B-cell AML, T-cell AML), myelodysplastic syndrome, myeloproliferative neoplasm, chronic myelomonocytic leukemia (CMML) and chronic myelogenous leukemia (CML) (e.g., B-cell CML, T-cell CML)) and lymphocytic leukemia such as acute lymphocytic leukemia (ALL) (e.g., B-cell ALL, T-cell ALL) and chronic lymphocytic leukemia (CLL) (e.g., B-cell CLL, T-cell CLL)); brain cancer (e.g., meningioma, glioblastomas, glioma (e.g., astrocytoma, oligodendroglioma), medulloblastoma); lung cancer (e.g., bronchogenic carcinoma, small cell lung cancer (SCLC), non-small cell lung cancer (NSCLC), adenocarcinoma of the lung); acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendocrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

By "control" or "reference" is meant a standard of comparison. In one aspect, as used herein, "changed as compared to a control" sample or subject is understood as having a level that is statistically different than a sample from a normal, untreated, or control sample. Control samples include, for example, cells in culture, one or more laboratory test animals, or one or more human subjects. Methods to select and test control samples are within the ability of those in the art. Determination of statistical significance is within the ability of those skilled in the art, e.g., the number of standard deviations from the mean that constitute a positive result.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation.

As used herein, the term "next-generation sequencing" or "NGS" can refer to sequencing technologies that have the capacity to sequence polynucleotides at speeds that were unprecedented using conventional sequencing methods (e.g., standard Sanger or Maxam-Gilbert sequencing methods). These unprecedented speeds are achieved by performing and reading out thousands to millions of sequencing reactions in parallel. NGS sequencing platforms include, but are not limited to, the following: Massively Parallel Signature Sequencing (Lynx Therapeutics); 454 pyro-sequencing (454 Life Sciences/Roche Diagnostics); solid-phase, reversible dye-terminator sequencing (Solexa/Illumina); SOLiD technology (Applied Biosystems); Ion semiconductor sequencing (ion Torrent); and DNA nanoball sequencing (Complete Genomics). Descriptions of certain NGS platforms can be found in the following: Shendure, er al., "Next-generation DNA sequencing," Nature, 2008, vol. 26, No. 10, 135-1145; Mardis, "The impact of next-generation sequencing technology on genetics," Trends in Genetics, 2007, vol. 24, No. 3, pp. 133-141; Su, et al., "Next-generation sequencing and its applications in molecular diagnostics" Expert Rev Mol Diagn, 2011, 11 (3):333-43; and Zhang et al., "The impact of next-generation sequencing on genomics", J Genet Genomics, 201, 38(3): 95-109.

As used herein, the term "subject" includes humans and mammals (e.g., mice, rats, pigs, cats, dogs, and horses). In many embodiments, subjects are mammals, particularly primates, especially humans. In some embodiments, subjects are livestock such as cattle, sheep, goats, cows, swine, and the like; poultry such as chickens, ducks, geese, turkeys, and the like; and domesticated animals particularly pets such as dogs and cats. In some embodiments (e.g., particularly in research contexts) subject mammals will be, for example, rodents (e.g., mice, rats, hamsters), rabbits, primates, or swine such as inbred pigs and the like.

As used herein, the terms "treatment," "treating," "treat" and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment," as used herein, covers any treatment of a disease or condition in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

Unless specifically stated or obvious from context, as used herein, the term "or" is understood to be inclusive. Unless specifically stated or obvious from context, as used herein, the terms "a", "an", and "the" are understood to be singular or plural.

The phrase "pharmaceutically acceptable carrier" is art recognized and includes a pharmaceutically acceptable material, composition or vehicle, suitable for administering compounds of the present disclosure to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect. It is further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

The term "pharmaceutically acceptable salts, esters, amides, and prodrugs" as used herein refers to those carboxylate salts, amino acid addition salts, esters, amides, and prodrugs of the compounds of the present disclosure which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the disclosure.

The term "salts" refers to the relatively non-toxic, inorganic and organic acid addition salts of compounds of the present disclosure. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethyl ammonium, methylamine, dimethylamine, trimethylamine, triethylamine, ethylamine, and the like. (See, for example, S. M. Barge et al., "Pharmaceutical Salts," J. Pharm. Sci., 1977, 66:1-19 which is incorporated herein by reference).

A "therapeutically effective amount" of an agent described herein is an amount sufficient to provide a therapeutic benefit in the treatment of a condition or to delay or minimize one or more symptoms associated with the condition. A therapeutically effective amount of an agent means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the disclosure will be apparent from the following description of the preferred embodiments thereof, and from the claims. Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All published foreign patents and patent applications cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

The following detailed description, given by way of example, but not intended to limit the disclosure solely to the specific embodiments described, may best be understood in conjunction with the accompanying drawings, in which:

FIG. 1A is a plot showing the number and frequency of recurrent mutations (left), with a gene-sample matrix of recurrently mutated genes (color-coded by type; center), ranked by their significance (MutSig2CV q-value; right). A graph of total mutation density across the cohort is also given (top). Asterisk indicates hypermutator case. Genes also identified by CLUMPS are in bold. FIG. 1B is an image of representative examples of binding pockets for products of genes that showed significant spacial clustering in protein structures (grey): TP53 (top; PDB:4MZR), BRAF (middle; PDB ID:4G9R), GNAI2 (bottom; PDB:1AGR). Mutated residues are shown in red and color intensity scales with number of mutations. Polar interactions are shown in dotted yellow lines. Frequently mutated residues are labeled in black. Co-crystalized proteins are shown in blue (Zn+, Type II Dihydroquinazoline inhibitor and GDP). FIG. 1C is an image of a co-crystal structure of RHOA (grey) and ARHGEF18 (cyan; PDB:4D0N) highlights mutational clustering at the RHOA-ARHGEF interface. Residues at the interface are in black.

FIG. 2A is a series of graphs of mutation signature analysis with the clustering information of mutations quantified by the nearest mutation distance (NMDs). The mutation signature analysis identifies three mutational signatures; C→T mutations at CpG islands (C→T CpG, hereafter "Aging"), canonical AID (cAID) and a secondary AID signature (AID2) in 303 DLBCL samples. One sample with a predominant contribution of the MSI signature activity (SNVs>5000; See Example 1) was excluded. FIG. 2B displays a series of graphs of signature activity (the number of mutations assigned to each signature) in each group of clustered (red; NMD≤1 kb) and non-clustered mutations (blue; NMD>1 kb) across 303 DLBCL samples sorted by decreasing mutation count. FIG. 2C shows a graph of relative enrichment of signature activities in significantly mutated genes having at least 10 mutations. Number of mutations per gene are displayed at right. Genes were sorted by prevalence of the aging signature. Error bars show the standard error.

FIG. 3A shows a an image of SVs of BCL2 (green) and partner genes (grey) visualized as Circos plots. FIG. 3B displays an image of BCL6 (blue) and partner genes (grey) visualized as Circos plots. FIG. 3C displays an image of MYC (red) and partner genes (grey) visualized as Circos plots. Genes also targeted by somatic mutations are highlighted in black, while thickness of partner linking lines indicates frequency (numbers indicate frequency >1) in FIGS. 3A to 3C. FIG. 3D displays a graph of breakpoints within BCL2 plotted in their indicated genomic context. FIG. 3E shows a graph of breakpoints within BCL6 plotted in their indicated genomic context. FIG. 3F displays a graph of breakpoints within MYC plotted in their indicated genomic context. Arrows indicate the transcription start site in the coding direction; boxes indicate exons including first coding exon (red); green bar below indicates which exons are protein coding. Translocation partners are indicated by the shading of the circle at the tip of each breakpoint (IgH, black; Igκ, dark grey; Igλ, light grey; non-Ig partners, white and name of partner gene above) in FIGS. 3D to 3F. FIG. 3G displays a circos plot of chromosomal rearrangements involving the PD-1 ligand loci, PD-L1 and PD-L2, (orange). Labeling for FIG. 3G is the same as labeling for FIGS. 3A to 3D. FIG. 3H displays a graph of stick figures for indicated translocations involving either PD-L1 or PD-L2 (refer to FIG. 3H for details). Raw reads count were visualized in FIG. H below. Reads mapping to the first and second partner gene are highlighted in green and orange, respectively. FIG. 3I displays a series of images of PD-L1/PAX5 (left panel, PD-L1, brown; PAX5, pink) and PD-L2 (middle panel; PD-L2, brown) immuno-histochemical analyses for the cases identified in FIG. 3H.

FIG. 4A displays an image of GISTIC2.0-defined recurrent copy number gains (red, left panel) and losses (blue, right panel) visualized as mirror GISTIC-plots, with arm-level events, left, and focal events, right. Chromosomes are displayed on the vertical axis. Green line denotes q-value of 0.1. SCNAs are labeled with their associated cytoband/arm followed in brackets by the frequency of the alteration, the number of total genes and COSMIC-defined cancer genes in GISTIC2.0-defined regions, respectively. For focal events, COSMIC cancer genes with a positive correlation to gene expression in our data (fold change >1.2, q<0.25) are indicated within the brackets. Genes that were also identified as significantly mutated (in black) or subject to chromo-somal rearrangement (n=>2, green) in the dataset are high-lighted after the brackets. Other important drivers are labeled in grey. FIG. 4B displays Kaplan Meier plots of individual genetic factors predictive for PFS in univariate and multivariate models; alterations present, dashed line; p-values derived from log-rank test. FIG. 4C displays forest plots which visualize the multivariate analysis of IPI risk groups and individual genetic factors for PFS.

FIG. 6A depicts a pie chart of the type of MYD88 mutations. In FIGS. 6E to 6I, cancer cell fractions (CCF) of clusters C1-C5 have been plotted and ranked by the fraction of clonal events of each landmark alteration (high to low, right panel). Median CCF in red bar, error bar represents the interquartile range. Mutations, black; CN gain, red; CN loss, blue; SVs, green. The threshold chosen for assigning an alteration to be "clonal" is a CCF of ≥0.9 (green dotted line). FIG. 6N displays a series of forest plots that visualize HR and p-values obtained from the multivariate analysis of¬ clusters and IPI for PFS.

FIGS. 9A to 9D show crystal structures of CREBBP (FIG. 9A: PDB:4pzt), KRAS (FIG. 9B: PDB:4lv6), MAP2K1 (MEK1, FIG. 9C: PDB:3w8q) and PTPN6 (SHP1, FIG. 9D: PDB:4grz) in grey. Mutated residues in red and color intensity scales with number of mutations. Polar interactions are shown in yellow. Ligands are respectively represented in blue (FIG. 9A: S-Co-enzyme A; FIG. 9B: GDP; FIG. 9C: ATPγS; FIG. 9D: phosphate). FIG. 9E shows BRAF mutations in the context of the functional domains of BRAF. Analysis revealed clustering of mutations in the P-loop (orange) and activation-loop (cyan) of the kinase domain. Structural and functional consequences for several of these BRAF mutations have been analyzed previously (S10-S12). Mutations that either activate the kinase domain by abolishing a hydrophobic interaction between P- and activation-loop (green) or result in a reduced kinase activity (red) are noted (S10-S12). Since kinase-death mutations transactivate RAF1, the downstream consequences of all mutations are identical—increased phosphorylation and signaling through ERK (S10-S12).

FIG. 10A shows the co-crystal structure of RHOA (grey) and ARHGEF18 (cyan, PDB:4D0N) as a representative example of clustered mutations at the interphase of RHOA to its ARHGEFs (left panel, side view; right panel, 90° rotation around vertical axis of left panel). Mutated residues are labeled in black and shown in red and color intensity scales with number of mutations. Previous studies also described RHOA mutations that perturb interactions with ARHGEFs in other tumors (S13, S14). FIG. 10B shows the crystal structure of RHOA (grey, PDB ID: 1dpf). Of note, mutations in RHOA do not affect the catalytic pocket surrounding GDP (blue); instead, the mutations perturb the interphase with ARHGEFs (highlighted in yellow; Mega Table Supplementary Table 3c presents a list of all CLUMPS at interfaces/EMPRINT results). FIG. 10C depicts a model of RHOAwt (top) and RHOAmut (bottom) function. ARHGEFs serve as guanosine exchange factors (GEF) facilitating the replacement of GDP (blue) by GTP (red). Active RHOAwt-GTP blocks migration and Pi3K/AKT signaling. Mutations in RHOA (RHOAmut) prevent the binding of ARHGEFs, keeping RHOAmut in its inactive GDP state and preventing negative regulation of migration and Pi3K/AKT signaling. FIG. 10D shows the co-crystal structure of FBXW7 (grey) and cyclin E1 (CCNE1, blue). Mutations in FBXW7 at the interphase to the CCNE1 degron are labeled in black. FIG. 10E depicts a model of FBXW7mut function. The SCFFBXW7-wt (complex of SKP1, CUL1 and FBXW7 wt) recognizes and targets cyclin E1 (CCNE1) for proteasomal degradation by ubiquitination (Ub). Mutations in FBXW7 (FBXW7mut) perturb the recognition of cyclin E1 and its subsequent proteasomal degradation.

FIG. 11A shows de novo signature extraction for 304 DLBCL samples identified a putative microsatellite instability (MSI) signature in addition to two signatures, 304-B and 304-C. FIG. 11G), the paired sample set analyzed with the matched normal samples (PAIRED-SET-TN, n=134; FIG. 11H), and the paired sample set analyzed without the matched normal (PAIRES-SET-TO, n=134, FIG. 11I); FIG. 11J shows a heatmap of the cosine similarity of three signatures among COMBINE-SET, PAIRED-SET-TN, and PAIRED-SET-TO; FIG. 11Q shows cosine similarity of Aging (left), cAID (middle), and AID2 (right) signature extracted for 500 pooled sample sets as a function of a fraction of FFPE samples. In each experiment, randomly chosen fresh-frozen samples were replaced by the same number of random FFPE samples.

FIG. 12A shows a schematic overview of the analytical pipeline to detect SVs and their CCF. The outputs of four different detectors, dRanger (S15), SVaBA, Lumpy (S16) and BreaKmer (S17), were clustered and inputted into Breakpointer (S15) to obtain supporting split read evidence and a unified count read of the reference and alternate allele. SVs found with less than 4 total reads, SVs found in a Panel of Normals (PoNs), SV that were part of polymorphic Ig and TCR regions and artifacts in manual review were filtered out. For the remainder of events, the CCF was calculated as described in the Methods. FIG. 12B depicts a Venn Diagram visualizing the overlap of SVs identified by each detector. FIG. 12C shows a heatmap illustrating the detector evidence for chromosomal rearrangements involving BCL2, BCL6 and MYC. FIG. 12D presents a summary of SV types. Of note, translocations of BCL2 and BCL6 were largely mutual exclusive (p=8.6730e-04). FIG. 12E presents a summary of the most frequent SVs ranked by frequency.

FIGS. 13A to 13F show circos plots of all detected chromosomal rearrangements involving the IgH (FIG. 13A), Igk (FIG. 13B), Igl (FIG. 13C), TBL1XR1 (FIG. 13D), TP63 (FIG. 13E) and CIITA (FIG. 13F) loci. Line thickness correlates to number of events. Partner genes in grey, if significantly mutated in black. For consistency, BCL2, BCL6 and MYC are in green, blue and red, as in FIGS. 3A to 3I above. FIG. 13G shows selected translocations between IgH and partner genes, plotted in their genomic context. Breakpoints are visualized by an arrow; the two numbers on the arrow indicate split read count followed by read pair count supporting this chromosomal rearrangement. Boxes indicate exons; red box, indicates first coding exon; ORF in green; enhancer element in black. Translocations are activating (orange partner gene) or inactivating by destroying the ORF (dark blue). All diagrams display the IgH partner in the coding direction. FIG. 13H shows color-coded matrices that visualize significant mutual exclusivity of SVs and CN gains in BCL2 (top, p=0.038), co-occurring of SV and mutations in BCL2 (middle, p=8.25e-36) and co-occurring of single CN loss and mutations in TP53 (bottom, p=4.98e-14). Mutations, black; SV, green; single CN loss, cyan; low grade CN gain, pink; high grade CN gain, red. Contingency table and p-value obtained by a Fisher's Exact test are displayed to the right. FIG. 13I depicts a color-coded matrix that shows genetic alterations in indicated immune evasion molecules. (See color code legend of FIGS. 4A to 4C above.)

FIGS. 14A and 14B show the result of assessing individual genetic features detected in ≥3% of the R-CHOP cohort (150 genetic drivers) for their association to PFS (FIG. 14A) and OS (FIG. 14B) in univariate Cox regression models (q-value <0.2). Volcano plots show hazard ratio (x-axis) vs. significance (y-axis). Size of dots represent the number of mutations; the color of dots represent significance (p-value <0.05, light red; p-value >0.05, grey). Alterations with significant p-values are labeled (q-value <0.2: CN gains, red; CN loss, blue; SVs, green; q-value >0.2: Mutations, grey; CN gain, pale light red; CN blue: light blue). FIG. 14C shows Kaplan Meier plots for significant factors in univariate model predicting OS that were also independent to each other in a multivariate model; alterations absent, solid line; alterations present, dashed line; p-values derived from log-rank test. FIG. 14D shows forest plots that visualize the multivariate analysis of IPI risk groups and individual genetic factors for OS.

FIG. 15A is a series of consensus plots for k=4 to k=10 cluster solutions. FIG. 15B is a line plot of cophenetic coefficient for k=4 to k=10 cluster solutions.

FIG. 17A shows the incidence of MYD88 and CD79B mutations in clusters C0-C5 (FIGS. 4A to 4C above). Types of MYD88 mutations are color-coded (MYD88L265P, blue; MYD88other, pink). In cluster C5, MYD88 and CD79B mutations were identified as more frequent, MYD88 mutations were more likely to be MYD88L265P and MYD88 and CD79B mutations were more likely to be concordant. FIG. 17B shows drivers SCNAs by cluster. FIG. 17C shows mutation density by cluster. p-values in FIGS. 17B and 17C were obtained using a Kruskal-Wallis test. FIG. 17D shows the fraction of mutational signature activity by cluster. FIG. 17E shows the incidence of TP53 mutations and 17p loss across clusters C0-C5. Bi-allelic inactivation of TP53 in cluster 2 was significantly more frequent than in other clusters (p<0.0001; Fisher's exact test). FIG. 17F shows a gene set enrichment analysis (GSEA) plot of BCL6 and NOTCH2 target gene sets (S18) in C1 DLBCLs compared to other DLBCLs. FIG. 17G shows GSEA of a functionally defined EZH2 target gene list (S19) in C3 DLBCLs compared to other DLBCLs. FIG. 17H shows GSEA of E2F and TP53 target genes (MSigDB; software.broadinstitute.org/gsea/msigdb; (S20)) in C2 DLBCLs compared to the other DLBCLs.

FIG. 18A shows a Kaplan Meier (KM) plot for OS for all clusters, C0 (grey), C1 (purple), C2 (cyan), C3 (orange), C4 (turquoise), C5 (red) to the left. FIG. 18B shows a KM plot for OS for favorable DLBCL clusters (C0, C1, C4) in black, C2-DLBCLs in blue and unfavorable DLBCLs (C3, C5) in pink. The p-value obtained using the log-rank test. FIG. 18C presents forest plots used to visualize HR and p-values obtained from the multivariate analysis of OS including clusters and IPI. FIG. 18D shows a KM plot for OS for the two genetically distinct GCB-DLBCLs (left), ABC-DLBCLs (middle) and C2 DLBCLs. The p-value obtained using the log-rank test. FIG. 18E shows a KM plot for PFS (upper row) and OS (lower row) for all C3 DLBCLs (left), C3 DLBCLs split by presence/absence of SV-MYC (middle) and C3 DLBCLs split by presence/absence of concurrent SV-MYC and SV-BCL2 (right). The p-value obtained using the log-rank test.

BRIEF DESCRIPTION OF THE TABLES

Figure 1A:
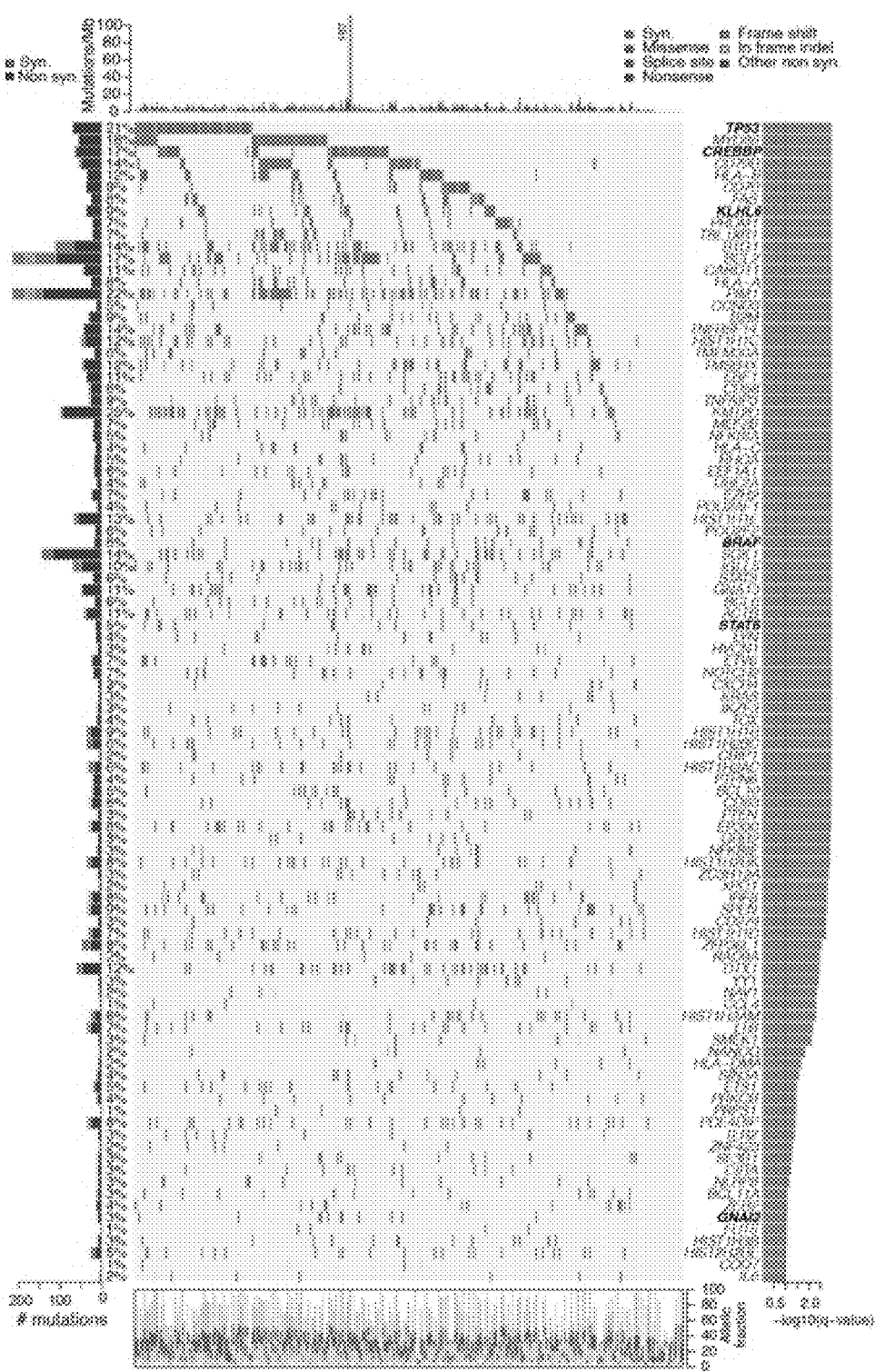
FIGS. 1A to 1C show a series of plots and images depicting recurrently mutated genes in 304 primary DLBCLs.
Figure 1B:
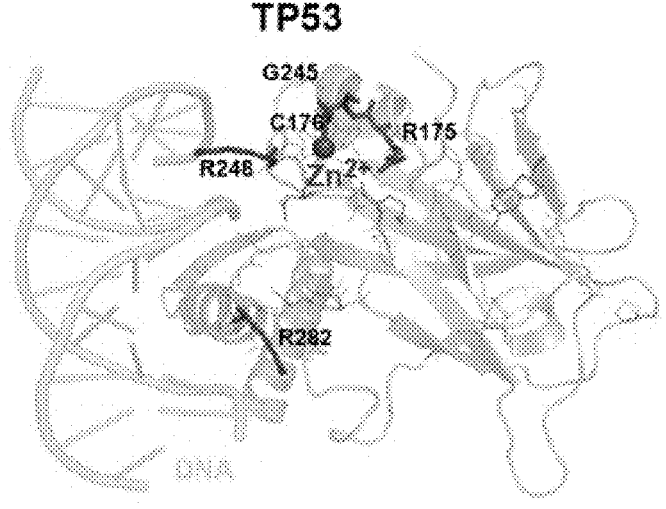
Figure 1B:
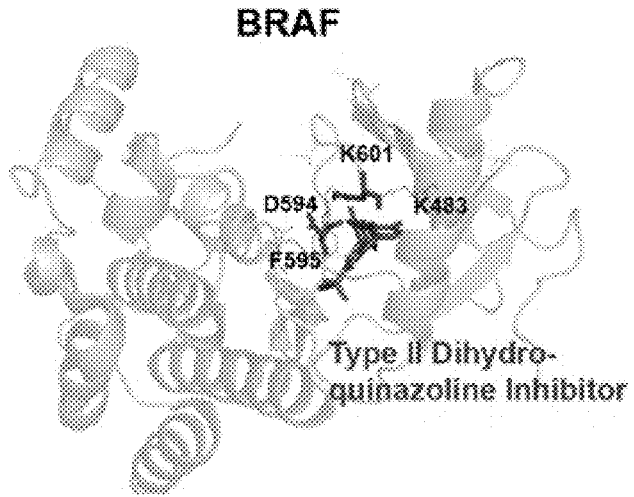
Figure 1B:
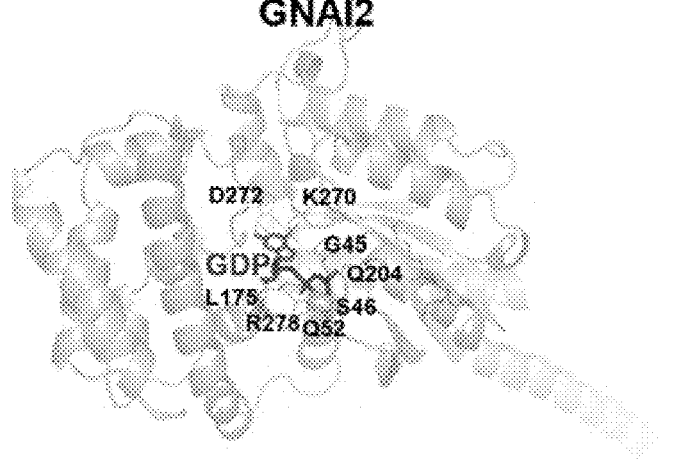
Figure 1C:
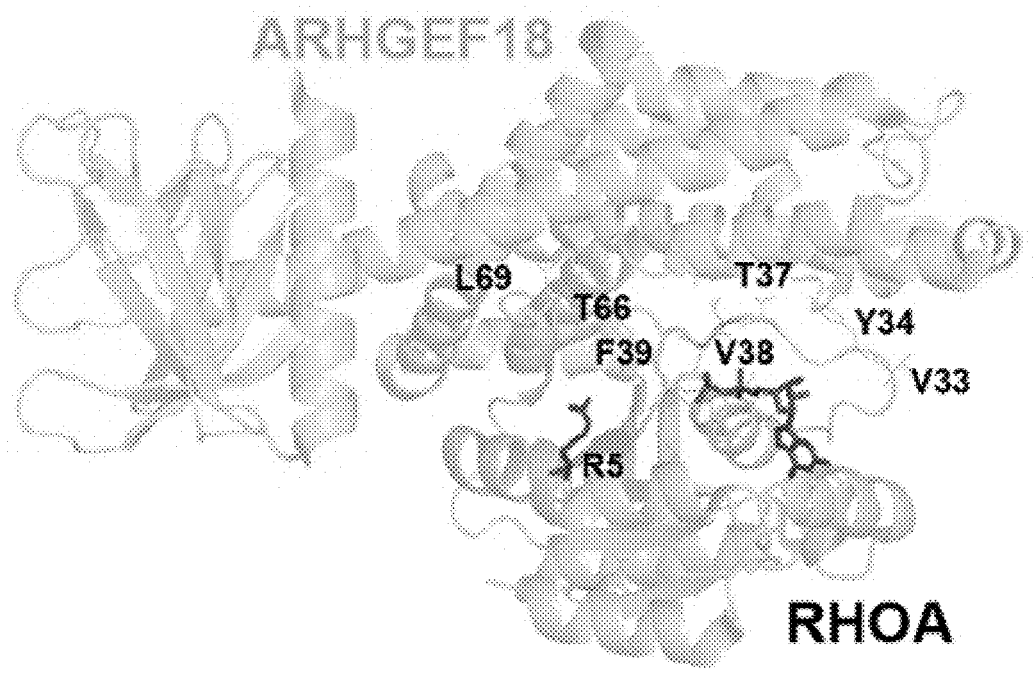

The accompanying mega table comprises the following tables:

Summary information for each sample of the instant disclosure is listed in Table S1, including sample ID, cohort, tissue type (frozen/FFPE), availability of paired normal, cell of origin (COO) and comprehensive consensus clustering (CCC) subtypes, QC metrics (coverage tumor and normal, TiN, etc.), purity, ploidy, cluster association, summary statistics for EBV and genetic features (total mutation count and density, driver mutation count and density, non-synonymous mutation rate, total and driver CNAs, number of chromosomal rearrangements).

Patient characteristics data are contained in Table S2a and Table S2b. Overall, patient characteristics are summarized in Table S2a, including ID, cohort, age, gender, morphological subtype, IPI and its factors, PFS, OS, R-CHOP-like treatment (yes/no). Patient characteristics by cohort are summarized in Table S2b.

Tables S3a to S3f contain data of significantly mutated genes. Mutated genes ranked by their significance values obtained from MutSig2CV are summarized in Table S3a. Genes with significant spatial clustering within a protein structure as detected by CLUMPS are summarized in Table S3b. Genes with significant spatial clustering at protein-protein interfaces as detected by EMPRINT are summarized in Table S3c. MAF file of all mutations of samples with a paired normal are summarized in Table S3d. Values ranked by q-value from Fisher's exact test comparing frequencies of CCGs in tumor-only and tumor-normal paired samples are summarized in Table S3e. Values from Fisher's exact test comparing frequencies of CCGs in samples obtained from FFPE and fresh-frozen samples after removal of the focal copy number gain peak 21q22.3 are summarized in Table S3f.

Table S4: Data of mutational signature analyses are displayed in Tables S4a to S4f. Table S4a shows mutational signature activity data in 304 samples. Mutational signature activity data including clustering in 303 samples are summarized in Table S4b. Aging signature enrichment data by gene are summarized in Table S4c. Table S4d contains cAID signature enrichment data by gene. AID2 signature enrichment data by gene are summarized in Table S4e. Cosine similarity data of mutational signatures discovered in test sets to evaluate germline and FFPE contamination are supplied in Table S4f.

Tables S5a to S5d contain chromosomal rearrangement data. Regions of the targeted bait set for structural variants (SV) detection are supplied in Table S5a. Chromosomal rearrangements as reported by the newly developed Break-pointer pipeline are supplied in Table S5b. For each event, the table summarizes the chromosomal position of the first and second gene, type of rearrangement, support by which detection algorithm, supporting split read and read pair count of the alternate and reference alleles as well as the calculated cancer cell fractions (CCFs). A matrix of frequent (at least in 2 samples) chromosomal rearrangement by sample is given in Table S5c. Chromosomal rearrangements and the reported CCFs involving MYC, BCL2 and BCL6 in 31 LBCL cell lines are supplied in Table S5d. Table S5d is in the same format as Table S5b.

Figure 17A:
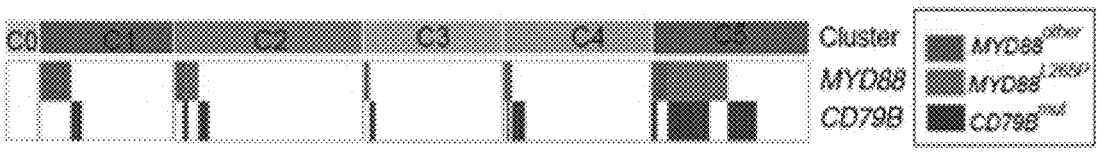
FIGS. 17A to 17H display a summary of genetic alterations by cluster.
Figure 17B:
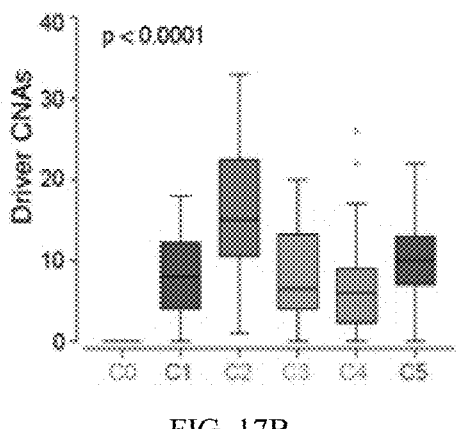
Figure 17C:
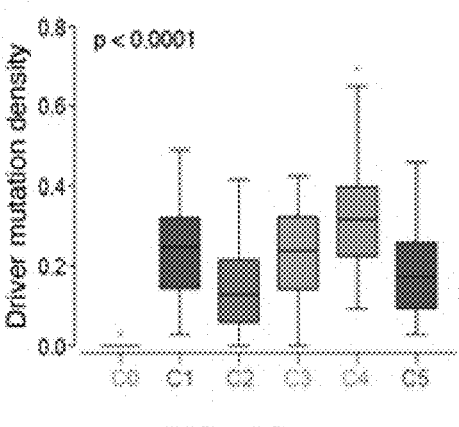
Figure 17D:
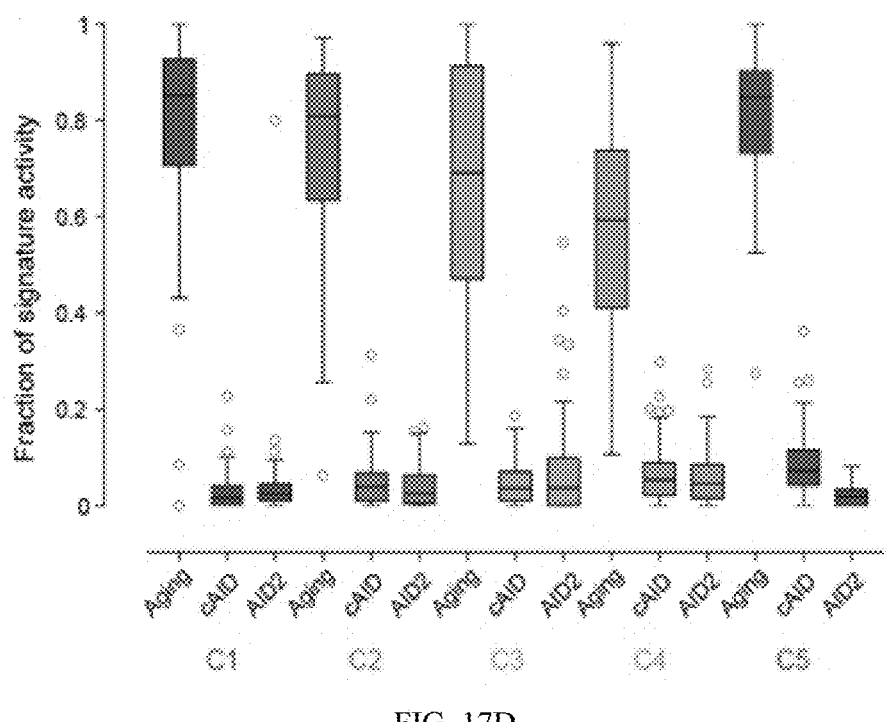
Figure 17E:
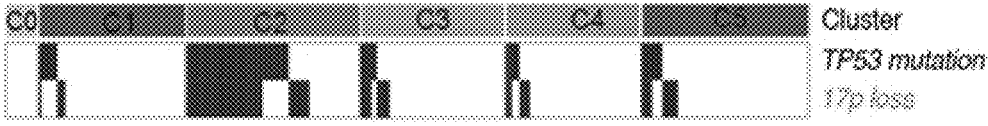
Figure 17F:
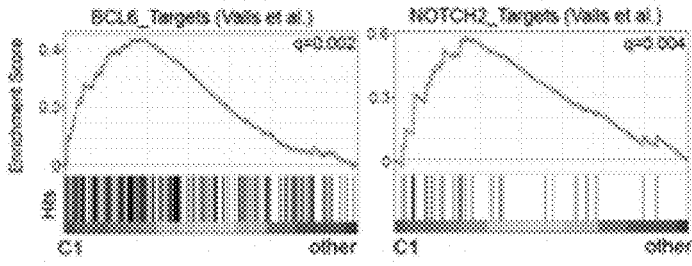
Figure 17G:
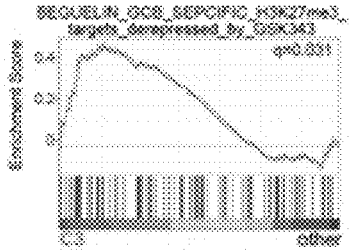
Figure 17H:
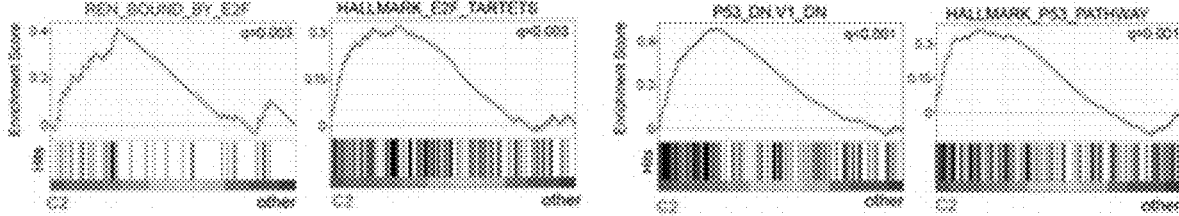

Tables S6a to S6h contain data of significant CNAs and correlation to gene expression. Table S6a is a list of significant arm-level and focal CNAs (CN gain and CN loss) with FDR <0.1 as identified by GISTIC2.0. Summary data of focal peaks are given in Table S6b. For Table S6b, wide peak coordinates, genes within wide peaks and summary statistics of within-peak genes with positive correlation to gene expression are listed. A detailed list of all genes with significant correlation between focal-peaks and associated cis-acting gene expression (FDR<0.25; FC>1.2) is given in Table S6c. Summary data of arm-level alterations are supplied in Table S6d. Genes within arm-level alterations and summary statistics of arm-level genes with positive correlation to gene expression are listed. A detailed list of all genes with significant correlation (FDR<0.25; FC>1.2) between arm-level alterations and associated cis-acting gene expression is supplied in Table S6e. Summary data of focal plus arm-level alterations are supplied in Table S6f. Wide peak coordinates of focal-peaks, genes within wide peaks and summary statistics of within-peak genes with positive correlation between arm-level or focal-peaks to gene expression are listed. A detailed list of all genes with significant correlation (FDR<0.25; FC>1.2) between focal and arm-level alterations and associated cis-acting gene expression is supplied in FIG. S6g. Gene sets used in gene set enrichment analysis in FIGS. 17F to 17H are supplied in Table S6h.

Data of univariate and multivariate outcome associations of genetic drivers are shown in Tables S7a and S7b. Values, ranked by significance (q-value), for univariate Cox model for all genetic driver alterations with at least 3% events in the R-CHOP treated cohort (n=259) for PFS and OS are summarized in Table S7a. Values for Cox regression models of IPI with all significant factors from the univariate analyses for PFS and OS are summarized in Table S7b.

Tables S8a to S8c contain date of gene sample matrix and features of consensus clusters. Gene sample matrix data are summarized in Table S8a. For each of the 304 samples, each of the 159 genetic "drivers" with a frequency ≥3% are listed. For these data, the following labeling conventions were used: Mutations (0, absent; 1, synonymous; 2, non-synonymous); CNAs (no CNA, 0; low grade CNA, 1; high grade CNA, 2); Chromosomal Rearrangements (SV; absent, 0; present, 3). Table S8b summarizes consensus clustering results with the following labeling conventions: Cophenetic coefficient for k=4 to k=10 clusters, membership of each sample and silhouette values for "Best cluster" (k=5). Feature selections for each cluster by Fisher test are shown in Table S8c.

Tables S9a and S9b contain clinical features, features across clusters and gene sets tested for an enrichment. Table S9a is a summary table of clinical features by cluster. Pairwise comparisons of significant results from Table S9a are shown in Table S9b.

Tables S10a to S10c contain ordering analyses. CCF-Matrix for all 158 driver alterations are shown in Table S10a. Occurring and modelling of clonal-subclonal pairs by cluster are given in Table S10b. Results of ordering analyses for clonal-subclonal pairs powered to achieve a q-value <0.1 are contained in Table S10c.

Outcome analyses of clusters are contained in Tables S11a and S11b. PFS and OS survival proportions every 12 months for each cluster are given in Table S11a. Multivariate model of clusters and IPI (with comparison to IPI-only model) for PFS and OS are shown in Table S11b.

DETAILED DESCRIPTION OF THE INVENTION

The present disclosure is directed, at least in part, to the discovery that diffuse large B-cell lymphoma (DLBCL) can be classified into five distinct classes, C1-C5, each of which exhibits a distinct pathogenic mechanism and outcome, which respectively implicates a selection of a preferred treatment and/or prevention strategy for each such class of DLBCL. Compositions and methods for use of the instantly described DLBCL classifier are described in additional detail below.

DLBCL is a genetically heterogeneous disorder with multiple low-frequency mutations, SCNAs and SVs (1-9). Currently, these tumors are thought to arise from antigen-exposed B-cells that transit through the germinal center (GC) (1). Aspects of the GC environment, including the high proliferation rate, physiologic activation-induced cytidine deaminase (AID)-mediated immunoglobulin receptor editing and aberrant somatic hypermutation (SHM) are conducive to malignant transformation (1).

The heterogeneity of DLBCL is reflected in transcriptionally defined subtypes that provide insights into disease pathogenesis and candidate treatment targets (10-15). The cell-of-origin (COO) classification identifies activated B-cell (ABC)- and GC B-cell (GCB)-type DLBCLs (1, 10). Without wishing to be bound by theory, ABC-DLBCLs are currently thought to be derived from B-cells that have passaged through the GC and are committed to plasmablastic differentiation (1). These tumors have increased NF-kB activity and a subset exhibit genetic alterations in NF-kB modifiers and proximal components of the B-cell receptor (BCR) pathway and perturbed terminal B-cell differentiation (1, 12, 14, 16). In contrast, GCB-DLBCLs are postulated to originate from light-zone GC B-cells (1). A subset of these tumors have alterations in chromatin-modifying enzymes, PI3K signaling and Gα-migration pathway components and frequent SVs of BCL2 (1, 17-19). Although patients with ABC-DLBCLs are reported to have less favorable responses to standard therapy than those with GCB-DLBCLs (8, 10, 20), targeted analyses of select alterations suggest additional genetic complexity remains to be defined (2, 12, 19, 21, 22). Despite the recognized clinical and molecular heterogeneity in DLBCL, previous genomic studies of this disease have largely focused on single types of alterations—mutations, SCNAs or SVs.

Herein, a comprehensive genetic analysis of 304 primary DLBCLs has been performed (via whole exome sequencing (WES) with an expanded bait set of 304 DLBCLs from newly diagnosed patients, 85% of whom were uniformly treated with R-CHOP and had long-term follow-up, a subset of these patients were enrolled in the prospective multi-center RICOVER60 trial (23)). This analysis of a representative and clinically annotated DLBCL cohort has identified low-frequency alterations and has captured recurrent mutations, somatic copy number alterations (SCNAs) and structural variants (SVs), and has defined coordinate signatures in patients with available outcome data. These genetic drivers have been integrated using consensus clustering and five robust DLBCL subsets have been newly identified (including three outcome-associated coordinate genetic signatures that were previously undescribed): a previously unrecognized group of low-risk ABC-DLBCLs of extrafollicular/ marginal zone origin; two distinct subsets of GCB-DLBCLs that exhibit different outcomes and targetable alterations; and an ABC/GCB-independent group that exhibits biallelic inactivation of TP53, CDKN2A loss and associated genomic instability. The genetic features of the newly characterized subsets, their mutational signatures and the temporal ordering of identified alterations have provided new insights into DLBCL pathogenesis. Significantly, the coordinate genetic signatures have also allowed for outcome predictions that are independent of the clinical International Prognostic Index and have indicated new treatment strategies (optionally including administration of combination therapies) based upon the herein described DLBCL classification groups. As such, a roadmap for further actionable DLBCL classification is also provided herein.

Outcome and treatment decisions in DLBCL are currently made using clinical parameters and/or RNA-based transcriptional signatures. However, these features are insufficiently precise to guide the development of new targeted agents in this disease. Here, compelling evidence of previously unrecognized genetically distinct DLBCL subsets has been provided.

The instant disclosure has expanded the landscape of recurrent genetic drivers in DLBCL through increased sample size and technical innovations, including analyses of WES data in the absence of paired normal samples. Such alterations have also been temporally ordered, which has yielded insight into biologic function of certain mutations by overlaying them onto 3D protein structure, and the instant studies have also identified the dominant mutational processes in DLBCL exomes. The instant studies have highlighted the complexity of DLBCLs, which possess a median of 17 different genetic alterations per tumor.

By integrating recurrent mutations, SCNAs and SVs, five distinct DLBCL subsets have been identified, including previously unappreciated favorable risk ABC-DLBCLs that exhibit genetic features of an extrafollicular, possibly marginal zone origin (C1); poor risk GCB-DLBCLs that tend to possess BCL2 SVs and alterations of PTEN and epigenetic enzymes (C3); a newly defined group of good-risk GCB-DLBCLs with distinct alterations in BCR/PI3K, JAK/STAT and BRAF pathway components and multiple histones (C4); and a COO-independent group of tumors that exhibit biallelic inactivation of TP53, 9p21.3/CDKN2A and associated genomic instability (C2). The key genetic features of these DLBCLs included mutations, SCNAs and SVs, indicating that assessment of all three types of alterations were needed to capture disease heterogeneity and outcome differences. Moreover, DLBCL cluster-defining genes were perturbed by multiple mechanisms.

The instant approach to define genetically distinct DLBCL subsets has not only identified a prognostic classifier of clinical significance for treatment of DLBCL but also has provided a framework for assessing previously unrecognized heterogeneity in transcriptionally defined subsets, linking mutational signatures with cluster-predominant pathogenetic mechanisms, assessing genetic bases of extranodal disease tropism and developing faithful murine models of human tumors. Significantly, the DLBCL outcome-associated genetic signatures identified herein are capable of guiding rational administration, as well as further development, of single-agent and combination therapies in patients possessing significant therapeutic needs.

DLBCL Classification

The methods and compositions described herein relate to identification of a new and clinically useful classifier for DLBCL, the development of which is based upon an assessment of a significantly powered cohort of DLBCL samples for variants across whole exome sequences, where such variant assessment included identification and evaluation of each of the following types of variation: somatic single nucleotide variants (SNVs), small insertions and deletions (Indels), somatic copy number alterations (SCNAs) and structural variants (SVs), including identification of variation across all cancer causing genes (CCGs). Specific components of the instant DLBCL classifier include the following.

Reference Sequences

In certain aspects, the instant disclosure provides methods and kits that involve and/or allow for assessment of the presence or absence of one or more sequence variants and/or mutations in a test subject, tissue, cell or sample, as compared to a corresponding reference sequence. In particular embodiments, a subject, tissue, cell and/or sample is assessed for one or more variants and/or sites of copy number variation within the sequences/sequence locations displayed in FIG. 8.

For the instantly exemplified classification, up to five alteration types were measured and can be used for the classifier (i.e., a prognostic classifier as exemplified herein):

1.) Mutations (single nucleotide variants and/or InDels)
2.) Copy number alterations (CN gain, amplifications, CN losses, Deletions)
3.) Structural variants (chromosomal translocations, inversions, tandem duplications, etc.)
4.) Genome doublings
5.) Mutational Signatures The variants (1-3) were called as described in the methods section using the hg19 as a reference (FASTA version downloadable at ftp.broadinstitute.org/pub/seq/references/ Homo_sapiens_assembly19.fasta, which largely builds on the GRCH37.p13 of the genome reference consortium (www.ncbi.nlm.nih.gov/grc/human/ data?asm=GRCh37.p13) with an extra contig NC_007605.1 "EBV type 1" (Epstein Barr). For classifier performance consistent with the exemplar described below as "Neural Network classifier" the somatic variants (1-5) should be detected with at least 90% sensitivity and less than 5% false detection rate.

Mutations in Candidate Cancer Genes (CCGs), hereafter referred to as driver mutations, were identified with MutSig2CV and CLUMPS. These driver mutations are a list of 105 unique genes (98 MutSig2CV genes, as listed in Table S3a, q<0.1 and 7 unique CLUMPS genes in Table S3b/c).

Recurrent copy number alterations were identified using GISTIC2.0. The exact boundaries of these focal and arm level events are listed at Table S6a and genes within these peaks that had a significant association to gene expression were listed in Table S6b-g Genome doublings were assessed using the ABSOLUTE algorithm as described in the methods, Tumors with a ploidy (an output of ABSOLUTE)>3 were assigned to harbor a genome doubling.

Mutation discovery was performed as described in the methods section and C1 and C5 DLBCLs had significantly different cAID signature activity.

It is expressly contemplated that either all or a subset of these five types of alterations, with any combination of the individual members of each class, or even other genes, can be used within a classifier of the instant disclosure.

Amplification and Sequencing Oligonucleotides

Figure 8:
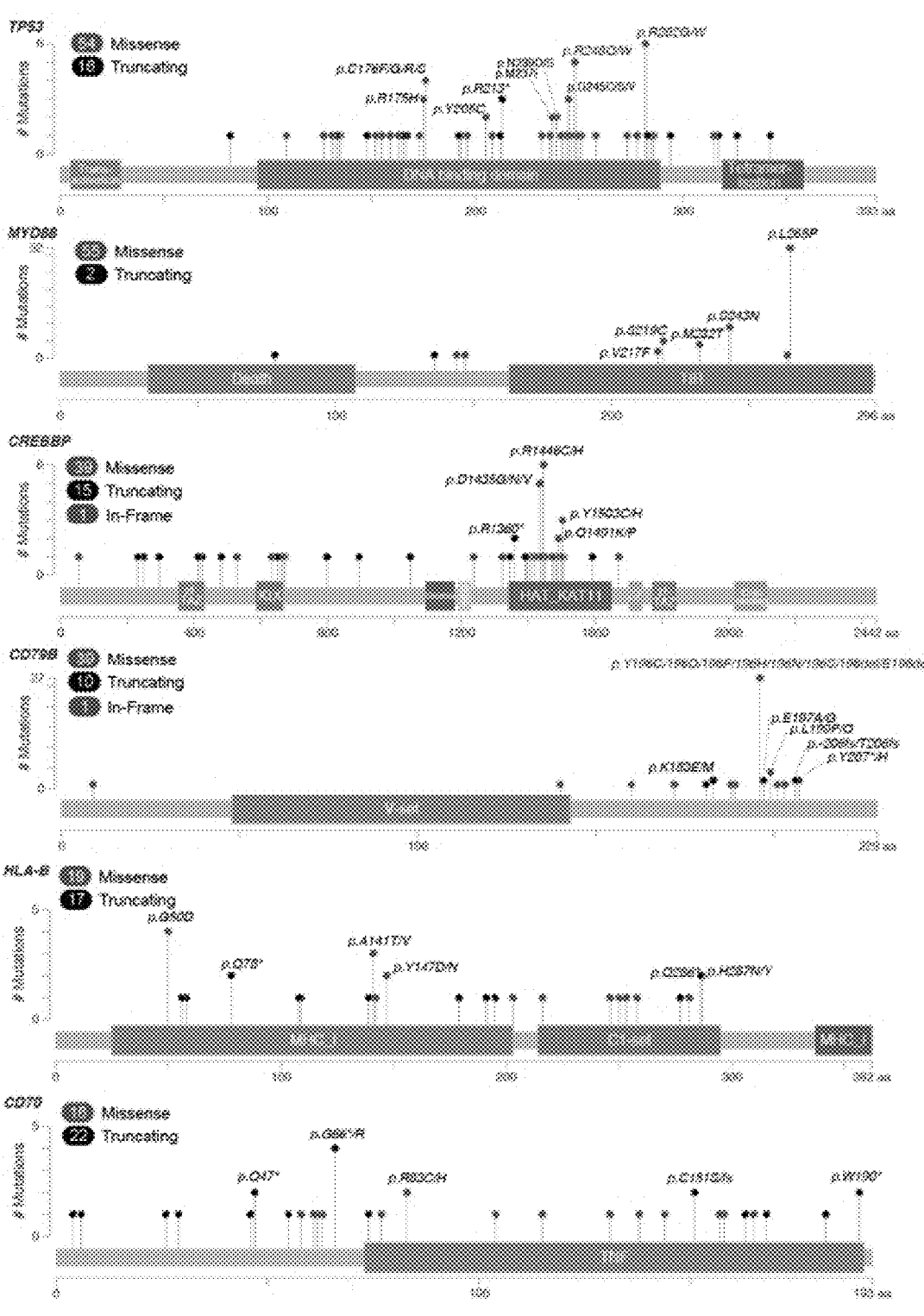
FIG. 8 shows an alphabetic index for mutation diagrams (lollipop figures) for all significantly mutated genes. For each significantly mutated gene, all non-synonymous muta-tions were visualized within the functional domains of the respective protein using MutationMapper v1.0.18,9. Genes have been ordered by significance (MutSig2CV q-value).
Figure 8:
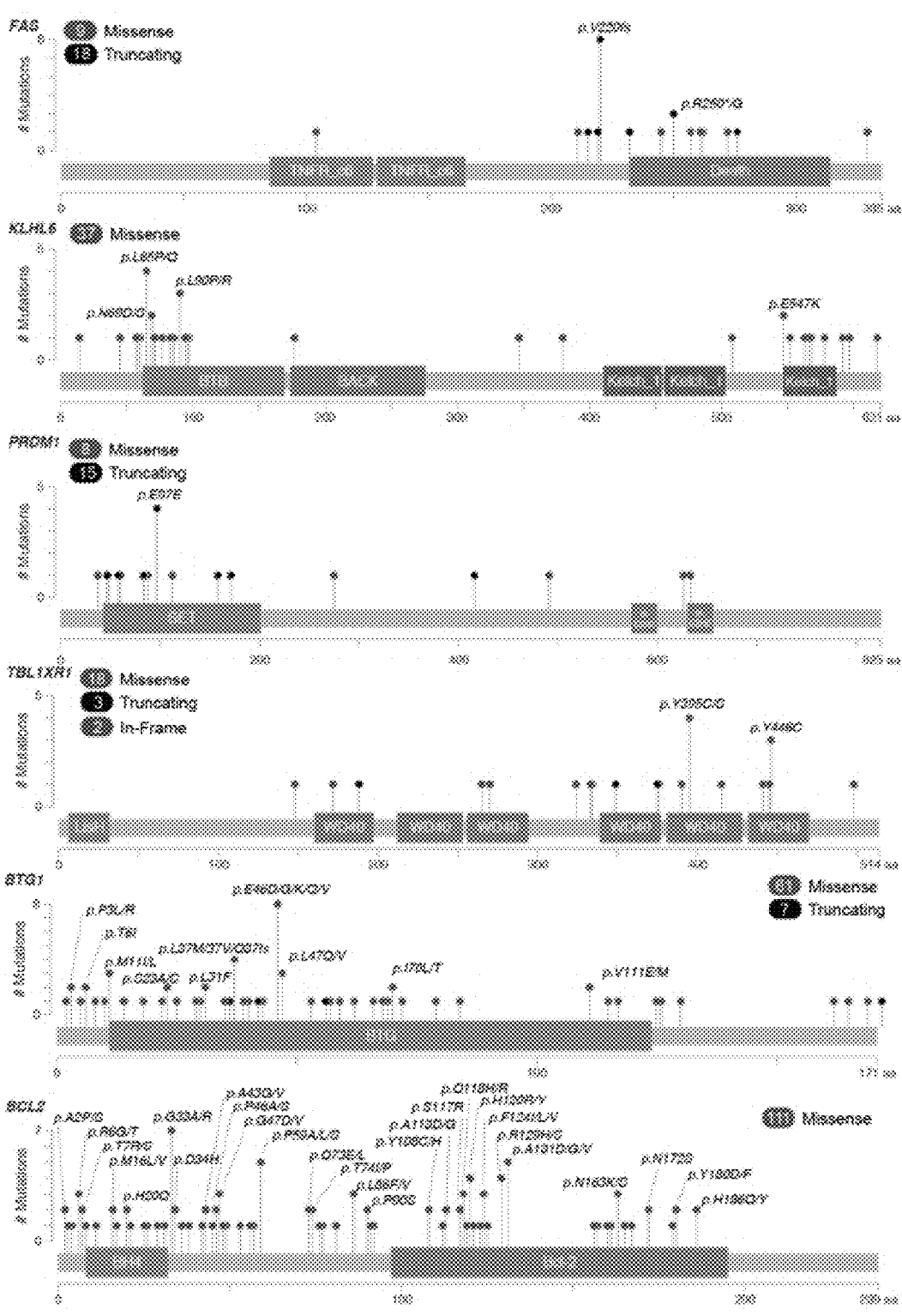
Figure 8:
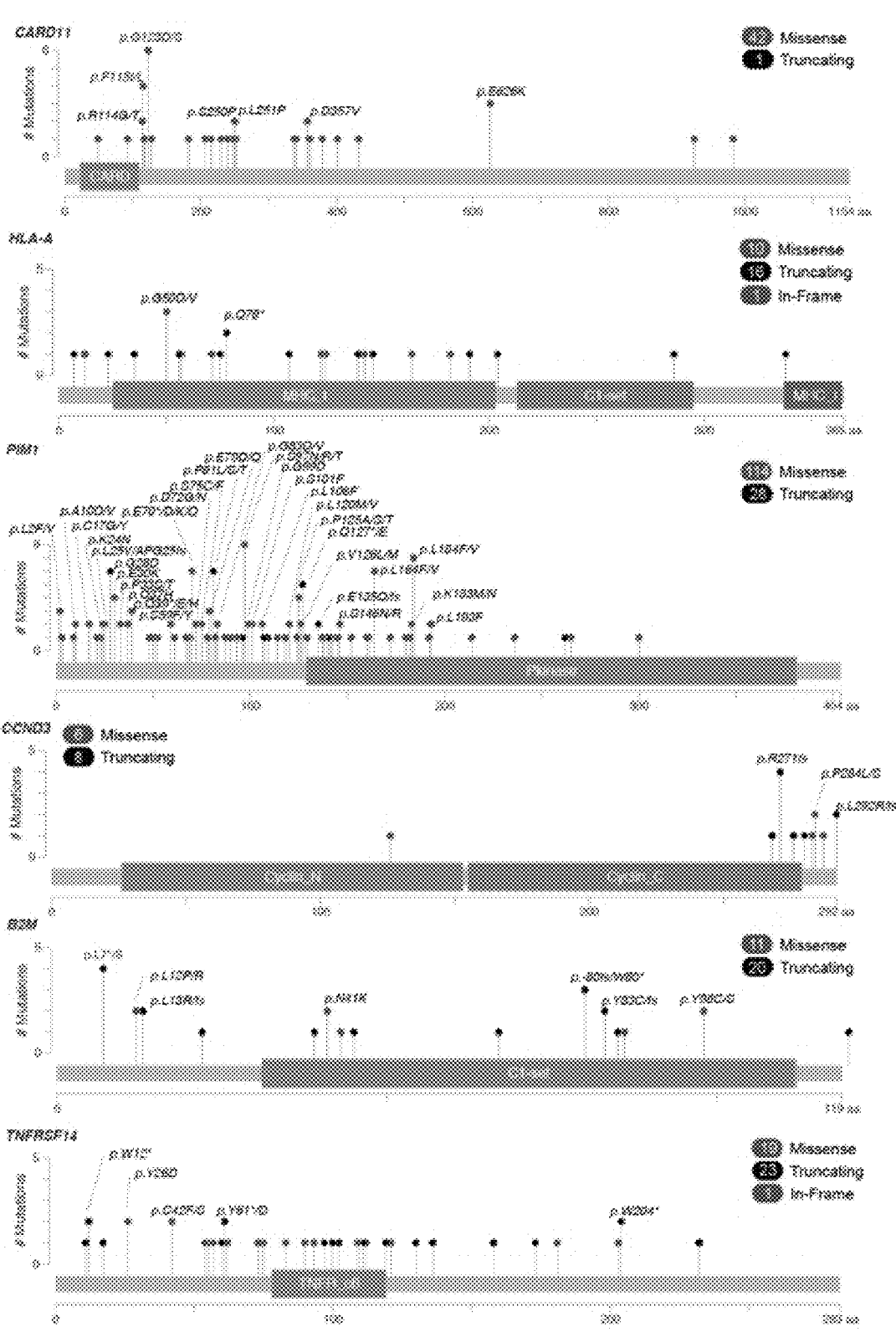
Figure 8:
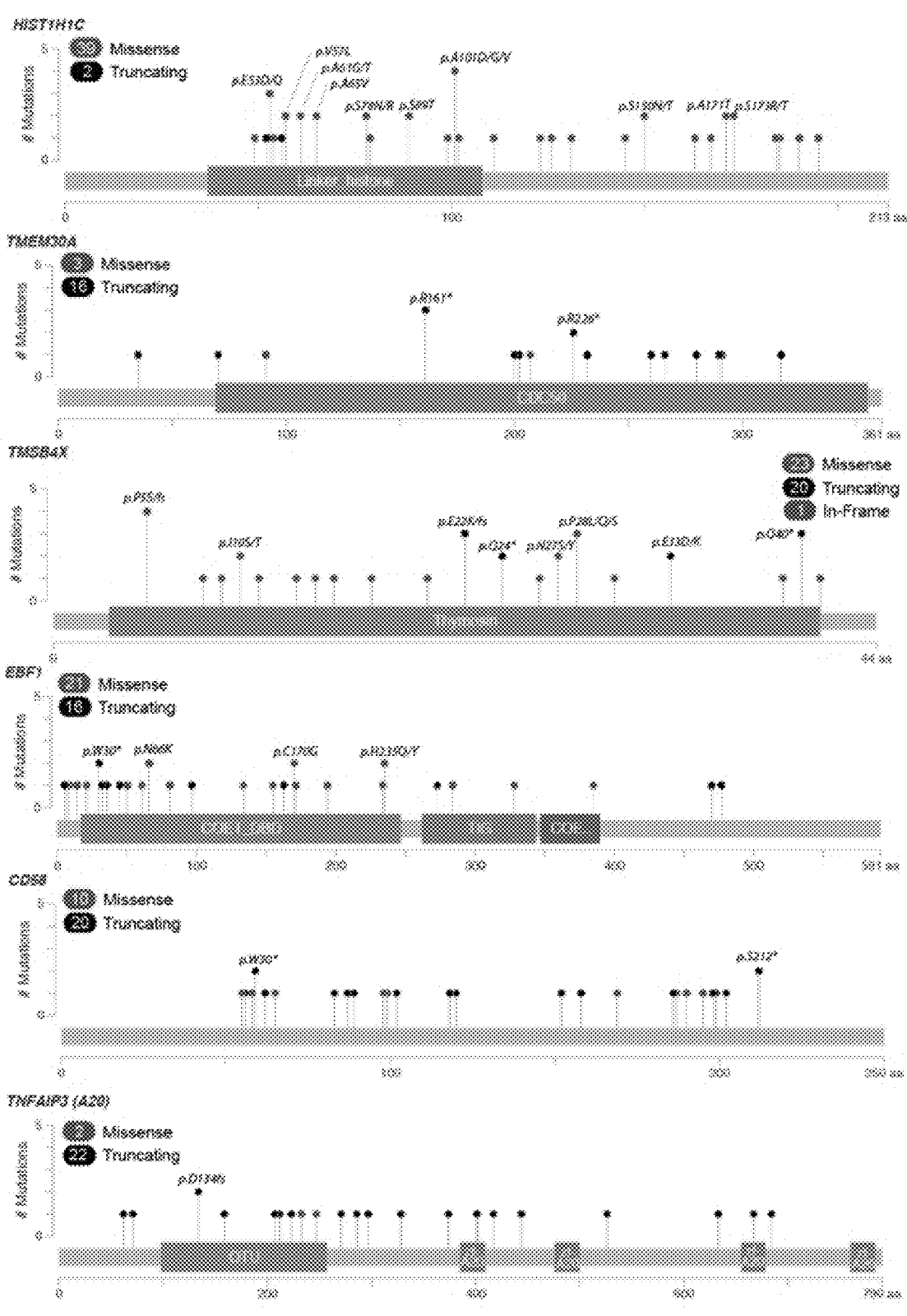
Figure 8:
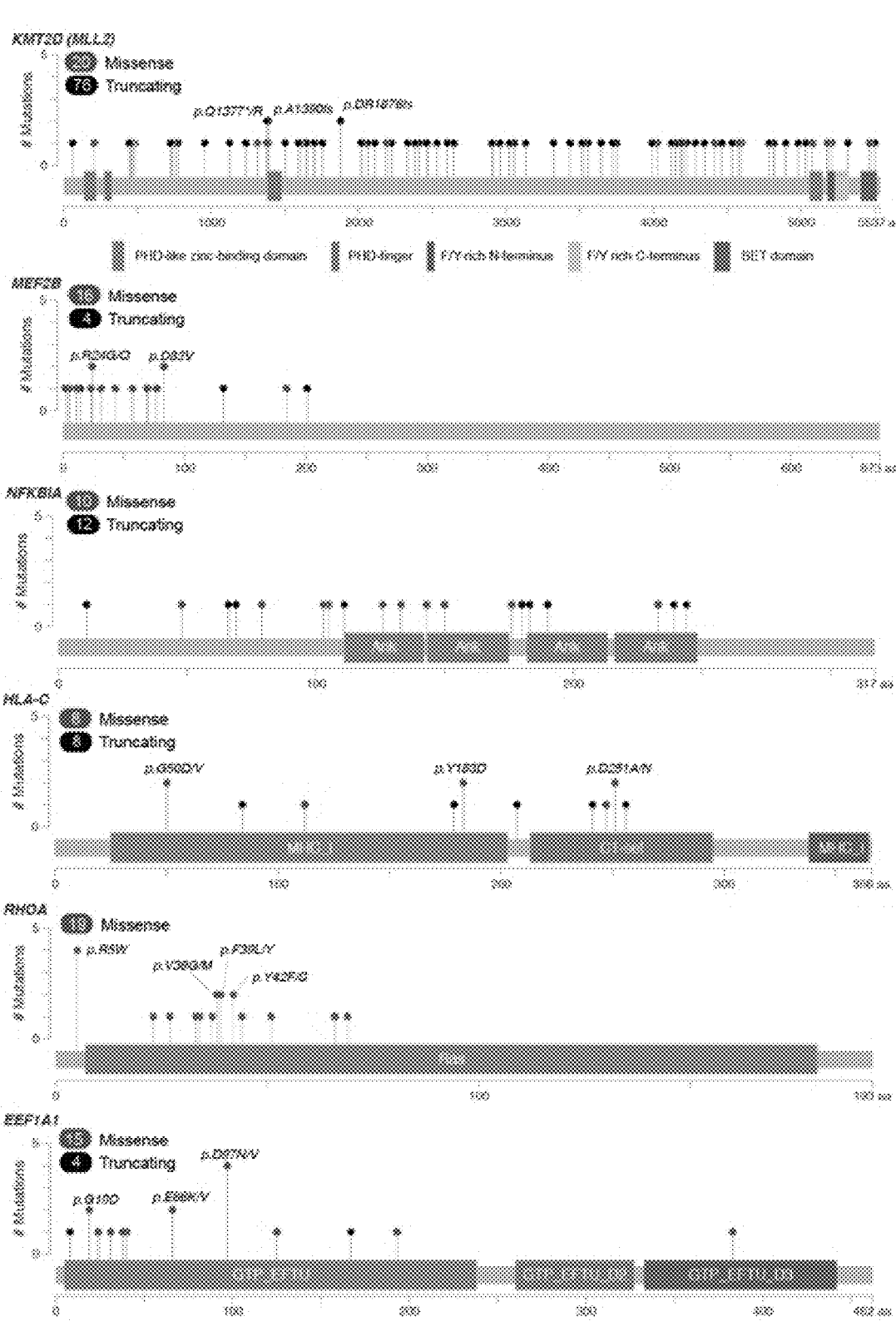
Figure 8:
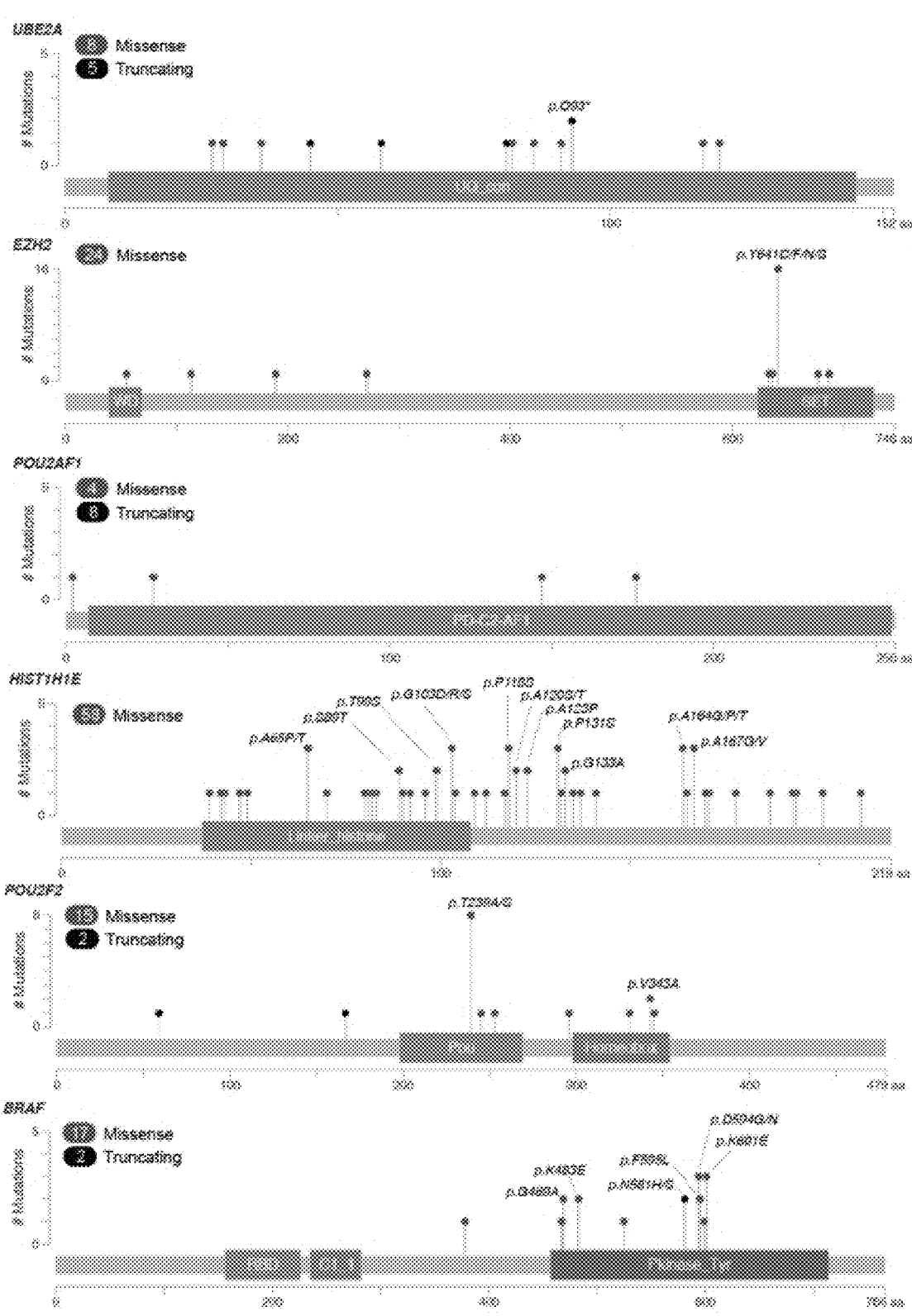
Figure 8:
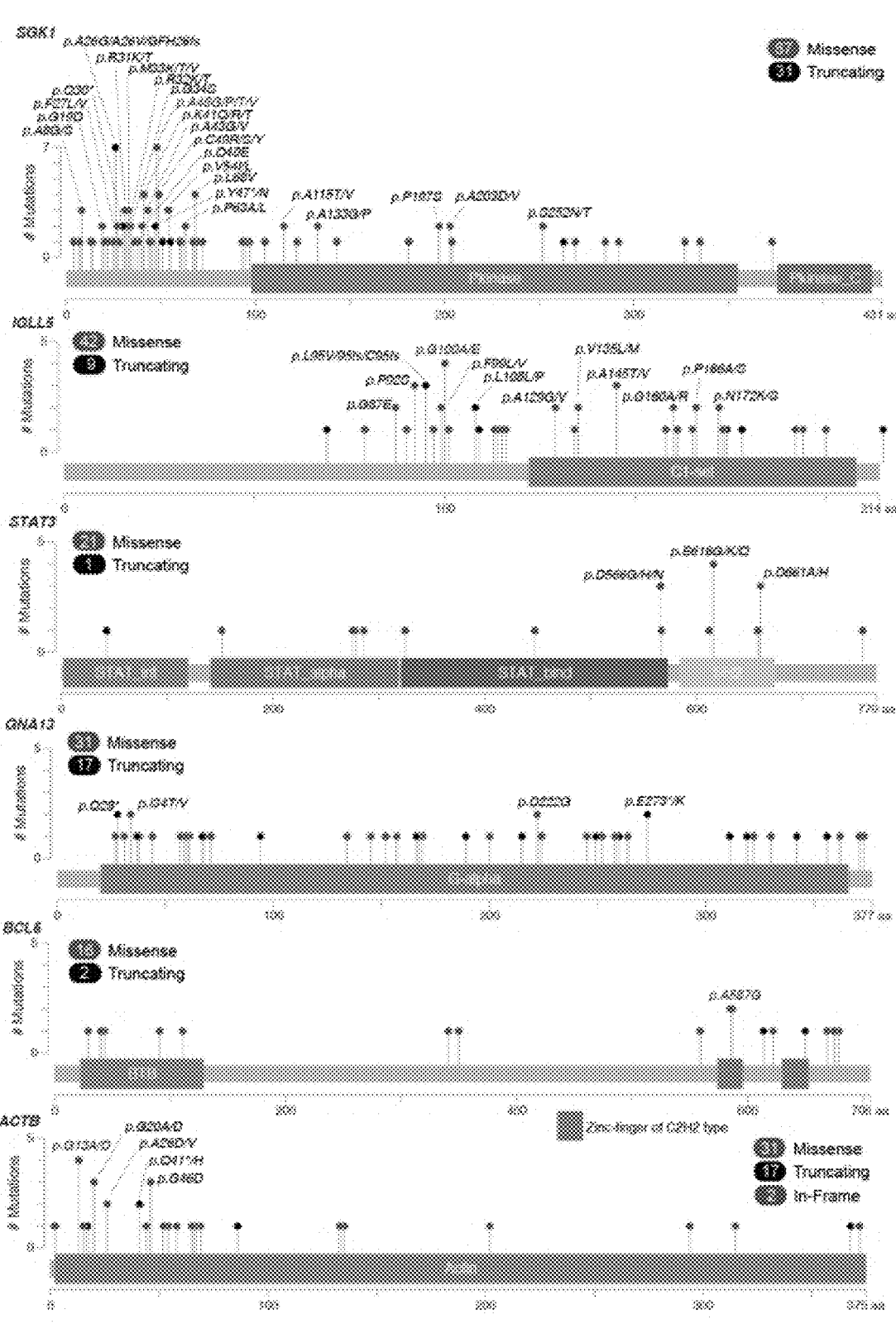
Figure 8:
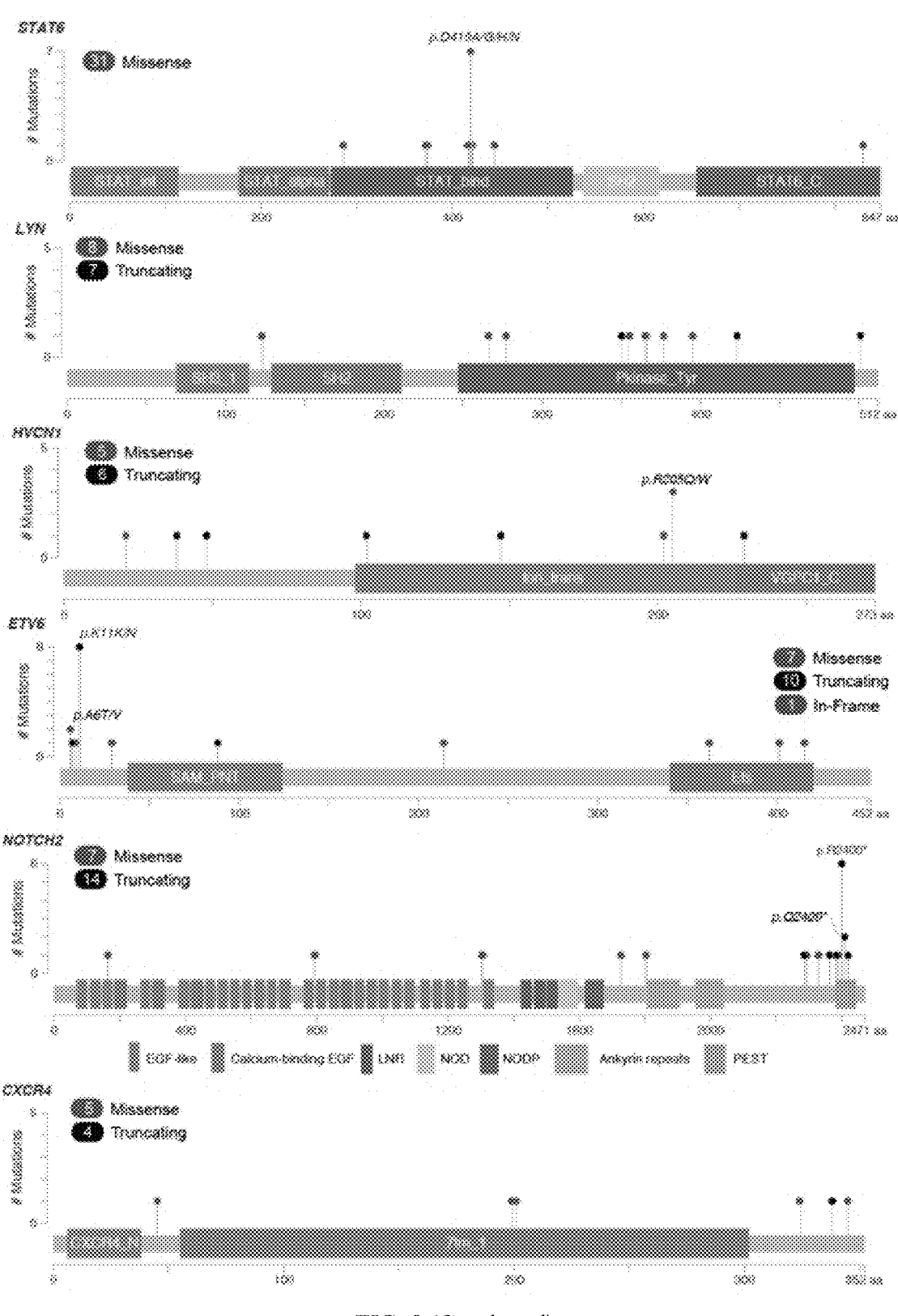
Figure 8:
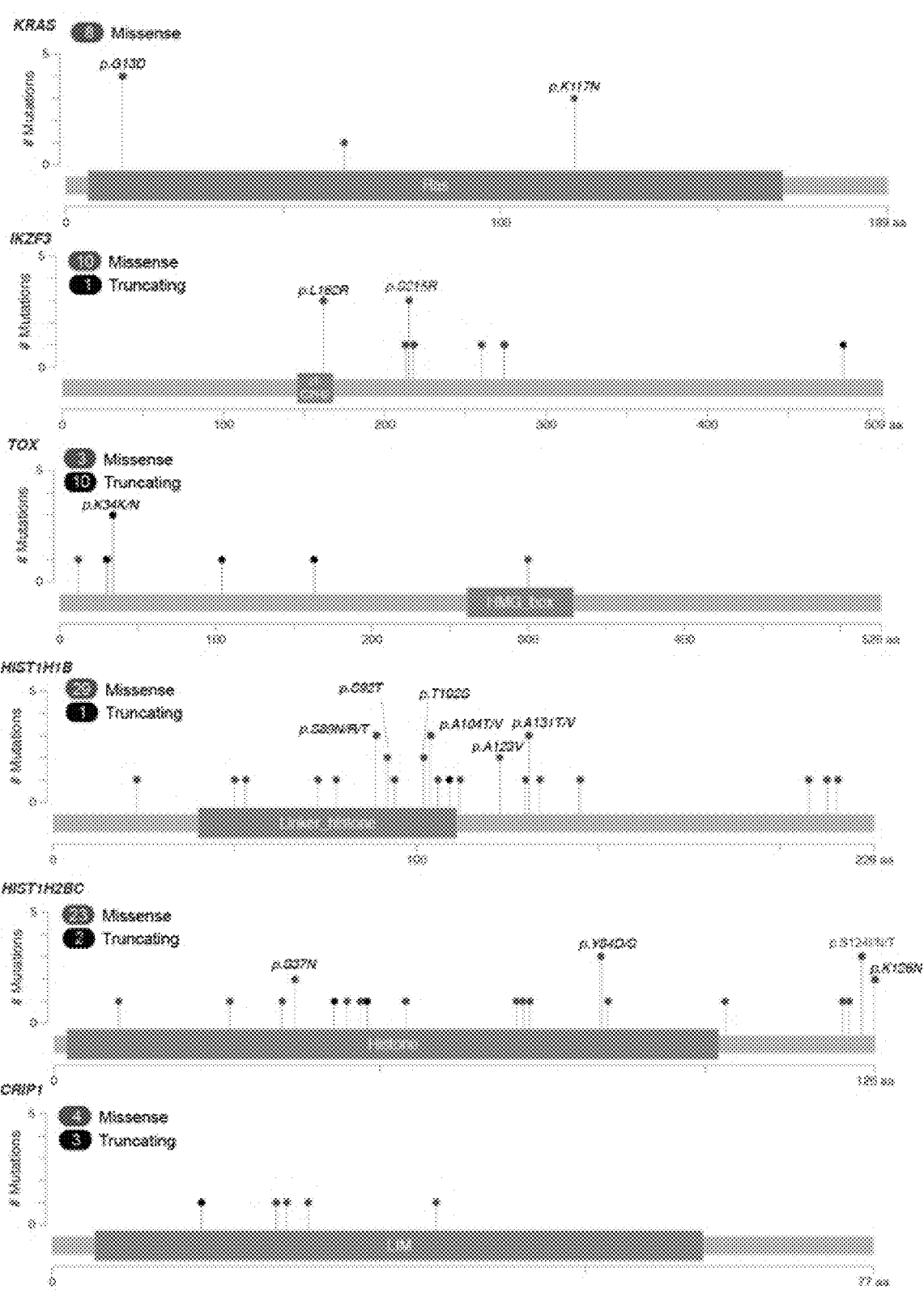
Figure 8:
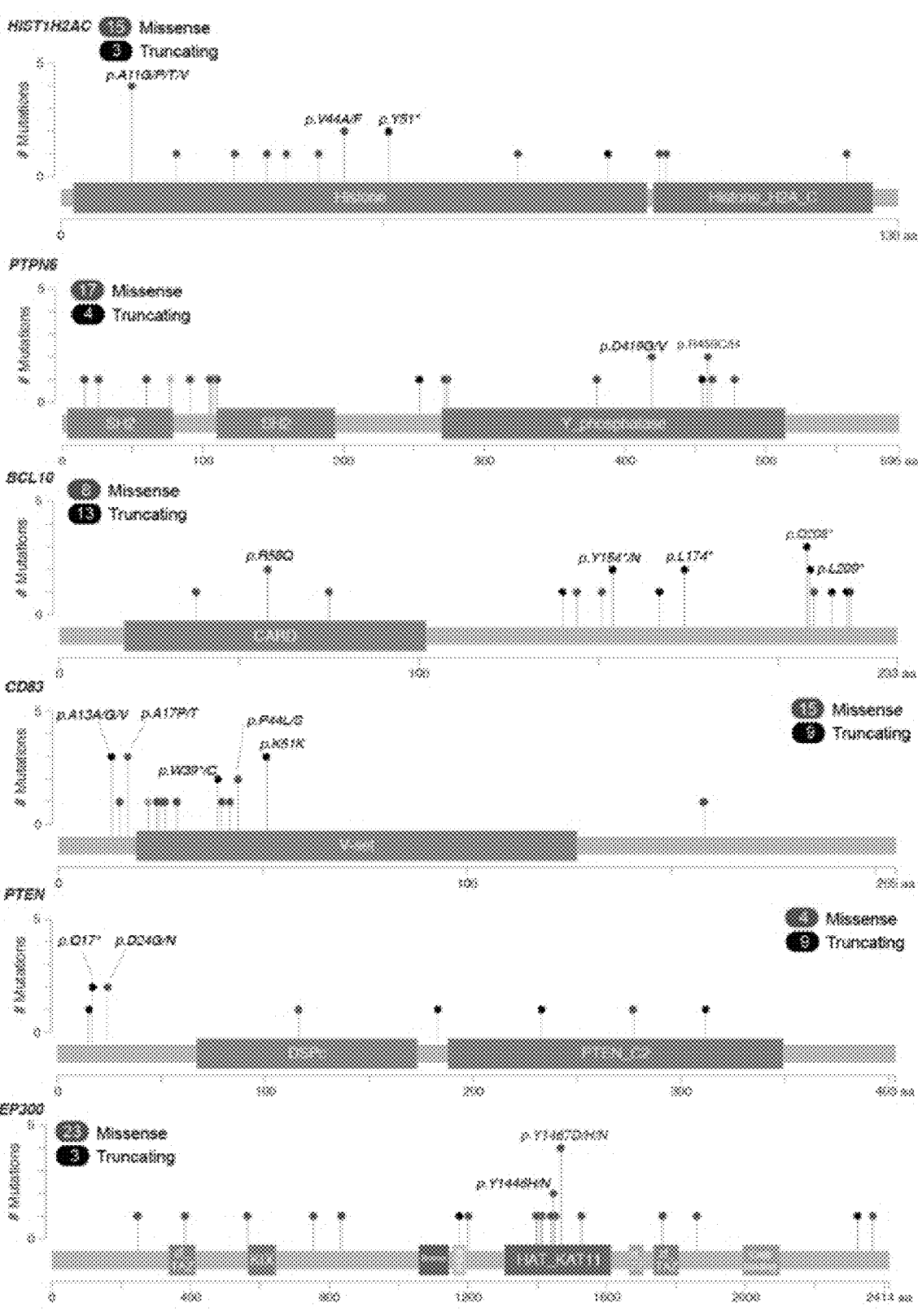
Figure 8:
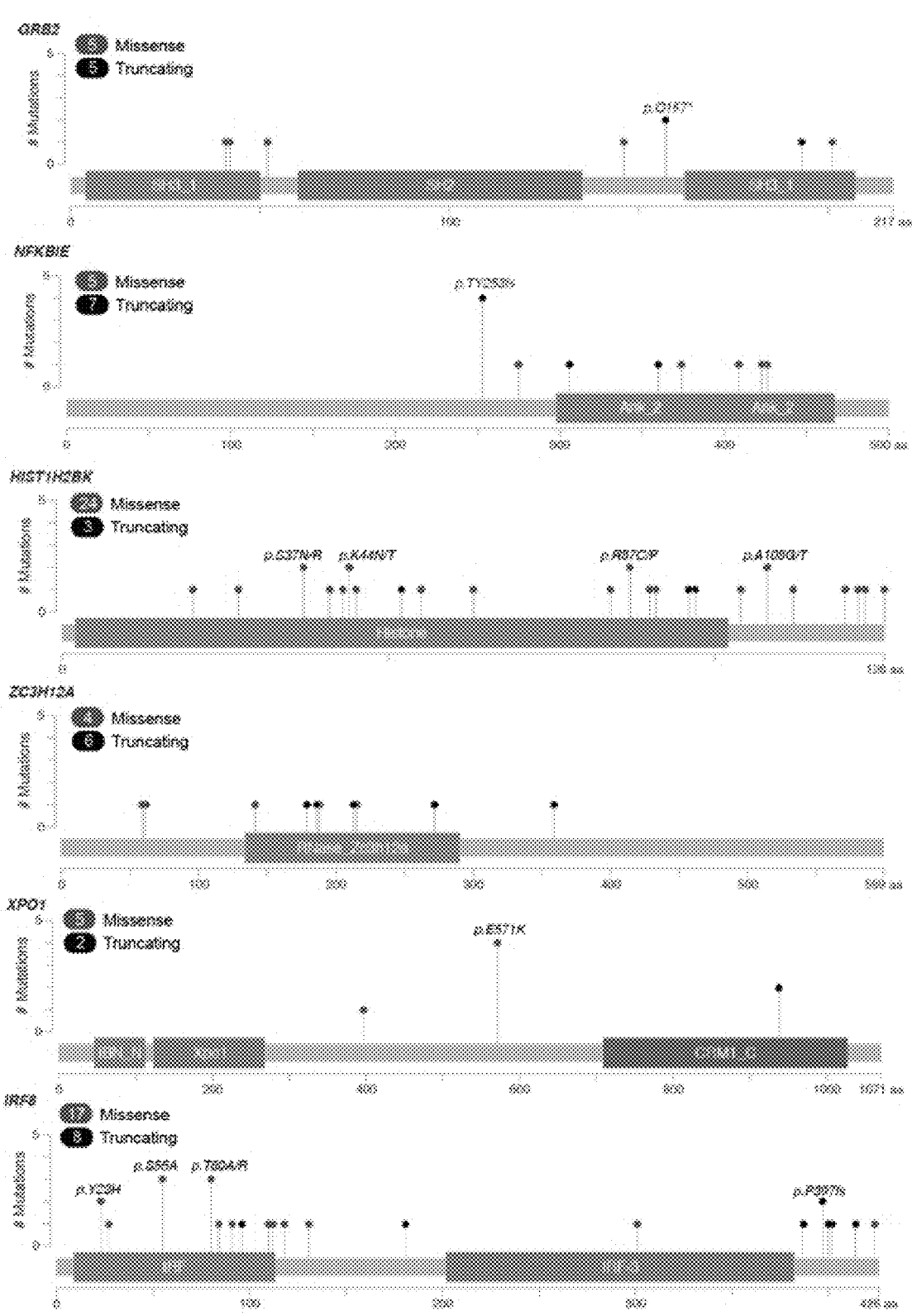
Figure 8:
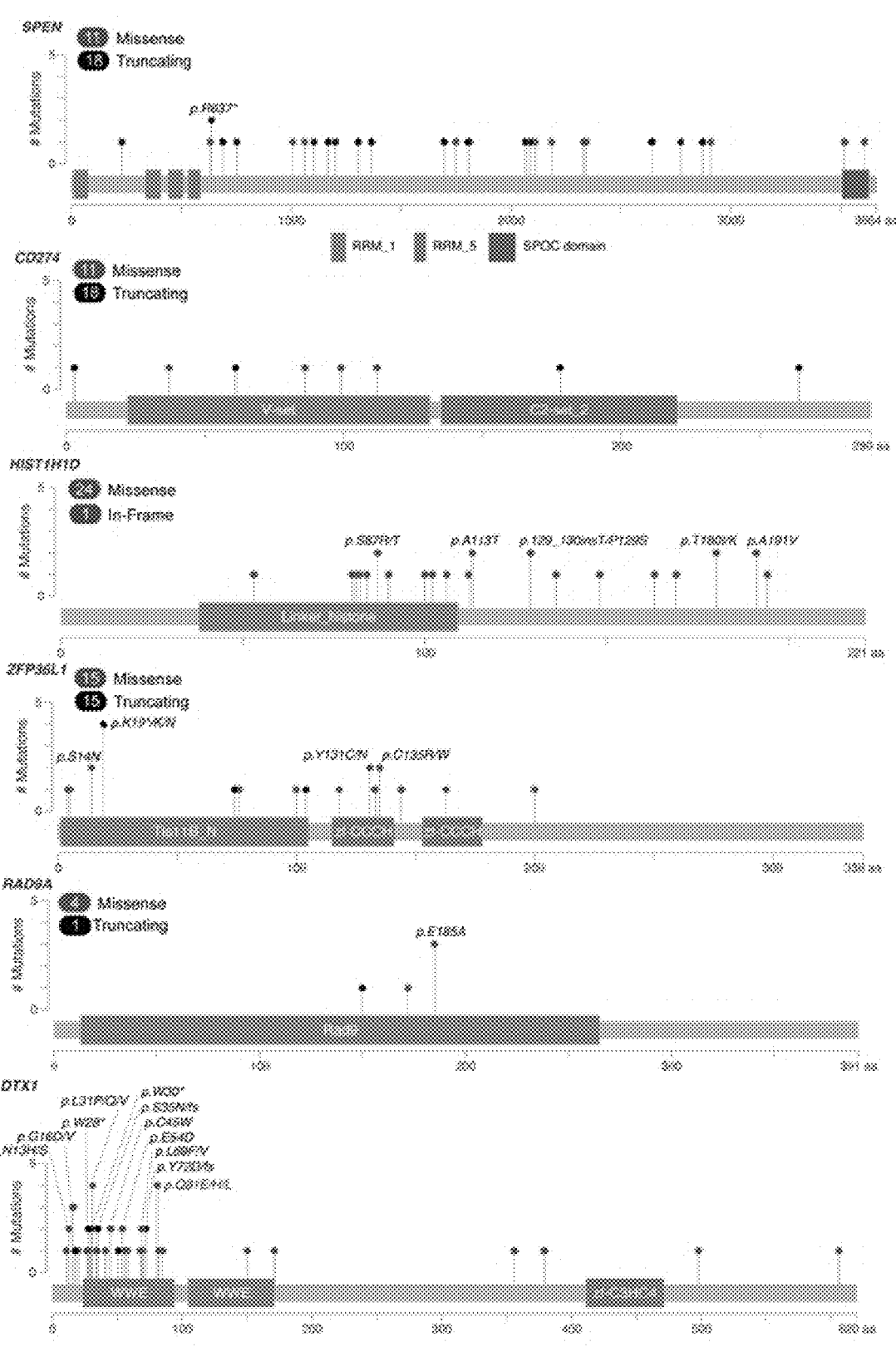
Figure 8:
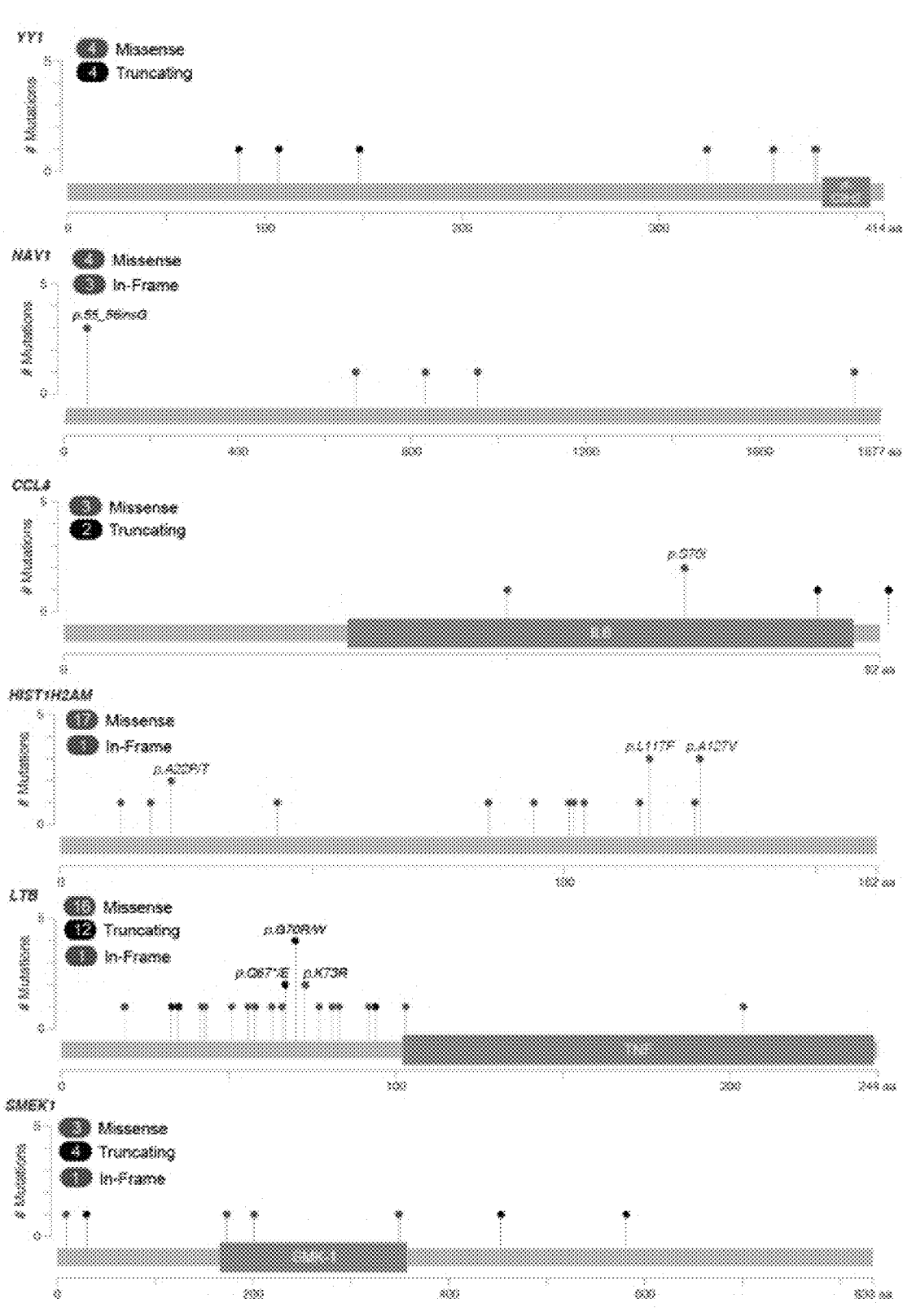
Figure 8:
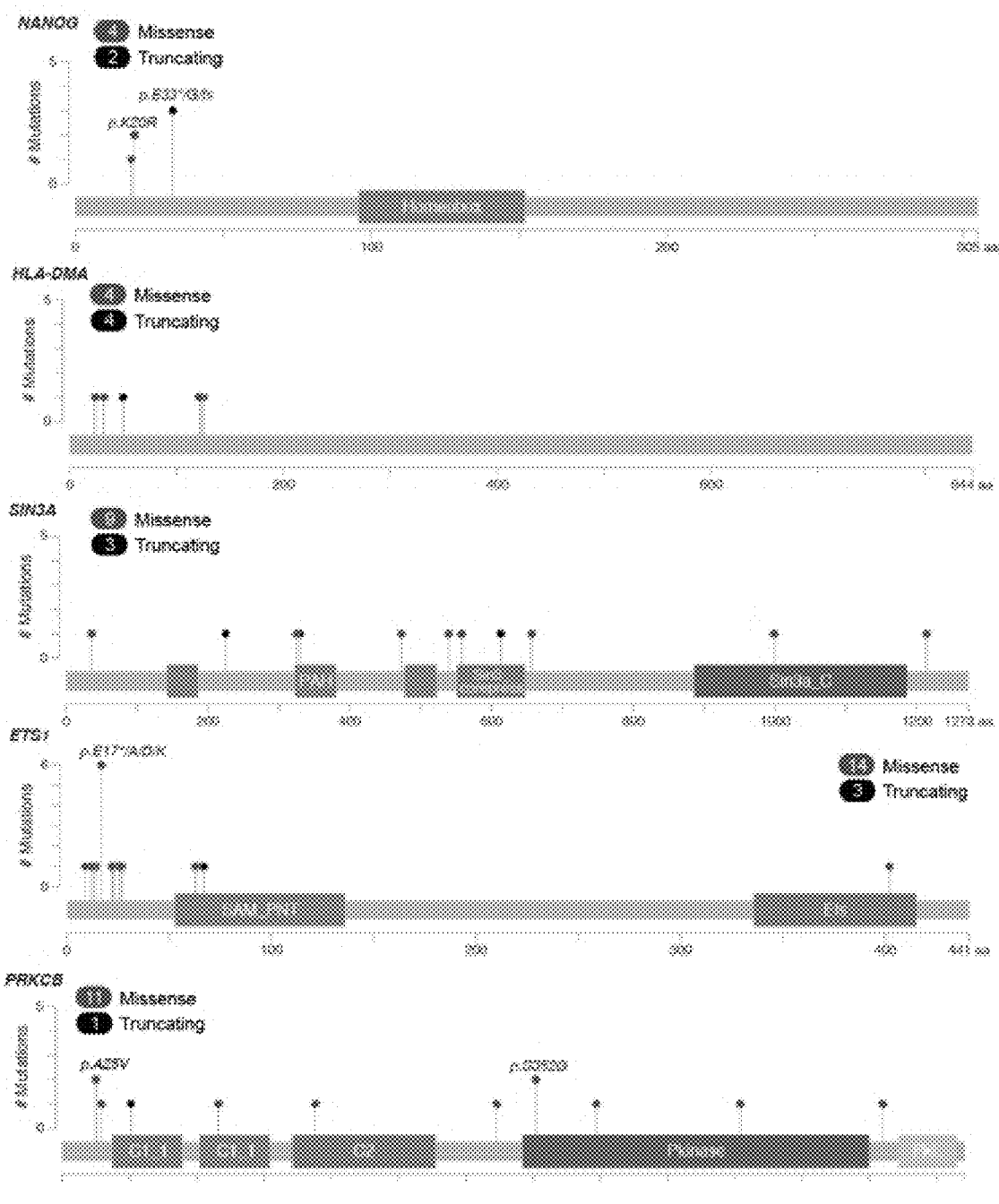
Figure 8:
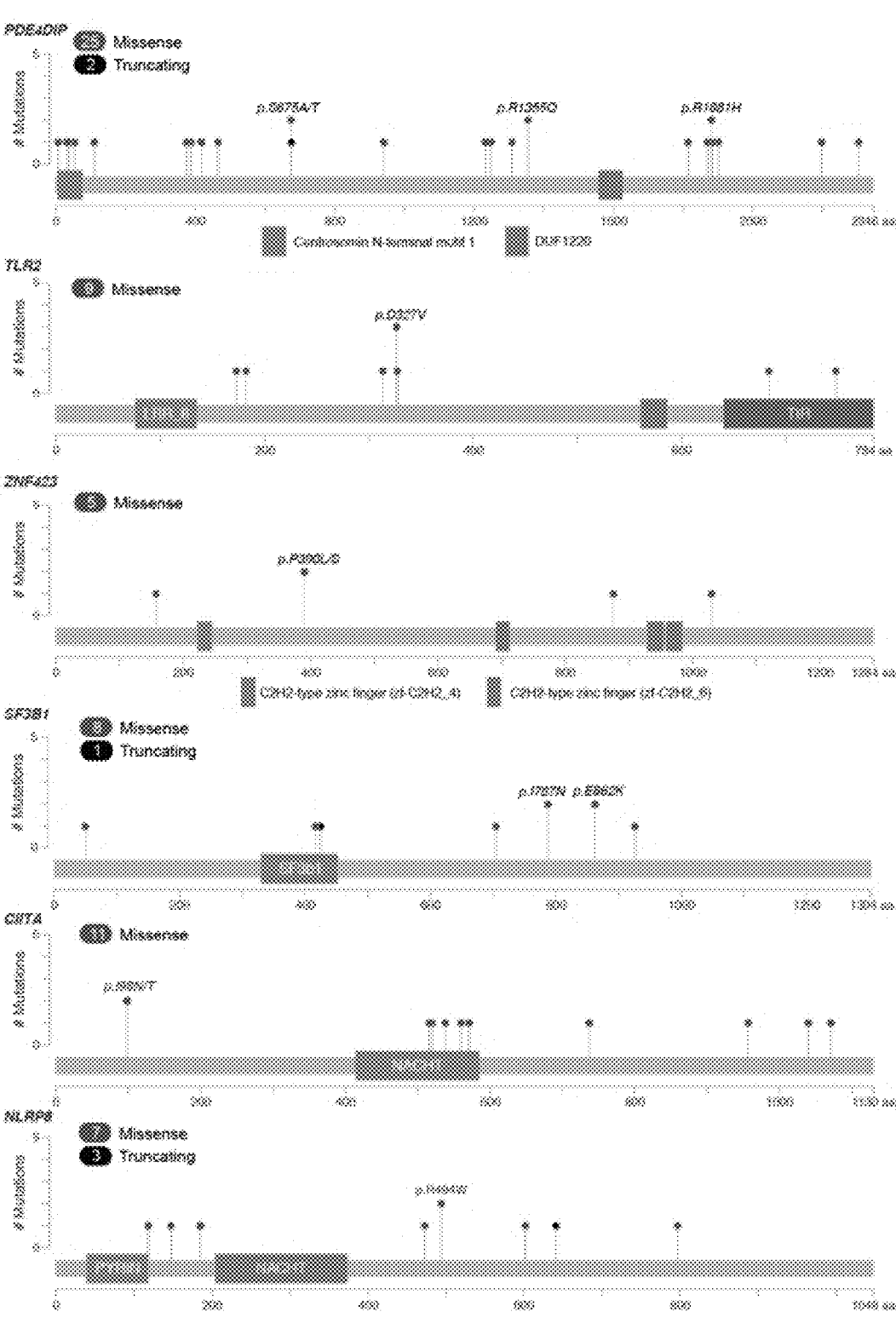
Figure 8:
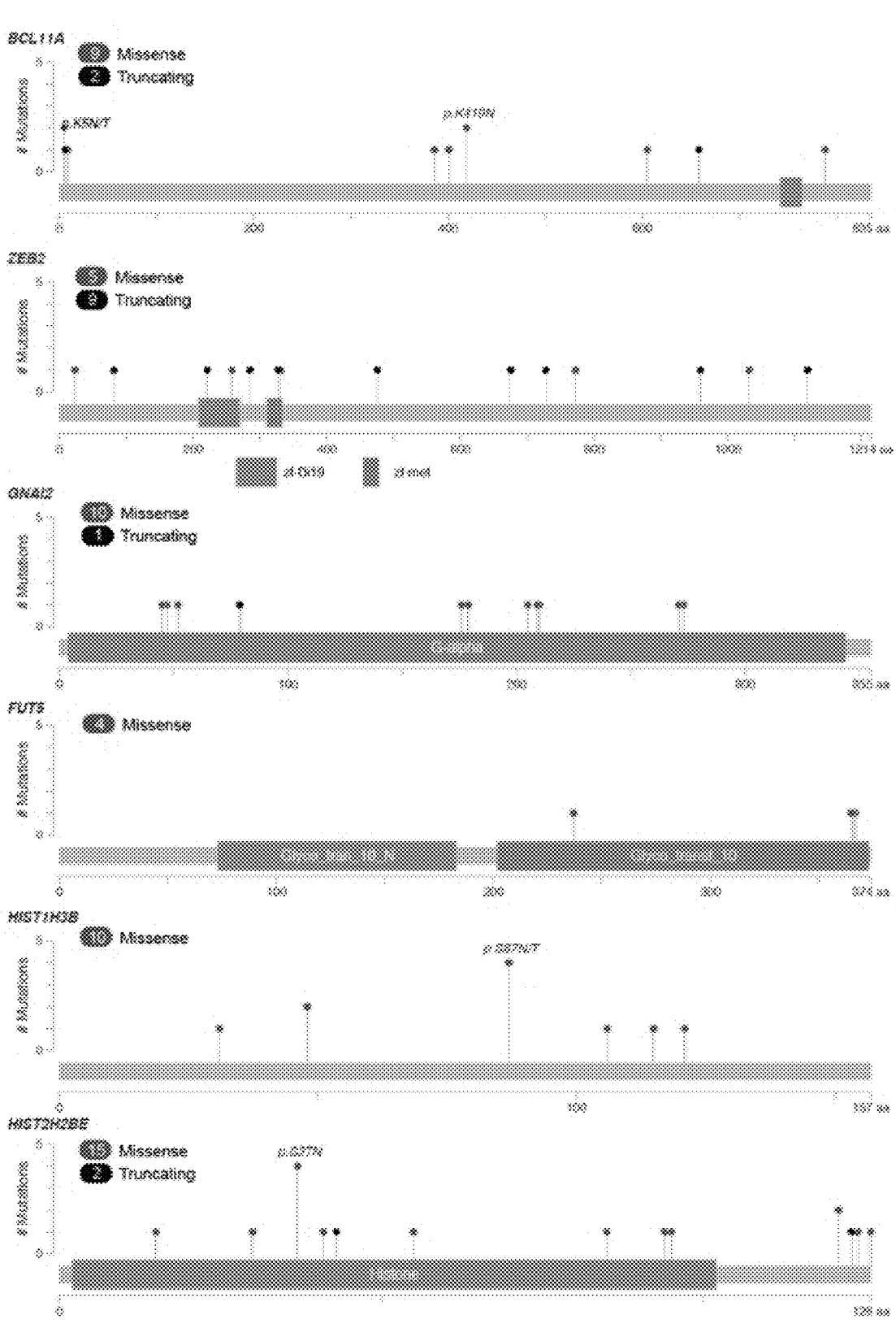
Figure 8:
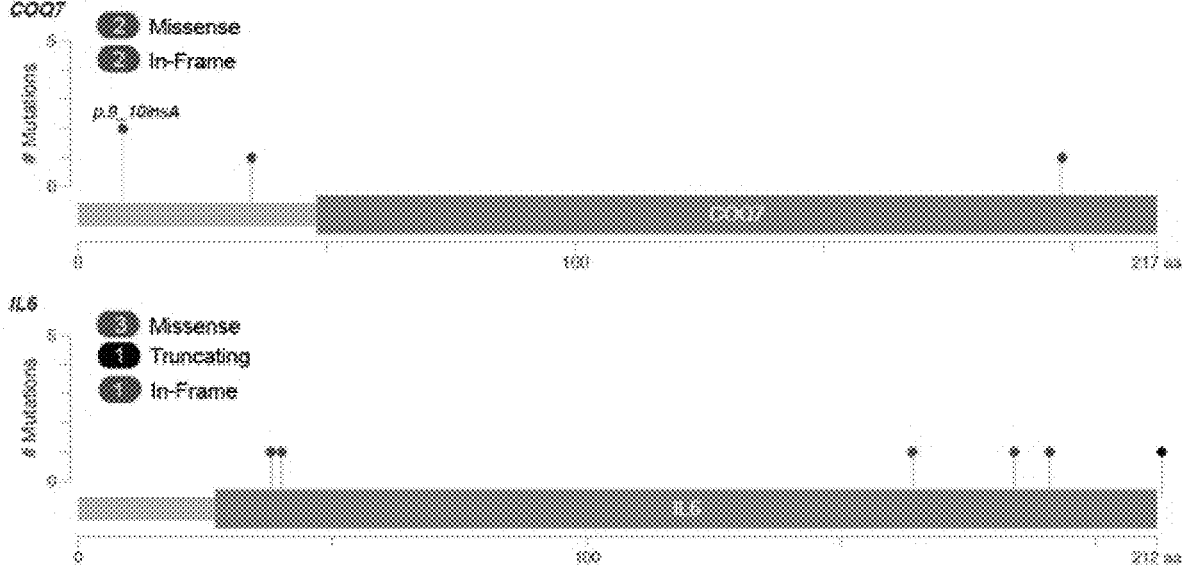

In some aspects, exome sequencing is performed upon a test sample for purpose of detecting variants and/or copy number variation as described herein and identifying DLBCL classification and selecting a therapy. In certain embodiments, assessment of candidate and/or test DLBCL samples can be performed using one or more amplification and/or sequencing oligonucleotides flanking the above-referenced variant sequence and/or copy number variation regions (e.g., regions as shown in FIG. 8, or as described above). Design and use of such amplification and sequencing oligonucleotides, and/or copy number detection probes/oligonucleotides, can be performed by one of ordinary skill in the art, in possession of the instantly disclosed reference sequence information and/or information provided in FIG. 8 or as described above.

As will be appreciated by one of ordinary skill in the art, any such amplification sequencing and/or copy number detection oligonucleotides can be modified by any of a number of art-recognized moieties and/or exogenous sequences, e.g., to enhance the processes of amplification, sequencing reactions and/or detection. Exemplary oligonucleotide modifications that are expressly contemplated for use with the oligonucleotides of the instant disclosure include, e.g., fluorescent and/or radioactive label modifications; labeling one or more oligonucleotides with a universal amplification sequence (optionally of exogenous origin) and/or labeling one or more oligonucleotides of the instant disclosure with a unique identification sequence (e.g., a "bar-code" sequence, optionally of exogenous origin), as well as other modifications known in the art and suitable for use with oligonucleotides.

Neural Network Classification

In certain exemplified aspects, a neural network classifier has been employed to define DLBCL classification groups. As would be appreciated by one of ordinary skill in the art, other forms of classifier (e.g., nearest-neighbor and various others) can be applied to variant and/or copy number data, to perform such test sample classification.

A neural network consists of units (neurons), arranged in layers, which convert an input vector into some output. Each unit takes an input, applies a (often nonlinear) function to it and then passes the output on to the next layer. Generally the networks are defined to be feed-forward: a unit feeds its output to all the units on the next layer, but there is no feedback to the previous layer. Weightings are applied to the signals passing from one unit to another, and it is these weightings which are tuned in the training phase to adapt a neural network to the particular problem at hand. This is the learning phase.

Neural networks have found application in a wide variety of problems. These range from function representation to pattern recognition, with pattern recognition being the focus of use of neural net classifiers of the instant disclosure.

Clinical Classifier Scoring Algorithm

As an example, a neural net classifier was developed to prospectively identify DLBCL patients with the respective genetic signatures. The exemplified classifier utilizes 75 variants that were selected based on a Fisher Test to be specific markers for each DLBCL genetic cluster. A network with these 75 input variants (including MYD88 L265, non-L265, and genome doubling) provided 78% agreement with the DLBCL clusters in a random subset of 72 tumors (using the other 212 for training the network). In this subset, 57 of the 72 test-tumors were classified with "High Confidence" ($p\_max>0.7$, where $p\_max$ is the maximum network output among the 5 clusters) with an agreement of 84%.

The 75 variants of the presently exemplified classifier are included below in alphabetical order.

1P13.1:DEL
1P31.1:DEL
1P36.11:DEL
2P16.1:AMP
3P:AMP
3P21.31:DEL
3Q:AMP
4Q21.22:DEL
4Q35.1:DEL
5P:AMP
9P21.3:DEL
9Q21.13:DEL
10Q23.31:DEL
14Q32.31:DEL
16Q12.1:DEL
17P:DEL
17Q25.1:DEL
18P:AMP
18Q:AMP
19P13.2:DEL
19Q:AMP
19Q13.42:AMP
21Q:AMP
B2M
BCL2
BCL10
BRAF
CD58
CD70
CD79B
CD83
CREBBP
ETV6
EZH2
FAS
GENOME_DOUBLING
GNA13
GNAI2
GRHPR
HIST1H1B
HIST1H1C
HIST1H1D
HIST1H1E
HIST1H2BC
HLA-B
HVCN1
IRF8
KLHL6
KMT2D
MEF2B
MYD88:L265
MYD88:OTHER
NFKBIA

US 12,571,049 B2

27

NFKBIE
NOTCH2
PIM1
POU2F2
PTEN
SGK1
SPEN
STAT3
SV:BCL2
SV:BCL6
SV:CD274/PDCD1LG2
SV:MYC
SV:TP63
TBL1XR1
TMEM30A
TNFAIP3
TNFRSF14
TP53
UBE2A
ZC3H12A
ZEB2
ZFP36L1

It is expressly contemplated that a classifier of the instant disclosure can be used to link discrete genetic signatures, clinical outcome and specific targeted therapy in clinical trials and in practice. Specifically, it is contemplated that tumors of patients with DLBCL can be analyzed prospectively with an exemplified classifier or other classifier within the scope of the instant disclosure. The resulting cluster identifications are predictive of the likelihood of response to standard combination chemotherapy and suggest rational targeted therapies based on cluster-specific biology. It is further expressly contemplated that a classifier of the instant disclosure can also be applied retrospectively to archival tissue from patients on specific clinical trials or therapies.

Treatment Selection

The methods described herein can be used for selecting, and then optionally administering, an optimal treatment for a subject. Thus the methods described herein include methods for the treatment of cancer, particularly DLBCL. Generally, the methods include administering a therapeutically effective amount of a treatment as described herein, to a subject who is in need of, or who has been determined to be in need of, such treatment.

As used in this context, to "treat" means to ameliorate at least one symptom of the cancer. For example, a treatment can result in a reduction in tumor size, tumor growth, cancer cell number, cancer cell growth, or metastasis or risk of metastasis.

For example, the methods can include selecting and/or administering a treatment that includes a therapeutically effective amount of a BCR/TLR signaling inhibitor and/or a BCL2 inhibitor, to a subject having a select DLBCL cancer/tumor (e.g., a DLBCL of the C5 class, as defined herein).

Therapeutic agents specifically implicated for administration in using the instant DLBCL classifier include inhibitors of the following genetic targets:

BCL-2

B-cell lymphoma 2 (BCL-2) is the founding member of the Bcl-2 family of regulator proteins that regulate apoptosis. Bcl-2 is considered an important anti-apoptotic protein but not a proto-oncogene. Targeted selective BCL-2 inhibitors for clinical use include oblimersen, ABT-263, and Venetoclax (ABT-199).

BCL-6

B-cell lymphoma 6 (BCL-6) is an evolutionarily conserved zinc finger transcription factor and contains an N-terminal POZ/BTB domain. This protein acts as a sequence-specific repressor of transcription and has been shown to modulate the STAT-dependent Interleukin 4 (IL-4) responses of B cells. This gene is found to be frequently translocated and hypermutated in diffuse large B cell lymphoma (DLBCL) and contributes to the pathogenesis of DLBCL. An exemplary BCL6 inhibitor is 79-6-Calbiochem from Millipore.

BCR/TLR Pathway

The B-cell receptor (BCR) protein controls the activation of B-cells. Toll-like receptors (TLRs) are a class of proteins that play a key role in the innate immune system. TLR's are single, membrane-spanning, non-catalytic receptors typically expressed on cells such as macrophages and dendritic cells. TLR's recognize structurally conserved molecules derived from microbes. BCR and TLR signaling synergizes for induction of activation-induced cytidine deaminase (AID) and immunoglobulin class-switching.

Notch

The Notch signaling pathway is a highly conserved cell signaling system present in most multicellular organisms. Mammals possess four different notch receptors, NOTCH1, NOTCH2, NOTCH3, and NOTCH4. Notch signaling promotes proliferative signaling during neurogenesis, and its activity is inhibited by Numb to promote neural differentiation. NOTCH also plays a major role in the regulation of embryonic development. No approved NOTCH small molecule inhibitors are currently in use.

PI3K

Phosphatidylinositol-4,5-bisphosphate 3-kinases, also called phosphatidylinositol-3-kinases (PI3K), are enzymes involved in cellular functions such as cell growth, proliferation, differentiation, motility, survival and intracellular trafficking. PI3Ks perform their functions through phosphorylating the 3 position hydroxyl group of the inositol ring of phosphatidylinositol. All PI3-kinases are inhibited by the drugs wortmannin and LY294002.

EZH2

Enhancer of zeste homolog 2 (EZH2) is a histone-lysine N-methyltransferase enzyme (EC 2.1.1.43) that participates in histone methylation and, ultimately, transcriptional repression. Methylation activity of EZH2 facilitates heterochromatin formation thereby silences gene function. EZH2 is also the functional enzymatic component of the Polycomb Repressive Complex 2 (PRC2), which is responsible for healthy embryonic development through the epigenetic maintenance of genes responsible for regulating development and differentiation. Several inhibitors of EZH2 have been developed as of 2015, including 3-deazaneplanocin A (DZNep), EPZ005687, EI1, GSK126, and UNC1999. UNC1999 was developed as an analogue of GSK126, and was the first orally bioavailable EZH2 inhibitor to show activity. However, UNC1999 also binds to EZH1 and may have off-target effects.

CREBBP

CREB-binding protein (CREBBP), is a protein that carries out its function by activating transcription. Interaction with transcription factors is managed by one or more CREB domains: the nuclear receptor interaction domain (RID), the KIX domain (CREB and MYB interaction domain), the cysteine/histidine regions (TAZ1/CH1 and TAZ2/CH3) and the interferon response binding domain (IBiD). A small molecule inhibitor (I-CBP112) binding to the bromodomain domain of CBP/p300 has been developed for leukaemia therapy.

JAK/STAT

The Janus kinase/signal transducer and activator of transcription (JAK/STAT) signaling pathway transmits information from extracellular chemical signals to the nucleus resulting in DNA transcription and expression of genes involved in immunity, proliferation, differentiation, apoptosis and oncogenesis. JAK-STAT signaling consists of three main components: a cell surface receptor, a JAK and two STAT proteins. An example JAK/STAT small molecule inhibitors is ruxolitinib.

BRAF/MEK1 Blockade

BRAF is a human gene that encodes a protein called B-Raf. The gene is also referred to as proto-oncogene B-Raf, v-Raf murine sarcoma viral oncogene homolog B, and serine/threonine-protein kinase B-Raf. B-Raf protein is involved in internal cell signaling that directs cell growth. Mitogen-activated protein kinase kinase (MEK1 or MAP2K1), is a chromosome-axis-associated kinase that slows sister chromatid recombination. BRAF/MEK1 inhibition is possible with Vemurafenib and Cobimetinib, small molecule inhibitors currently used for advanced melanoma treatment.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Combination Treatments

The compositions and methods of the present disclosure may be used in the context of a number of therapeutic or prophylactic applications. In order to increase the effectiveness of a treatment with the compositions of the present disclosure, e.g., a BCL-2 inhibitor selected and/or administered as a single agent, or to augment the protection of another therapy (second therapy), it may be desirable to combine these compositions and methods with one another, or with other agents and methods effective in the treatment, amelioration, or prevention of diseases and pathologic conditions, for example, cancers, e.g., DLBCL.

Administration of a composition of the present disclosure to a subject will follow general protocols for the administration described herein, and the general protocols for the administration of a particular secondary therapy will also be followed, taking into account the toxicity, if any, of the treatment. It is expected that the treatment cycles would be repeated as necessary. It also is contemplated that various standard therapies may be applied in combination with the described therapies.

Pharmaceutical Compositions

Agents of the present disclosure can be incorporated into a variety of formulations for therapeutic use (e.g., by administration) or in the manufacture of a medicament (e.g., for treating or preventing a DLBCL cancer) by combining the agents with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols.

Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

Further examples of formulations that are suitable for various types of administration can be found in Remington's Pharmaceutical Sciences, Mace Publishing Company, Philadelphia, PA, 17th ed. (1985). For a brief review of methods for drug delivery, see, Langer, Science 249: 1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink.

Similar diluents can be used to make compressed tablets. Both tablets and capsules can be manufactured as sustained release products to provide for continuous release of medi- cation over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacte- riostats, and solutes that render the formulation isotonic with the blood of the intended recipient, and aqueous and non- aqueous sterile suspensions that can include suspending agents, solubilizers, thickening agents, stabilizers, and pre- servatives.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commen- surate with a reasonable benefit/risk ratio. Pharmaceutically acceptable salts of amines, carboxylic acids, and other types of compounds, are well known in the art. For example, S. M. Berge, et al. describe pharmaceutically acceptable salts in detail in J Pharmaceutical Sciences 66 (1977): 1-19, incor- porated herein by reference. The salts can be prepared in situ during the final isolation and purification of the compounds (e.g., FDA-approved compounds) of the application, or separately by reacting a free base or free acid function with a suitable reagent, as described generally below. For example, a free base function can be reacted with a suitable acid. Furthermore, where the compounds to be administered of the application carry an acidic moiety, suitable pharma- ceutically acceptable salts thereof may, include metal salts such as alkali metal salts, e.g. sodium or potassium salts; and alkaline earth metal salts, e.g. calcium or magnesium salts. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsul- fate, ethanesulfonate, formate, fumarate, glucoheptonate, glycerophosphate, gluconate, hemisulfate, heptanoate, hexanoate, hydroiodide, 2-hydroxy-ethanesulfonate, lacto- bionate, lactate, laurate, lauryl sulfate, malate, maleate, malonate, methanesulfonate, 2-naphthalenesulfonate, nico- tinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammo- nium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers to esters that hydrolyze in vivo and include those that break down readily in the human body to leave the parent compound (e.g., an FDA-approved com- pound where administered to a human subject) or a salt thereof. Suitable ester groups include, for example, those derived from pharmaceutically acceptable aliphatic carbox- ylic acids, particularly alkanoic, alkenoic, cycloalkanoic and alkanedioic acids, in which each alkyl or alkenyl moeity advantageously has not more than 6 carbon atoms. Examples of particular esters include formates, acetates, propionates, butyrates, acrylates and ethylsuccinates.

Furthermore, the term "pharmaceutically acceptable prodrugs" as used herein refers to those prodrugs of the certain compounds of the present application which are, within the scope of sound medical judgment, suitable for use in contact with the issues of humans and lower animals with undue toxicity, irritation, allergic response, and the like, commensurate with a reasonable benefit/risk ratio, and effective for their intended use, as well as the zwitterionic forms, where possible, of the compounds of the application. The term "prodrug" refers to compounds that are rapidly transformed in vivo to yield the parent compound of an agent of the instant disclosure, for example by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharma- ceutical Association and Pergamon Press, (1987), both of which are incorporated herein by reference.

The components used to formulate the pharmaceutical compositions are preferably of high purity and are substan- tially free of potentially harmful contaminants (e.g., at least National Food (NF) grade, generally at least analytical grade, and more typically at least pharmaceutical grade) Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental adminis- tration are also sterile, substantially isotonic and made under GMP conditions.

Formulations may be optimized for retention and stabili- zation in a subject and/or tissue of a subject, e.g., to prevent rapid clearance of a formulation by the subject. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of the agent, such as a BCL2 inhibitor, PI3K inhibitor, BCR/TLR signaling inhibitor, JAK/STAT inhibi- tor, etc., in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross- linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the individual instant disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an agent described herein may be used (e.g., administered to an individual, such as a human individual, in need of treatment with a BCL2 inhibitor, PI3K inhibitor, BCR/TLR signaling inhibitor, JAK/STAT inhibitor, etc.) in accord with known methods, such as oral administration, intravenous administration as a bolus or by continuous infusion over a period of time, by intramuscular, intraperitoneal, intracerobrospinal, intracranial, intraspinal, subcutaneous, intraarticular, intrasynovial, intrathecal, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan. Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In Toxicokinetics and New Drug Development, Yacobi et al., Eds, Pergamon Press, New York 1989, pp. 42-46.

For in vivo administration of any of the agents of the present disclosure, normal dosage amounts may vary from about 10 ng/kg up to about 100 mg/kg of an individual's and/or subject's body weight or more per day, depending upon the route of administration. In some embodiments, the dose amount is about 1 mg/kg/day to 10 mg/kg/day. For repeated administrations over several days or longer, depending on the severity of the disease, disorder, or condition to be treated, the treatment is sustained until a desired suppression of symptoms is achieved.

An effective amount of an agent of the instant disclosure may vary, e.g., from about 0.001 mg/kg to about 1000 mg/kg or more in one or more dose administrations for one or several days (depending on the mode of administration). In certain embodiments, the effective amount per dose varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

An exemplary dosing regimen may include administering an initial dose of an agent of the disclosure of about 200 µg/kg, followed by a weekly maintenance dose of about 100 µg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, or about 2 mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the agent(s) administered, can vary over time independently of the dose used.

Pharmaceutical compositions described herein can be prepared by any method known in the art of pharmacology. In general, such preparatory methods include the steps of bringing the agent or compound described herein (i.e., the "active ingredient") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, Poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methyl cellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of an agent (e.g., a BCL2 inhibitor, PI3K inhibitor, BCR/TLR signaling inhibitor, JAK/STAT inhibitor, etc.) described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the compound in powder form through the outer layers of the skin to the dermis are suitable.

Formulations suitable for topical administration include, but are not limited to, liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other ophthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

FDA-approved drugs provided herein are typically formulated in dosage unit form for ease of administration and uniformity of dosage. It will be understood, however, that the total daily usage of the agents described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The agents and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the agent or pharmaceutical composition described herein is suitable for topical administration to the eye of a subject.

The exact amount of an agent required to achieve an effective amount will vary from subject to subject, depending, for example, on species, age, and general condition of a subject, severity of the side effects or disorder, identity of the particular agent, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of an agent (e.g., a BCL2 inhibitor, PI3K inhibitor, BCR/TLR signaling inhibitor, JAK/STAT inhibitor, etc.) described herein.

As noted elsewhere herein, a drug of the instant disclosure may be administered via a number of routes of administration, including but not limited to: subcutaneous, intravenous, intrathecal, intramuscular, intranasal, oral, transepidermal, parenteral, by inhalation, or intracerebroventricular.

The term "injection" or "injectable" as used herein refers to a bolus injection (administration of a discrete amount of an agent for raising its concentration in a bodily fluid), slow bolus injection over several minutes, or prolonged infusion, or several consecutive injections/infusions that are given at spaced apart intervals.

In some embodiments of the present disclosure, a formulation as herein defined is administered to the subject by bolus administration.

The FDA-approved drug or other therapy is administered to the subject in an amount sufficient to achieve a desired effect at a desired site (e.g., reduction of cancer size, cancer cell abundance, symptoms, etc.) determined by a skilled clinician to be effective. In some embodiments of the disclosure, the agent is administered at least once a year. In other embodiments of the disclosure, the agent is administered at least once a day. In other embodiments of the disclosure, the agent is administered at least once a week. In some embodiments of the disclosure, the agent is administered at least once a month.

Additional exemplary doses for administration of an agent of the disclosure to a subject include, but are not limited to, the following: 1-20 mg/kg/day, 2-15 mg/kg/day, 5-12 mg/kg/day, 10 mg/kg/day, 1-500 mg/kg/day, 2-250 mg/kg/day, 5-150 mg/kg/day, 20-125 mg/kg/day, 50-120 mg/kg/day, 100 mg/kg/day, at least 10 µg/kg/day, at least 100 µg/kg/day, at least 250 µg/kg/day, at least 500 µg/kg/day, at least 1 mg/kg/day, at least 2 mg/kg/day, at least 5 mg/kg/day, at least 10 mg/kg/day, at least 20 mg/kg/day, at least 50 mg/kg/day, at least 75 mg/kg/day, at least 100 mg/kg/day, at least 200 mg/kg/day, at least 500 mg/kg/day, at least 1 g/kg/day, and a therapeutically effective dose that is less than 500 mg/kg/day, less than 200 mg/kg/day, less than 100 mg/kg/day, less than 50 mg/kg/day, less than 20 mg/kg/day, less than 10 mg/kg/day, less than 5 mg/kg/day, less than 2 mg/kg/day, less than 1 mg/kg/day, less than 500 µg/kg/day, and less than 500 µg/kg/day.

In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of an agent (e.g., a BCL2 inhibitor, PI3K inhibitor, BCR/TLR signaling inhibitor, JAK/STAT inhibitor, etc.) described herein. In certain embodiments, a dose described herein includes independently between 1 mg and 3 mg, inclusive, of an agent (e.g., a BCL2 inhibitor, PI3K inhibitor, BCR/TLR signaling inhibitor, JAK/STAT inhibitor, etc.) described herein. In certain embodiments, a dose described herein includes independently between 3 mg and 10 mg, inclusive, of an agent (e.g., a BCL2 inhibitor, PI3K inhibitor, BCR/TLR signaling inhibitor, JAK/STAT inhibitor, etc.) described herein. In certain embodiments, a dose described herein includes independently between 10 mg and 30 mg, inclusive, of an agent (e.g., a BCL2 inhibitor, PI3K inhibitor, BCR/TLR signaling inhibitor, JAK/STAT inhibitor, etc.) described herein. In certain embodiments, a dose described herein includes independently between 30 mg and 100 mg, inclusive, of an agent (e.g., a BCL2 inhibitor, PI3K inhibitor, BCR/TLR signaling inhibitor, JAK/STAT inhibitor, etc.) described herein.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

It will be also appreciated that an agent (e.g., a BCL2 inhibitor, PI3K inhibitor, BCR/TLR signaling inhibitor, JAK/STAT inhibitor, etc.) or composition, as described herein, can be administered in combination with one or more additional pharmaceutical agents (e.g., therapeutically and/or prophylactically active agents), which are different from the agent or composition and may be useful as, e.g., combination therapies. The agents or compositions can be administered in combination with additional pharmaceutical agents that improve their activity (e.g., activity (e.g., potency and/or efficacy) in treating a disease in a subject in need thereof, in preventing a disease in a subject in need thereof, in reducing the risk of developing a disease in a subject in need thereof, in inhibiting the replication of a virus, in killing a virus, etc. in a subject or cell. In certain embodiments, a pharmaceutical composition described herein including an agent (e.g., a BCL2 inhibitor, PI3K inhibitor, BCR/TLR signaling inhibitor, JAK/STAT inhibitor, etc.) described herein and an additional pharmaceutical agent shows a synergistic effect that is absent in a pharmaceutical composition including one of the agent and the additional pharmaceutical agent, but not both.

In some embodiments of the disclosure, a therapeutic agent distinct from a first therapeutic agent of the disclosure is administered prior to, in combination with, at the same time, or after administration of the agent of the disclosure. In some embodiments, the second therapeutic agent is selected from the group consisting of a chemotherapeutic, an antioxidant, an antiinflammatory agent, an antimicrobial, a steroid, etc.

The agent or composition can be administered concurrently with, prior to, or subsequent to one or more additional pharmaceutical agents, which may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease described herein. Each additional pharmaceutical agent may be administered at a dose and/or on a time schedule determined for that pharmaceutical agent. The additional pharmaceutical agents may also be administered together with each other and/or with the agent or composition described herein in a single dose or administered separately in different doses. The particular combination to employ in a regimen will take into account compatibility of the agent described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include, but are not limited to, additional BCL2 inhibitors, PI3K inhibitors, BCR/TLR signaling inhibitors, JAK/STAT inhibitors, other epigenetic modifier inhibitors, etc., other anti-cancer agents, immunomodulatory agents, anti-proliferative agents, cytotoxic agents, anti-angiogenesis agents, anti-inflammatory agents, immunosuppressants, anti-bacterial agents, anti-viral agents, cardiovascular agents, cholesterol-lowering agents, anti-diabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine kinase inhibitors), modulators of protein stability (e.g., proteasome inhibitors), Hsp90 inhibitors, glucocorticoids, all-trans retinoic acids, and other agents that promote differentiation. In certain embodiments, the agents described herein or pharmaceutical compositions can be administered in combination with an anti-cancer therapy including, but not limited to, surgery, radiation therapy, transplantation (e.g., stem cell transplantation, bone marrow transplantation), immunotherapy, and chemotherapy.

Dosages for a particular agent of the instant disclosure may be determined empirically in individuals who have been given one or more administrations of the agent.

Administration of an agent of the present disclosure can be continuous or intermittent, depending, for example, on the recipient's physiological condition, whether the purpose of the administration is therapeutic or prophylactic, and other factors known to skilled practitioners. The administration of an agent may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the instant disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Kits

The instant disclosure also provides kits containing agents of this disclosure for use in the methods of the present disclosure. Kits of the instant disclosure may include one or more containers comprising an agent (e.g. a BCL2 inhibitor, PI3K inhibitor, BCR/TLR signaling inhibitor, JAK/STAT inhibitor, etc.) of this disclosure and/or may contain agents (e.g., oligonucleotide primers, probes, etc.) for identifying a cancer or subject as possessing one or more variant sequences. In some embodiments, the kits further include instructions for use in accordance with the methods of this disclosure. In some embodiments, these instructions comprise a description of administration of the agent to treat or diagnose, e.g., a DLBCL, according to any of the methods of this disclosure. In some embodiments, the instructions comprise a description of how to detect a DLBCL class of cancer, for example in an individual, in a tissue sample, or in a cell. The kit may further comprise a description of selecting an individual suitable for treatment based on identifying whether that subject has a specific type of DLBCL.

The instructions generally include information as to dosage, dosing schedule, and route of administration for the intended treatment. The containers may be unit doses, bulk packages (e.g., multi-dose packages) or sub-unit doses. Instructions supplied in the kits of the instant disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a class of DLBCL, in a subject. Instructions may be provided for practicing any of the methods described herein.

The kits of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). In certain embodiments, at least one active agent in the composition is a BCL2 inhibitor, PI3K inhibitor, BCR/TLR signaling inhibitor, JAK/STAT inhibitor, an epigenetic modifier, an epigenetic modifier inhibitor, etc. The container may further comprise a second pharmaceutically active agent.

Kits may optionally provide additional components such as buffers and interpretive information. Normally, the kit comprises a container and a label or package insert(s) on or associated with the container.

The practice of the present disclosure employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992), Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986); Westerfield, M., The zebrafish book. A guide for the laboratory use of zebrafish (Danio rerio), (4th Ed., Univ. of Oregon Press, Eugene, 2000).

Unless otherwise defined, all technical and scientific terms used herein have the same meaning as commonly understood by one of ordinary skill in the art to which this disclosure belongs. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Reference will now be made in detail to exemplary embodiments of the disclosure. While the disclosure will be described in conjunction with the exemplary embodiments, it will be understood that it is not intended to limit the disclosure to those embodiments. To the contrary, it is intended to cover alternatives, modifications, and equivalents as may be included within the spirit and scope of the disclosure as defined by the appended claims. Standard techniques well known in the art or the techniques specifically described below were utilized.

EXAMPLES

Example 1: Materials and Methods

Patient Samples

Figure 7:
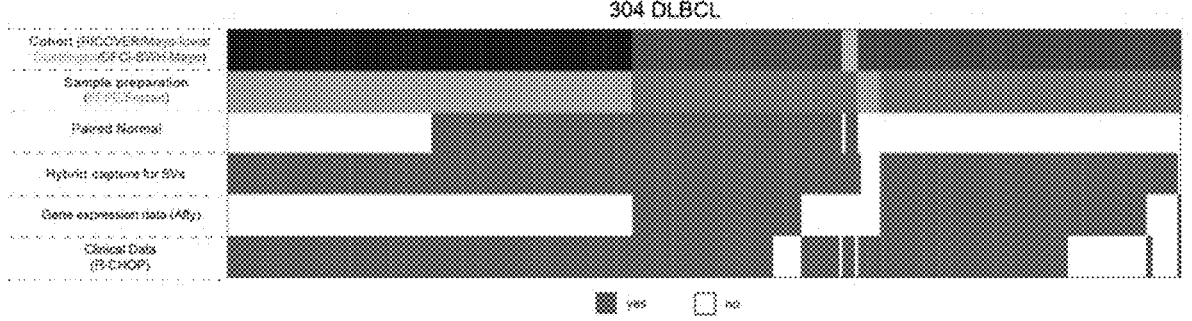
FIG. 7 presents a chart that depicts the composition of the dataset. The dataset included 304 newly diagnosed DLBCLs from 4 cohorts (129 samples from the RICOVER60 trial1; 67 samples from a Mayo/Iowa cohort, of which 51 WES were previously reported (2, 3); 5 samples from the Uni-versity of Gottingen, Germany; 103 samples from a DFCI/BWH/Mayo cohort (4); top row) including DNA-derived from formalin-fixed paraffin embedded (FFPE) or frozen tissue (second row). DLBCLs with paired normal samples are indicated (third row). Samples used for targeted sequenc-ing analyses of recurrent structural variants (SVs) (fourth row) and transcriptional profiling (fifth row) are noted. DLBCLs from patients who were treated with state-of-the-art therapy (R-CHOP) and which had long-term follow-up are also indicated below (bottom line).

A cohort of 351 patient samples diagnosed with a previously untreated, primary diffuse large B-cell lymphoma (DLBCL) was assembled, of which 304 passed all below described quality controls. This 304 sample dataset was obtained from four sources: 129 samples from patients enrolled in the prospective, randomized, multi-center RICOVER60 trial (S1); 103 samples from a DFCI/BWH cohort; 67 samples from the Mayo Clinic and University of Iowa Specialized Program of Research Excellence (SPORE) (51 previously reported WES analysis (S2, S3)); and 5 samples from the University of Gottingen, Germany. Forty-four percent (135/304) of samples had a paired normal specimen and 55% (168/304) of samples were obtained from formalin-fixed paraffin embedded (FFPE) tissue (FIG. 7 and Table S1). All patients had a diagnosed primary DLBCL per WHO criteria; this diagnosis was confirmed for all RICOVER60 samples by a central pathological review as previously described (S1), and all DFCI/BWH and Mayo cases were confirmed by an expert hematopathologist (SJR). The patient characteristics were equally distributed across the different sources and have been summarized in Table 2 of the associated mega table. A total of 85% (259/304) of patients were uniformly treated with state-of-the-art therapy (rituximab-containing CHOP-like regimen) and had long-term follow-up (median: 78.5 months). This study was approved by the institutional review board (IRB) of the Dana-Farber Cancer Institute and the IRBs of all other participating institutions.

Whole Exome Sequencing (WES)

DNA quality control. Tumor and normal DNA were extracted as previously described from lymph node samples, blood and 31 B-cell lymphoma cell lines, respectively (S2, S4). DNA quality control was performed as previously described (S22, S23). Briefly, genomic DNA was quantified using Quant-iT PicoGreen® dsDNA Assay Kit (ThermoFisher Scientific, USA) and identities of all tumor/normal DNA pairs were confirmed by mass spectrometric fingerprint genotyping of common SNPs.

Figure 12A:
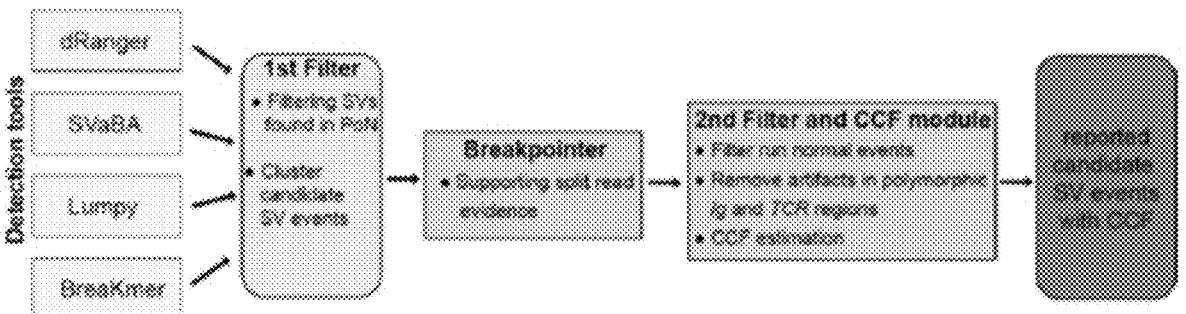
FIGS. 12A to 12E depict chromosomal rearrangements—pipeline and summary statistics.
Figure 12B:
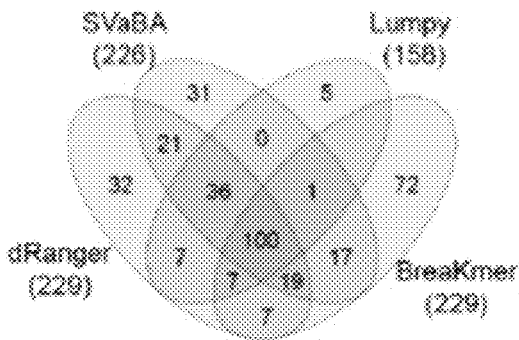
Figure 12C:
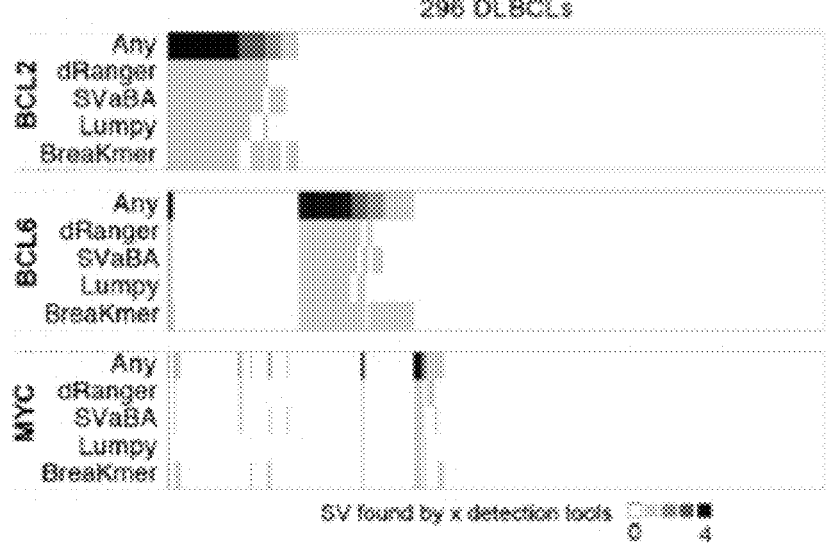
Figure 12D:
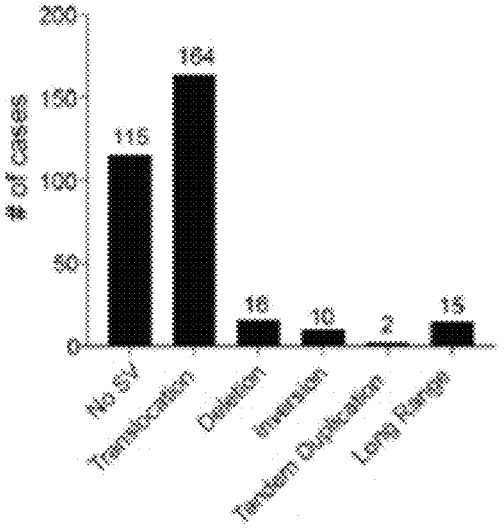
Figure 12E:
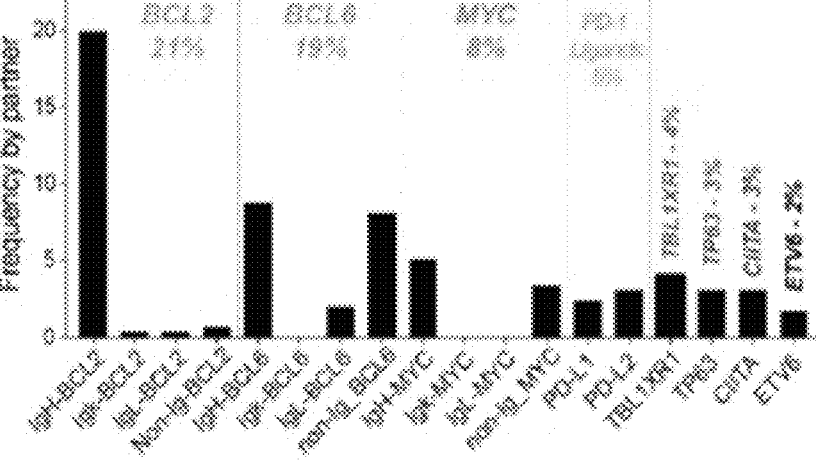

Exome sequencing. Whole exome capture was performed using the Agilent SureSelect Human All Exon 44 Mb v2.0 bait set (Agilent Technologies, USA) as previously described (S24-S26). In summary, genomic DNA was sheared, end repaired, ligated with barcoded Illumina sequencing adapters, amplified, size selected and subjected to in solution hybrid capture using the Agilent SureSelect Human All Exon v2.0 bait set (S24, S25). Resulting exome Illumina sequencing libraries were then qPCR quantified, pooled, and sequenced with 76 base paired-end reads using Illumina GAII or HiSeq 2000 sequencers (Illumina, USA). In addition, raw sequencing reads of previously in house generated and published WES data for 49 DLBCL tumor/normal paired samples (S2) were processed through identical pipelines as the newly generated WES data (FIG. 12A). Exome sequencing of cell lines with the spiked-in bait set for SV detection was performed as previously described (S26, S27). The new WES data has been deposited in the dbGAP database (www.ncbi.nlm.nih.gov/gap) with the updated accession number phs000450.v1.p1 (currently being updated).

Alignment and Quality Control. To prepare read alignments for analysis, all sequence data were processed through the Broad Institute's data processing pipeline, "Picard" (picard.sourceforge.net/) as previously described (S26). For each sample, this pipeline combines data from multiple libraries and flow cell runs into a single BAM file. This file contains reads aligned to the human genome with quality scores recalibrated using the TableRecalibration tool from the Genome Analysis Toolkit (GATK) (S28). Reads were aligned to the Human Genome Reference Consortium build 37 (GRCh37) using BWA (version 0.5.9-tpx bio-bwa-.sourceforge.net/). Variant detection and analysis of the BAM files were performed using the Broad Institute's Cancer Genome Analysis infrastructure program "Firehose" (archive.broadinstitute.org/cancer/cga/firehose). Firehose facilitates comparison of BAM files from matched tumor/normal pairs and coordinates the execution of specific modules including quality control, local realignment, mutation calling, small insertion and deletion identification, rearrangement detection, variant annotation, computation of mutation rates and calculation of sequencing metrics. Module versioning and logging of the specific analytical parameters was also tracked.

The amount of cross-individual contamination for tumor-normal pairs was estimated by ContEst (S29) and the median contamination was 0.3% (interquartile-range 0.1-0.4%). Due to the lack of methods for estimating cross-individual contamination without a paired normal, tumor-only samples were assumed to have 2% contamination, which is higher than 98% of the contamination estimates determined by ContEst in the paired samples.

A total of 47 samples were omitted due to quality control concerns, including 12 that failed sequencing (no BAM file), 23 samples had coverage that was too low to analyze (less than 75% of exome was callable), 1 was removed because of a high ContEst value (greater than 5%) and 11 were removed due to pervasive realignment artifact. Of the remaining 304 samples, one sample was treated as a tumor-only because its paired normal showed evidence of high tumor in normal contamination and two samples where the tumor and normal samples were mixed up. The median sequencing depth of the exome region in the tumor samples meeting all quality control cut offs is 87.6× (range: 39-206.8).

Copy Number Analysis from WES data. Initial estimates of exome-wide copy number profiles were determined using ReCapseq (S5) which created a copy number profile based on coverage across the exome and a panel of normals which obviated the need for a paired normal. The allele-specific copy number was determined using Allelic Capseq as previously described (S21, S30, S31). For paired samples, Allelic Capseq called heterozygous sites from the paired normal, while for the tumor-only samples heterozygous sites were called from the tumor itself. While this method possesses lower sensitivity for discovering sites with loss of heterozygosity (LOH) in the tumors, when paired samples are run with this method, they show high fidelity to the results when run with a paired normal.

Significance analysis of recurrent SCNAs using GIS-TIC2.0. Arm-level and focal peaks of recurrent copy number alterations were identified from the results of Allelic Capseq using GISTIC2.0 (version 129) as previously described (S32). Regions with germline copy number variants were excluded from the analysis. Events with a q-value of less than 0.1 were reported significant. A 99% confidence interval was specified to determine wide peak boundaries.

Chromothripsis Assessment

Due to the lack of full genome sequencing, the instant studies were limited to only one method of detection of chromothripsis as described in the literature (S33). To this end, each chromosome found to have been split into at least 10 segments longer than 100 exons in which there is at least one deletion of log 2(CN/2)<0.25 and at least one gain of log 2(CN/2)>0.25 and a variance at least 0.25 was tested to determine if the distances between the breakpoints were consistent with an exponential distribution, because it has been reported (S33) that chromothripsis tends to deviate from this model while other mechanisms of copy number alterations do not.

Mutation Calling. Somatic single nucleotide variants (SNVs) and small insertions and deletions (Indels) were identified using MuTect (Firehose CallSomaticMutations v131 (S34), and Indelocator (Firehose CallIndelsPipeline v77 (S22)), respectively. When a paired normal was not available, a normal sample was chosen from the instant DLBCL cohort that showed no evidence of tumor in normal contamination and otherwise acceptable QC metrics to remove common germline and potentially remove artifacts resulting from batch effect. Mutations were annotated using the oncotator tool (v68) (S35). Of note, a total of 67,518 unfiltered mutations were detected in tumor samples with a paired normal and 364,692 in samples without a paired normal. Stringent filtering as described below reduced the numbers to 20,328 and 31,586 for samples with and without paired normal, respectively. All significant analyses (MutSig2CV, CLUMPS, SignatureAnalyser tool) were performed on the filtered MAF file. The True-Positive-Rate=Sensitivity (=detected true mutations/all true mutations) for MuTect in tumor/normal (TN) pairs was above 90% in a blind simulated competition among algorithms called "Dream challenge 3" (www.synapse.org/#!Synapse: syn312572/wiki/63089). For the instant tumor-only pipeline, the sensitivity was higher than 90% relative to TN pair detection (FIG. 8G).

Estimation of and correction for tumor in normal content (deTiN). As described previously (S21), tumor in normal contamination significantly decreased the ability to detect somatic mutations. Therefore, the presence of tumor contamination was estimated in matched normal samples when available using the deTiN algorithm (S21) (manuscript in preparation, Taylor-Weiner et al.). Briefly, deTiN uses candidate somatic nucleotide variants and allelic copy number events to infer the fraction of tumor cells in a matched normal sample. This estimate was then used to recover somatic events that otherwise would have been rejected by MuTect or Indelocator due to low-allele fraction presence in the normal.

Artifact Filtering. OxoG-artifacts were filtered as previously described (S36). In brief, OxoG is an artifact signature that has long been known to result from oxidative damage to guanine during library preparation, which causes guanine to pair with adenine instead of cytosine, ultimately causing an observed G>T mutation. These artifacts will only occur on one strand whereas a somatic event will show the change on both strands of DNA, and this orientation bias is used to distinguish real events from artifacts. This cohort also had single nucleotide artifacts resulting from the use of FFPE samples, wherein formaldehyde causes deamination of cytosine resulting in C>T mutations similar to that of the aging signature but with the same orientation bias observed in OxoG events, allowing here for use of the same algorithm for determining orientation bias which has previously been used on FFPE samples (S37). In addition to the canonical OxoG and FFPE artifacts, this cohort had an artifact characterized by recurrent mutations in repetitive regions that have many potential sites for mapping in the genome. To control for this, SNV-containing regions were first realigned with Novoalign v3.02.08 (novocraft.com) and those variants that showed evidence in both sets of BAMs (S38) were preserved. Subsequently, SNV- and Indel-containing regions were reassembled using an approach similar to that of Haplotype caller (S28, S39; software.broadinstitute.org/ gatk/documentation/tooldocs/current/org-broadinstitute_gatk_tools_walkers_cancer_m2_MuTect2. php). Variants in regions with sufficient coverage after reassembly that did not have evidence of an alternate allele were rejected.

Panel of Normals (PoNs) Filtering. To remove sequencing artifacts and frequent germline events (for tumor only samples), SNVs and Indels were filtered using version 8 of the in-house PoNs which includes 8334 WES normals (S21, S38). Briefly, the panel includes for each site 8 values, which describe the percent of normals, different modes of artifact and the likelihood that the event is a germline event at that site.

Estimation of purity, ploidy and cancer cell fraction (CCF) using ABSOLUTE. For paired samples, purity, ploidy and cancer cell fraction (CCF) estimates for mutations and copy number were determined applying the ABSOLUTE algorithm as previously described (S40). Candidate models were reviewed by three independent reviewers (BC, AJD, CS) and discordances in the solution picks were resolved by discussion. ABSOLUTE models based on AllelicCapseq results and mutation calls from tumor only samples were similarly reviewable to those that came from paired samples. Due to the prevalence of heterozygous germline sites in the mutations going into ABSOLUTE, the solutions called were more driven by the ABSOLUTE copy number profile than the allele frequency distribution in tumor only samples than for paired samples. However, when ABSOLUTE solutions were called, independently, on 147 available paired lymphoma samples and those same sample samples run without pairs, there was a high correlation in calls of ploidy and purity.

Germline Somatic Log odds Filter for Tumor Only Samples. For each event that passed all preceding filters (SNV or Indel), its CCF, purity, ploidy and local copy number were used to determine the log ratio of the probability that its allele fraction is consistent with the allele fraction modeled for a hypothetical germline event and the probability it is consistent with a modeled somatic event. First, the total amount of DNA per cell (in units of copy number) was calculated as follows:

$$D = (1-\alpha)N + (1-C_{CNV})\alpha N + \alpha C_{CNV}(\mu + M)$$

Where $\alpha$ is the sample purity, N is the normal copy number at the site (2 for autosomes, 2 for X in females and 1 for X in males), $C_{CNV}$ is the CCF of any potential copy number alterations at that site, and $\mu$ and M are the minor and major allele counts of the copy number. Because heterozygous germline sites should always be at 50% allele fraction in the normal component of the tumor, only copy number alterations should affect the predicted allele fraction. Thus, there are two models for germline event allele fraction, depending on whether the germline event is on the minor allele ($G_1$) or major allele ($G_2$) of a copy number event in the region:

$$G_1 = \frac{(1 - \alpha) + (1 - C_{CNV})\alpha + \alpha C_{CNV}\mu}{D}$$

$$p_{G_1} = \beta(G_1, n_{ALT} + 1, n_{REF} + 1)$$

$$G_2 = \frac{(1 - \alpha) + (1 - C_{CNV})\alpha + \alpha C_{CNV}M}{D}$$

$$p_{G_2} = \beta(G_2, n_{ALT} + 1, n_{REF} + 1)$$

Where $G_1$ is the modeled allele fraction for when the germline site event is on the minor allele, and $G_2$ is the modeled allele fraction for when the germline event is on the major allele. The probability that the observed allele fraction is consistent with this model is calculated based on a beta ($\beta$) probability distribution function, where the modeled hypothesis is tested against the actual counts of reference ($n_{REF}$) and variant ($n_{ALT}$) reads. For somatic events, 6 separate models must be evaluated depending on the order in which events happen in a tumor. Specifically, the models account for the minor and major allele when a somatic event co-occurs with a copy number event ($S_1+S_2$), occurs before a copy number event ($S_3+S_4$), occurs after a copy number event ($S_5$), or if it occurs in a different subclone ($S_6$):

$$S_1 = \frac{\alpha C_{mut} C_{CNV} M}{D}$$

$$p_{S_1} = \beta(S_1, n_{ALT} + 1, n_{REF} + 1)$$

$$S_2 = \frac{\alpha C_{mut} C_{CNV} \mu}{C}$$

$$p_{S_2} = \beta(S_2, n_{ALT} + 1, n_{REF} + 1)$$

$$S_3 = \frac{\alpha C_{mut}(1 - C_{CNV}) + \alpha C_{mut} C_{CNV} M}{D}$$

$$p_{S_3} = \beta(S_3, n_{ALT} + 1, n_{REF} + 1)$$

$$S_4 = \frac{\alpha C_{mut}(1 - C_{CNV}) + \alpha C_{mut} C_{CNV} \mu}{D}$$

$$p_{S_4} = \beta(S_4, n_{ALT} + 1, n_{REF} + 1)$$

$$S_5 = \frac{\alpha C_{mut} C_{CNV}}{D}$$

$$p_{S_5} = \beta(S_5, n_{ALT} + 1, n_{REF} + 1)$$

$$S_6 = \frac{\alpha C_{mut}(1 - C_{CNV}))}{D}$$

$$p_{S_6} = \beta(S_6, n_{ALT} + 1, n_{REF} + 1)$$

Where $C_{mut}$ is the CCF of the somatic event as calculated by ABSOLUTE. Once the probability that each model is consistent with the data, the log odds ratio of the most likely germline and somatic model, L, becomes the statistic to apply the filter on:

$$p_G = \max(p_{G1}, p_{G2})$$

$$p_S = \max(p_{S_1}, p_{S_2}, p_{S_3}, p_{S_4}, p_{S_5}, p_{S_6})$$

-continued $$L = \log\frac{p_G}{p_S}$$

Because the allele fraction of a clonal heterozygous somatic event will be similar to a germline heterozygous site at high purity, but falls as the purity goes down, the divergence in L between putative somatic events (events present in the paired analysis) and putative germline events (events present only when paired samples are run without their paired normals) differs greatly depending on purity, meaning that while for impure samples we can use a very stringent cutoff of 0, for higher purity samples the cutoff must be relaxed to prevent the removal of true somatic events with high clonality.

To calibrate the cutoff, the data consisting of the 147 available non-hypermutator lymphoma samples with paired normal was split into two training sets, each set was split into 10 bins with similar purity and cutoffs were found that preserved 99% of the putative somatic events in each bin and then used to fit a linear model determining the best cutoff depending on purity. After applying this filter, the less pure samples of our cohort show nearly the same mutation rate as when run through the pipeline with their paired normal. While this step filters out many of the remaining germline events, no sample reports fewer events after this filter than in the paired pipeline.

ExAC Filtering. After applying the Germline Somatic Log odds filter, the ExAC database was used as a final criterion for excluding potential germline events (S41). Using 147 paired non-hypermutator samples, the allele frequency in ExAC that yielded 98% sensitivity which cut out 50% of the remaining putative germline events was selected.

Significance analysis of recurrently mutated genes (Mutsig2CV). Significantly mutated genes were identified applying the MutSig2CV algorithm and genes with a q-value of less than 0.1 were reported as significant (S6, S42). Notably, with the increased background mutation rate from 3.3/MB to 6.6/MB, the power to detect CCGs present in 10% of patients dropped from 100% to 98% in tumor-only samples.

Measuring the effect of remaining germline events on determination of significant mutated genes using the tumor-only pipeline. To evaluate the performance of the newly developed tumor only pipeline, the paired normals of the instant DLBCL cohort were run as tumor only samples through the tumor only pipeline as a null model, using one of the paired normal as the "normal" for the others, leaving a total of 134 samples run through this pipeline. Despite the size of the cohort, when running Mutsig2CV on these samples after all filtering 0 to 3 (assigning each normal its paired tumor's purity, assuming 10% or 90% purity) significant genes were found, suggesting that any germline sites remaining after this pipeline are most likely randomly distributed throughout the genome and unlikely to affect the significantly mutated genes detected by Mutsig2CV (S21). Additionally, a beta binomial test was performed to determine if the number of mutations from tumor only samples occurring in SMGs was significantly overrepresented. The p-value was calculated as:

$$P = \sum_{MTO}^{MTO+MTN} \beta b(x, MTO + MTN, NTO + 1, NTN + 1) = 0.41$$

Where βb is the beta-binomial probability density function, NTO is the number of tumor-only samples (NTO=169), NTN is the number of tumor-normal paired samples (NTN=134), MTO is the number of non-silent SMGs detected in tumor-only samples (MTO=1516), and MTN is the number of non-silent SMGs detected in tumor-normal paired samples (MTN=1033).

Clustering and visualization of mutations in protein structures. The identified missense mutations found in the instant cohort were overlaid onto protein structures from the Protein Data Bank (RCSB PDB; www.rcsb.org) (S43) and the recently reported CLUMPS algorithm (S13) was applied to identify significant spatial clustering of mutations in protein structures. Briefly, CLUMPS summarizes the pairwise three-dimensional Euclidean distances between mutated residues into a score function and compares the score to a null model obtained by randomly scattering the mutations across residues covered in the structure (10,000,000 times). Both native (human) and homologous (>20% amino acid sequence identity) protein 3D structures were used in this analysis. Protein structures containing mutations from fewer than 5 samples were not analyzed because the results from such structures may lack robustness. In addition, CLUMPS was also used to assess enrichment of mutations at protein-protein interaction interfaces; this algorithm counts the mutations at residues located at protein interfaces and compares the count to a null model created by random mutational scattering of mutations across the structures. Images showing protein structures were created with Pymol v1.8.0.5 (pymol.org). Mutation diagrams (lollipop figures) of mutations were generated using Mutations Mapper (www.cbio-portal.org/mutation_mapper.jsp) (S8, S9).

Correlation between driver genes and GISTIC2.0 peaks. To investigate whether driver genes were more likely to be mutated in copy number regions or not, non-silent coding genes in the cohort were categorized by whether they were in a GISTIC peak that was affected by a copy number alteration in its patient, and whether it was in one of the driver genes identified as significantly mutated by CLUMPS or MutSig2CV. Fisher's exact test was then used to determine if mutations in driver genes co-occurred with significant copy number alterations more frequently than would be expected by random chance.

Mutational Signature Analysis

Methods and Algorithms. The mutational signatures discovery is a process of de-convoluting cancer somatic mutations counts, stratified by mutation contexts or biologically meaningful subgroups, into a set of characteristic patterns (signatures) and inferring the activity of each of the discovered signatures across samples (S44). For this purpose, a Bayesian variant of non-negative matrix factorization (Bayesian NMF) recently implemented and applied to several cancer genome projects was exploited (see S45 and S46 for additional background and technical details regarding the Bayesian NMF methodology). Bayesian NMF exploits a shrinkage or automatic relevance determination (ARD) technique to allow a sparse representation for both signatures and activities as well as an optimal inference for the number of signatures (K) by iteratively pruning away irrelevant components in balancing between a data-fidelity and a complexity (S47). The same parameters set as previously described were used (S45, S46). All SNVs were classified to 96 possible mutation types or categories based on six base substitutions (C>A, C>G, C>T, T>A, T>C, and T>G) within the tri-nucleotide sequence context including the base immediately 5' and 3' to the mutated base.

Figure 11A:
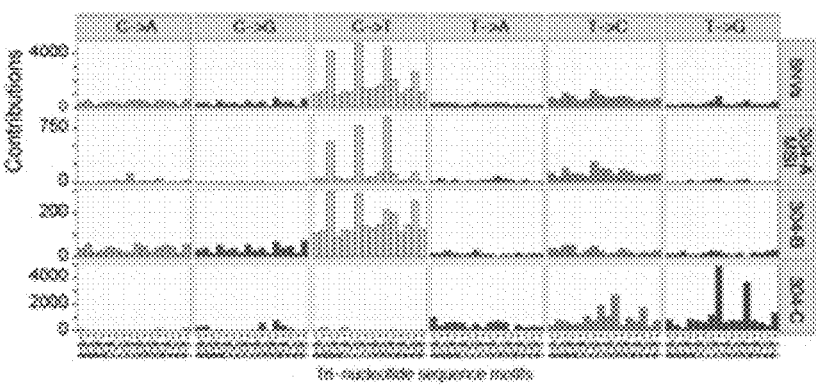
FIGS. 11A to 11Q depict supporting data for mutational signature analysis.

Signature discovery in DLBCL 304 WES samples and identification of a micro-satellite unstable tumor. A de-novo signature extraction for 304 DLBCL WES samples with the BayesNMF applied to SNVs stratified by 96 tri-nucleotide mutation contexts identified three major mutational processes (FIG. 11A). The similarity of these signatures to known 30 COSMIC signatures at cancer.sanger.ac.uk/cosmic/signatures was computed with a cosine similarity. The first signature (S304A; first de novo signature detected in 304 samples) characterized by a predominance of C>T mutations at CpG sites with minor contributions in C>A and T>C mutations was most similar to COSMIC6 (cosine similarity 0.87) and was exclusive to one sample with the highest mutation burden. The second signature (S304B; second de novo signature detected in 304 samples) characterized by a superposition of elevated C>T mutations at CpG sites with a background broad spectrum of base substitutions was most similar to the COSMIC1 (cosine similarity 0.86) and pervasive across samples, explaining about 64% overall mutations. The third signature (S304C; third de novo signature detected in 304 samples) was characterized by dominant T>G mutations at [C/G/T]pTpT sites with explaining about 7% overall mutations, but did not match 30 COSMIC signatures with the cosine similarity >=0.78. Interestingly, the highest mutation burden sample (DLBCL-MAY-O_DLBCL_234-Tumor; 5956 mutation) had a significantly higher activity of S304A (97% SNVs were associated with S304A). Since the signature profile of S304A most resembled the COSMIC6, which is known to be associated with defective DNA mismatch repairs and found in micro-satellite unstable tumors, it was further explored if this tumor had additional characteristics of the micro-satellite instability (MSI). This sample was identified to possess a pathogenic splice site mutation in MLH1 (chr3: 37083822G>A) with a significant enrichment of insertions and deletions (14% in all variants). It was also noted that the third highest mutation sample (DLBCL-RICOVER_787-Tumor-SM-4MILK) also had a relatively high activity of S304A (53% SNVs), and this sample had a pathogenic nonsense mutation in MSH6 (R298*) with no indel enrichment.

Figure 11B:
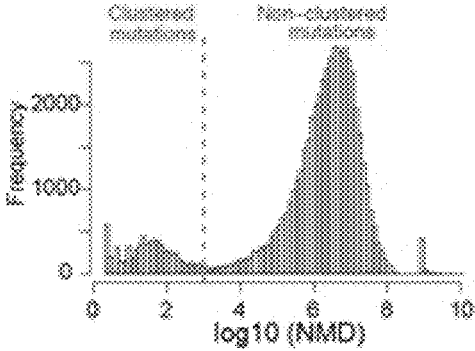
FIG. 11B shows that based on the bimodal distribution of nearest mutational distance (NMD), all SNV mutations were partitioned into two groups of clustered ($NMD \leq 1$ kb) and non-clustered mutations ($NMD > 1$ kb).

Signature discovery in DLBCL 303 WES samples and identification of activation-induced cytidine deaminase signatures. To minimize a possible interference between the MSI signature (S304A) and the aging signature (S304B), which shared similar hotspot motifs, C>T at CpG sites, the putative MSI sample with the highest mutation burden was excluded in all downstream analyses and re-generate a de-novo signature extraction for 303 WES samples. In addition to 96 tri-nucleotide mutation types, the clustering information of mutations was considered as an additional feature to capture a signal of the mutational process related to the activation-induced cytidine deaminase (AID signature). As was previously demonstrated (S46), there was a substantial difference in mutation spectra between clustered and non-clustered mutations due to a differential activity of both canonical and non-canonical AID signatures. NMDs (Nearest Mutation Distance) were first computed for all SNVs, a minimum genomic distance to all other mutations on the same chromosome in the same patient, and partitioned them into 'clustered' (NMD<=1 kb) and 'nonclustered' groups (NMD>1 kb) (FIG. 11B). The threshold (1 kb) was manually chosen from a bimodal feature of the NMD distribution. Then, we separately counted clustered and non-clustered mutations across 96 mutation channels and split mutations in each sample into two columns representing clustered and non-clustered mutational groups, giving rise to the mutation count matrix X (96 by 2M, M is the number of samples). This mutation count matrix was ingested as an input for the BayesNMF and factored into two matrices, W' (96 by K) and H' (K by 2M), approximating X by W'H'. It should be noted that clustered and non-clustered mutations from the same patient were separately handled to capture a characteristic signal from clustered mutations. Through a scaling transformation, X~W'H'=WH, W=W'U−1 and H=UH' where U is a K-by-K diagonal matrix with the element corresponding to the 1-norm of column vectors of W', resulted in the final signature loading matrix W and the activity loading matrix H.

All fifty independent BayesNMF runs converged to the three signatures solution, identifying the aging signature (Aging), the canonical AID signature (cAID), and the secondary AID signature (AID2). The overall activity of discovered signatures was determined by summing up the activities of three signatures assigned to both clustered and non-clustered mutations. The aging signature was characterized by pronounced C>T mutations at CpG sites superimposed with a background broad base substitutions, most similar to COSMIC1 (cosine similarity 0.93), and its activity was mostly attributed to non-clustered mutations (98% in non-clustered vs 2% in clustered aging mutations), explaining overall 80% SNVs across samples. The cAID signature had characteristic peaks of C>T and C>G mutations at GCT context corresponding to one of AID known hotspot motifs at RCY (R=A/G, Y=C/T), and its activity was much higher in clustered mutations (70% in clustered mutations) consistent to known AID biology. About 47% mutations related to the cAID signature was C>T or C>G mutations at RCY motifs. Interestingly, the third signature characterized by T>G mutations at [C/G]TT contexts also showed an enrichment of its activity in clustered mutations (36% in clustered mutations), and the signature profile was most similar to COSMIC9 (cosine similarity 0.75) corresponding to the non-canonical AID activity related to the error-prone DNA polymerase eta. Indeed, 50% mutations associated with the AID2 signature were A>[T/C/G] at WA (W=A/T) motifs corresponding to the hotspot motifs of non-canonical AID.

Figure 11C:
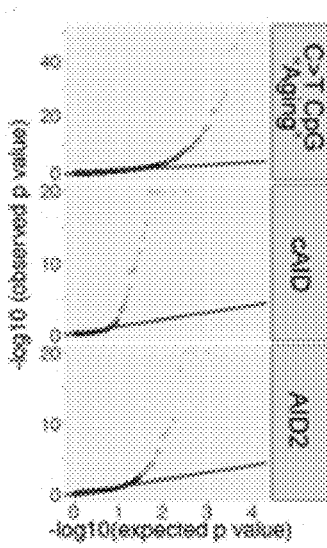
FIG. 11C displays the Q-Q plots for the gene-level signature enrichment analysis (see Methods for details).
Figure 11D:
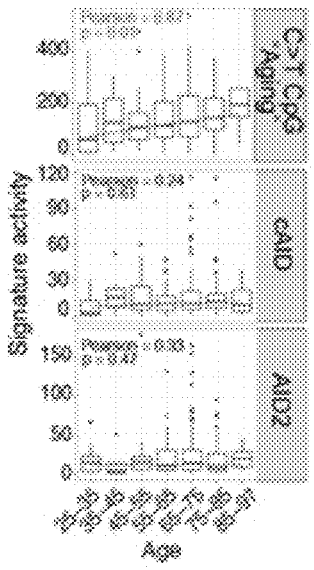
FIG. 11D shows correlations of signature activity to the age at diagnosis across seven age groups. Box plots represent a distribution of each signature activity of samples belonging to each age bin. The Pearson correlation was calculated between the median signature activity and the median age in each age group.
Figure 11E:
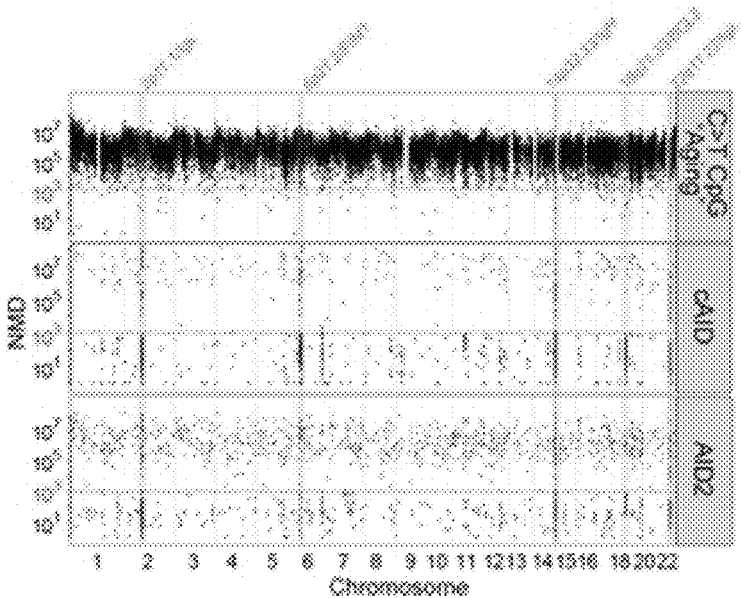
FIG. 11E shows rainfall plots of all mutations by mutational signature. Vertical axis illustrates the NMD, horizontal axis the genomic location. Ig loci as loci of physiologic hypermutation are highlighted in blue, 6p21.2/PIM1 and 18q21.33/BCL2 as loci of aberrant somatic hypermutation are visualized in pink. Clustered mutations ($NMD \leq 1$ kb) below the dotted red line.
Figure 11F:
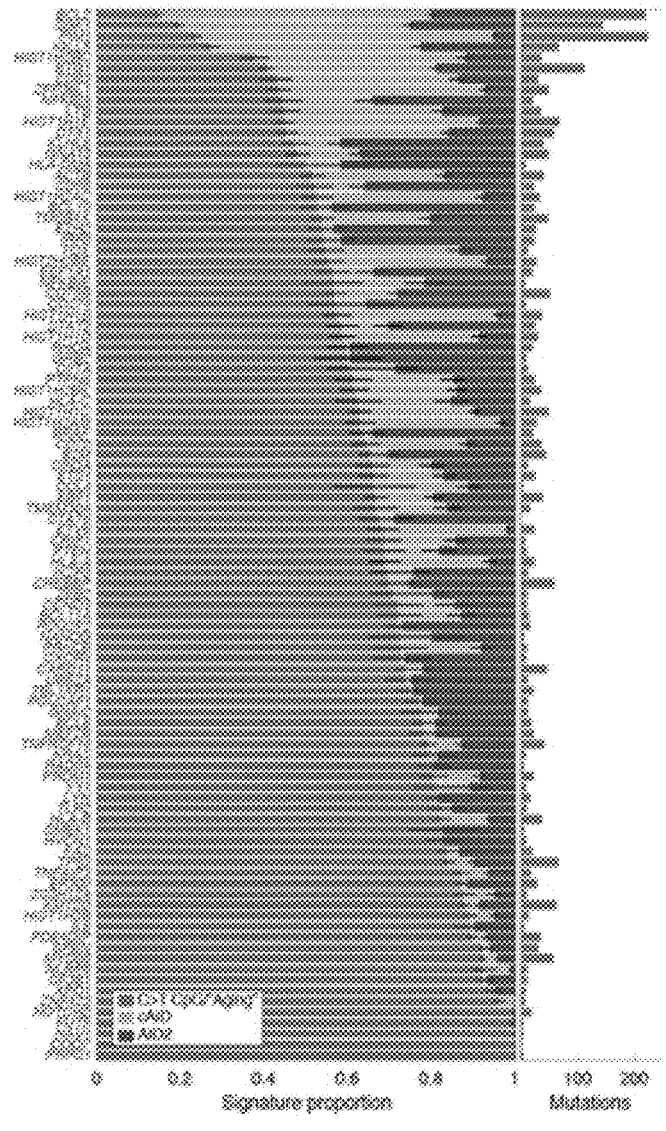
FIG. 11F shows, for all significantly mutated genes, the relative contribution of each mutational process (C>T CpG/"Aging", purple; cAID, cyan; AID2, blue). Genes were ordered from top to bottom by the fraction of aging signature. Histogram to the right reports the number of mutations.
Figure 11G:
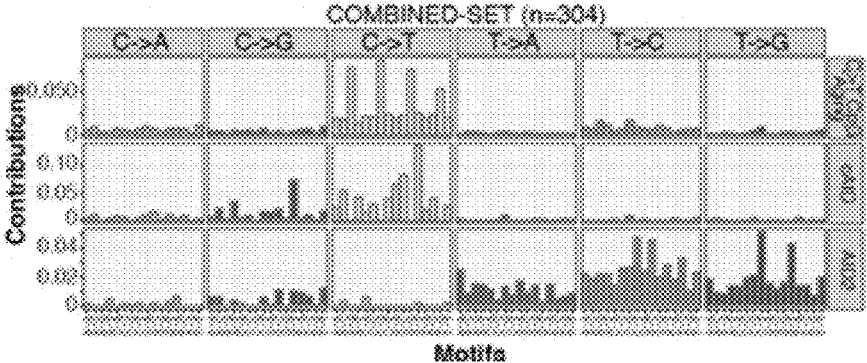
FIGS. 11G to 11I show normalized signature profiles determined by de-novo signature extraction for the combined sample set (COMBINED-SET, n=303.
Figure 11H:
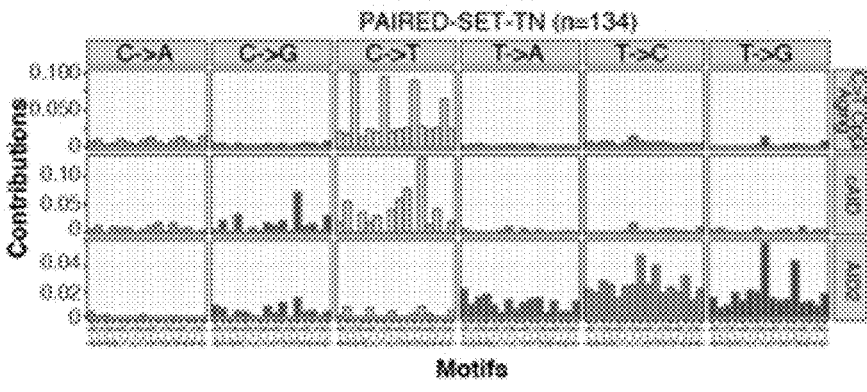
Figure 11I:
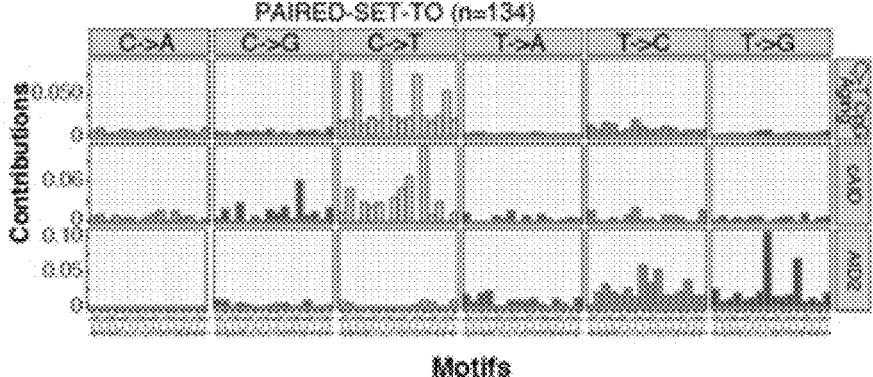
Figure 11J:
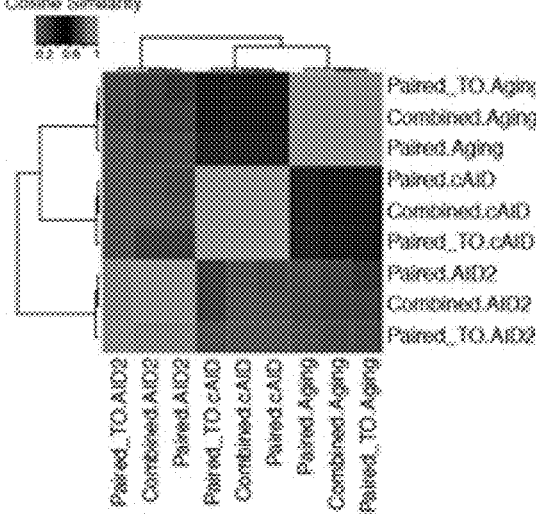
Figure 11K:
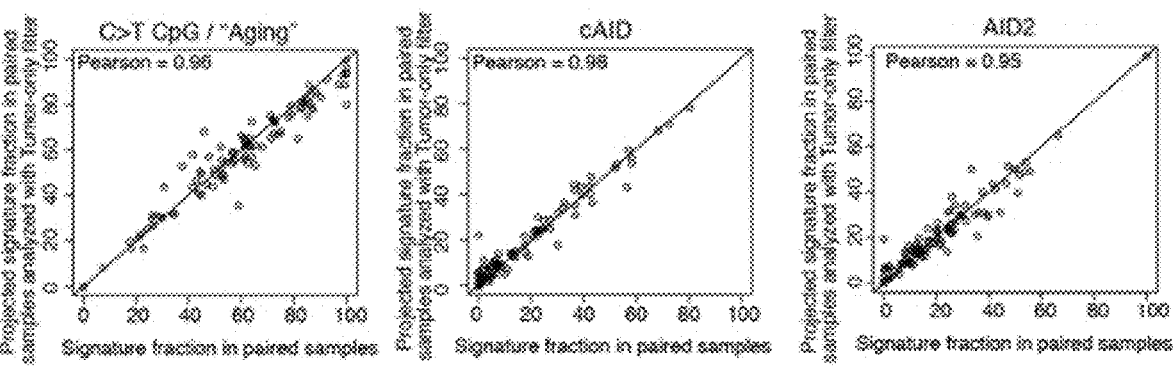
FIG. 11K), Gene-level signature fraction of the C>T CpG/Aging signature (left), cAID signature (middle), and AID2 signature (right) across CCGs (n=>10 mutations) between PAIRED-SET-TN (x-axis) and PAIRED-SET-TO (y-axis). Note that the activity of PAIRED-SET-TO was determined by the projection onto the signature profiles of PAIRED-SET-TN.
Figure 11L:
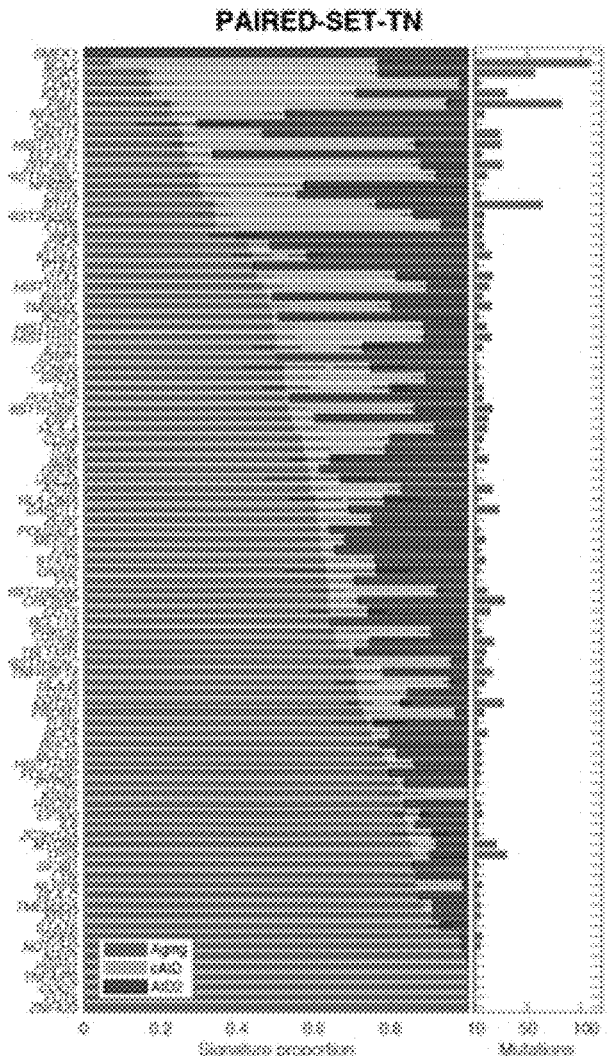
FIGS. 11L and 11M show signature fractions for CCGs by using (FIG. 11L) or not using (FIG. 11M) the patient-matched normal sample. See FIG. 11F for details.
Figure 11M:
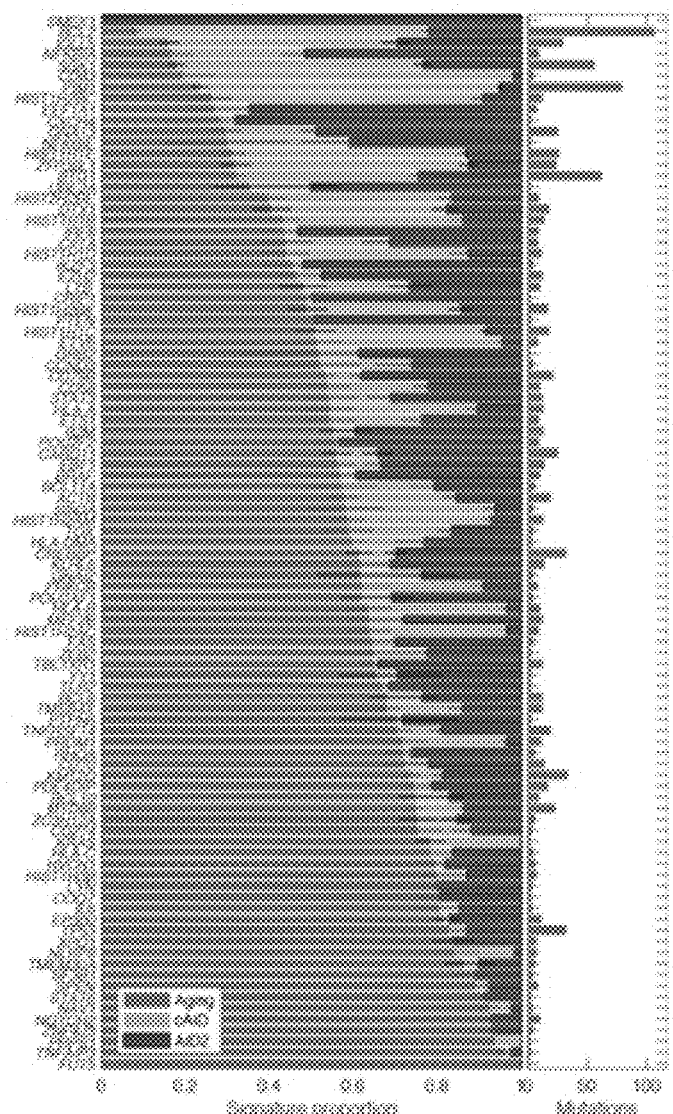

Assessment of the impact of a germline component in the mutational signature discovery. To address the impact of the germline contents in our tumor-only pipeline on the mutational signature discovery, a signature discovery was separately performed for the 134 samples with available patient-matched paired normals using either the tumor-normal pipeline (PAIRED-SET-TN, FIG. 11H) or the tumor-only pipeline (PAIRED-SET-TO, FIG. 11I). In both PAIRED-SET-TN and PAIRED-SET-TO, SignatureAnalyzer discovered three similar signatures highly concordant to those discovered in the COMBINED-SET (n=303, FIG. 11G) irrespective of whether the samples were analyzed with their respective patient-matched normal samples or with our tumor-only pipeline (cosine similarity in Table S4f and FIG. 11J). Given that the germline component in tumor-only samples did not negatively impact the discovery of mutational signatures, it was next evaluated if it skews the gene-level signature fractions for the significantly mutated genes (SMGs). To remove an additional confounding factor from the signature differences between PAIRED-SET-TN and PAIRED-SET-TO, a projection approach was applied to infer the signature activity of PAIRED-SET-TO samples onto the signature profiles of PAIRED-SET-TN. More specifically, the projection was done by minimizing the Kulbeck-Leibler divergence while the signature-loading matrix, W, comprised of the column vectors corresponded to normalized signature profiles of PAIRED-SET-TN (Aging, cAID, and AID2) is frozen, and the activity-loading matrix H is iteratively updated to best approximate the mutation count matrix of PAIRED-SET-TO, X. The resulting row vectors in H represent a de-convoluted signature activity of PAIRED-SET-TO samples onto the signatures of PAIRED-SET-TN. A strong correlation of the paired signature fraction for all SMGs for the aging, cAID signature and AID2 signature (Pearson correlation=0.96, 0.98 and 0.95, respectively; FIGS. 11K to 11M) was found.

Figure 11N:
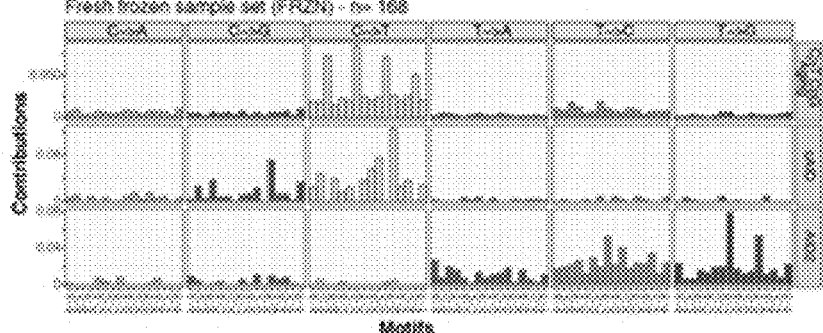
FIGS. 11N and 11O show normalized signature profiles determined by de-novo signature extraction for fresh frozen samples (FRZN-SET, n=168) (FIG. 11N) and for FFPE samples (FFPR-SET, n=136) (FIG. 11O).
Figure 11O:
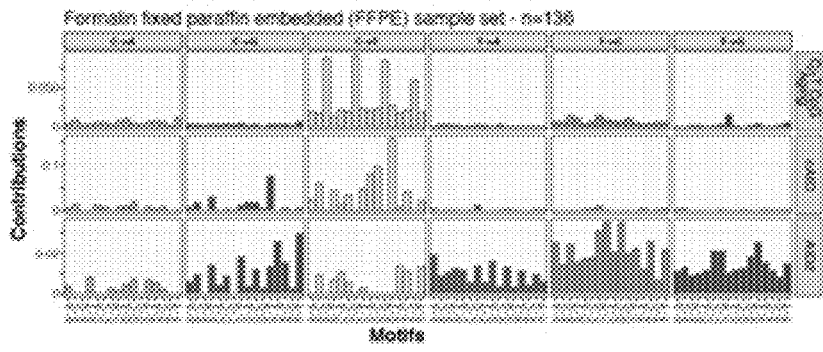
Figure 11P:
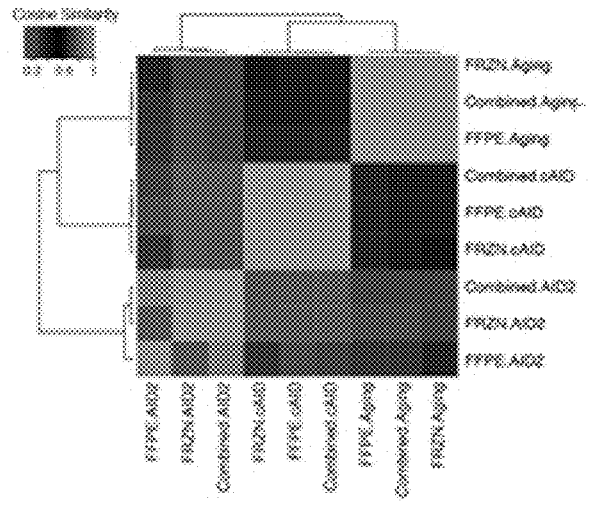
FIG. 11P shows a heatmap of the cosine similarity of three signatures among FRZN-SET, FFPE-SET, and COMBINE-SET.
Figure 11Q:
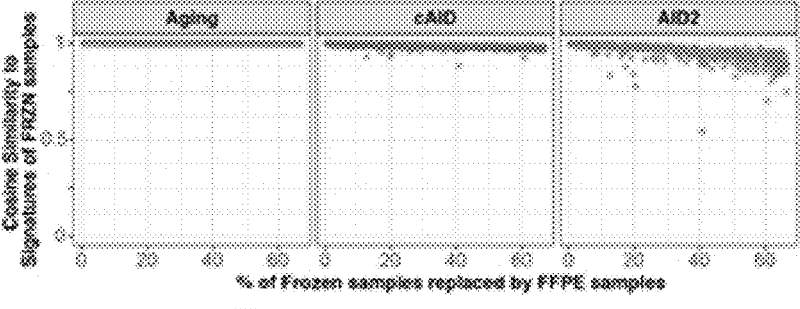

Assessment of the impact of FFPE artifacts in the mutational signature discovery. Additional analyses were also performed to assess the impact of FFPE bias on mutational signature discovery. SignatureAnalyzer was separately applied to tumors from frozen (FRZN-SET, FIG. 11N) and FFPE tissue (FFPE-SET, FIG. 11O) and compared discovered signatures to those in COMBINED-SET (FIG. 11P, Table S4g). The cosine similarity of both C>T_CpG and cAID signatures was observed to be very high among the three sets (FIG. 11P, Table S4g), while the AID2 signature in FFPE-SET had a slightly reduced similarity. To investigate the effects of FFPE samples more systematically a series of signature discoveries were performed for the pooled sample sets generated by randomly replacing fresh-frozen samples by the same number of random FFPE samples (500 experiments). Strong stability was observed in the cosine similarities of both aging and cAID signatures, but a subtle drop was observed in the AID2 signature with incremental fractions of FFPE samples (FIG. 11Q). However, it could not be ruled out that this reduced cosine similarity of the AID2 signature might have been attributed to the sample heterogeneity between FRZN-SET and FFPE-SET.

Signature enrichment analysis. Each mutation was first annotated with the probability (likelihood of association) that it was generated by each of the discovered mutational signatures, Pms, where 'm' denoted a mutation and 's' refers to the signature. More specifically, the likelihood of association to the k-th signature for a set of mutations corresponding to i-th mutation context and j-th clustered or non-clustered mutation group was defined as [wkhk/Σ (wkhk)]ij, where wk and hk correspond to the k-th column vector and k-th row vector of W and H, respectively. The relative activity enrichment for candidate cancer genes (CCGs) with at least 10 mutations was determined by taking an average of Pms for all mutations in each CCGs. For the gene-level signature-enrichment analysis, it was first attempted to identify a hotspot mutation motif out of 96 contexts in each signature by considering coding mutations only with Pms>=0.75, identifying 40 and 50 characteristic motifs with non-zero probability for cAID and AID2, respectively. Note that keeping mutations with a higher Pms, filtered out mutations shared by multiple signatures and enabled the discovery of more distinct mutation motifs characteristic to each signature. To take into account sequence composition variation across the genome, all available tri-nucleotide contexts across coding genes were enumerated and genes having non-zero mutations with Pms>=0.75 in each signature were considered. This information was used to estimate the background mutation rates at the hotspot motifs in each signature, resulting in rAging=4.3 per Mb, rcAID=7.5 per Mb and rAID2=2.4 per Mb for the aging, cAID, and AID2 signatures, respectively. Then, for given mutation counts with Pms>=0.75, x, at hotspot motifs and available sequence context, n, in each gene, a binomial test was performed with the estimated background mutation rate to assess the significance of the enrichment of each signature across 11898 genes for the aging, 315 genes for cAID, and 917 genes for AID2 signature having non-zero mutations with Pms>=0.75 (Tables S4b to S4d). Multiple hypotheses were corrected for and genes were identified that were associated with each signature using a q-value cutoff of 0.1 (see Q-Q plots in FIG. 11C).

Statistical analysis related to signatures. The age correlation with three signatures in FIG. 11D was performed by binning the age into seven groups and calculating a Pearson correlation between the median age and the median activity in each age group. To determine if the AID mutations discovered in a cohort had clustering around the transcription start site (TSS) (S48), a Fisher's exact test was applied to determine if AID mutations (PcAID+PAID2>0.75) in the instant 98 CCG were more frequently within +/−2000 base pairs of its TSS. A Wilcoxon rank sum test was used to determine if mutations from the 98 CCGs attributed to either of the two AID signature had a significantly higher proportion of silent mutations than mutations not attributed to either AID signature.

Integrative Analysis of Gene Expression and Copy Number Data

Gene expression profiling and data normalization. RNA samples from 52 samples with available WES data were transcriptionally profiled using an U133plus2 Affymetrix gene expression array as previously described (batch1) (S4). The data have been uploaded to GEO with the accession GSE98588. Additional expression profiles from 85 samples with available WES data were generated and published previously (GSE34171, batch2) (S4). The Affymetrix gene expression profiles were normalized using Robust Multi-Array Average (RMA) (S49) and Brainarray custom chip definition files (Version 16) based on Ensemble IDs (S50). Gene expression values were adjusted for batch effect using a linear regression model of each gene against the batch variable (batch1 vs. batch2). The batch-corrected gene expression values are the residuals of the linear regression plus the intercept. Log 2-transformed batch-corrected gene expression was used for differential analysis. The following analyses were performed using the integrative (Epi)DNA-to-Gene Expression analysis package (iEDGE, manuscript in preparation).

Cis-analysis. Genomic coordinates of genes within SCNAs were determined using R Bioconductor annotation package TxDb.Hsapiens.UCSC.hg19.knownGene. Genes within arm-level alterations were considered for within-arm differential expression analysis (Table S6a). Genomic boundaries of chromosome arms were defined by the start, centromere, and end coordinates of each chromosome as annotated in the UCSC hg19 cytoband annotation file. Separately, genes with coordinates within wide peak limits of each GISTIC2-defined copy number alteration with a FDR q-value <0.1 were considered for within-peak differential expression analysis (Table S6a).

Expression of the genes within each GISTIC-defined alteration peak was tested for association with the corresponding peak's copy number alteration (CNA) status (presence or absence of copy gain or loss) by a differential expression test using the R package limma (S51). One-sided p-values were estimated, since the associations of interest are gene expression up-regulation among samples with copy gain and gene expression down-regulation among samples with copy loss. The p-values for all genes across all alteration peaks were corrected for multiple hypothesis testing using the false discovery rate (FDR) estimation (S52). Genes with FDR<0.25 and a fold change of >1.2 were considered significant "cis-acting" genes. 3 types of differential expression analysis were performed: 1. Arm-levels:

Integrating arm-level CNA status and expression of genes on each arm (Tables S6b and S6c); 2. Focal alterations: Integrating focal CNAs and expression of genes in focal peaks (Tables S6d and S6e), and 3. focal or arm: comparing focal or arm level CNA status and expression of genes in focal peak. In this case, the copy number alteration status of the sample is considered altered if it is altered in the focal peak or the arm that harbors the focal peak. (Tables S6f and S6g)

Cell-of-origin (COO) assignment. The COO phenotype was assigned for 80% (242/304) of samples. For the newly gene expression profiled fresh frozen samples (GSE98588, batch1), the COO assignment was performed using a linear-predictive-score classifier as previously published (Table S1) (S4, S53, S54). The COO phenotypes for the 85 previously published samples (GSE34171, batch2) were previously reported (Table S1) (S4). NanoString-based COO assignment using the Lymph2Cx assay (S55) was performed for additional 102 FFPE samples as recently reported (Table S1) (S56).

Gene Set Enrichment Analysis (GSEA). For samples with paired available gene expression data, GSEA was performed as previously described (S4, S20, S57). Indicated target gene sets (FIGS. 17F to 17H, Table S9c) were tested for an enrichment in a given DLBCL clusters vs. the union of samples in the other DLBCL clusters (excluding C0 DLBCLs).

Targeted DNA-Sequencing for the Detection of Chromosomal Rearrangements

Library Construction, sequencing and pre-analysis processing. Targeted rearrangements (Table S5a) were captured from either leftover uncaptured libraries from WES or genomic DNA, sequenced using an Illumina sequencing platform, de-multiplexed and aligned to the reference sequence b37 edition from the Human Genome Reference Consortium with bwa (S58) as described previously (S26, S27). A total of 296/304 samples had a mean read depth is 221.4× and met all quality control checkpoints and 99% of samples had a power greater than 0.996 to detect chromosomal rearrangements.

Chromosomal rearrangement pipeline. Somatic rearrangements were detected using four different calling algorithms, BreaKmer (S17), Lumpy (S16), dRanger (S15) and SVaBA (S59), followed by Breakpointer validation, filtering and a CCF estimation module (FIG. 12A) as described below.

Chromosomal rearrangement detection. BreaKmer (S17), Lumpy (S16) and dRanger (S15) were applied as previously described to generate a separate list of candidate rearrangements.

SVaBA. SVaBA identified rearrangements by performing de novo local assembly across every 25 kb region in the genome, with 1 kb overlaps. Assembly within SVaBA was achieved through a modified version of SGA (S60), which assembled reads with gapped alignments, unmapped pair mates, clipped alignments and reads with an aligned insert size that differed substantially from the mean. The assembled contigs were re-aligned within SVaBA to the reference genome using an in-memory implementation of BWA-MEM (S61, S62). Contigs with multi-part alignments were used to infer candidate rearrangements, excluding contigs with low alignment quality. Within each local assembly window, rearrangements were genotyped by finding the optimal alignment of the sequencing reads to either the variant-supporting contig or the reference genome. Rearrangements obtained from contigs with breakpoints supported by >4 tumor reads and no normal reads were classified as somatic. In addition to detecting rearrangements from assembled contigs, discordant reads were clustered as a second signal for rearrangements. In the absence of a supporting contig, discordant read clusters required a minimum of 8 tumor read pairs with a high alignment quality, and no normal read pairs, to be called as a somatic rearrangement. The discordant read clusters were further compared with the rearrangements obtained from the contig assemblies to obtain the total number of variant supporting reads for each somatic rearrangement.

Filtering and Breakpointer module. The candidate rearrangements detected by each detector were filtered for variants found in 342 in house normal samples from the Broad Institute based on a 5 kb window to match candidate rearrangements. The remaining variants were clustered based on a 50 bp window and the union of all unique clustered candidate rearrangements was passed to Breakpointer (S15) (FIG. 12A). Breakpointer scans for additional supporting split read evidence to confirm breakpoint junctions in the tumor sample and to reject candidate somatic rearrangements with evidence of the rearrangement appearing in matched normal samples. A combined total of at least 4 supporting reads, either read pairs or split reads, were required following Breakpointer. A panel of an additional 21 normal samples sequenced with the same targeted bait set and protocol were also used. A 5 kb window was used to match candidate rearrangements. In addition, all intrachromosomal rearrangements (deletions and tandem fusions) involving the IGH, IGK, IGL, TRA, TRB, TRG loci and translocations between two loci, both not part of the bait set, were filtered out.

A total of 3293 structural variants were called and passed all standard panel of normal filtering steps (1355 from dRanger, 514 from SVaBA, 453 from Breakmer and 1775 from Lumpy). Subsequent clustering, Breakpointer validation, filtering events found in 19 similar processed normal samples and post-processing review resulted in 413 reported SVs (Table S5).

CCF calculation for SVs. For SVs, a novel algorithm was applied for determining CCF ($C_{SV}$) based on local copy number and allele fraction. The calculation here is roughly equivalent of the ABSOLUTE recipe of mutation CCFs, except that SVs consist of two breakpoints, each with its own estimated allele fraction, underlying copy number, and multiplicity. SV multiplicity has the same meaning as mutation multiplicity: the number of SV events per cell. With targeted data, there is an additional complication in that not all the breakpoints occur within targeted regions, which leaves the observed allele counts biased against the reference allele. For this reason, only breakpoints found within a targeted region are used in SV CCF estimates. At a given breakpoint, the DNA copy state At a given breakpoint, the DNA copy state is defined according to:

$$D=(T_a+T_b)*C_{CNV}*\alpha+(N_a+N_b)*(1-C_{CNV}*\alpha)$$

Where

α=tumor purity $C_{CNV}$=Cancer Cell Fraction of cells with SCNA state $T_a$=minor copy number allele in tumor cells $T_b$=major copy number allele in tumor cells $N_a$=minor copy number allele in normal cells $N_b$=major copy number allele in tumor cells SV breakpoints often occur at edges of copy number segments, which introduces some ambiguity regarding the relevant copy number state. The copy number estimates used here are those within the SV alternate allele, which corresponds to a window upstream (3' direction in reference coordinates) of forward mapped alt supporting reads and downstream (5') of reverse mapped alt supporting reads for each breakpoint. A 10 kb window was used, which was roughly consistent with the breakpoint resolution of the instant copy number segmentation algorithm (ReCapseq). Estimates of $T_a$, $T_b$, and $C_{CNV}$ were based on ABSOLUTE and AllelicCapseq. Although the copy number state and the SV allele fractions may not be the same at both breakpoints for a given SV, the SV CCF is constrained to be the same at both breaks. At each break, the CCF is estimated as a CCF probability density distribution (pdf) and the combined SV CCF is the joint pdf from the two breakpoint CCF pdfs. In cases where only one of the two breakpoints was contained within a targeted region, only the targeted breakpoint CCF pdf was used to estimate the SV CCF. The expected allele fraction for a given SV breakpoint was calculated for different somatic variant configurations similar to the different scenarios modeled when calculating the germline/somatic for point mutations. There are three basic SV event scenarios that depend on the ordering of events (SV comes before or after the SCNA) and whether or not the SV occurs in tumor cells with or without the somatic copy number variant:

1) The SV variant occurs on cells with somatic copy number variants ($T_a$ or $T_b$) with multiplicity m. In this scenario the SV event occurs chronologically after the copy number event so the multiplicity (m) should be 1.

$$AF_1 = \frac{\alpha m C_{SV}}{D}$$

2) The SV variant occurs in tumor cells without the somatic copy number alteration with multiplicity 1.

$$AF_2 = \frac{\alpha C_{SV}}{D}$$

3) The SV variant occurs in all cells with the the somatic copy number alteration Ta or Tb with multiplicity m and a fraction of cells without the somatic copy number alteration. In this scenario the SV event occurs chronologically before the copy number event.

$$AF_3 = \frac{\alpha(C_{SV} + (m-1)*C_{CNV})}{D}$$

$C_{SV}$, the CCF of the structural variant, from f 0 to 1 in increments of 0.01 to construct the $C_{SV}$ pdf. The $C_{SV}$ pdf is based on the beta pdf of the estimated AF with the observed read depth d, and the counts of alternate allele supporting reads a.

$$pdf(a \,|\, d, C_{SV}) = \beta(AF_i, a+1, d-a+1) = \frac{AF_i^a (1 - AF_i)^{d-a} * \Gamma(d+2)}{\Gamma(a+1)\Gamma(d-a+1)}$$

where β is the beta probability density distribution for observing a alt reads, from a total of d with allele fraction $AF_i$. The scenario with the maximum pdf mode was chosen to represent the SV breakpoint. This boils down to a choice between scenario 3 and 1 since scenario 1 and 2 are mathematically equivalent when the SV multiplicity is 1. The combined SV CCF from both breakpoints is the joint pdf:

$$pdf(a_1,a_2|d_1,d_2,C_{SV})=pdf(a_1|d_1,C_{SV})*pdf(a_2|d_1,d_2, C_{SV})$$

The $C_{SV}$ value for a given SV is the mode of the CCF pdf distribution and the 95% confidence interval for $C_{SV}$ is the 95% region of the normalized pdf around the mode.

Validation of CCF in LBCL Cell Lines.

The CCF calculation for structural variants was also applied to 31 B-cell lymphoma (DLBCL and follicular lymphoma) cell lines as a validation test of the method, with the assumption that the bulk of known driver SV events in these cell lines should be clonal. Sequencing data for the 31 cell lines used the same protocol with as the targeted data for the detection of SVs in DLBCL. The bulk of driver translocations IgH-BCL2, IgH-BCL6 and IgH-MYC were found to be clonal with CCFs exceeding 0.9. Only one cell line, Ly18, had driver SVs but neither of the balanced translocations between MYC and IGH had CCF 95% CI's that excluded CCF >0.9. 8 cell lines lacked a clear driver SV and the remaining 22 cell lines had at least one clonal driver SV.

Visualization. Rearrangements were visualized either as circos plots circos.ca) or as stick figures plotting the breakpoint in its genomic context.

Immunohistochemistry of PD-1 Ligands

Double staining of PD-L1 (clone 405.9A11) and PAX5 (24/Pax-5, BD Biosciences, San Jose, CA) and staining of PD-L2 (clone 366C.9E5) was performed with an automated staining system (Bond III; Leica Biosystems, Buffalo Grove) as previously described (S26, S63).

Consensus Clustering of Genetic Alterations

Generation of gene sample matrix. All significant mutated genes (MutSig2CV and CLUMPS, q-value ≤0.1 and frequency ≥3%), significant regions of SCNAs (GISTIC2.0, q-value ≤0.1 and frequency ≥3%) and chromosomal rearrangements (frequency ≥3%) were assembled into a gene sample matrix (Table S9a; Non-synonymous mutations, 2; synonymous mutations, 1; no-mutation, 0; High grade CN gain [CN ≥3.7 copies], 2; low grade CN gain [3.7 copies≥CN≥2.2 copies], 1; CN neutral, 0; low grade CN loss [1.1≤CN≤1.6 copies]; high grade CN loss [CN≤1.1 copies]; chromosomal rearrangement present, 3; chromosomal rearrangement absent, 0; chromosomal rearrangements not assessed, na).

Assessing bias in individual genetic alterations due to remaining germline and FFPE artifacts. Fisher's exact test was applied to each putative genetic driver alteration in the gene sample matrix to determine if any of the putative genetic drivers occurred more than expected by random chance in tumor-only samples compared to patient-matched tumor-normal samples. This analysis revealed no outliers after FDR correction, suggesting that there was not a strong bias of remaining germline effect in the discovery of CCGs (Table S3e). The same Fisher's exact test was applied to assess if a putative driver was overrepresented in FFPE tissue compared to fresh-frozen tissue. After calculating the false discovery rate using the Benjamini-Hochberg, one focal amplification, 21q22.3, was highly significant and the 15 focal amplifications were exclusively found in FFPE samples (Table S3f). To further investigate the quality of this focal peak, the distribution of the difference in amplitude of adjacent targets as a noise measurement was plotted against other focal peaks, where the distribution was found to be more irregular and to have the highest standard deviation. The higher noise level of the focal amplification 21q22.3, combined with the fact that it only appeared in FFPE samples and the event was exclusively subclonal served as justification for removal of the event as a likely FFPE artifact. After the removal of this event, no other genetic alterations were significantly overrepresented in FFPE after false discovery rate correction (Table S3f).

Figure 16:
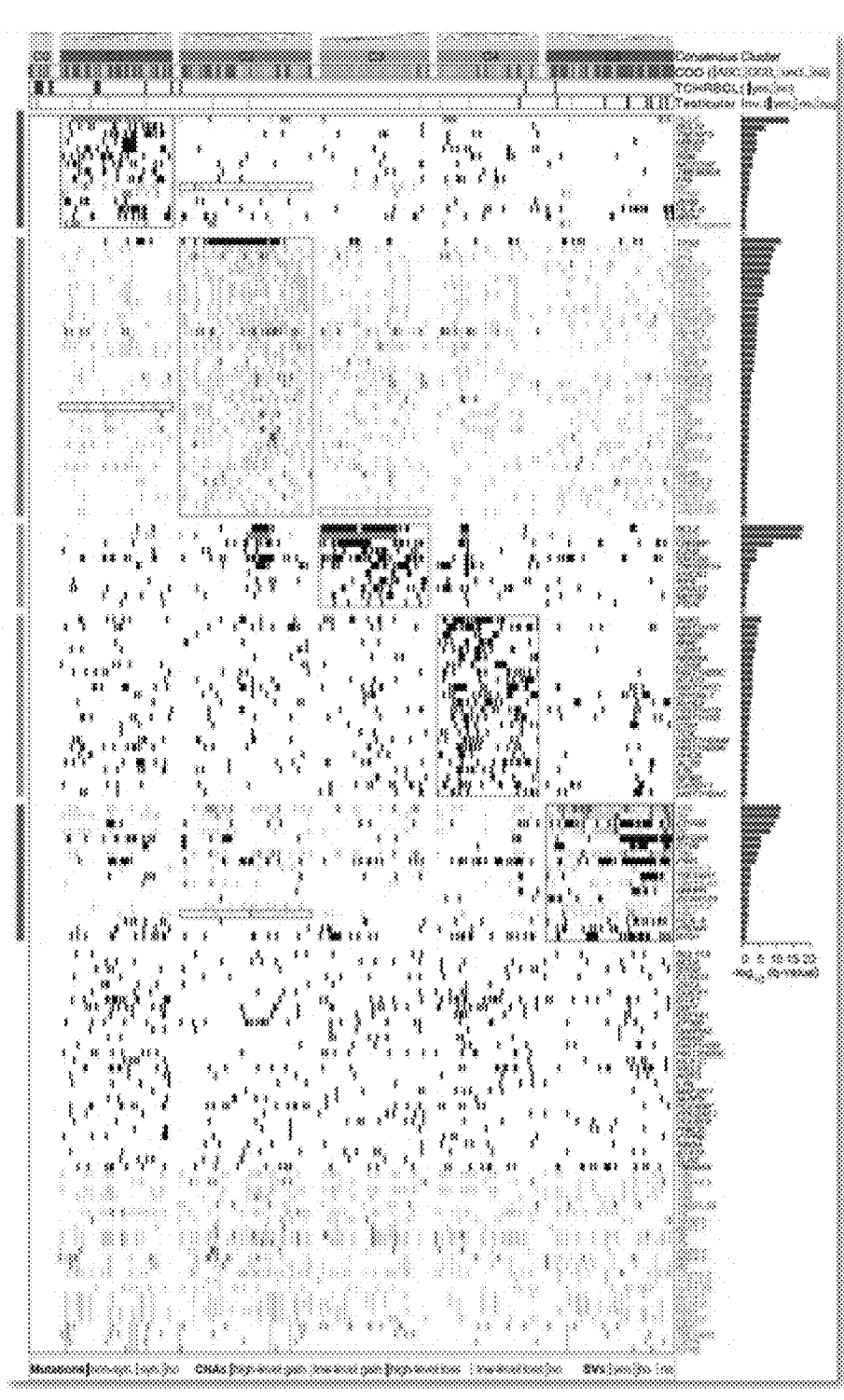
FIG. 16 shows an expanded consensus clustering gene-sample matrix. Clusters C1-C5 with their associated landmark genetic alterations are visualized as in FIGS. 4A to 4C. At the bottom, the additional recurrent alterations that were not associated with specific clusters are shown. See also legend of FIG. 5 above.

Non-Negative matrix factorization consensus clustering. To robustly identify tumors with shared genetic features, a non-negative matrix consensus clustering algorithm (S64) with slight modifications was applied. Briefly, the gene sample matrix containing mutations, CNAs and chromosomal rearrangements (Table S9a) was passed to the NMF consensus clustering algorithm (input parameters k=4-10) bypassing the matrix normalization so that the cluster distance metric depended directly on the variant number in the gene-sample matrix. The NMF consensus clustering algorithm provided the cluster membership of each sample, the cophenetic coefficient for k=4 to k=10 clusters and silhouette values for the "Best cluster" (k=5) (Table S9b). Samples without genetic drivers in the input matrix to the clustering were assigned to cluster C0. In addition, marker genes were identified that were associated with each cluster by applying a fisher test (2×2 table with variant present or absent as one dimension and within-cluster or outside-cluster the second dimension) and the p-values were corrected using the FDR procedure (Table S9c). Features with a q-value ≤0.1 were selected as cluster features (Table S9d) and visualized as a color-coded heatmap using GENE-E (FIGS. 5 and 16; software.broadinstitute.org/GENE-E/).

Mutual exclusivity/co-occurrence estimations. For each gene of interest, the significance of the co-occurrence or mutual exclusivity for each pair of different events (mutations, amplification, deletion or structural variant) that affected that gene was calculated using a Fisher test, and then corrected for false discovery using the Benjamini-Hochberg method.

Inferred Timing of Genetic Alterations

CCF matrix of putative drivers. First, for each of the 158 candidate driver events (for criteria, see generation of gene sample matrix above) the cancer cell fraction was assembled. When multiple events appeared in the same patient, the estimate based on the event with the highest coverage was used for mutations and SVs, while the one based on the longest segment was used for copy number alterations, as in each case this should represent the best-measured estimate (Table S10a). In addition to the actual CCF value, for each genetic feature a binary distinction was added if this is clonal or subclonal alteration with 0.9 being the threshold.

Event ordering analysis. To infer the timing of genetic events in each cluster and the overall cohort, we applied the method previously described for mutation ordering (S21). Briefly, for all driver alterations event pairs were first identified where events occurred such that one event was subclonal and the other was clonal (Table S10b). The "effect-size" to quantify alteration pairs according to clonal and sub-clonal mixtures was simply the difference in counts of clonal and subclonal samples. Next, a null model was assumed in which the timing of genetic events was random, allowing for performance of a formal binomial test to determine if one event was more frequently clonal than the null model (Table S10c). Of note, the test was restricted to those event pairs that were powered to achieve a significant result (q-value ≤0.1) when occurring as maximal effect.

Code Availability

Data processing was performed in the Broad Firehose computing environment (archive.broadinstitute.org/cancer/ cga/firehose). Code for modules from firehose as well as visualization and post-processing scripts are available upon request.

Clinical Endpoint Analyses

Statistical analyses were performed using R v3.3.2 with additional packages survival v2.41-2 for survival analyses, qvalue v2.6.0 for false discovery rate control, and knitr v1.15.1 for reproducible research.

Overall survival (OS) was defined as time from treatment until death from any cause. Subjects not confirmed dead were censored at the time last known to be alive. Progression-free survival (PFS) was defined as time from treatment until the earliest time of progression or death from any cause, and censored at time last known to be alive and free of progression.

Univariate and multivariable analyses of time-to-event endpoints were performed on the R-CHOP treated cohort (n=259) using Cox regression and genetic features had to be present in at least 3% of samples of the R-CHOP treated cohort to be tested for outcome associations. Hazard ratios (HR) with 95% confidence intervals (CI) and Wald p-values were reported for model covariates; likelihood-ratio tests and p-values were reported for multivariable models. Log-likelihoods of nested models were compared using a chi-square test to assess improvement in model fits. Median event times were estimated using the method of Kaplan and Meier (KM) and reported with 95% CIs; Greenwood's formula was used to approximate the variance of KM estimate, and 95% CIs were generated using the log-log transformation. Differences in survival curves were assessed using log-rank tests. Median follow-up time was estimated using the reverse KM method.

Fisher's exact test was used to test for association between categorical variables. Odds ratios (OR) and 95% CIs were calculated for binary outcomes from contingency tables or logistic regression for continuous predictors. The Wilcoxon or Kruskal-Wallis rank-sum test was used to assess a location shift in the distribution of continuous variables between two or more than two groups, respectively. Descriptive statistics (proportions, medians, etc.) were reported with 95% exact binomial CIs or range. All p-values were two-sided, and adjustments for multiple hypothesis testing was performed using the method of Benjamini and Hochberg; p- and q-value thresholds for significance were set at 0.05 and 0.2, respectively.

Example 2: Significantly Mutated Driver Genes

Mutations were detected from WES data of 304 primary DLBCLs, 55% of which lacked patient matched normal samples (Methods, FIG. 7). To include all 304 samples in the discovery cohort for candidate cancer genes (CCGs), new computational methods were developed to filter germline variants and artifacts from tumor-only samples (Methods, FIGS. 2 and 3). After filtering, a median of 3.3 and 6.6 mutations/Mb was found in the paired and tumor-only samples, respectively, suggesting that on average 3.3 germline variants per megabase persisted after filtering. Multiple lines of evidence indicated that these rare germline variants were spread throughout the genome and had minimal effect on the detection of CCGs (P=0.4; Methods, FIGS. 2 and 3).

MutSig2CV (24) was applied to the 304 DLBCLs and detected 98 CCGs (FIG. 1, Table S3a, q-value <0.1). The CCG list includes previously reported mutational drivers, including the tumor suppressor, TP53; the chromatin modifiers, KMT2D (MLL2), CREBBP and EP300; components of the BCR, Toll-like receptor (TLR) and NF-kB signaling pathways, CD79B, MYD88, CARD11 and TNFAIP3 (A20); certain components of the RAS pathway, KRAS, BRAF; NOTCH2 and the NOTCH signaling modifier, SPEN; and immunomodulatory pathway components, B2M, CD58, CD70 and CIITA (FIG. 1A) (3-8). Due to improved methodology and increased sample size, an additional 40 previously undescribed CCGs in DLBCL were identified (8), many of which have defined roles in other lymphoid malignancies or cancers. These included additional modifiers of the BCR and TLR signaling pathways, PTPN6 (SHP1), LYN, HVCN1, PRKCB and TLR2; additional histone genes, HIST1H1B, HIST1H1C, HIST1H1D, HIST1H2AC, HIST1H2AM, HIST1H2BK, HIST1H3B, HIST2H2BE; the BAF SWI/SNF chromatin remodeling complex member, BCL11A; IL6; the chemokine CCL4 (MIP-1β) and the PD-1 ligand, CD274 (PD-L1) (FIGS. 1A and 10).

Figure 9A:
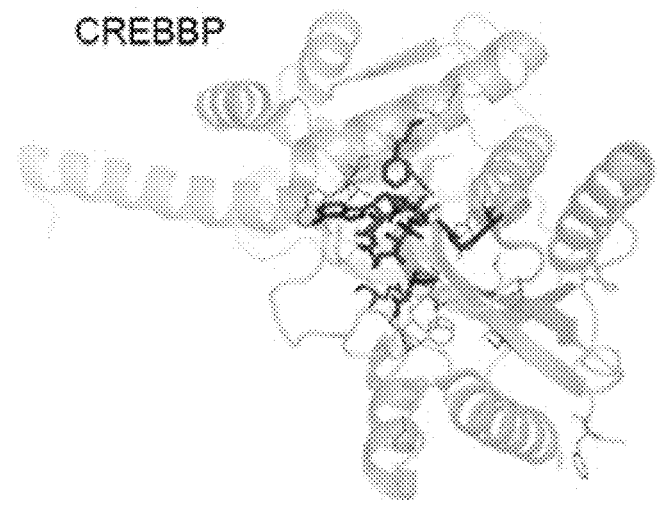
FIGS. 9A to 9E show significant mutation clustering at protein structures, as well as additional BRAF mutation details.
Figure 9B:
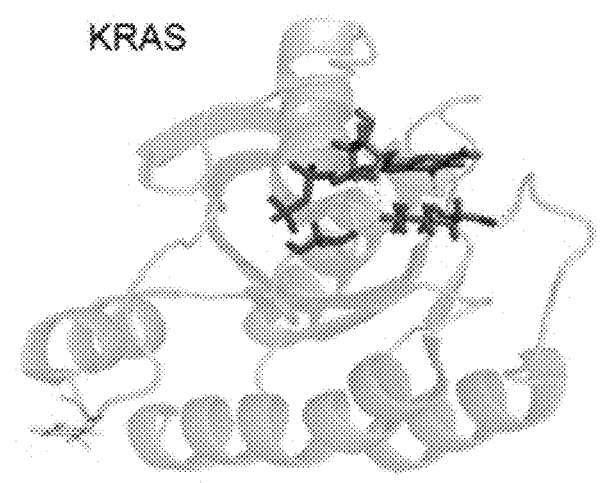
Figure 9C:
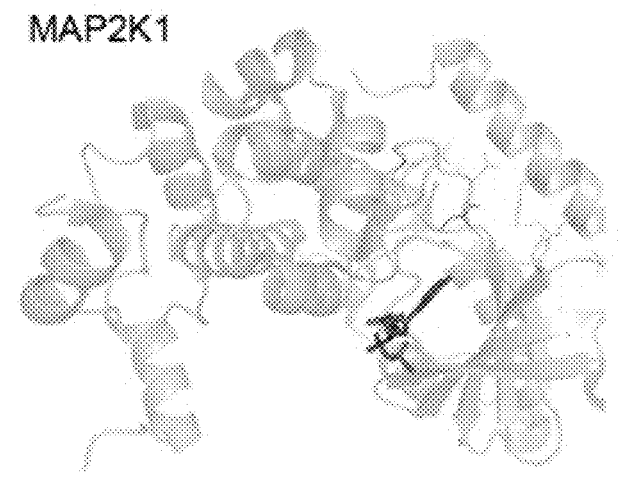
Figure 9D:
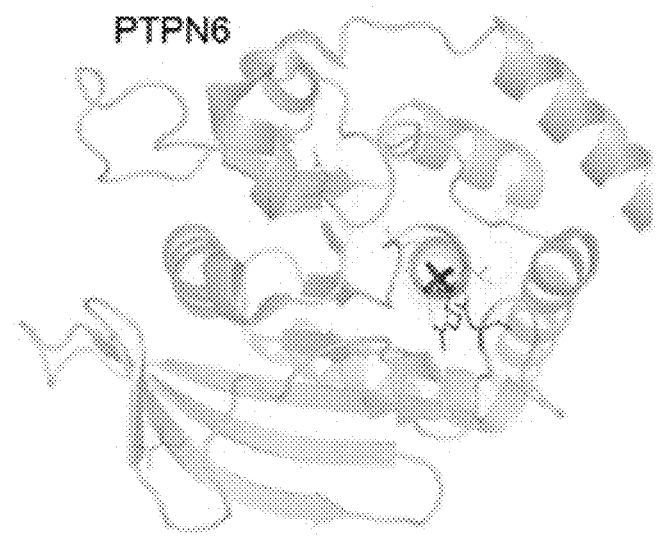
Figure 9E:
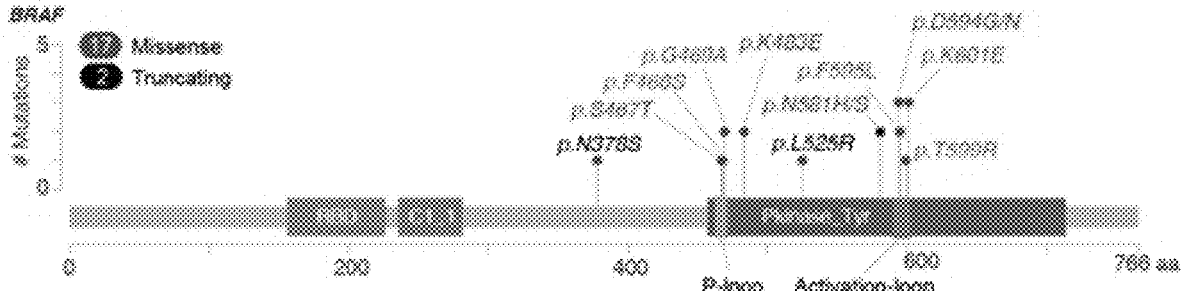
Figure 10A:
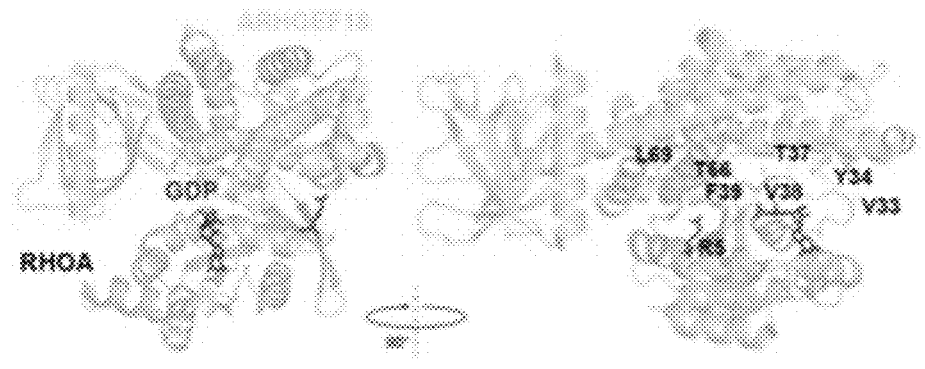
FIGS. 10A to 10E show significant mutation clustering at protein interfaces.
Figure 10B:
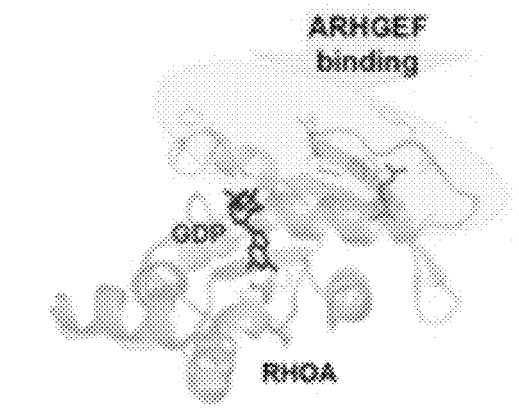
Figure 10C:
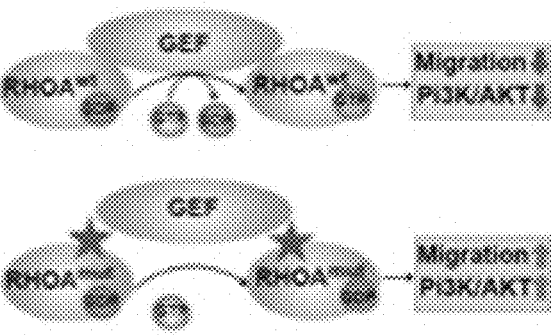
Figure 10D:
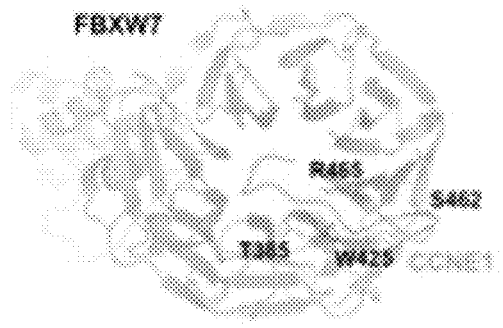
Figure 10E:
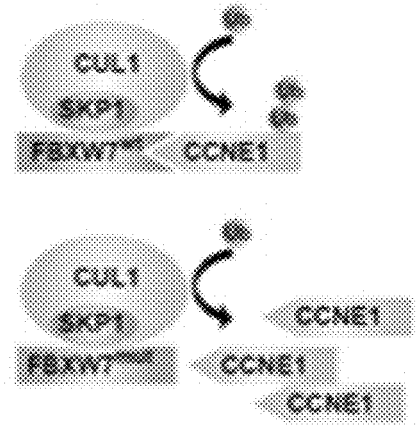

To identify genes with significant clustering in 3-dimensional protein structures, CLUMPS (25) was applied which revealed 22 CCGs (q-value <0.1). Notably, 7/22 CCGs were not captured by MutSig2CV, including an additional member of the KRAS-BRAF-MEK1 pathway, MAP2K1 (MEK1) (FIG. 11 and Table S3b). CLUMPS also provided insights into the putative function of mutations: TP53 alterations clustered in 2 distinct regions of the protein, the DNA binding site and the $Zn^{2+}$-atom coordinating residues required for p53 structural integrity (FIG. 1B); clustered mutations in CREBBP, PTPN6 (SHP1) and GNAI2 abolished polar interactions around the catalytic pocket (FIGS. 1B and 11); and non-canonical BRAF mutations perturbed the autoinhibitory interaction of the P- and activation-loops (FIG. 9E). A second step in CLUMPS (called EMPRINT) identified enrichment of mutations at protein-protein interfaces. For example, RHOA mutations cluster at the binding interface with multiple ARHGEFs, keeping RHOA in its inactive form and de-repressing PI3K signaling and Ga-migration (FIGS. 1C and 10A to 10C; Table S3c) (1). Additionally, CLUMPS identified mutation clustering at the acceptor groove of FBXW7 that limits CCNE1 recognition and CUL1/SKP1/FBXW7-mediated degradation—a previously reported tumor suppressor mechanism in other cancers (FIGS. 10D and 10E, Table S3c) (26).

Example 3: Mutational Processes

Figure 2A:
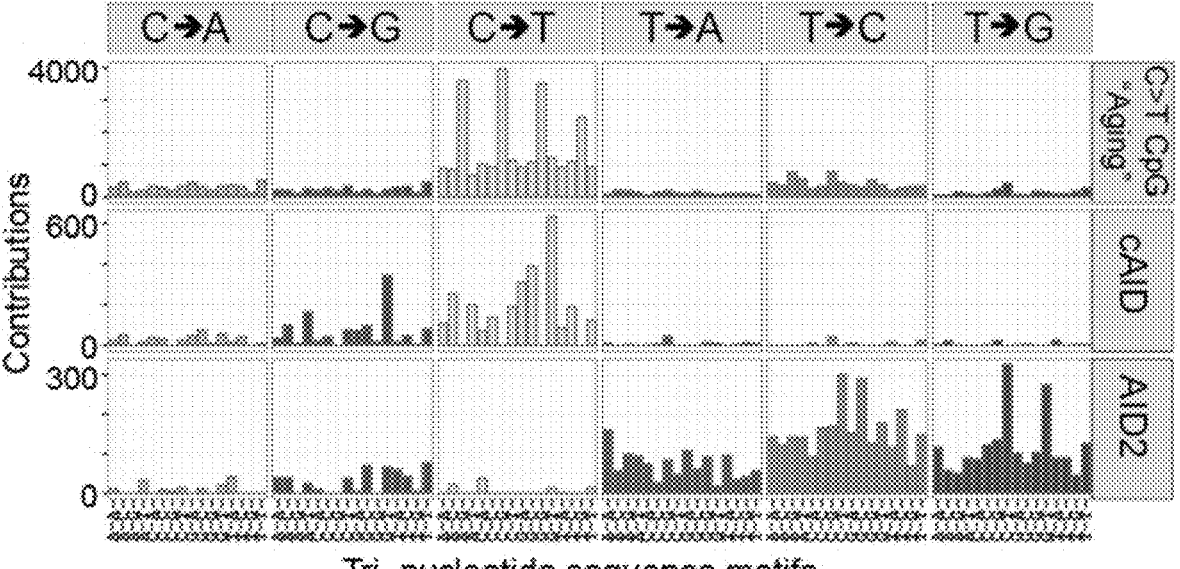
FIGS. 2A to 2C display a series of graphs of mutational signatures operating in primary DLBCLs.
Figure 2B:
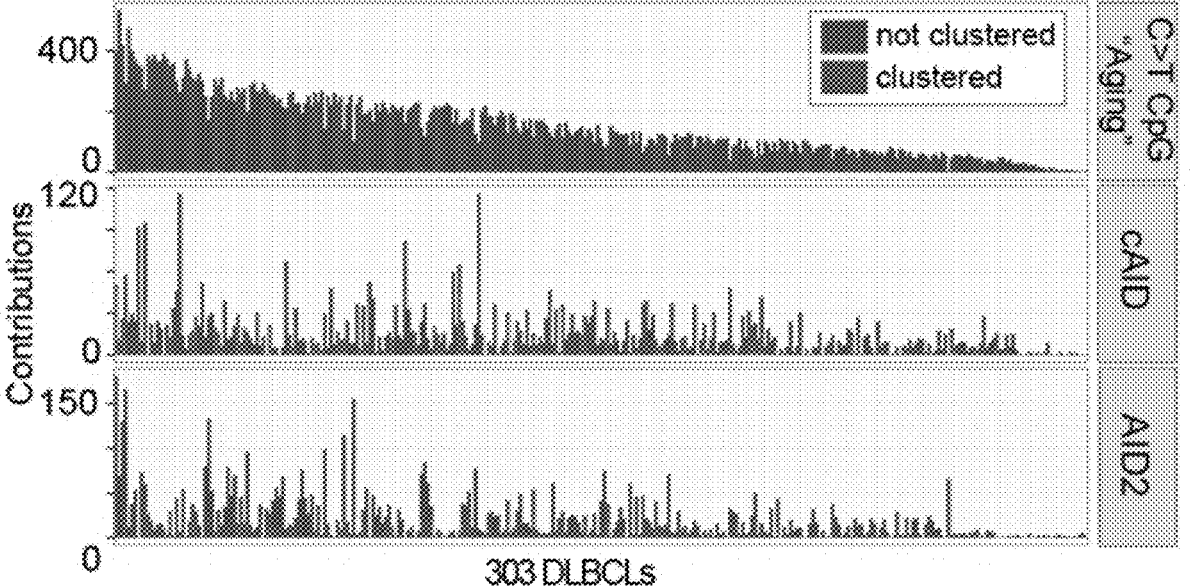
Figure 2C:
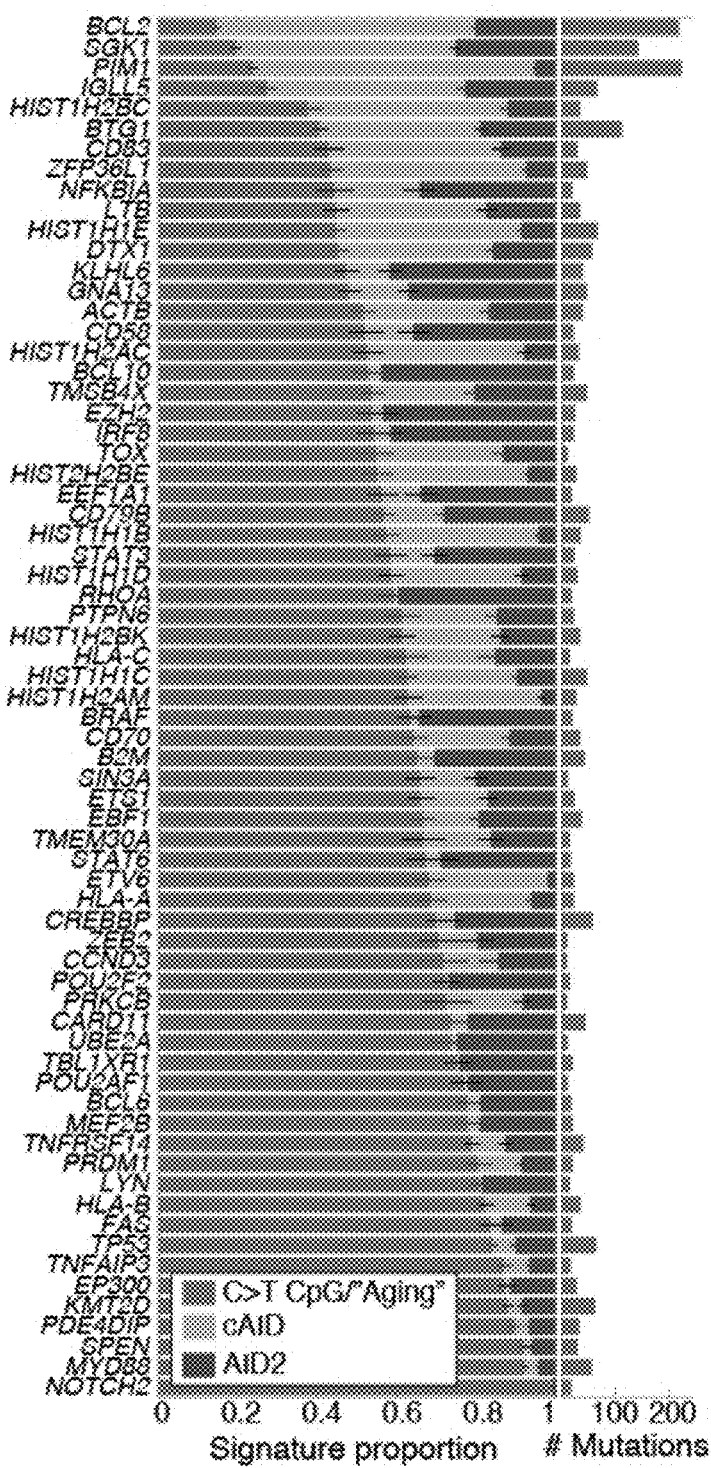

Each mutational process leaves a characteristic imprint, a mutational signature, in the cancer genome that reflects both DNA damage and repair (27). A SignatureAnalyzer tool (28) was applied that uses both the 3-base mutational sequence context and mutational clustering in genome coordinates to discover four signatures (three signatures after removal of a single microsatellite instability case; Methods; FIGS. 2A, 11B and 11C; Table S4b). The predominant mutational signature, which explained 80% of all mutations, was spontaneous deamination at CpG sites (C>T_CpG, hereafter "Aging"; FIGS. 2A, 2B and 13). Consistent with the underlying etiology of this signature, older patients had more mutations driven by spontaneous deamination (FIG. 11D). Also identified were two AID-driven signatures, canonical AID (c-AID) and AID2 that reflect different repair mechanisms following AID-induced deamination of cytosine to uracil. The cAID signature was characterized by increased C>T/G mutations at a known AID hotspot, the RCY-motif (R=A/G, Y=C/T), representing mutations caused by UNG-mediated repair of AID-induced genetic lesions (28, 29). Consistently, cAID activity was enriched at sites of both physiologic and aberrant somatic hypermutation (SHM, FIGS. 2A, 2B and 11E; Tables S3d and S3e) (30). The AID2 signature was dominated by A>[T/C/G] mutations at WA(W=A/T)-motifs and shared some properties of the COSMIC9/non-canonical AID signature (28, 29).

Next, the relative contributions of aging, cAID and AID2 mutational processes to each CCG in DLBCL (FIGS. 2C and 11F) were determined. Genes that are known targets of aberrant SHM, including BCL2, SGK1, PIM1, IGLL5 (FIG. 2C; Tables S3d and S3e) (28), exhibited predominant AID signatures (cAID+AID2), comprised of mutations with the lowest ratio of non-silent to silent mutations (Fisher's Exact test, $P=1.97\times10^{-4}$) that clustered within 2 kb of the transcription start site (Fisher's Exact test, $P=2\times10^{-41}$), consistent with the AID mechanism. In contrast, genes including MYD88, KMT2D (MLL2), EP300, TNFAIP3 (A20), TP53 and PRDM1 (BLIMP1), exhibited predominant aging mutational signatures (FIGS. 2C, 11F and 11G; Table S3c).

Example 4: Chromosomal Rearrangements and SCNAs

Figure 13A:
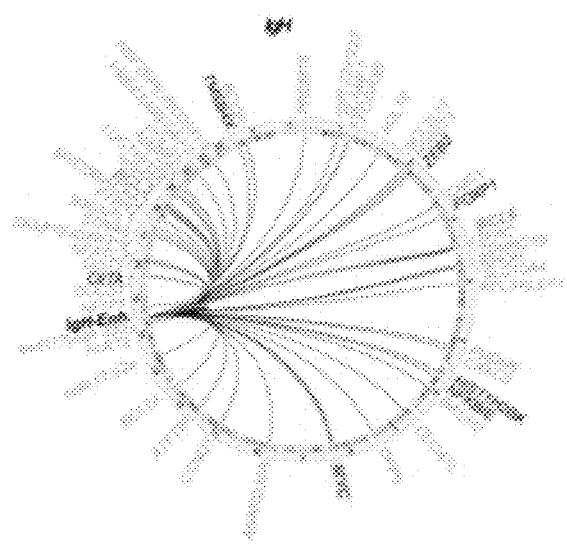
FIGS. 13A to 13I depict additional chromosomal rearrangements and mutual exclusivity/co-occurrence.
Figure 13B:
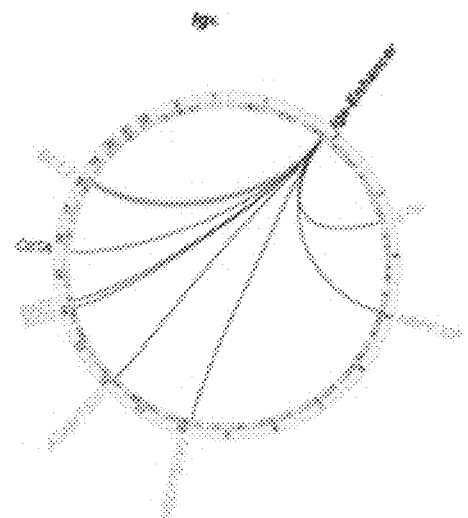
Figure 13C:
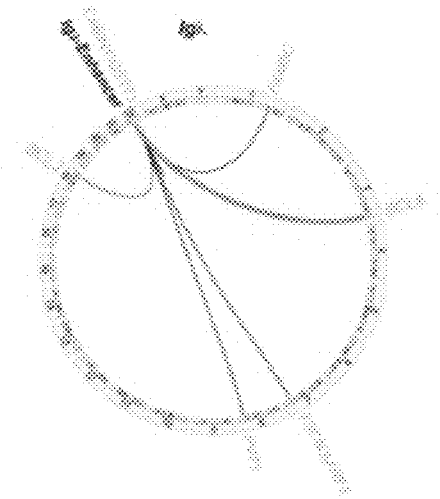
Figure 13D:
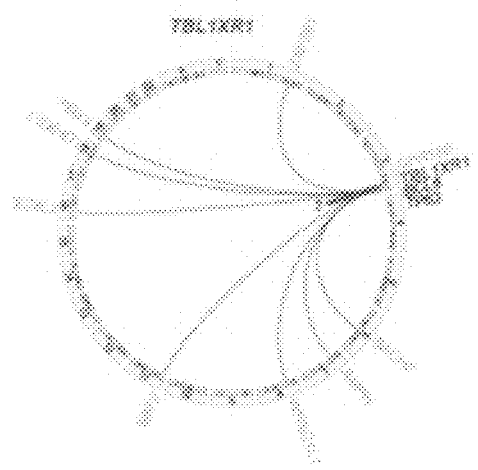
Figure 13E:
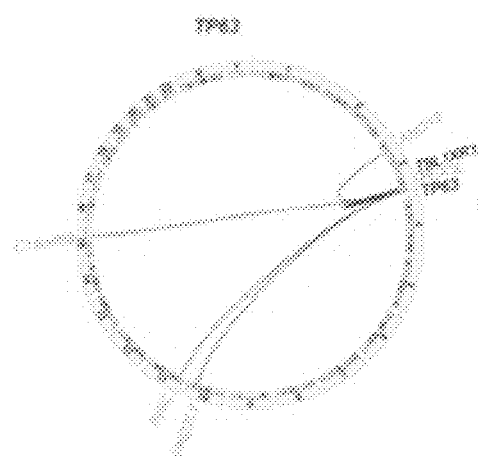
Figure 13F:
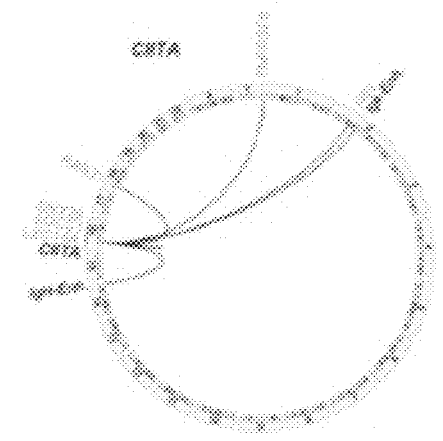
Figure 13G:
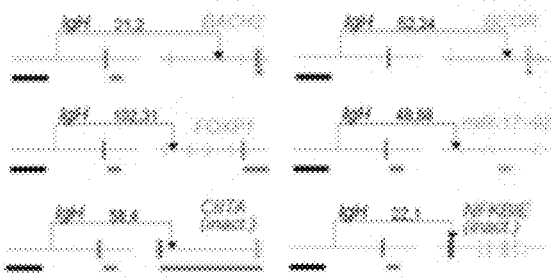
Figure 13H:
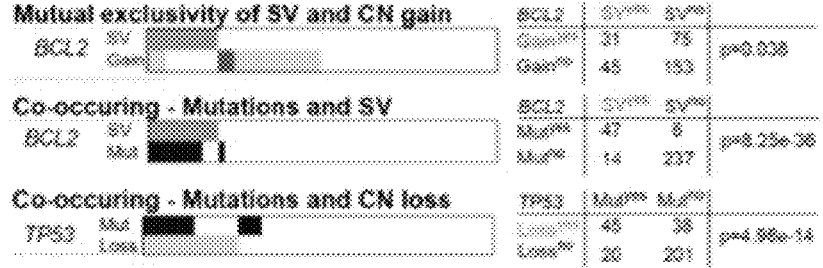
Figure 13I:
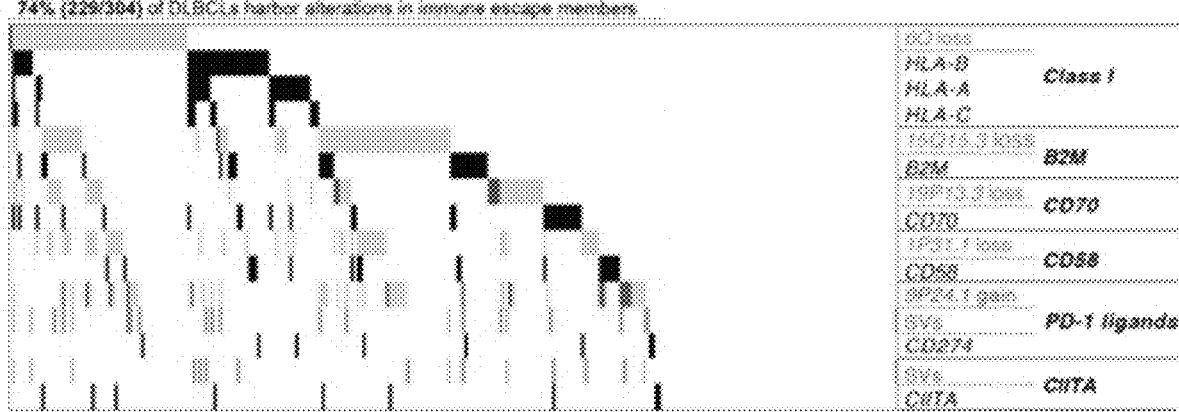

Recurrent SVs were assessed using a previously described targeted sequencing approach (31) and a pipeline that included 4 different algorithms followed by a filtering and split-read validation step (Methods, FIGS. 7 and 13A to 13D; Table S5). At least 1 SV was identified in 64% (189/296) of tumors; translocations that juxtaposed genes to strong regulatory elements were the most common SVs (FIGS. 3 and 13D).

Figure 3A:
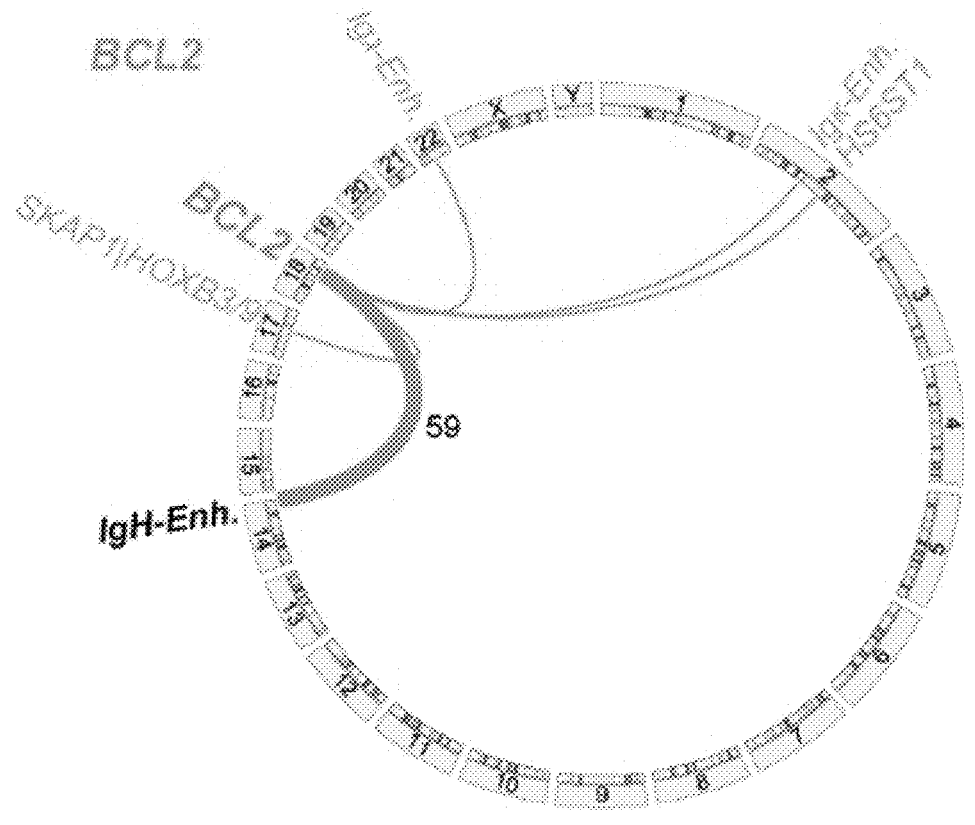
FIGS. 3A to 3I display graphs and images of chromosomal rearrangements identified in primary DLBCLs.
Figure 3B:
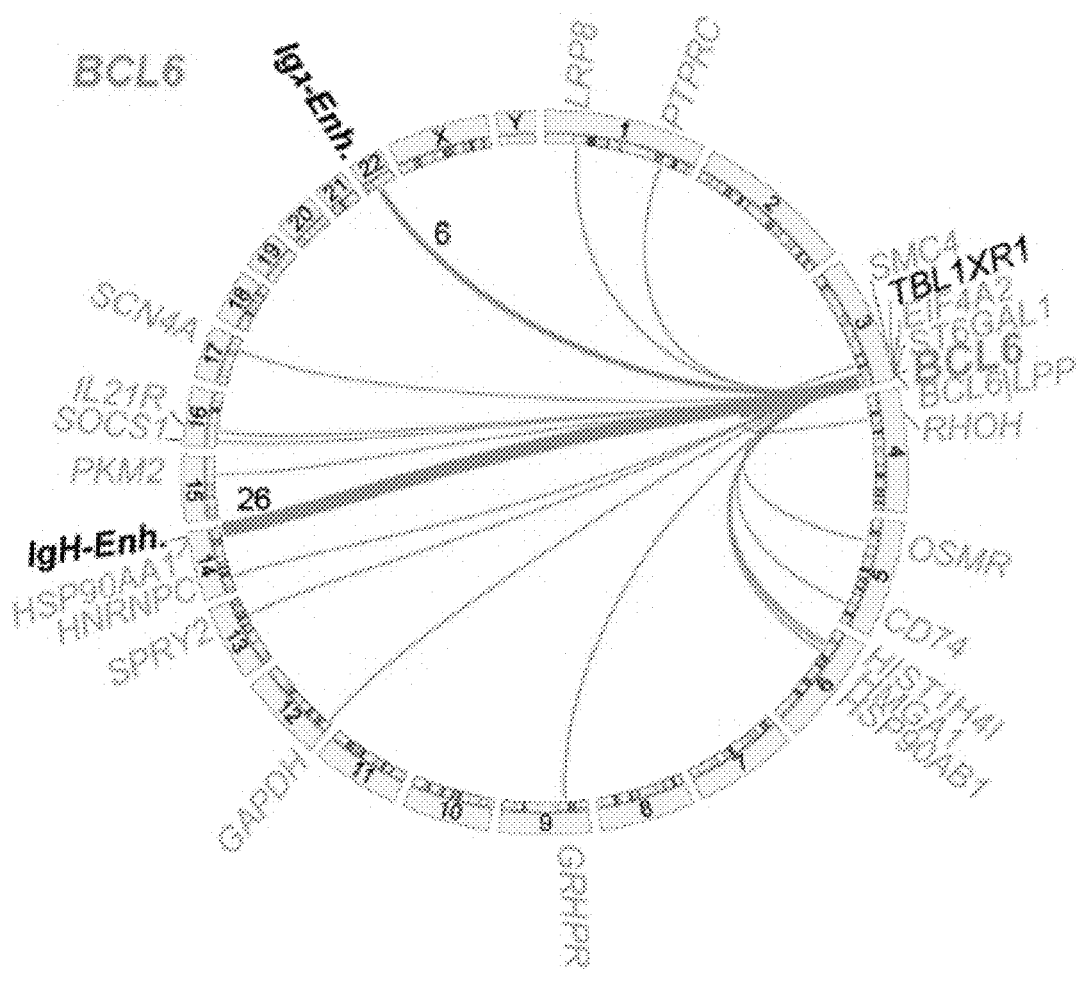
Figure 3C:
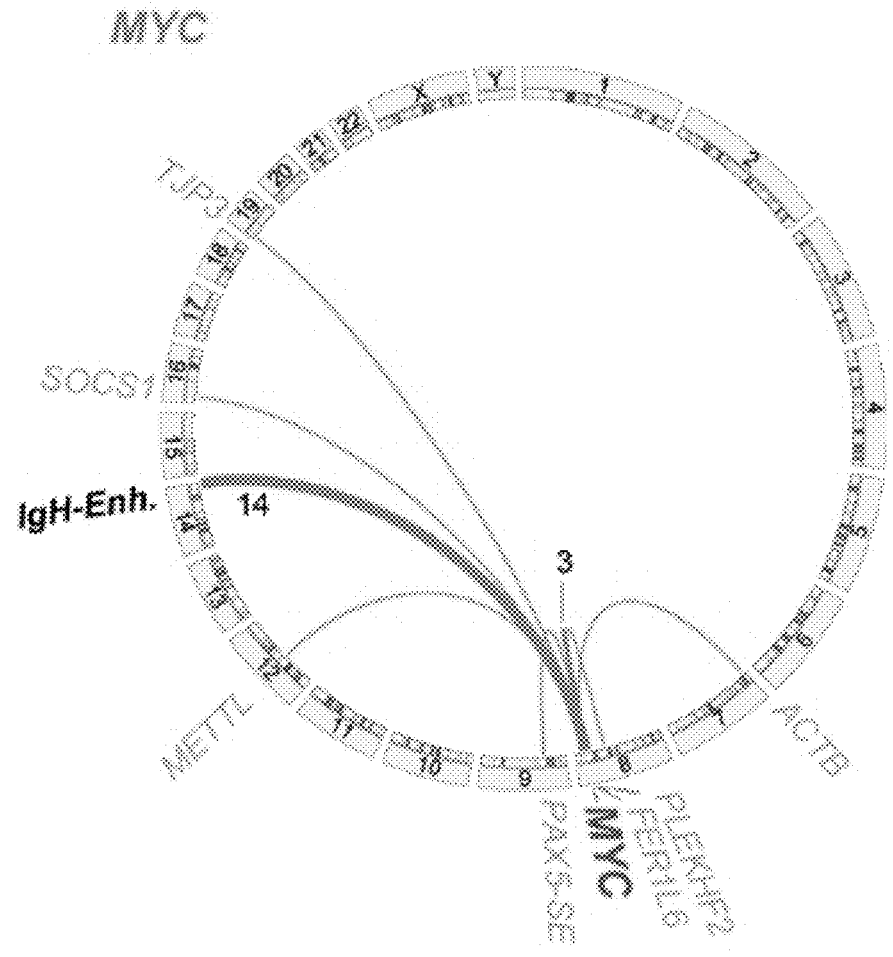
Figure 3D:
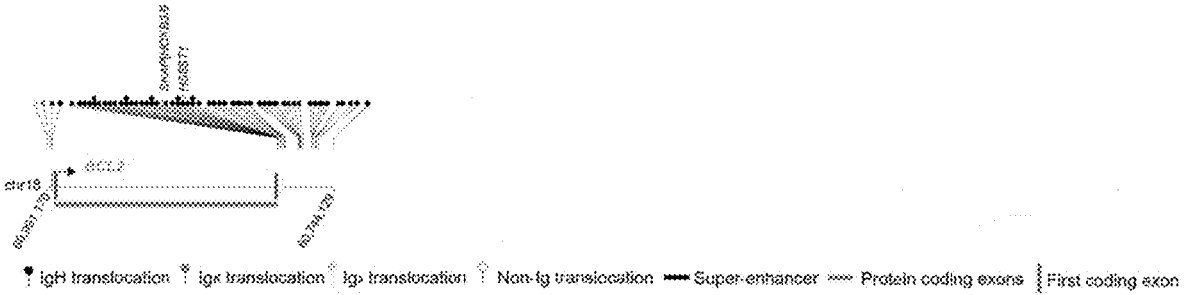
Figure 3E:
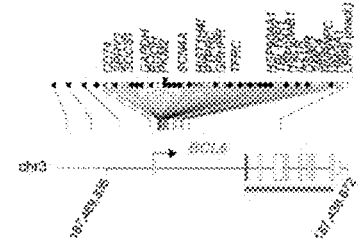
Figure 3F:
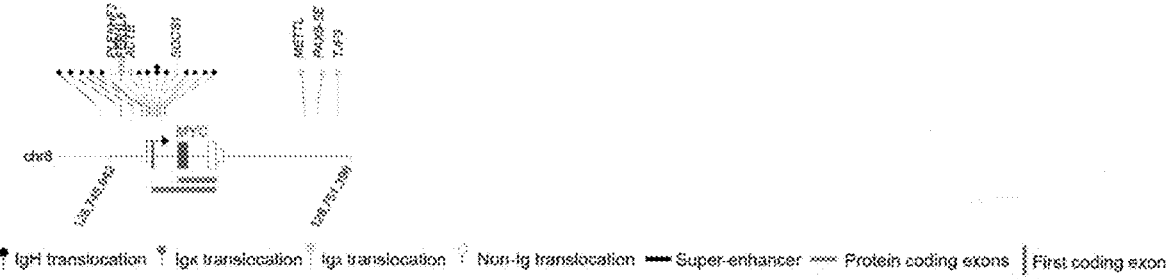
Figure 3G:
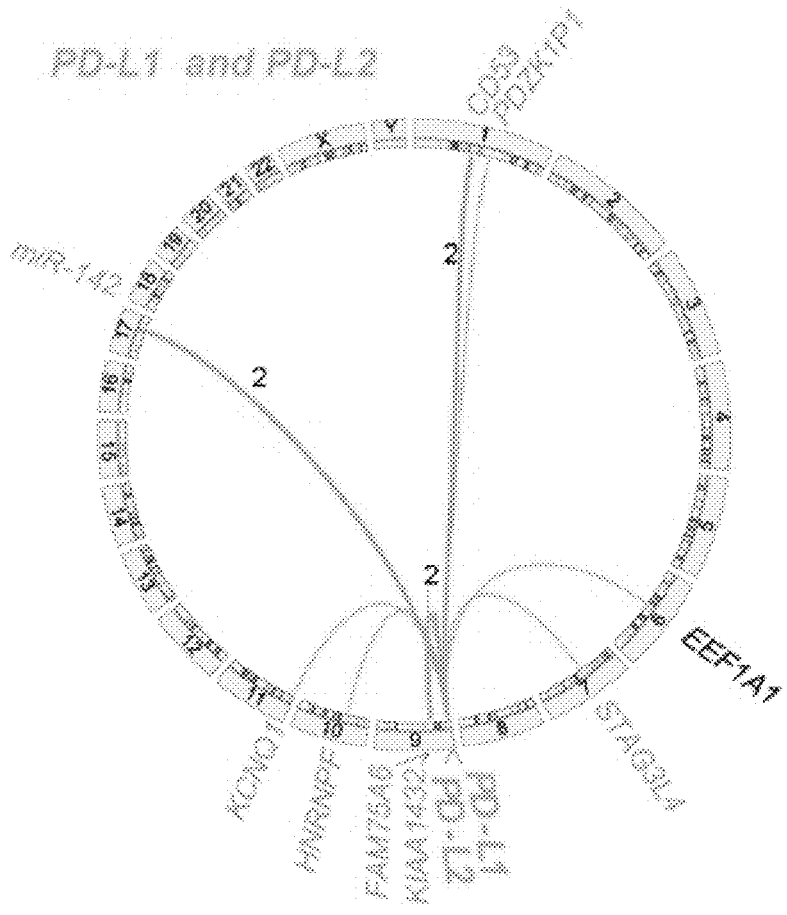
Figure 3H:
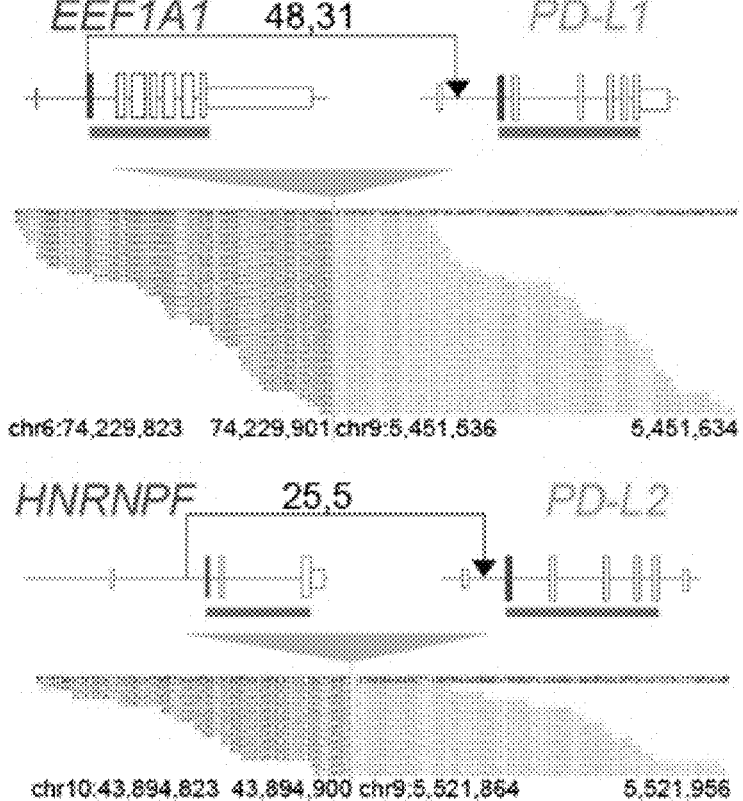
Figure 3I:
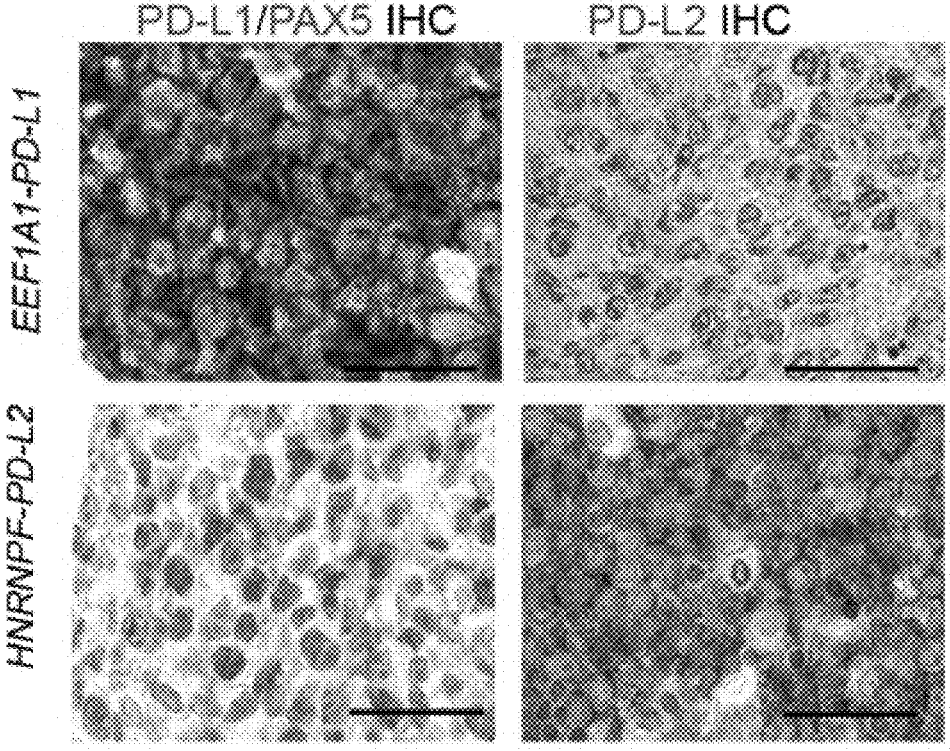

As expected (1, 32, 33), IGH, BCL2, BCL6 and MYC were the most frequently rearranged genes (40%, 21%, 19% and 8%, respectively) followed by the PD-1 ligands, PD-L1 and PD-L2 (5%), then TBL1XR1 (4%), TP63 (3%), CIITA (3%) and ETV6 (2%) (FIGS. 3A to 3G, 13E, 14A, 14D and 16E). The IgH enhancer region was the predominant rearrangement partner (97%) of BCL2, and breakpoints were almost exclusively distal to the BCL2 open reading frame (ORF) (FIGS. 3A and 3D). Although Ig loci enhancers were the most common rearrangement partners for BCL6 and MYC (57% and 58%, respectively), multiple additional partners were identified; breakpoints in BCL6 and MYC were predominantly proximal to the ORFs (FIGS. 3B, 3C, 3E and 3F). PD-L1 and PD-L2 SVs involved multiple regulatory elements juxtaposed to intact ORFs with increased expression of the respective protein (FIGS. 3G to 3I), as previously described (31). Less frequently, Ig-regulatory elements (IgH, Igκ, Igγ) were juxtaposed to additional partners with known roles in GC B-cells (BACH2, BCOR, FOXP1, miR 17-92, CCND1, CIITA, SOCS1, NFKBIE) (FIGS. 13A to 13C and 13G).

Figure 4A:
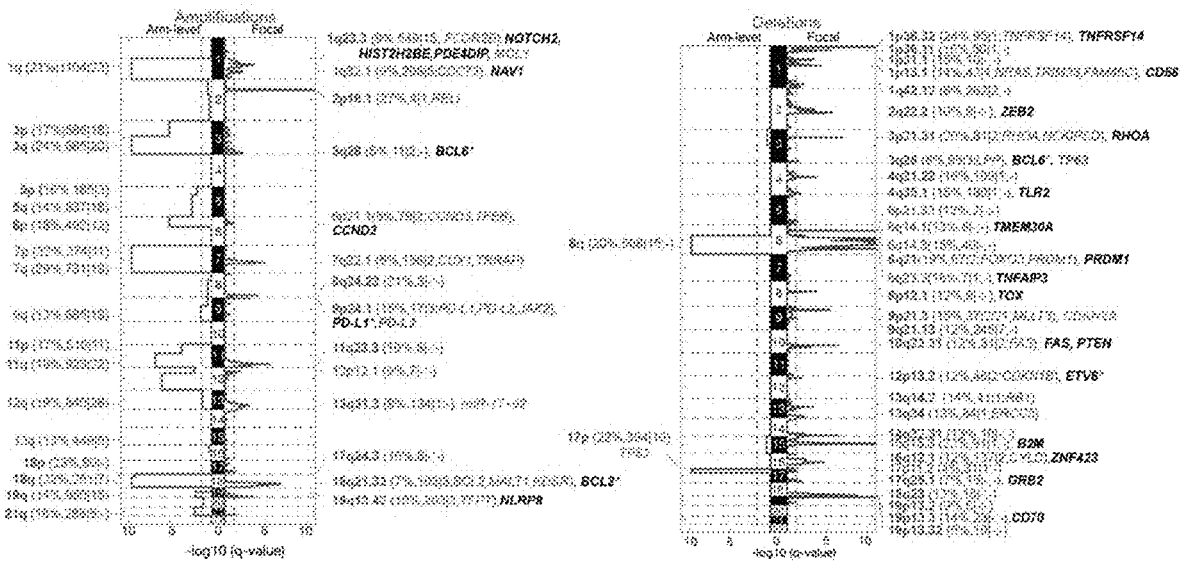
FIGS. 4A to 4C display graphs and charts of recurrent SCNAs and outcome association of individual genetic factors.

Next, significantly recurrent SCNAs were identified with the GISTIC2.0 program based on the WES data. Detected were 18 arm-level and 18 focal regions of copy gain and 2 arm-level and 32 focal regions of copy loss (q-value ≤0.1, f≥3%; FIG. 4A). The frequencies of these SCNAs ranged between 5-32% and the number of genes within focal peaks varied from 4 (2p16 gain) to 549 (1q23.3 gain). Chromothripsis was not observed in the dataset (Methods).

To provide insights regarding candidate driver genes in SCNAs, available gene expression data was leveraged and an integrative analysis (2) performed (Methods, Table S6). For each focal alteration, genes from the COSMIC Cancer Gene Census (34) with a significant association between transcript abundance and SCNA were identified (FIG. 4A, Table S6). In DLBCLs with focal 13q31.3 gain, the transcript with the highest fold change was miR-17-92 (FIG. 4A, Table S6).

Figure 15A:
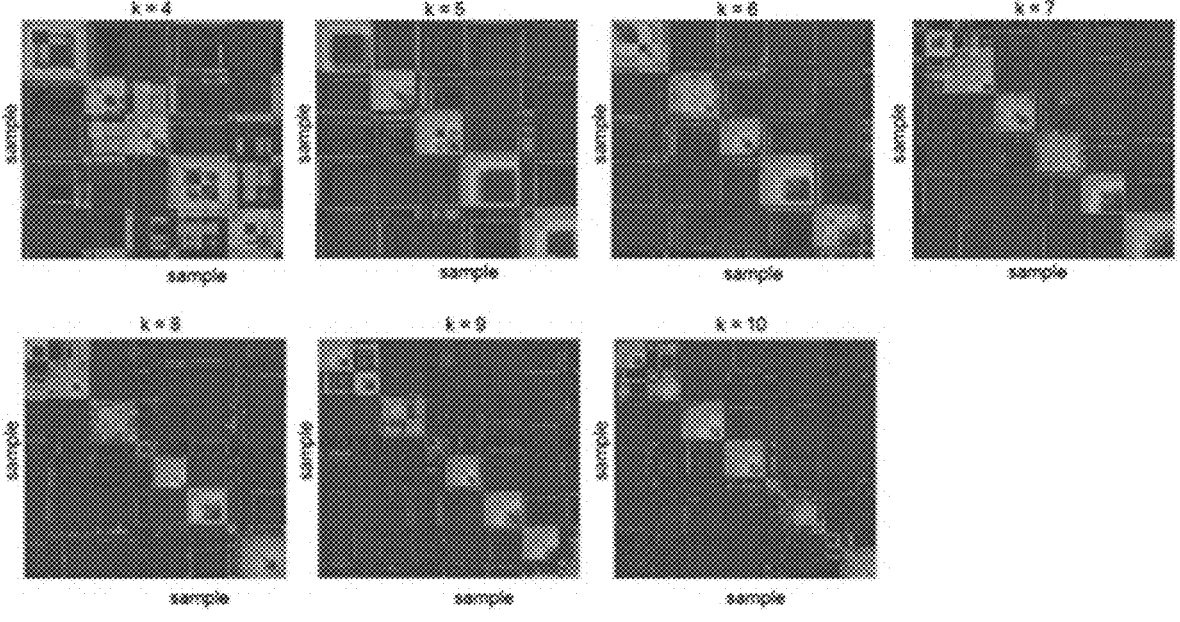
FIGS. 15A and 15B present a series of graphs of consensus clustering.
Figure 15B:
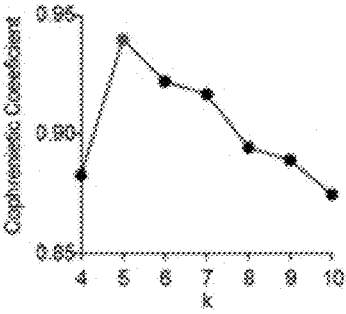

CCGs were significantly more likely to reside within focal SCNAs (Fisher Exact test, $P=1\times10^{-44}$; FIG. 4A), suggesting that these driver genes were perturbed by multiple mechanisms. Significant genes altered by mutations, CN gain and/or SVs included NOTCH2 (1q23.3), CCND3 (6p21.1), PD-L1/PD-L2/JAK2 (9p24.1) and BCL2 (18q/18q21.33); those perturbed by mutations and CN losses included CD58 (1q13.1), TNFAIP3 (6q23.3), PRDM1 (BLIMP1; 6q21), B2M (15q15.3), PTEN/FAS (10q23.31), CD70 (19p13.3), RHOA (3p21.31), TMEM30A (6q14.1) and TP63 (3q28). Of note, 74% of DLBCLs exhibited genetic bases of immune escape (7, 31, 35-37) including alterations of MHC class I loci, B2M, CD70, CD58, CD274 (PD-L1), PDCD1LG2 (PD-L2) and CIITA (FIG. 15I).

Example 5: Association of Individual Genetic Features to Outcome

Figure 4B:
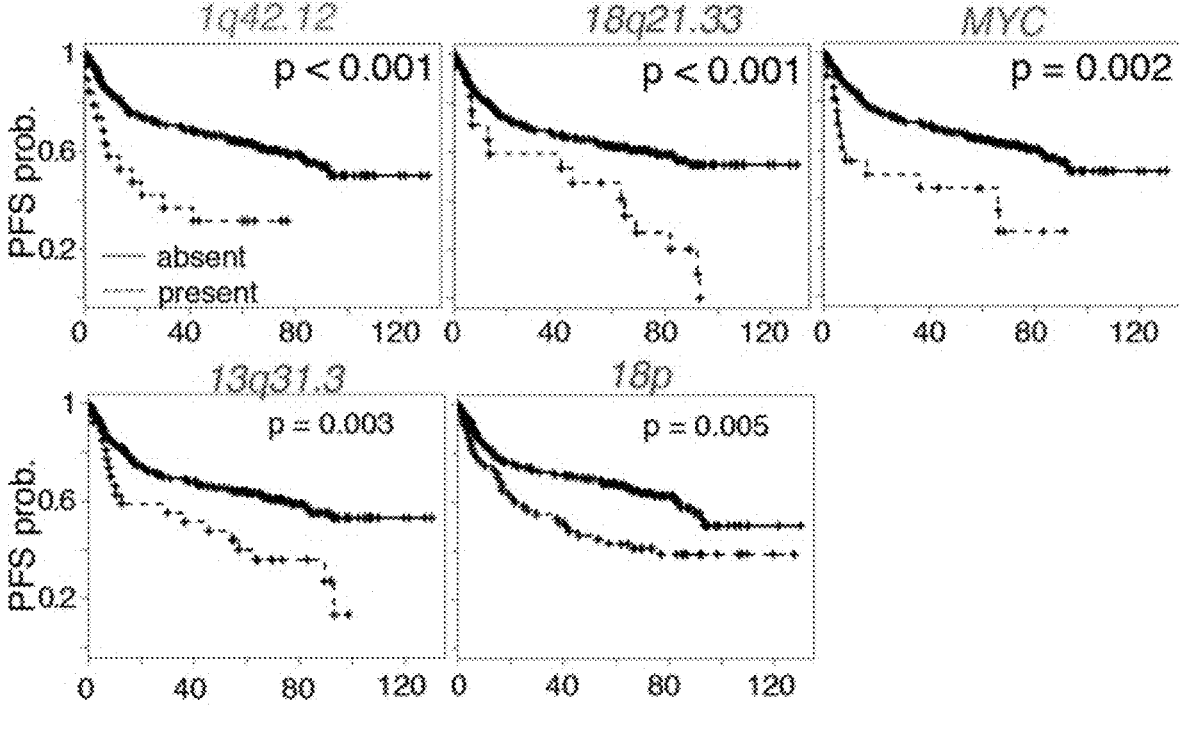
Figure 4C:
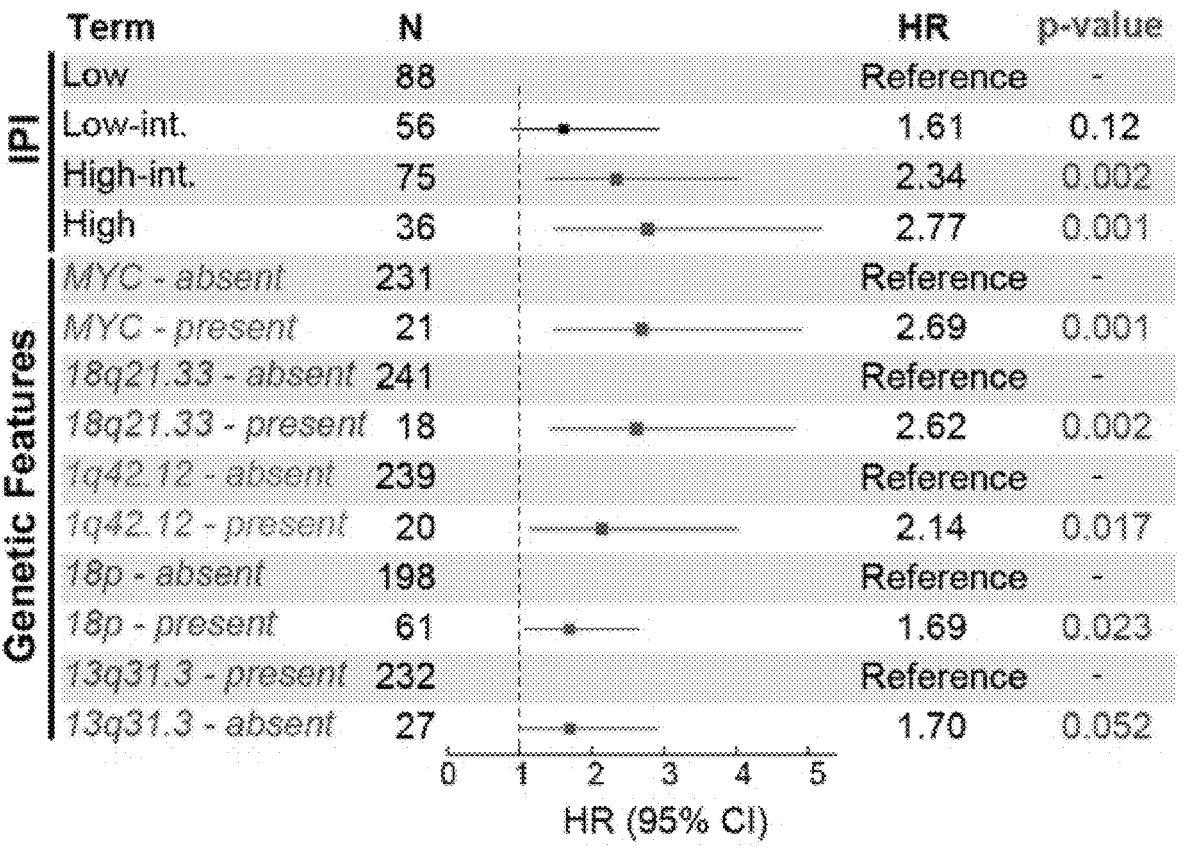
Figure 14A:
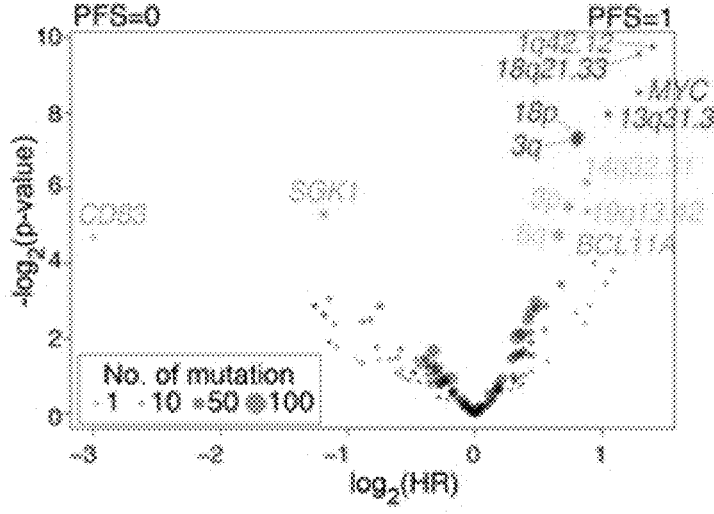
FIGS. 14A to 14D present supporting outcome analyses of individual genetic alterations.
Figure 14B:
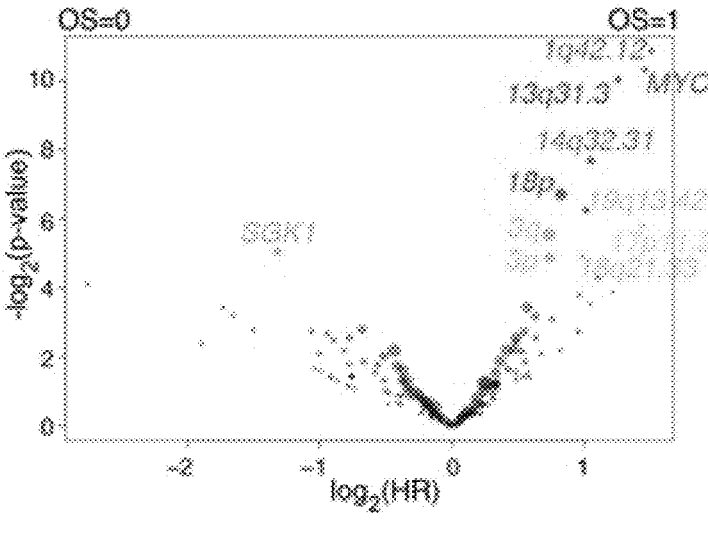
Figures 14C, 14D:
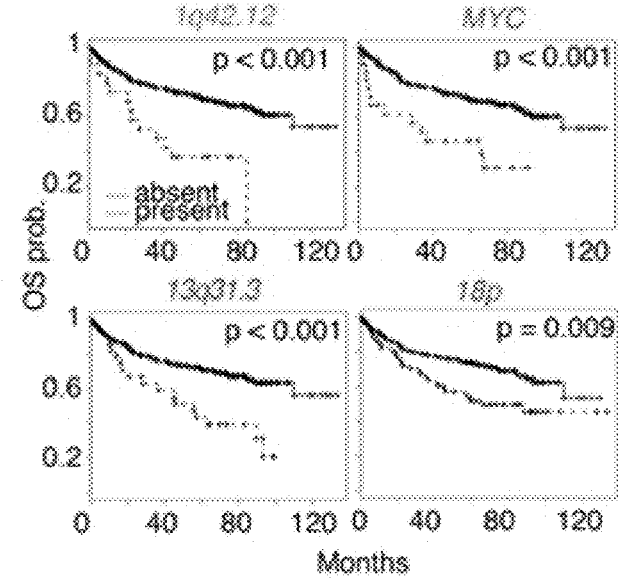

Next, the prognostic value of our identified genetic drivers was assessed for progression-free survival (PFS) and overall survival (OS) in the subset of patients who were treated with R-CHOP-like therapy (n=259, median follow-up 78.5 months). Loss of 1q42.12, MYC SVs and gains of 18q21.33/BCL2, 13q31.3/miR-17-92 and 18p, were independently predictive of inferior PFS; all retained significance when added to IPI risk groups (FIGS. 4B, 4C and 14A). MYC SVs, 13q31.3 gain and 1q41.12 loss were also associated with shortened OS alone and when added to IPI risk groups (FIGS. 14B to 14D). Notably, the prognostically significant individual alterations were SCNAs or SVs rather than mutations (Fisher's Exact test; PFS, P=0.007; OS, P=0.02).

Example 6: Coordinate Genetic Signatures Capture Biologic Heterogeneity

DLBCLs in this series harbored a median of 17 (range: 0-48) genetic drivers prompting additional analyses of co-occurring alterations. Non-negative matrix factorization (NMF) consensus clustering (38) was applied to the 158 identified genetic driver alterations and discovered 5 robust subsets of tumors (clusters) with discrete genetic signatures (hereafter coordinate genetic signatures; C1-C5; 51 to 72 samples each) and an additional subset without detectable alterations (C0; 12 samples) (Methods, FIGS. 5 and 17, Tables S7, S8).

Figure 5:
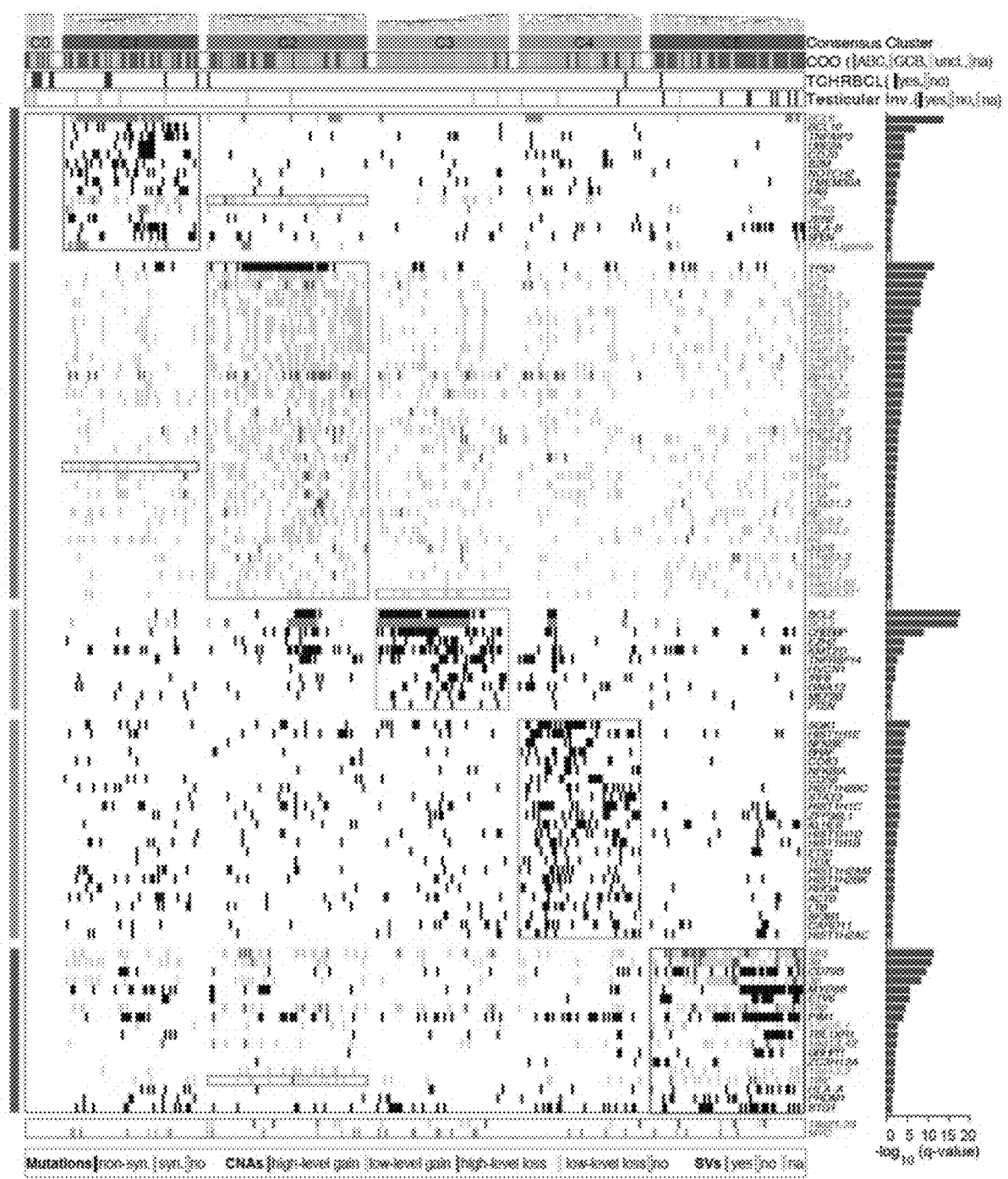
FIG. 5 displays an image in which groups of tumors possessing coordinate genetic signatures were identified. Non-negative matrix factorization consensus clustering was performed using all cancer causing genes (CCGs), somatic copy number alterations (SCNAs) and structural variants (SVs) in the 304 DLBCL samples (columns). Clusters C1-C5 with their associated landmark genetic alterations were visualized (boxed for each cluster). Samples without driver alterations have been represented as Cluster C0. Genetic alterations are ranked by significance. Significance, obtained from a Fisher test, has been visualized at right as a bar graph, while the green line denotes a q value of 0.1. Labeling is as follows: non-synonymous mutations, black; synonymous mutations, grey; single CN loss (1.1≤CN≤1.6 copies), cyan; double CN loss (CN≤1.1), blue; low level CN gain (3.7 copies≥CN≥2.2 copies), pink; high grade CN gain (CN≥3.7 copies), red; chromosomal rearrangement, green; no alterations, white; grey-crossed, not assessed. Header shows cluster association (C0, grey; C1, purple; C2, blue; C3, orange; C4, green; C5, yellow), COO classification (ABC, red; GCB, cyan; unclassifiable, yellow; not assessed, grey), TCHRBCL cases (red, yes; white, no), and testicular involvement (black, yes; white, no; grey, na). Outcome-associated alterations that are not part of a specific cluster, SVs of MYC and 18q21.33 copy gain, are below.

Cluster 5 (C5): The 60 C5 DLBCLs exhibited near-uniform 18q gain likely increasing expression of BCL2 and other candidate drivers, such as MALT1 (22, 39, 40). These tumors also had frequent mutations in CD79B (48% [29/60]) and MYD88 (50% [30/60]), alterations previously associated with ABC-type DLBCLs (12, 14, 21). Notably, MYD88 mutations selectively involved L265P and often occurred in association with CD79B mutations (Fisher's Exact test, P=0.036; FIGS. 5, 6A, 6B and 17A). Additional alterations linked to ABC-DLBCLs, including gains of 3q, 19q13.42 and inactivation of PRMD1, were observed in this cluster (2, 41-43), as were the prognostically significant 18p copy gains (FIGS. 4B and 5). In this cluster, 96% (45/47) of tumors with available COO designations typed as ABC-DLBCLs (Fisher Exact test, p<0.001).

Figure 6A:
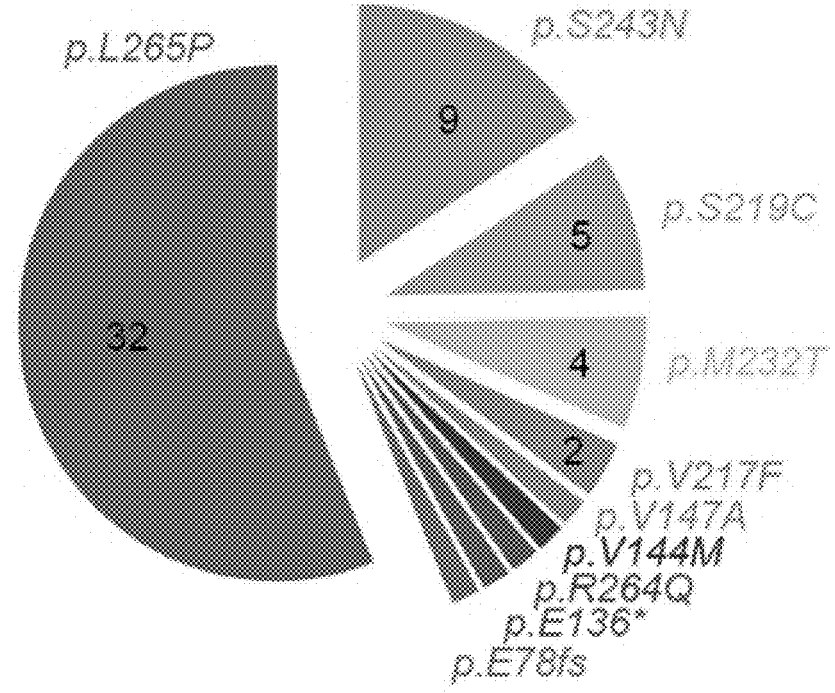
FIGS. 6A to 6N display graphs and schematics showing the type and incidence of MYD88 mutations, cAID muta-tional signature activity, inferred timing of genetic drivers and outcome association of DLBCL clusters.
Figure 6B:
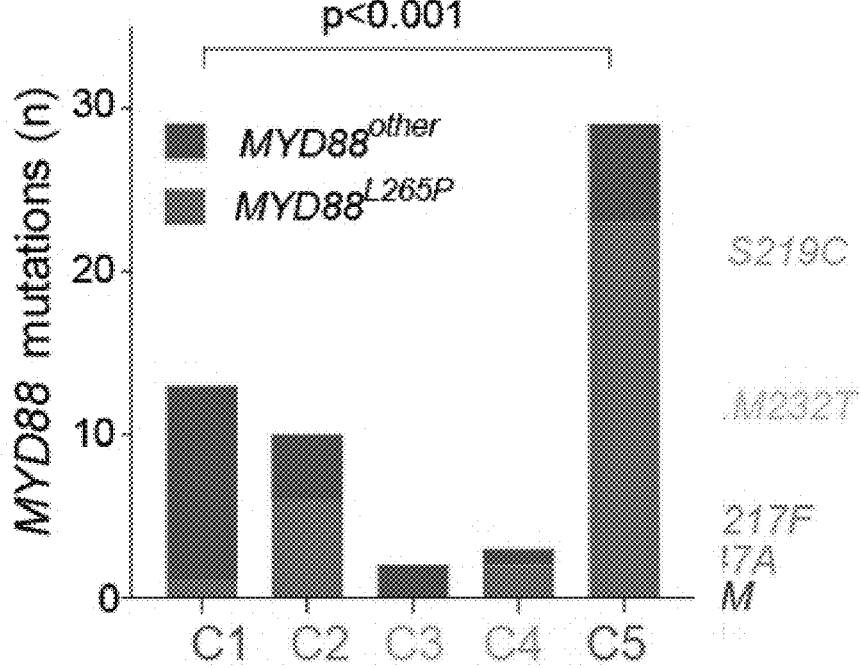
FIG. 6B displays a graph of the frequency of $MYD88^{L265P}$ and $MYD88^{other}$ mutations across clusters C1-C5; p-value by Fisher's Exact test.
Figure 6C:
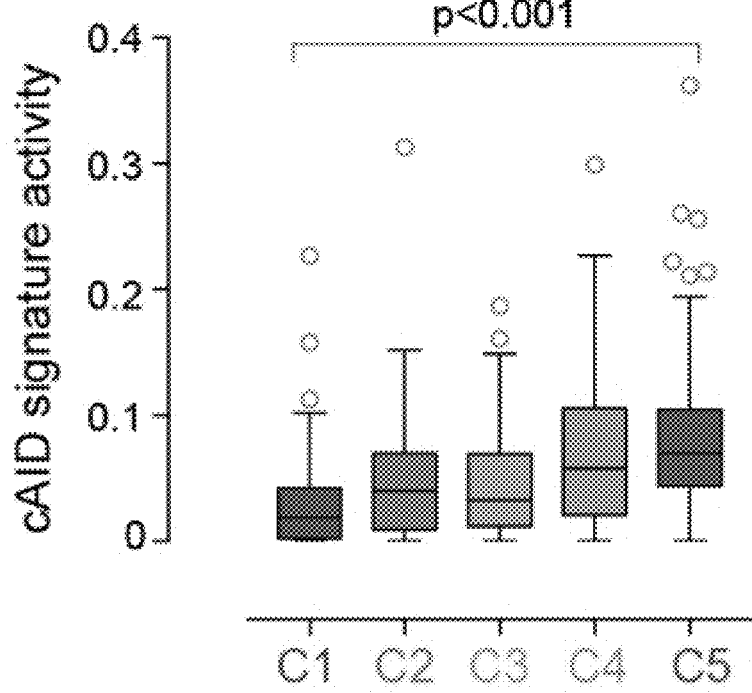
FIG. 6C displays a graph of the fraction of cAID mutational signature activity by cluster; p-values by Mann-Whitney U test.

Major components of the C5 signature, including frequent BCL2 gain, concordant $MYD88^{L265P}$/CD79B mutations and additional mutations of ETV6, PIM1, GRHPR, TBL1XR1 and BTG1 (FIG. 5), were similar to those recently described in primary CNS and testicular lymphoma (31, 44). Therefore, systemic DLBCLs with CNS or testicular involvement were identified, and it was found that 8/9 patients with testicular disease were in this cluster (Fisher's Exact test, P<0.001) as was 1 of 2 patients with CNS involvement. These data suggested that the C5 coordinate genetic signature was associated with extranodal tropism and extended the findings of targeted sequencing studies linking MYD88$^{L265P}$ with extranodal disease (45-47). C5 DLBCLs possessed the highest contribution of cAID and associated aberrant SHM indicative of tumors that have passaged through the GC (FIG. 6C) (1).

Cluster 1 (C1): The majority of the 51 C1 DLBCLs exhibited BCL6 SVs in combination with mutations of NOTCH2 signaling pathway components, predominantly PEST-domain mutations of NOTCH2 and truncating mutations of its negative regulator, SPEN. C1 CLBCLs also had increased transcriptional abundance of NOTCH2 and BCL6 target genes by gene set enrichment analysis (GSEA) (FIG. 19). Additionally, these tumors harbored frequent mutations of the NF-kB pathway members, BCL10 and TNFAIP3 (A20), and FAS (FIGS. 5 and 10). Alterations in NOTCH and NF-kB pathway components and FAS mutations were previously found in low grade marginal zone lymphomas (MZLs) (48-51) and BCL6 translocations were described in transformed MZL (52).

C1 DLBCLs had no histologic features of MZLs, suggesting that these tumors were either occultly transformed prior to diagnosis or that they derived de novo from a common extrafollicular B-cell precursor with shared genetic features. MZLs typically arise in a setting of chronic inflammation, often in response to pathogen-driven antigen stimulation (53). Interestingly, C1 DLBCLs exhibited multiple genetic bases of immune escape, including inactivating mutations in B2M, CD70, FAS and SVs of PD-L1 and PD-L2 (FIGS. 5 and 10) (31, 35, 54).

The majority of C1 DLBCLs were classified as ABC-type tumors by transcriptional profiling (Fisher's Exact test, P=0.01). Although 25% (13/51) of C1 DLBCLs exhibited MYD88 mutations, these were almost exclusively MYD88$^{non-L265P}$ in contrast to the predominant MYD88$^{L265P}$ found in C5 ABC DLBCLs (p<0.001, FIGS. 6A, 6B and 17A). MYD88$^{L265}$ and MYD88$^{non-L265P}$ differ in their ability to coordinate IRAK1/IRAK4-containing signaling complexes and activate NF-kB (12). C5 and C1 ABC-DLBCLs also differ in the contribution of cAID to their mutational spectrum (FIG. 6C, C1 vs. C5, P<0.001; C1 vs. rest, P<0.001). In contrast to C5 tumors, C1 DLBCLs possessed low to absent cAID activity, providing additional evidence of an extrafollicular origin and an associated lower rate of SHM (FIG. 6C) (55).

Taken together, the coordinate genetic signatures of C1 and C5 ABC-type DLBCLs defined subsets of tumors with distinct pathogenetic mechanisms. These findings (FIGS. 5 and 6B) also indicated different targeted treatment strategies in the genetically distinct ABC-DLBCLs—inhibition of proximal BCR/TLR signaling and BCL2 in C5 ABC-DLBCLs and perturbation of NOTCH and BCL6 signaling and immune evasion mechanisms in C1 ABC-DLBCLs.

Cluster 3 (C3): The majority of the 53 C3 DLBCLs harbored BCL2 mutations with concordant SVs that juxtaposed BCL2 to the IgH enhancer (Fisher Exact test, P=3.3× 10$^{-35}$; FIGS. 5 and 9E). C3 DLBCLs also exhibited frequent mutations in chromatin modifiers, KMT2D, CREBBP and EZH2, and increased transcriptional abundance of EZH2 targets by GSEA (FIG. 17G). These tumors also had alterations of the B-cell transcription factors, MEF2B and IRF8, and indirect modifiers of BCR- and PI3K-signaling, TNFSF14 (HVEM), HCNV1 and GNA13 (FIGS. 5 and 10).

Additionally, these tumors exhibited 2 alternative mechanisms of inactivating PTEN—focal 10q23.31/PTEN loss and predominantly truncating PTEN mutations (FIG. 5). The 2 types of PTEN alterations are noteworthy because the PTEN N-terminal and C-terminal domains have distinct roles in antagonizing PI3K/AKT signaling, maintaining genomic stability and inducing murine B-cell lymphomas (FL((19, 56, 57). C3 genetic alterations have been described in follicular lymphoma and de novo GCB-type B-cell lymphomas (4, 17-19, 41, 58-63). Consistent with this finding, 95% (38/40) of C3 DLBCLs with available COO designations were GCB-type (FIG. 5).

Cluster 4 (C4): The 56 C4 DLBCLs were characterized by mutations in 4 linker and 4 core histone genes, multiple immune evasion molecules (CD83, CD58, CD70), BCR/Pi3K signaling intermediates (RHOA, GNA13, SGK1), NF-kB modifiers (CARD11, NFKBIE, NFKBIA) and RAS/JAK/STAT pathway members (BRAF, STAT3).

C4 DLBCLs were primarily GCB-type (Fisher's Exact test, P=0.01), indicating that C4 and C3 DLBCLs represented genetically distinct subsets of GCB-tumors (FIG. 5). Comparison of the C3 and C4 genetic signatures further indicated that these GCB-DLBCLs utilized distinct mechanisms to perturb common pathways such as PI3K signaling. In contrast to C3 DLBCLs, C4 tumors rarely exhibited PTEN alterations but harbored more frequent RHOA mutations (FIG. 5). Additionally, C4 DLBCLs rarely exhibited BCL2 alterations.

Unlike C3 tumors, C4 DLBCLs largely lacked alterations in chromatin modifying enzymes but frequently exhibited mutations in H1 linker histones and additional core histones that have also been described in FL (62, 64, 65). The identified mutations in the globular or C-terminal domains of H1 linker histones likely reduce their association with chromatin and/or perturb interactions with additional effector molecules (FIG. 8) (64-66). H1 linker and core histone alterations may increase mutation rates by opening chromatin and exposing DNA to ongoing AID activity; indeed, C4 tumors exhibited a significantly higher mutational density (p<0.0001; FIG. 17C).

The distinct genetic features of C3 and C4 GCB-DLBCLs also newly indicated use of specific targeted therapies including inhibition of BCL2, PI3K and the epigenetic modifiers, EZH2 and CREBBP, in C3 GCB tumors and JAK/STAT and BRAF/MEK1 blockade in C4 GCB-DLBCLs.

Figure 6D:
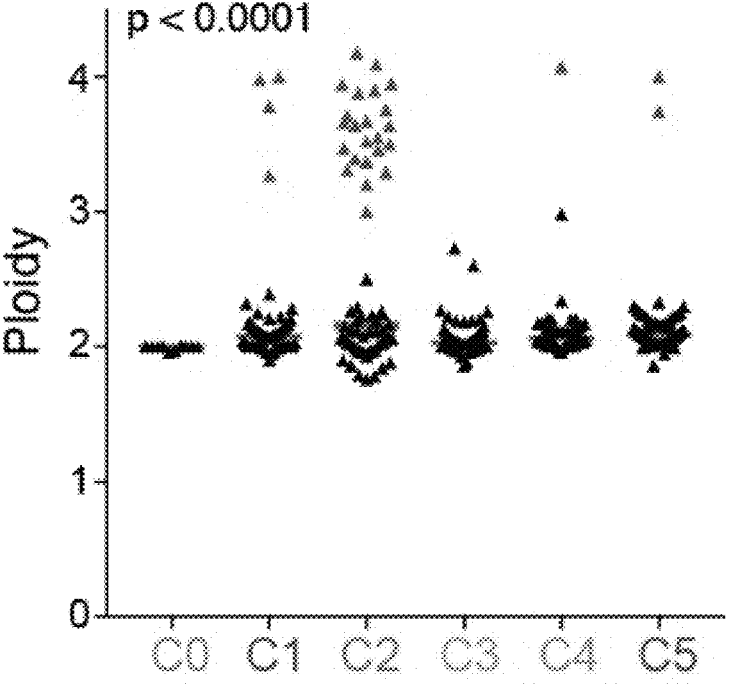
FIG. 6D displays a graph of ploidy as inferred by ABSOLUTE by cluster. DLBCLs with an inferred ploidy ≥3 are indicated in red; p-value by Fisher's Exact test.

Cluster 2 (C2): The 72 C2 DLBCLs harbored frequent bi-allelic inactivation of TP53 by mutations and 17p copy loss (FIGS. 5 and 17E). Additionally, C2 tumors often exhibited copy loss of 9p21.13/CDKN2A and 13q14.2/RB1, which perturb chromosomal stability and cell cycle (2). Consistent with these findings, transcriptionally profiled C2 DLBCLs exhibited decreased abundance of TP53 targets and increased levels of E2F targets by GSEA (FIG. 17H). C2 tumors also exhibited significantly more driver SCNAs (P<0.0001) and a higher proportion of genome doubling events (FIG. 6D, P<0.001; FIGS. 17B to 17D). This cluster included both GCB- and ABC-DLBCLs, as did prior DLBCL cohorts with TP53 mutations in targeted analyses (67). C2 DLBCLs shared features of previously described DLBCLs with TP53 alterations and multiple SCNAs of p53/cell cycle modifiers (2). These tumors also exhibited more frequent copy gains of 1q23.3 MCL1 and 9p24.1/PD-L1/PD-L2. Prognostically significant SCNAs, including 13q31.31/miR-17-92 copy gain and 1q41.12 copy loss, were also more common in these DLBCLs (FIG. 5). Treatment of C2 cluster tumors with CDK inhibitors is expressly contemplated (refer to U.S. Pat. No. 9,890,429 for exemplary use of CDK inhibitors in treatment).

Cluster 0 (C0): A small subset of 12 DLBCLs lacked defining genetic drivers. Significance analyses (MutSig2CV and GISTIC2.0) restricted to C0 DLBCLs were also unrevealing. This group included increased numbers of T-cell/histocyte-rich LBCLs (Fisher's Exact test P<0.001), a morphologically defined subtype with a brisk inflammatory/immune cell infiltrate (11). The absence of detectable drivers in these DLBCLs may reflect lower tumor purity or different pathogenetic events.

Recently, subsets of tumors with co-occurring BCL2 and MYC and/or BCL6 SVs and/or increased protein expression have been described and associated with poor outcome ("double and triple hit" DLBCLs) (68). Notably, prognostically significant MYC SVs and focal 18q21.33/BCL2 gain were detected (FIG. 5, bottom) and additional alterations that perturbed the expression of BCL2, BCL6 and MYC target genes in multiple clusters were also observed (FIG. 5; 18q gain, C5; BCL2 SVs, C3; 13q14.2/miR-15/16 loss, C2; BCL6 SVs, C1; 13q31.3/miR-17-92 gain (69), C2). However, tumors possessing co-occuring BCL2 and MYC SVs were significantly more frequent in C3 DLBCLs (Fisher's exact test, p=0.003). Taken together, these findings indicated that current definitions of "double and triple hit" DLBCLs may be insufficiently precise.

Example 7: Temporal Ordering of Genetic Events in DLBCL Clusters

Figure 6E:
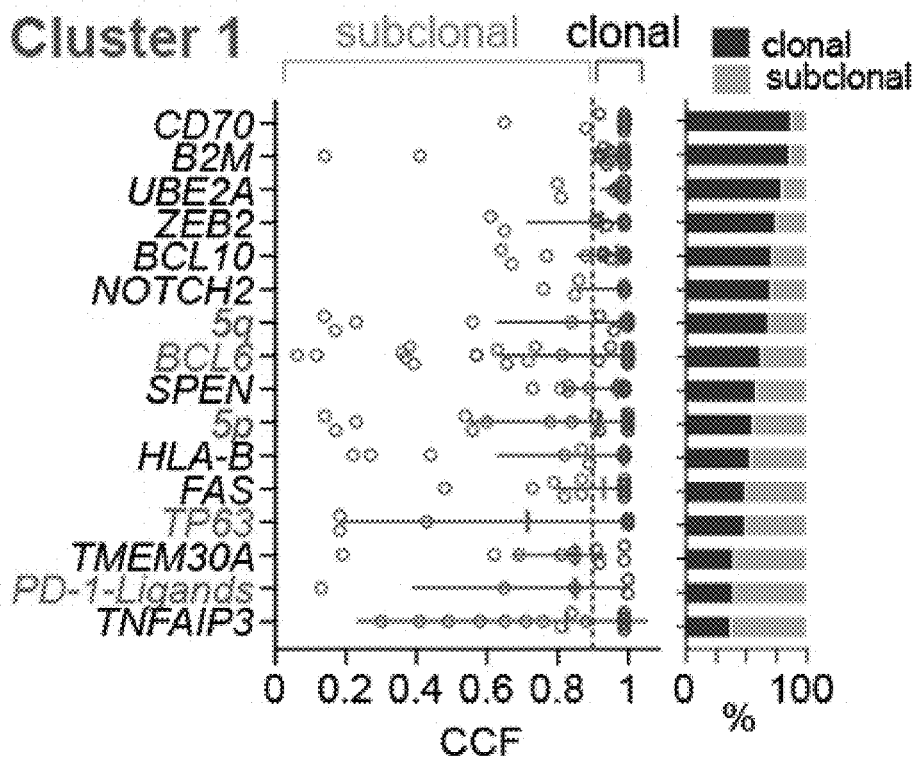
FIG. 6E displays a graph of cluster 1 cancer cell fractions.
Figure 6F:
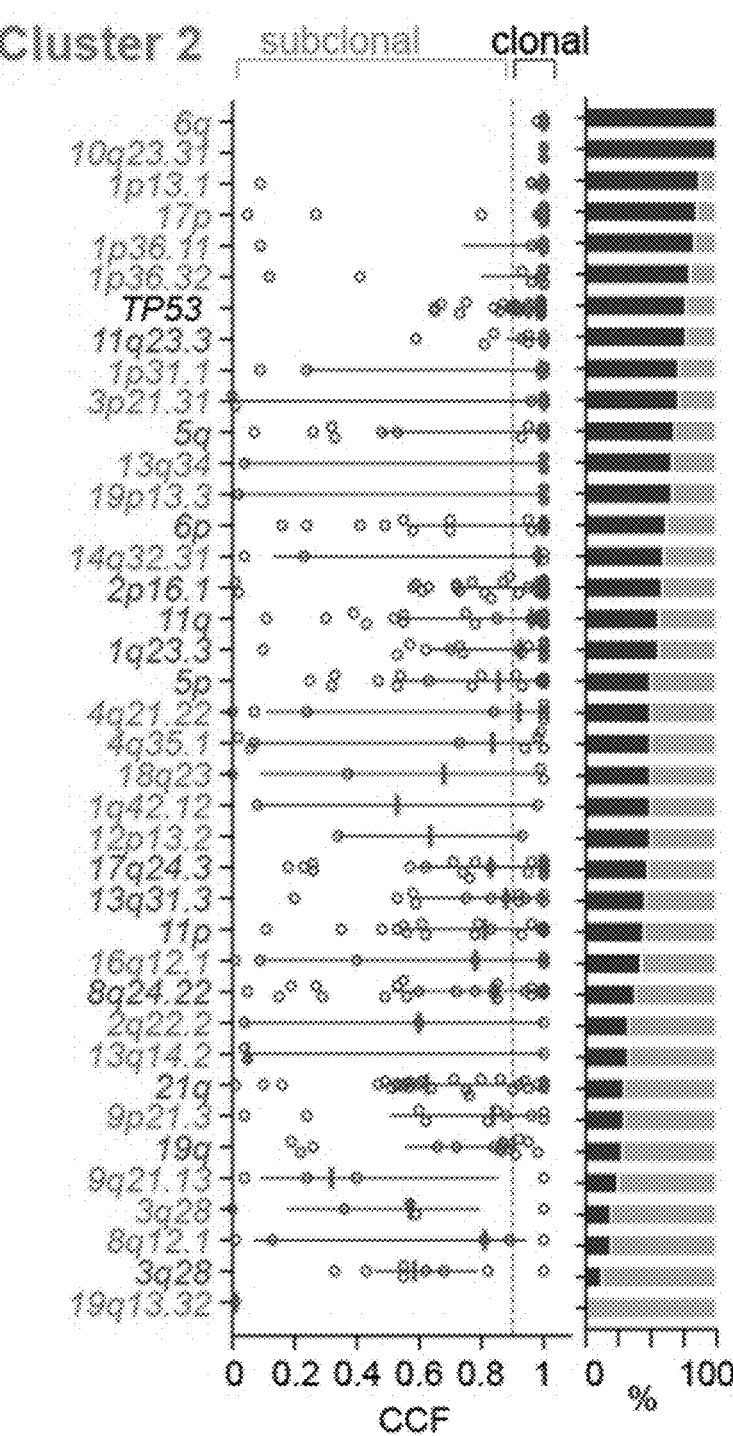
FIG. 6F displays a graph of cluster 2 cancer cell fractions.
Figure 6G:
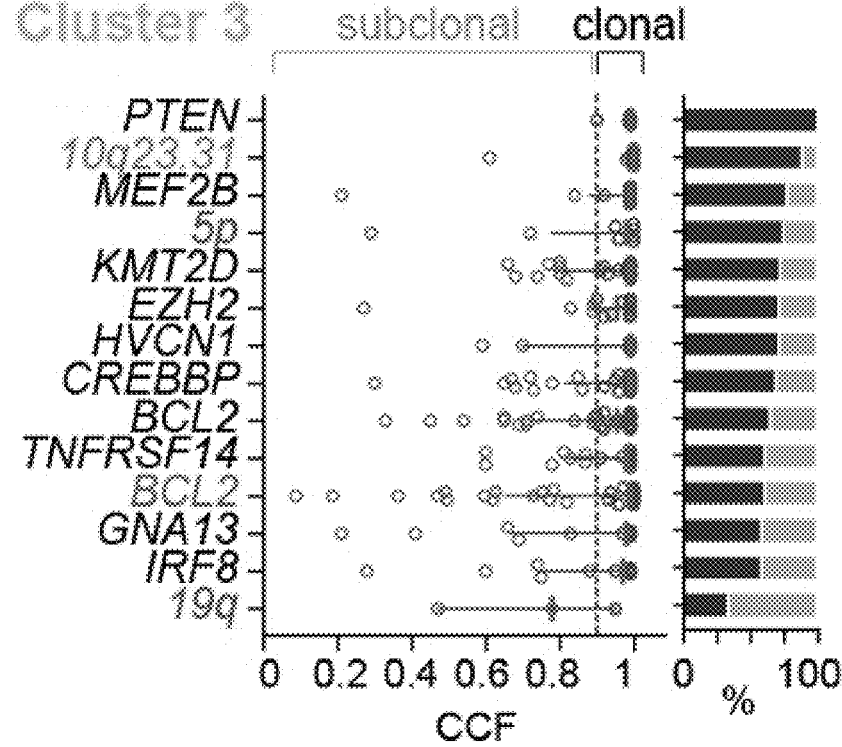
FIG. 6G displays a graph of cluster 3 cancer cell fractions.
Figure 6H:
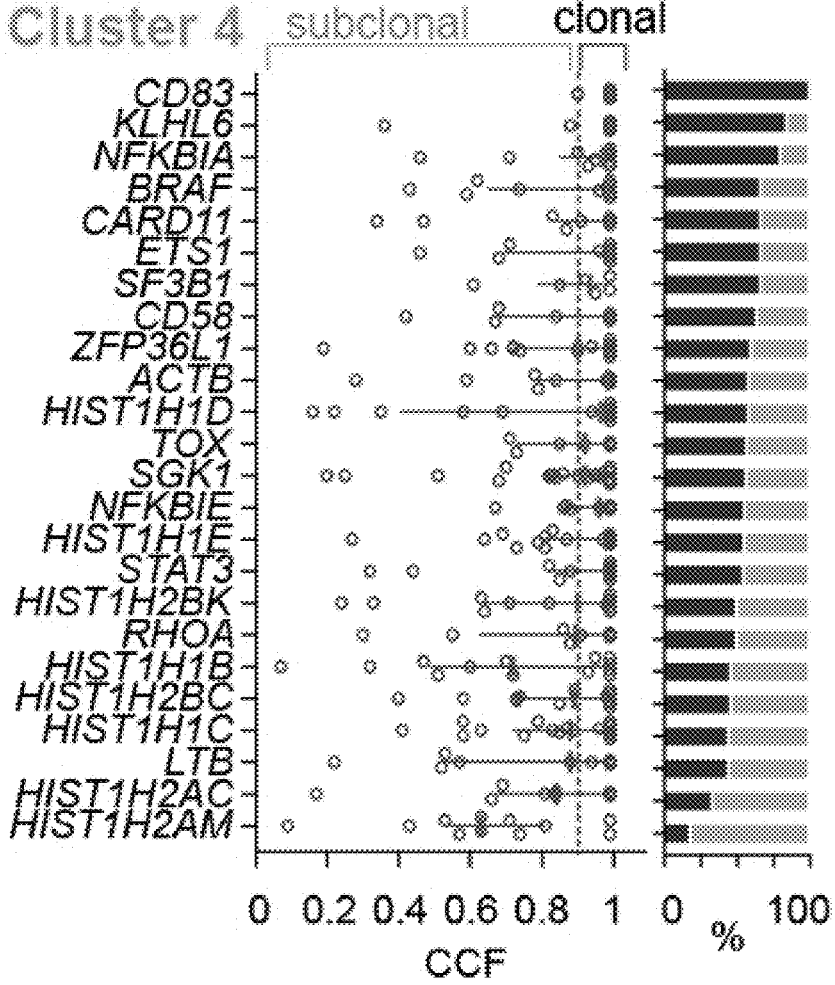
FIG. 6H displays a graph of cluster 4 cancer cell fractions.

The cancer cell fraction (CCF) (70) for each genetic driver was next determined and a CCF threshold of 0.9 was used to identify each alteration as clonal or subclonal; 74% of mutations, 49% of SCNAs and 57% of SVs were clonal in this series (FIG. 20, Table S10a and Methods). Each of the above-mentioned mutational signatures (FIG. 2) contributed to subclonal mutations, which indicated that all mutational processes were ongoing. A method for mutation ordering was also applied (71) in tumors that harbored pairs of alterations that were clonal and subclonal. Pairs that exhibited an excess of clonal to subclonal events were identified and highly significant pairs were highlighted (q-value <0.1; FIGS. 6J, 21, Table S10 and Methods) (70). As clonal alterations occur prior to subclonal events, this method allowed for ordering of the timing of genetic alterations to be established (FIGS. 6E to 6J) (70).

Figure 6I:
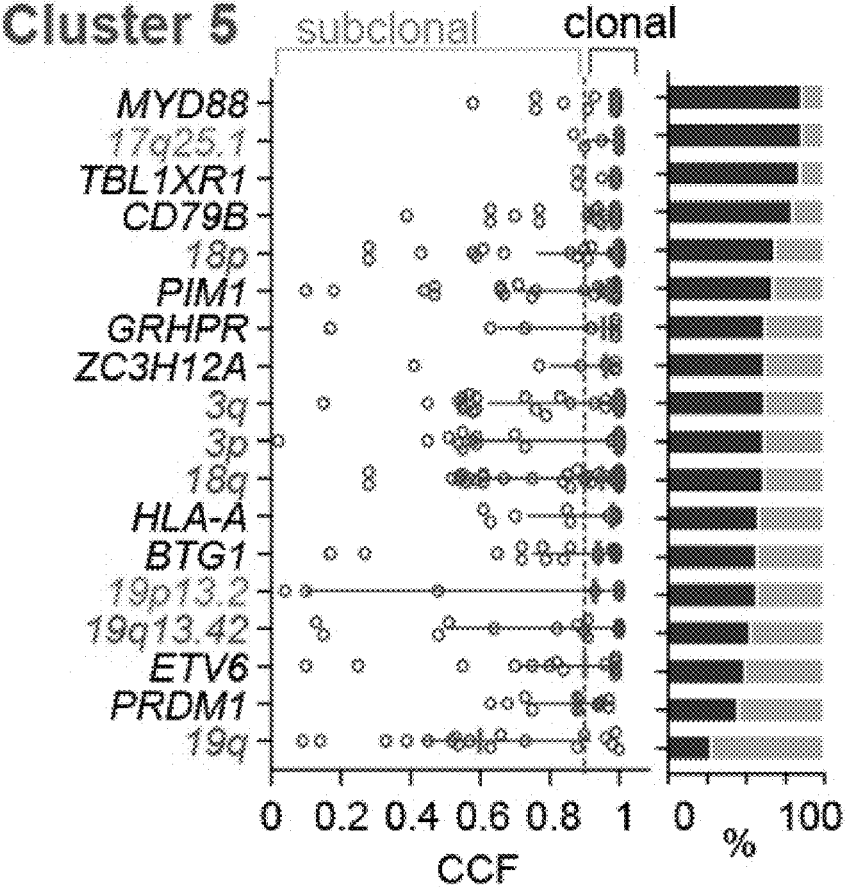
FIG. 6I displays a graph of cluster 5 cancer cell fractions.
Figure 6J:
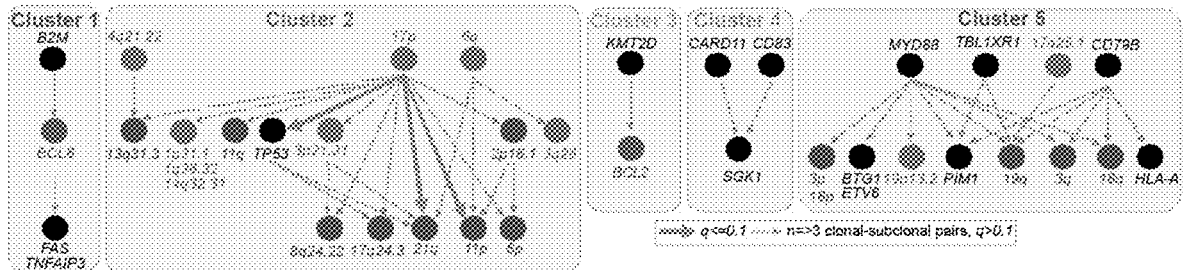
FIG. 6J displays a schematic of the timing of cluster-associated alterations. The timing of cluster-associated alterations has been visualized with early events at top; late events at bottom. Color indicates alteration type as above. Arrows between 2 alterations are drawn when 2 drivers are found in one sample with an excess of clonal to subclonal events. Line type of arrows indicates significance derived from a binomial test (solid thick arrow, q value <0.1; dotted line, too few clonal-subclonal pairs to formally test with binominal test).

In C5 ABC-DLBCLs, defining mutations of CD79B, MYD88 and TBL1XR1 were largely clonal, whereas additional genetic events including 18q copy gain and PIM1, BTG1 and ETV6 mutations were more frequently subclonal (FIGS. 6I and 6J). In C1 ABC-DLBCLs, mutations associated with MZL, NOTCH2, SPEN and BCL10, and immune evasion, CD70 and B2M, were largely clonal, whereas FAS and TNFAIP3 mutations and BCL6 and PD-1 ligand SVs were often subclonal (FIG. 6E). In informative tumors, the ordering of paired alterations supported the hypothesis that BCL6 SVs were later, potentially transforming, events (FIG. 6J).

The alterations in C3 GCB-DLBCLs were largely clonal (FIG. 6G), although a subset of BCL2 SVs were subclonal (FIGS. 6G and 6J). In C4 primarily GCB-DLBCLs, defining alterations of immune evasion molecules, BCR/PI3K signaling intermediates, NF-kB modifiers and RAS/JAK/STAT pathways members were largely clonal (FIG. 6H). In contrast, mutations of linker and core histone genes were variably clonal and subclonal (FIG. 6H), which indicated that at least some of these alterations were later events.

C2 DLBCLs were largely characterized by clonal loss of 17p, followed by TP53 mutations (FIGS. 6F and 6J). Certain prognostically significant genetic alterations, 18q21.33 copy gain and MYC SVs, were often subclonal (FIGS. 4 and 6).

Example 8: Outcome Associations of DLBCL Clusters

Figure 6K:
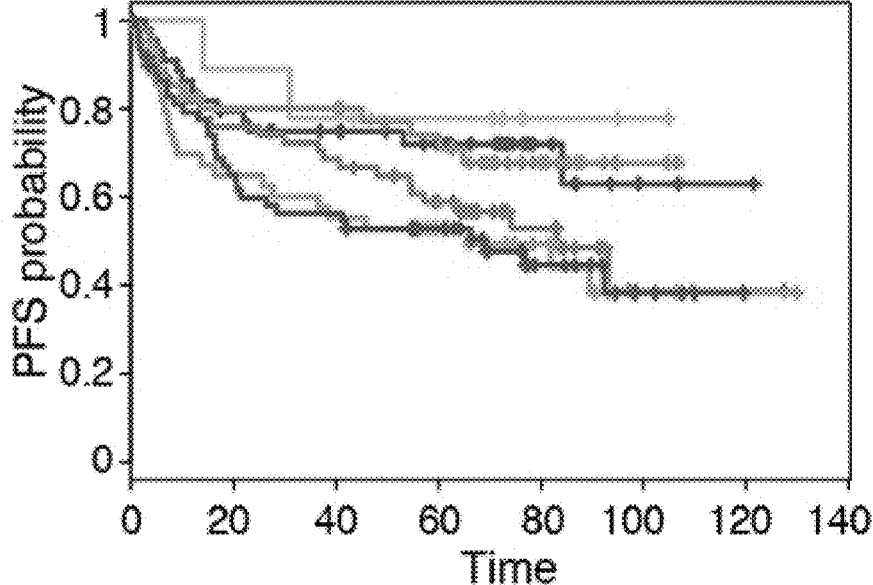
FIG. 6K displays a series of Kaplan Meier plots for PFS for all clusters, C0 (grey), C1 (purple), C2 (cyan), C3 (orange), C4 (turquoise), C5 (red); p-values obtained by log-rank test.
Figure 6L:
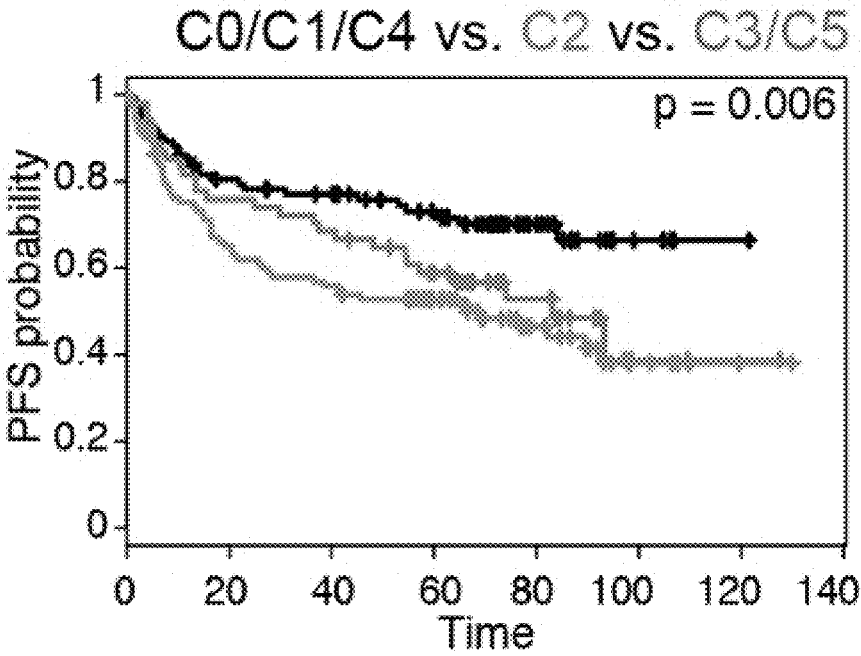
FIG. 6L displays a KM plot for PFS for favorable DLBCL clusters (C0, C1, C4) in black, C2-DLBCLs in blue and unfavorable DLBCLs (C3, C5) in pink. The p-value obtained using the log-rank test.
Figure 6M:
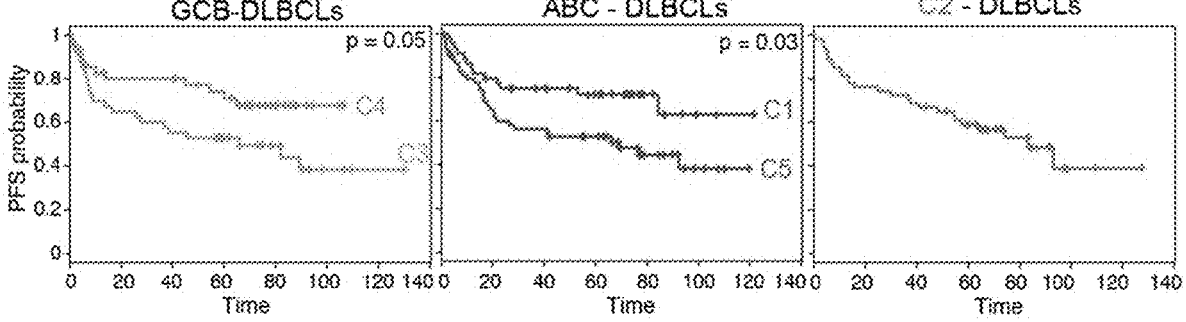
FIG. 6M displays a KM plot for PFS for the genetically distinct GCB-DLBCL (germinal center B-cell) clusters (C3 and C4; left), the ABC-DLBCL (activated B-cell-DLBCL) clusters (C1 and C5; middle) and C2 DLBCLs. The p-value obtained using the log-rank test.
Figure 18A:
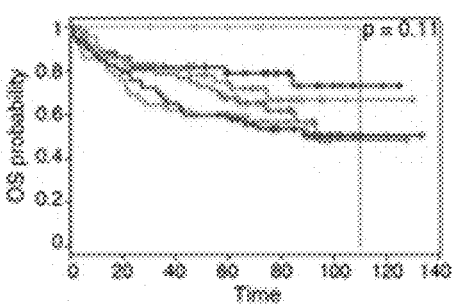
FIGS. 18A to 18E show the association of coordinate genetic signatures with overall survival (OS).
Figure 18B:
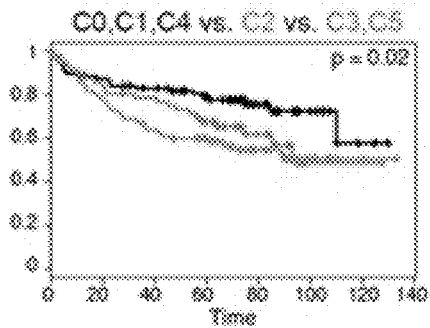
Figure 18C:
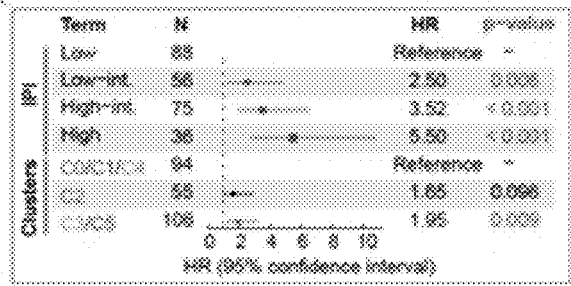
Figure 18D:
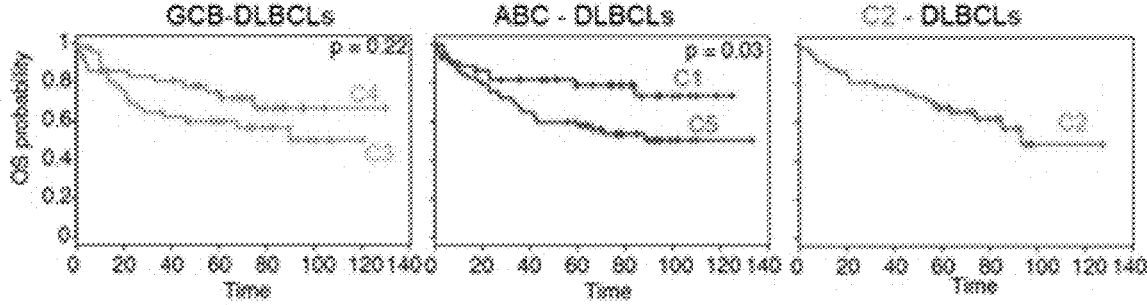
Figure 18E:
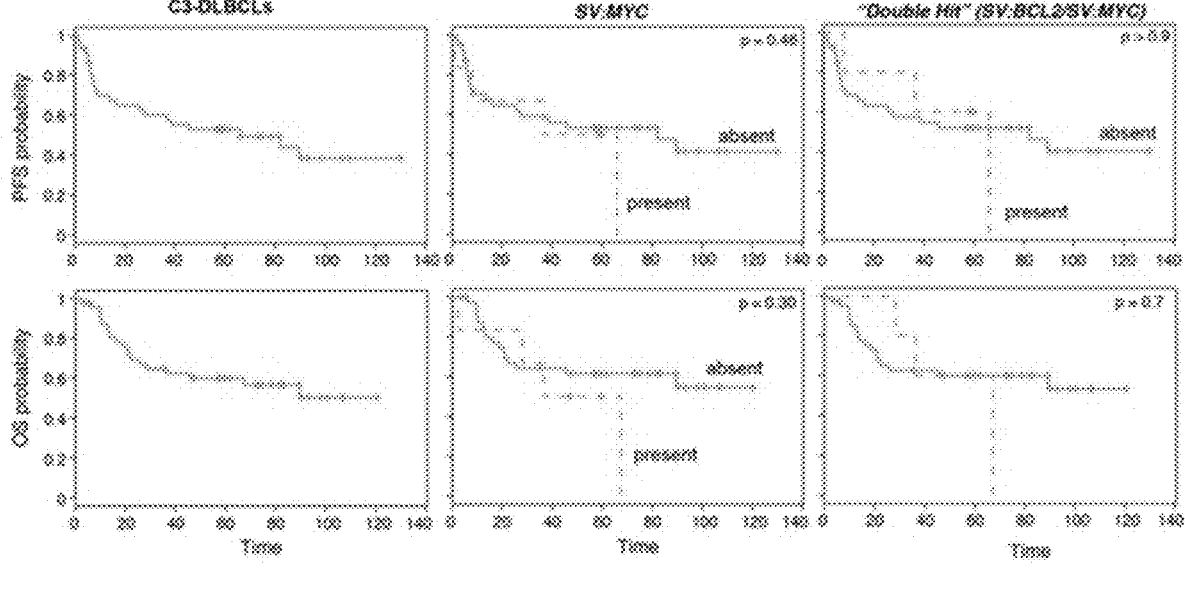

The prognostic significance of the newly defined coordinate genetic signatures was next assessed and significant differences in PFS and OS were identified (FIGS. 6K, 6L, 18A and 18B). Patients with C0, C1 and C4 DLBCLs exhibited more favorable outcomes whereas those with C3 and C5 tumors exhibited less favorable outcomes (FIGS. 6K, 6L, 18A and 18B). Notably, in patients with C3 tumors, outcomes were not dependent on co-occurring MYC/BCL2 SVs (FIG. 18E). Patients with C2 DLBCLs had a distinct trajectory and a steady rate of progression over time (FIGS. 6K, 6L and 18A). The genetically distinct COO subtypes (C1 and C5 ABC-DLBCLs; C3 and C4 GCB-DLBCLs) exhibited marked differences in PFS and OS, with more favorable outcomes in the newly defined C1 ABC- and C4 GCB-DLBCLs (FIGS. 6M and 18D).

Without wishing to be bound by theory, these findings likely explained the reported clinical and genetic heterogeneity within transcriptionally defined COO subsets (10, 20-22). For example, recent targeted studies have identified poor prognosis subsets of ABC DLBCLs having BCL2 copy gain and GCB tumors having BCL2 SVs, defining alterations of the genetically distinct C5 ABC and C3 GCB DLBCLs (FIGS. 5, 6M and 18D) (22).

Figure 6N:
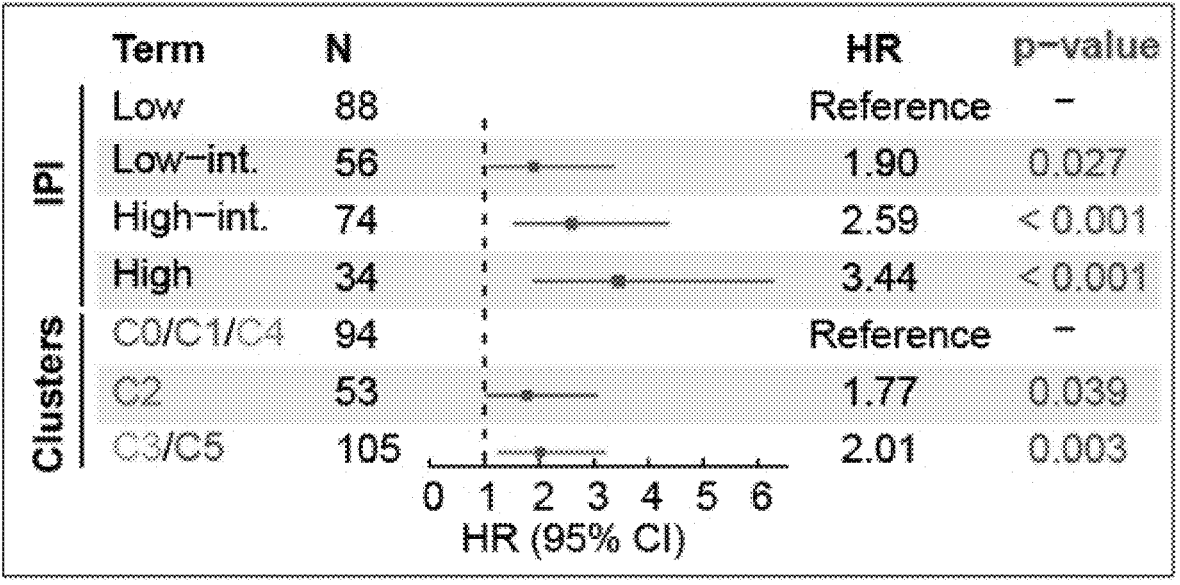

A multivariate model was next constructed that considered both IPI and genetic signatures as variables, with low-risk IPI and favorable (C0/C1/C4) genetic signatures as reference (FIGS. 6N [PFS] and 18C [OS]). For low-risk IPI patients, those with C5 features exhibited a hazard ratio (HR) of 2.01 compared to patients with favorable genetic signatures (FIG. 6N). For patients with favorable genetic features, those with high-risk IPIs had a HR of 3.44 compared to those with low-risk IPIs (FIG. 6N). Patients with C5 features and high-risk IPI had a HR of 6.91 (3.44×2.01) compared to the reference group. Therefore, the coordinate genetic signatures captured outcome differences that were independent of the IPI (FIGS. 6N and 18C; Table S11).

Example 9: Clinical Classification and Treatment Selection for DLBCL Cancers

An exemplary prognostic DLBCL cancer classifier suitable for clinical use has been designed and described herein. Specifically, a neural net classifier has been developed to prospectively identify patients possessing respective genetic signatures (as described above). The classifier utilizes 75 variants that were selected based on a Fisher Test to be specific markers for each DLBCL genetic cluster. The 75 variants assessed by the instant prognostic DLBCL cancer classifier are listed in alphabetical order: 1P13.1:DEL; 1P31.1:DEL; 1P36.11:DEL; 2P16.1:AMP; 3P:AMP; 3P21.31:DEL; 3Q:AMP; 4Q21.22:DEL; 4Q35.1:DEL; 5P:AMP; 9P21.3:DEL; 9Q21.13:DEL; 10Q23.31:DEL; 14Q32.31:DEL; 16Q12.1:DEL; 17P:DEL; 17Q25.1:DEL; 18P:AMP; 18Q:AMP; 19P13.2:DEL; 19Q:AMP; 19Q13.42:AMP; 21Q:AMP; B2M; BCL2; BCL10; BRAF; CD58; CD70; CD79B; CD83; CREBBP; ETV6; EZH2; FAS; genome doubling; GNA13; GNAI2; GRHPR; HISTI-HIB; HISTIHIC; HISTIHID; HIST1H1E; HIST1H2BC; HLA-B; HVCN1; IRF8; KLHL6; KMT2D; MEF2B;

MYD88:L265; MYD88:OTHER; NFKBIA; NFKBIE; NOTCH2; PIM1; POU2F2; PTEN; SGK1; SPEN; STAT3; SV:BCL2; SV:BCL6; SV:CD274/PDCD1LG2; SV:MYC; SV:TP63; TBL1XR1; TMEM30A; TNFAIP3; TNFRSFI4; TP53; UBE2A; ZC3H12A; ZEB2; and ZFP36L1.

A network with these 75 input variants (including MYD88 L265, non-L265, and genome doubling) has provided 78% agreement with the DLBCL clusters in a random subset of 72 tumors (using the other 212 for training the network). In this subset, 57 of the 72 test-tumors were classified with "High Confidence" (p_max>0.7, where p_max is the maximum network output among the five clusters) with an agreement of 84%.

As noted above, this exemplary classifier can be used to assess the mutation state of 75 variant sequences in a test sample (e.g., in a biopsy, blood, cells and/or other tissue of a subject, and/or in a cell line derived from a subject) and apply a weighting/scoring algorithm to each detected variant/reference sequence, thereby arriving at a classification of the test sample that designates the sample as DLBCL cancer class C0, C1, C2, C3, C4 or C5.

Example 10: Refinement of Prognostic Clinical Classifier for DLBCL Cancer Therapy The above-described prognostic DLBCL classifier is further refined, optionally via paring or expansion of the current 75 input variants, for example, 30-75 of the current input variants are retained and a further 0-200 input variants are added, for purpose of refining the currently exemplified classifier, e.g., to improve sensitivity and/or specificity of the classifier in performing the classification of DLBCL of a test sample into one of the five herein-described DLBCL groups, with treatment selection and/or administration to a subject having provided the test sample thereby proceeding in accordance with DLBCL grouping.

REFERENCES

1. Basso, K. & Dalla-Favera, R. Germinal centres and B cell lymphomagenesis. Nat Rev Immunol 15, 172-184, doi:10.1038/nri3814 (2015).
2. Monti, S. et al. Integrative Analysis Reveals an Outcome-Associated and Targetable Pattern of p53 and Cell Cycle Deregulation in Diffuse Large B Cell Lymphoma. Cancer Cell 22, 359-372, doi:10.1016/j.ccr.2012.07.014 (2012).
3. Pasqualucci, L. et al. Analysis of the coding genome of diffuse large B-cell lymphoma. Nat Genet 43, 830-837, doi:10.1038/ng.892 (2011).
4. Morin, R. D. et al. Frequent mutation of histone-modifying genes in non-Hodgkin lymphoma. Nature 476, 298-303, doi:10.1038/nature10351 (2011).
5. Morin, R. D. et al. Mutational and structural analysis of diffuse large B-cell lymphoma using whole-genome sequencing. Blood 122, 1256-1265, doi:10.1182/blood-2013-02-483727 (2013).
6. Lohr, J. G. et al. Discovery and prioritization of somatic mutations in diffuse large B-cell lymphoma (DLBCL) by whole-exome sequencing. Proc Natl Acad Sci USA 109, 3879-3884, doi:10.1073/pnas.1121343109 (2012).
7. de Miranda, N. F. et al. Exome sequencing reveals novel mutation targets in diffuse large B-cell lymphomas derived from Chinese patients. Blood 124, 2544-2553, doi:10.1182/blood-2013-12-546309 (2014).
8. Reddy, A. et al. Genetic and Functional Drivers of Diffuse Large B Cell Lymphoma. Cell 171, 481-494 e415, doi:10.1016/j.cell.2017.09.027 (2017).

9. Morin, R. D. et al. Genetic Landscapes of Relapsed and Refractory Diffuse Large B-Cell Lymphomas. Clin Cancer Res 22, 2290-2300, doi:10.1158/1078-0432.CCR-15-2123 (2016).
10. Rosenwald, A. et al. The use of molecular profiling to predict survival after chemotherapy for diffuse large-B-cell lymphoma. N Engl J Med 346, 1937-1947, doi:10.1056/NEJMoa012914346/25/1937 [pii] (2002).
11. Monti, S. et al. Molecular profiling of diffuse large B-cell lymphoma identifies robust subtypes including one characterized by host inflammatory response. Blood 105, 1851-1861 (2005).
12. Ngo, V. N. et al. Oncogenically active MYD88 mutations in human lymphoma. Nature 470, 115-119, doi:nature09671 [pii]10.1038/nature09671 (2011).
13. Caro, P. et al. Metabolic signatures uncover distinct targets in molecular subsets of diffuse large B cell lymphoma. Cancer Cell 22, 547-560, doi:10.1016/j.ccr.2012.08.014 (2012).
14. Davis, R. E. et al. Chronic active B-cell-receptor signalling in diffuse large B-cell lymphoma. Nature 463, 88-92, doi:10.1038/nature08638 (2010).
15. Chen, L. et al. SYK inhibition modulates distinct PI3K/AKT-dependent survival pathways and cholesterol biosynthesis in diffuse large B cell lymphomas. Cancer Cell 23, 826-838, doi:10.1016/j.ccr.2013.05.002 (2013).
16. Lenz, G. et al. Oncogenic CARD11 mutations in human diffuse large B cell lymphoma. Science 319, 1676-1679, doi:1153629 [pii]10.1126/science.1153629 (2008).
17. Muppidi, J. R. et al. Loss of signalling via Galpha13 in germinal centre B-cell-derived lymphoma. Nature 516, 254-258, doi:10.1038/nature13765 (2014).
18. Morin, R. D. et al. Somatic mutations altering EZH2 (Tyr641) in follicular and diffuse large B-cell lymphomas of germinal-center origin. Nat Genet 42, 181-185, doi:ng.518 [pii]10.1038/ng. 518 (2010).
19. Pfeifer, M. et al. PTEN loss defines a PI3K/AKT pathway-dependent germinal center subtype of diffuse large B-cell lymphoma. Proc Natl Acad Sci USA 110, 12420-12425, doi:10.1073/pnas.1305656110 (2013).
20. Lenz, G. et al. Stromal Gene Signatures in Large-B-Cell Lymphomas. New England Journal of Medicine 359, 2313-2323, doi:doi:10.1056/NEJMoa0802885 (2008).
21. Dubois, S. et al. Biological and Clinical Relevance of Associated Genomic Alterations in MYD88 L265P and non-L265P-Mutated Diffuse Large B-Cell Lymphoma: Analysis of 361 Cases. Clin Cancer Res, doi:10.1158/1078-0432.CCR-16-1922 (2016).
22. Ennishi, D. et al. Genetic profiling of MYC and BCL2 in diffuse large B-cell lymphoma determines cell of origin-specific clinical impact. Blood, doi:10.1182/blood-2016-11-747022 (2017).
23. Pfreundschuh, M. et al. Six versus eight cycles of bi-weekly CHOP-14 with or without rituximab in elderly patients with aggressive CD20+ B-cell lymphomas: a randomised controlled trial (RICOVER-60). Lancet Oncol 9, 105-116, doi:10.1016/S1470-2045(08)70002-0 (2008).
24. Lawrence, M. S. et al. Mutational heterogeneity in cancer and the search for new cancer-associated genes. Nature 499, 214-218, doi:10.1038/nature12213 (2013).
25. Kamburov, A. et al. Comprehensive assessment of cancer missense mutation clustering in protein structures. Proc Natl Acad Sci USA 112, E5486-5495, doi:10.1073/pnas.1516373112 (2015).
26. Welcker, M. & Clurman, B. E. FBW7 ubiquitin ligase: a tumour suppressor at the crossroads of cell division, growth and differentiation. Nat Rev Cancer 8, 83-93, doi:10.1038/nrc2290 (2008).

27. Helleday, T., Eshtad, S. & Nik-Zainal, S. Mechanisms underlying mutational signatures in human cancers. Nat Rev Genet 15, 585-598, doi:10.1038/nrg3729 (2014).

28. Kasar, S. et al. Whole-genome sequencing reveals activation-induced cytidine deaminase signatures during indolent chronic lymphocytic leukaemia evolution. Nat Commun 6, 8866, doi:10.1038/ncomms9866 (2015).

29. Alexandrov, L. B. et al. Signatures of mutational processes in human cancer. Nature 500, 415-421, doi:10.1038/nature12477 (2013).

30. Pasqualucci, L. et al. AID is required for germinal center-derived lymphomagenesis. Nat Genet 40, 108-112, doi:10.1038/ng.2007.35 (2008).

31. Chapuy, B. et al. Targetable genetic features of primary testicular and primary central nervous system lymphomas. Blood 127, 869-881, doi:10.1182/blood-2015-10-673236 (2016).

32. Georgiou, K. et al. Genetic basis of PD-L1 overexpression in diffuse large B-cell lymphomas. Blood 127, 3026-3034, doi:10.1182/blood-2015-12-686550 (2016).

33. Scott, D. W. et al. TBL1XR1/TP63: a novel recurrent gene fusion in B-cell non-Hodgkin lymphoma. Blood 119, 4949-4952, doi:10.1182/blood-2012-02-414441 (2012).

34. Futreal, P. A. et al. A census of human cancer genes. Nat Rev Cancer 4, 177-183, doi:10.1038/nrc1299 (2004).

35. Challa-Malladi, M. et al. Combined genetic inactivation of beta2-Microglobulin and CD58 reveals frequent escape from immune recognition in diffuse large B cell lymphoma. Cancer Cell 20, 728-740, doi:10.1016/j.ccr.2011.11.006 (2011).

36. Steidl, C. et al. MHC class II transactivator CIITA is a recurrent gene fusion partner in lymphoid cancers. Nature 471, 377-381, doi:10.1038/nature09754 (2011).

37. Green, M. R. et al. Integrative analysis reveals selective 9p24.1 amplification, increased PD-1 ligand expression, and further induction via JAK2 in nodular sclerosing Hodgkin lymphoma and primary mediastinal large B-cell lymphoma. Blood 116, 3268-3277, doi:blood-2010-05-282780 [pii]10.1182/blood-2010-05-282780 (2010).

38. Brunet, J. P., Tamayo, P., Golub, T. R. & Mesirov, J. P. Metagenes and molecular pattern discovery using matrix factorization. Proc Natl Acad Sci USA 101, 4164-4169, doi:10.1073/pnas.0308531101 (2004).

39. Ferch, U. et al. Inhibition of MALT1 protease activity is selectively toxic for activated B cell-like diffuse large B cell lymphoma cells. J Exp Med 206, 2313-2320, doi:10.1084/jem.20091167 (2009).

40. Dierlamm, J. et al. Gain of chromosome region 18q21 including the MALT1 gene is associated with the activated B-cell-like gene expression subtype and increased BCL2 gene dosage and protein expression in diffuse large B-cell lymphoma. Haematologica 93, 688-696, doi:10.3324/haematol.12057 (2008).

41. Lenz, G. et al. Molecular subtypes of diffuse large B-cell lymphoma arise by distinct genetic pathways. Proc Natl Acad Sci USA 105, 13520-13525, doi:0804295105 [pii] 10.1073/pnas.0804295105 (2008).

42. Mandelbaum, J. et al. BLIMP1 is a tumor suppressor gene frequently disrupted in activated B cell-like diffuse large B cell lymphoma. Cancer Cell 18, 568-579, doi:S1535-6108(10)00432-0 [pii]10.1016/j.ccr.2010.10.030 (2010).

43. Calado, D. P. et al. Constitutive canonical NF-kappaB activation cooperates with disruption of BLIMP1 in the pathogenesis of activated B cell-like diffuse large cell lymphoma. Cancer Cell 18, 580-589, doi:S1535-6108(10)00485-X [pii]10.1016/j.ccr.2010.11.024 (2010).

44. Deckert, M., Montesinos-Rongen, M., Brunn, A. & Siebert, R. Systems biology of primary CNS lymphoma: from genetic aberrations to modeling in mice. Acta neuropathologica 127, 175-188, doi:10.1007/s00401-013-1202-x (2014).

45. Taniguchi, K. et al. Frequent MYD88 L265P and CD79B Mutations in Primary Breast Diffuse Large B-Cell Lymphoma. Am J Surg Pathol 40, 324-334, doi:10.1097/PAS.0000000000000592 (2016).

46. Pham-Ledard, A. et al. High frequency and clinical prognostic value of MYD88 L265P mutation in primary cutaneous diffuse large B-cell lymphoma, leg-type. JAMA Dermatol 150, 1173-1179, doi:10.1001/jamadermatol.2014.821 (2014).

47. Rovira, J. et al. MYD88 L265P Mutations, But No Other Variants, Identify a Subpopulation of DLBCL Patients of Activated B-cell Origin, Extranodal Involvement, and Poor Outcome. Clin Cancer Res 22, 2755-2764, doi:10.1158/1078-0432.CCR-15-1525 (2016).

48. Rossi, D. et al. The coding genome of splenic marginal zone lymphoma: activation of NOTCH2 and other pathways regulating marginal zone development. J Exp Med 209, 1537-1551, doi:10.1084/jem.20120904 (2012).

49. Spina, V. et al. The genetics of nodal marginal zone lymphoma. Blood 128, 1362-1373, doi:10.1182/blood-2016-02-696757 (2016).

50. Zhang, Q. et al. Inactivating mutations and overexpression of BCL10, a caspase recruitment domain-containing gene, in MALT lymphoma with t(1;14)(p22;q32). Nat Genet 22, 63-68, doi:10.1038/8767 (1999).

51. Kiel, M. J. et al. Whole-genome sequencing identifies recurrent somatic NOTCH2 mutations in splenic marginal zone lymphoma. J Exp Med 209, 1553-1565, doi:10.1084/jem.20120910 (2012).

52. Flossbach, L. et al. BCL6 gene rearrangement and protein expression are associated with large cell presentation of extranodal marginal zone B-cell lymphoma of mucosa-associated lymphoid tissue. Int J Cancer 129, 70-77, doi:10.1002/ijc.25663 (2011).

53. Zucca, E., Bertoni, F., Vannata, B. & Cavalli, F. Emerging role of infectious etiologies in the pathogenesis of marginal zone B-cell lymphomas. Clin Cancer Res 20, 5207-5216, doi:10.1158/1078-0432.CCR-14-0496 (2014).

54. Afshar-Sterle, S. et al. Fas ligand-mediated immune surveillance by T cells is essential for the control of spontaneous B cell lymphomas. Nat Med 20, 283-290, doi:10.1038/nm.3442 (2014).

55. MacLennan, I. C. et al. Extrafollicular antibody responses. Immunological reviews 194, 8-18 (2003).

56. Erdmann, T. et al. Sensitivity to PI3K and AKT inhibitors is mediated by divergent molecular mechanisms in subtypes of DLBCL. Blood, doi:10.1182/blood-2016-12-758599 (2017).

57. Sun, Z. et al. PTEN C-terminal deletion causes genomic instability and tumor development. Cell reports 6, 844-854, doi:10.1016/j.celrep.2014.01.030 (2014).

58. Ortega-Molina, A. et al. The histone lysine methyltransferase KMT2D sustains a gene expression program that represses B cell lymphoma development. Nat Med 21, 1199-1208, doi:10.1038/nm.3943 (2015).

59. Boice, M. et al. Loss of the HVEM Tumor Suppressor in Lymphoma and Restoration by Modified CAR-T Cells. Cell 167, 405-418 e413, doi:10.1016/j.cell.2016.08.032 (2016).

60. Ying, C. Y. et al. MEF2B mutations lead to deregulated expression of the oncogene BCL6 in diffuse large B cell lymphoma. Nat Immunol 14, 1084-1092, doi:10.1038/ni.2688 (2013).

61. Zhang, J. et al. The CREBBP Acetyltransferase Is a Haploinsufficient Tumor Suppressor in B-cell Lymphoma. Cancer discovery 7, 322-337, doi:10.1158/2159-8290.CD-16-1417 (2017).

62. Krysiak, K. et al. Recurrent somatic mutations affecting B-cell receptor signaling pathway genes in follicular lymphoma. Blood 129, 473-483, doi:10.1182/blood-2016-07-729954 (2017).

63. Beguelin, W. et al. EZH2 is required for germinal center formation and somatic EZH2 mutations promote lymphoid transformation. Cancer Cell 23, 677-692, doi:10.1016/j.ccr.2013.04.011 (2013).

64. Li, H. et al. Mutations in linker histone genes HIST1H1 B, C, D, and E; OCT2 (POU2F2); IRF8; and ARID1A underlying the pathogenesis of follicular lymphoma. Blood 123, 1487-1498, doi:10.1182/blood-2013-05-500264 (2014).

65. Okosun, J. et al. Integrated genomic analysis identifies recurrent mutations and evolution patterns driving the initiation and progression of follicular lymphoma. Nat Genet 46, 176-181, doi:10.1038/ng.2856 (2014).

66. Yang, S. M., Kim, B. J., Norwood Toro, L. & Skoultchi, A. I. H1 linker histone promotes epigenetic silencing by regulating both DNA methylation and histone H3 methylation. Proc Natl Acad Sci USA 110, 1708-1713, doi:10.1073/pnas.1213266110 (2013).

67. Xu-Monette, Z. Y. et al. Mutational profile and prognostic significance of TP53 in diffuse large B-cell lymphoma patients treated with R-CHOP: report from an International DLBCL Rituximab-CHOP Consortium Program Study. Blood 120, 3986-3996, doi:10.1182/blood-2012-05-433334 (2012).

68. Sesques, P. & Johnson, N. A. Approach to the diagnosis and treatment of high-grade B-cell lymphomas with MYC and BCL2 and/or BCL6 rearrangements. Blood 129, 280-288, doi:10.1182/blood-2016-02-636316 (2017).

69. Li, Y., Choi, P. S., Casey, S. C., Dill, D. L. & Felsher, D. W. MYC through miR-17-92 suppresses specific target genes to maintain survival, autonomous proliferation, and a neoplastic state. Cancer Cell 26, 262-272, doi:10.1016/j.ccr.2014.06.014 (2014).

70. Carter, S. L. et al. Absolute quantification of somatic DNA alterations in human cancer. Nat Biotechnol 30, 413-421, doi:10.1038/nbt.2203 (2012).

71. Landau, D. A. et al. Mutations driving CLL and their evolution in progression and relapse. Nature 526, 525-530, doi:10.1038/nature15395 (2015).

S1. Pfreundschuh, M. et al. Six versus eight cycles of bi-weekly CHOP-14 with or without rituximab in elderly patients with aggressive CD20+ B-cell lymphomas: a randomised controlled trial (RICOVER-60). Lancet Oncol 9, 105-116, doi:10.1016/S1470-2045(08)70002-0 (2008).

S2. Lohr, J. G. et al. Discovery and prioritization of somatic mutations in diffuse large B-cell lymphoma (DLBCL) by whole-exome sequencing. Proc Natl Acad Sci USA 109, 3879-3884, doi:10.1073/pnas.1121343109 (2012).

S3. Novak, A. J. et al. Whole-exome analysis reveals novel somatic genomic alterations associated with outcome in immunochemotherapy-treated diffuse large B-cell lymphoma. Blood cancer journal 5, e346, doi:10.1038/bcj.2015.69 (2015).

S4. Monti, S. et al. Integrative Analysis Reveals an Outcome-Associated and Targetable Pattern of p53 and Cell Cycle Deregulation in Diffuse Large B Cell Lymphoma. Cancer Cell 22, 359-372, doi:10.1016/j.ccr.2012.07.014 (2012).

S5. Lichtenstein, L., Wood, B., MacBeth, A., Birsoy, O. & Lennon, N. Abstract 3641: ReCapSeg: Validation of somatic copy number alterations for CLIA whole exome sequencing. Cancer Research 76, (14 Supplement) 3641; DOI: 3610.1158/1538-7445.AM2016-3641 (2016).

S6. Lawrence, M. S. et al. Mutational heterogeneity in cancer and the search for new cancer-associated genes. Nature 499, 214-218, doi:10.1038/nature12213 (2013).

S7. Reddy, A. et al. Genetic and Functional Drivers of Diffuse Large B Cell Lymphoma. Cell 171, 481-494 e415, doi:10.1016/j.cell.2017.09.027 (2017).

S8. Cerami, E. et al. The cBio cancer genomics portal: an open platform for exploring multidimensional cancer genomics data. Cancer discovery 2, 401-404, doi:10.1158/2159-8290.CD-12-0095 (2012).

S9. Gao, J. et al. Integrative analysis of complex cancer genomics and clinical profiles using the cBioPortal. Sci Signal 6, pl1, doi:10.1126/scisignal.2004088 (2013).

S10. Wan, P. T. et al. Mechanism of activation of the RAF-ERK signaling pathway by oncogenic mutations of B-RAF. Cell 116, 855-867 (2004).

S11. Dhillon, A. S. & Kolch, W. Oncogenic B-Raf mutations: crystal clear at last. Cancer Cell 5, 303-304 (2004).

S12. Holderfield, M. et al. RAF inhibitors activate the MAPK pathway by relieving inhibitory autophosphorylation. Cancer Cell 23, 594-602, doi:10.1016/j.ccr.2013.03.033 (2013).

S13. Kamburov, A. et al. Comprehensive assessment of cancer missense mutation clustering in protein structures. Proc Natl Acad Sci USA 112, E5486-5495, doi:10.1073/pnas.1516373112 (2015).

S14. Betts, M. J. et al. Mechismo: predicting the mechanistic impact of mutations and modifications on molecular interactions. Nucleic Acids Res 43, e10, doi:10.1093/nar/gku1094 (2015).

S15. Drier, Y. et al. Somatic rearrangements across cancer reveal classes of samples with distinct patterns of DNA breakage and rearrangement-induced hypermutability. Genome Res 23, 228-235, doi:10.1101/gr.141382.112 (2013).

S16. Layer, R. M., Chiang, C., Quinlan, A. R. & Hall, I. M. LUMPY: a probabilistic framework for structural variant discovery. Genome Biol 15, R84, doi:10.1186/gb-2014-15-6-r84 (2014).

S17. Abo, R. P. et al. BreaKmer: detection of structural variation in targeted massively parallel sequencing data using kmers. Nucleic Acids Res 43, e19, doi:10.1093/nar/gku1211 (2015).

S18. Valls, E. et al. BCL6 Antagonizes NOTCH2 to Maintain Survival of Human Follicular Lymphoma Cells. Cancer discovery 7, 506-521, doi:10.1158/2159-8290.CD-16-1189 (2017).

S19. Beguelin, W. et al. EZH2 is required for germinal center formation and somatic EZH2 mutations promote lymphoid transformation. Cancer Cell 23, 677-692, doi:10.1016/j.ccr.2013.04.011 (2013).

S20. Subramanian, A. et al. Gene set enrichment analysis: A knowledge-based approach for interpreting genome-wide expression profiles. PNAS 102, 15545-15550, doi: 10.1073/pnas.0506580102 (2005).

S21. Landau, D. A. et al. Mutations driving CLL and their evolution in progression and relapse. Nature 526, 525-530, doi:10.1038/nature15395 (2015).

S22. Chapman, M. A. et al. Initial genome sequencing and analysis of multiple myeloma. Nature 471, 467-472, doi:nature09837 [pii]10.1038/nature09837 (2011).

S23. Berger, M. F. et al. The genomic complexity of primary human prostate cancer. Nature 470, 214-220, doi:nature09744 [pii]10.1038/nature09744 (2011).

S24. Fisher, S. et al. A scalable, fully automated process for construction of sequence-ready human exome targeted capture libraries. Genome Biol 12, R1, doi:10.1186/gb-2011-12-1-r1 (2011).

S25. Gnirke, A. et al. Solution hybrid selection with ultra-long oligonucleotides for massively parallel targeted sequencing. Nat Biotechnol 27, 182-189, doi:10.1038/nbt.1523 (2009).

S26. Chapuy, B. et al. Targetable genetic features of primary testicular and primary central nervous system lymphomas. Blood 127, 869-881, doi:10.1182/blood-2015-10-673236 (2016).

S27. Chapuy, B. et al. Diffuse large B-cell lymphoma patient-derived xenograft models capture the molecular and biologic heterogeneity of the disease. Blood, doi: 10.1182/blood-2015-09-672352 (2016).

S28. McKenna, A. et al. The Genome Analysis Toolkit: a MapReduce framework for analyzing next-generation DNA sequencing data. Genome Res 20, 1297-1303, doi: 10.1101/gr.107524.110 (2010).

S29. Cibulskis, K. et al. ContEst: estimating cross-contamination of human samples in next-generation sequencing data. Bioinformatics 27, 2601-2602, doi:10.1093/bioinformatics/btr446 (2011).

S30. Giannikou, K. et al. Whole Exome Sequencing Identifies TSC1/TSC2 Biallelic Loss as the Primary and Sufficient Driver Event for Renal Angiomyolipoma Development. PLoS Genet 12, e1006242, doi:10.1371/journal.pgen.1006242 (2016).

S31. Burger, J. A. et al. Clonal evolution in patients with chronic lymphocytic leukaemia developing resistance to BTK inhibition. Nat Commun 7, 11589, doi:10.1038/ncomms11589 (2016).

S32. Mermel, C. H. et al. GISTIC2.0 facilitates sensitive and confident localization of the targets of focal somatic copy-number alteration in human cancers. Genome Biol 12, R41, doi:gb-2011-12-4-r41 [pii]10.1186/gb-2011-12-4-r41 (2011).

S33. Korbel, J. O. & Campbell, P. J. Criteria for inference of chromothripsis in cancer genomes. Cell 152, 1226-1236, doi:10.1016/j.cell.2013.02.023 (2013).

S34. Cibulskis, K. et al. Sensitive detection of somatic point mutations in impure and heterogeneous cancer samples. Nat Biotechnol 31, 213-219, doi:10.1038/nbt.2514 (2013).

S35. Ramos, A. H. et al. Oncotator: cancer variant annotation tool. Hum Mutat 36, E2423-2429, doi:10.1002/humu.22771 (2015).

S36. Costello, M. et al. Discovery and characterization of artifactual mutations in deep coverage targeted capture sequencing data due to oxidative DNA damage during sample preparation. Nucleic Acids Res 41, e67, doi: 10.1093/nar/gks1443 (2013).

S37. Giannakis, M. et al. Genomic Correlates of Immune-Cell Infiltrates in Colorectal Carcinoma. Cell reports 17, 1206, doi:10.1016/j.celrep.2016.10.009 (2016).

S38. Cancer Genome Atlas Research, N. Integrated genomic characterization of papillary thyroid carcinoma. Cell 159, 676-690, doi:10.1016/j.cell.2014.09.050 (2014).

S39. DePristo, M. A. et al. A framework for variation discovery and genotyping using next-generation DNA sequencing data. Nat Genet 43, 491-498, doi:10.1038/ng.806 (2011).

S40. Carter, S. L. et al. Absolute quantification of somatic DNA alterations in human cancer. Nat Biotechnol 30, 413-421, doi:10.1038/nbt.2203 (2012).

S41. Lek, M. et al. Analysis of protein-coding genetic variation in 60,706 humans. Nature 536, 285-291, doi: 10.1038/nature19057 (2016).

S42. Getz, G. et al. Comment on "The consensus coding sequences of human breast and colorectal cancers". Science 317, 1500, doi:10.1126/science. 1138764 (2007).

S43. Berman, H. M. et al. The Protein Data Bank. Nucleic Acids Res 28, 235-242 (2000).

S44. Alexandrov, L. B. et al. Clock-like mutational processes in human somatic cells. Nat Genet 47, 1402-1407, doi:10.1038/ng.3441 (2015).

S45. Kim, J. et al. Somatic ERCC2 mutations are associated with a distinct genomic signature in urothelial tumors. Nat Genet 48, 600-606, doi:10.1038/ng.3557 (2016).

S46. Kasar, S. et al. Whole-genome sequencing reveals activation-induced cytidine deaminase signatures during indolent chronic lymphocytic leukaemia evolution. Nat Commun 6, 8866, doi:10.1038/ncomms9866 (2015).

S47. Tan, V. Y. & Fevotte, C. Automatic relevance determination in nonnegative matrix factorization with the beta-divergence. IEEE Trans Pattern Anal Mach Intell 35, 1592-1605, doi:10.1109/TPAMI.2012.240 (2013).

S48. Di Noia, J. M. & Neuberger, M. S. Molecular mechanisms of antibody somatic hypermutation. Annu Rev Biochem 76, 1-22, doi:10.1146/annurev.biochem.76.061705.090740 (2007).

S49. Irizarry, R. A. et al. Exploration, normalization, and summaries of high density oligonucleotide array probe level data. Biostatistics 4, 249-264, doi:10.1093/biostatistics/4.2.249 (2003).

S50. Dai, M. et al. Evolving gene/transcript definitions significantly alter the interpretation of GeneChip data. Nucleic Acids Res 33, e175, doi:10.1093/nar/gni179 (2005).

S51. Ritchie, M. E. et al. limma powers differential expression analyses for RNA-sequencing and microarray studies. Nucleic Acids Res 43, e47, doi:10.1093/nar/gkv007 (2015).

S52. Benjamini, Y. & Hochberg, Y. Controlling the False Discovery Rate: A Practical and Powerful Approach to Multiple Testing. Journal of the Royal Statistical Society. Series B (Methodological) 57, 289-300 (1995).

S53. Monti, S. et al. Molecular profiling of diffuse large B-cell lymphoma identifies robust subtypes including one characterized by host inflammatory response. Blood 105, 1851-1861, doi:10.1182/blood-2004-07-2947 (2005).

S54. Wright, G. et al. A gene expression-based method to diagnose clinically distinct subgroups of diffuse large B cell lymphoma. Proceedings of the National Academy of Sciences 100, 9991-9996 (2003).

S55. Scott, D. W. et al. Determining cell-of-origin subtypes of diffuse large B-cell lymphoma using gene expression in formalin-fixed paraffin-embedded tissue. Blood 123, 1214-1217, doi:10.1182/blood-2013-11-536433 (2014).

S56. Staiger, A. M. et al. Clinical Impact of the Cell-of-Origin Classification and the MYC/BCL2 Dual Expresser Status in Diffuse Large B-Cell Lymphoma Treated Within Prospective Clinical Trials of the German High-Grade Non-Hodgkin's Lymphoma Study Group. J Clin Oncol 35, 2515-2526, doi:10.1200/JCO.2016.70.3660 (2017).

S57. Chapuy, B. et al. Discovery and characterization of super-enhancer-associated dependencies in diffuse large B cell lymphoma. Cancer Cell 24, 777-790, doi:10.1016/j.ccr.2013.11.003 (2013).

S58. Li, H. & Durbin, R. Fast and accurate short read alignment with Burrows-Wheeler transform. Bioinformatics 25, 1754-1760, doi:10.1093/bioinformatics/btp324 (2009).

S59. Wala, J. et al. Genome-wide detection of structural variants and indels by local assembly. bioRxiv (2017).

S60. Simpson, J. T. & Durbin, R. Efficient de novo assembly of large genomes using compressed data structures. Genome Res 22, 549-556, doi:10.1101/gr.126953.111 (2012).

S61. Wala, J. & Beroukhim, R. SeqLib: a C++ API for rapid BAM manipulation, sequence alignment and sequence assembly. Bioinformatics, doi:10.1093/bioinformatics/btw741 (2016).

S62. Li, H. Aligning sequence reads, clone sequences and assembly contigs with BWA-MEM. arXiv:1303.3997 (2015).

S63. Roemer, M. G. et al. PD-L1 and PD-L2 Genetic Alterations Define Classical Hodgkin Lymphoma and Predict Outcome. J Clin Oncol 34, 2690-2697, doi:10.1200/JCO.2016.66.4482 (2016).

S64. Brunet, J. P., Tamayo, P., Golub, T. R. & Mesirov, J. P. Metagenes and molecular pattern discovery using matrix factorization. Proc Natl Acad Sci USA 101, 4164-4169, doi:10.1073/pnas.0308531101 (2004).

All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

One skilled in the art would readily appreciate that the present disclosure is well adapted to carry out the objects and obtain the ends and advantages mentioned, as well as those inherent therein. The methods and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

In addition, where features or aspects of the disclosure are described in terms of Markush groups or other grouping of alternatives, those skilled in the art will recognize that the disclosure is also thereby described in terms of any individual member or subgroup of members of the Markush group or other group.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Embodiments of this disclosure are described herein, including the best mode known to the inventors for carrying out the disclosed invention. Variations of those embodiments may become apparent to those of ordinary skill in the art upon reading the foregoing description.

The disclosure illustratively described herein suitably can be practiced in the absence of any element or elements, limitation or limitations that are not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present disclosure provides preferred embodiments, optional features, modification and variation of the concepts herein disclosed may be resorted to by those skilled in the art, and that such modifications and variations are considered to be within the scope of this disclosure as defined by the description and the appended claims.

It will be readily apparent to one skilled in the art that varying substitutions and modifications can be made to the invention disclosed herein without departing from the scope and spirit of the invention. Thus, such additional embodiments are within the scope of the present disclosure and the following claims. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context. Those skilled in the art will recognize, or be able to ascertain using no more than routine experimentation, many equivalents to the specific embodiments of the disclosure described herein. Such equivalents are intended to be encompassed by the following claims.

We claim:

1. A method for selecting and administering an agent to a subject having or at risk of developing diffuse large B-cell lymphoma (DLBCL) comprising:

(a) obtaining a sample from a subject having or at risk of DLBCL;

(b) identifying the presence or absence in the sample of five or more sequence variants or sites of copy number variation selected from the group consisting of:

1P13.1:DEL;

1P31.1:DEL;

1P36.11:DEL;
2P16.1:AMP;
3P:AMP;
3P21.31:DEL;
3Q:AMP;
4Q21.22:DEL;
4Q35.1:DEL;
5P:AMP;
9P21.3:DEL;
9Q21.13:DEL;
10Q23.31:DEL;
14Q32.31:DEL;
16Q12.1:DEL;
17P:DEL;
17Q25.1:DEL;
18P:AMP;
18Q:AMP;
19P13.2:DEL;
19Q:AMP;
19Q13.42:AMP;
21Q:AMP;
a variant or copy number variation in B2M;
a variant or copy number variation in BCL2;
a variant or copy number variation in BCL10;
a variant or copy number variation in BRAF;
a variant or copy number variation in CD58;
a variant or copy number variation in CD70;
a variant or copy number variation in CD79B;
a variant or copy number variation in CD83;
a variant or copy number variation in CREBBP;
a variant or copy number variation in ETV6;
a variant or copy number variation in EZH2;
a variant or copy number variation in FAS;
a marker that indicates genome doubling;
a variant or copy number variation in GNA13;
a variant or copy number variation in GNA12;
a variant or copy number variation in GRHPR;
a variant or copy number variation in HIST1H1B;
a variant or copy number variation in HIST1H1C;
a variant or copy number variation in HIST1H1D;
a variant or copy number variation in HIST1H1E;
a variant or copy number variation in HIST1H2BC;
a variant or copy number variation in HLA-B;
a variant or copy number variation in HVCN1;
a variant or copy number variation in IRF8;
a variant or copy number variation in KLHL6;
a variant or copy number variation in KMT2D;
a variant or copy number variation in MEF2B;
MYD88:L265;
a non-L265 variant or copy number variation in
MYD88;
a variant or copy number variation in NFKBIA;
a variant or copy number variation in NFKBIE;
a variant or copy number variation in NOTCH2;
a variant or copy number variation in PIM1;
a variant or copy number variation in POU2F2;
a variant or copy number variation in PTEN;
a variant or copy number variation in SGK1;
a variant or copy number variation in SPEN;
a variant or copy number variation in STAT3;
a variant or copy number variation in SV:BCL2;
a variant or copy number variation in SV:BCL6;
a variant or copy number variation in SV:CD274/
PDCD1LG2;
a variant or copy number variation in SV:MYC;
a variant or copy number variation in SV:TP63;
a variant or copy number variation in TBL1XR1;

a variant or copy number variation in TMEM30A;
a variant or copy number variation in TNFAIP3;
a variant or copy number variation in TNFRSFI4;
a variant or copy number variation in TP53;
a variant or copy number variation in UBE2A;
a variant or copy number variation in ZC3H12A;
a variant or copy number variation in ZEB2; and
a variant or copy number variation in ZFP36L1;
  wherein the presence of at least one of said five or
    more sequence variants or sites of copy number
    variation is detected in the sample;
(c) detecting one of the following in the sample: increased
    abundance of NOTCH2 transcript and BCL6 transcript
    as compared to a control, biallelic inactivation of TP53
    and 17p copy loss, a mutation in BCL2 with concordant
    structural variant juxtaposing BCL2 to the IgH
    enhancer, a mutation in SGK1, or gain of 18q;
(d) analyzing the results of steps (b) and (c) to thereby
    assign the sample to one of five discrete classes of
    DLBCL selected from the group consisting of:
    Class 1: Activated B-cell (ABC)-type DLBCLs char-
      acterized by the presence of sequence variants or
      copy number variations associated with increased
      transcriptional abundance of NOTCH2 and BCL6,
      without sequence variants or copy number variations
      associated with 18q gain;
    Class 2: Mixed ABC-type and germinal center B-cell
      (GCB)-type DLBCLs characterized by the presence
      of sequence variants or copy number variations
      profiles associated with bi-allelic inactivation of
      TP53 by mutations and 17p copy loss;
    Class 3: GCB-type DLBCLs characterized by the pres-
      ence of BCL2 mutations with concordant structural
      variant juxtaposing BCL2 to the IgH enhancer, and
      mutations in chromatin modifiers KMT2D, CRE-
      BBP and EZH2, without sequence variants or copy
      number variations associated with mutations in
      linker and/or core histone genes, immune evasion
      molecules CD83, CD58, and/or CD70, BCR/Pi3K
      signaling intermediates RHOA, GNA13, and/or
      SGK1, NF-kB modifiers CARD11, NFKBIE, and/or
      NFKBIA and/or RAS/JAK/STAT pathway members
      BRAF, and/or STAT3;
    Class 4: GCB-type DLBCLs characterized by the pres-
      ence of sequence variants or copy number variations
      in linker and/or core histone genes, immune evasion
      molecules CD83, CD58, and/or CD70, BCR/Pi3K
      signaling intermediates RHOA, GNA13, and/or
      SGK1, NF-kB modifiers CARD11, NFKBIE, and/or
      NFKBIA and/or RAS/JAK/STAT pathway members
      BRAF, and/or STAT3, without BCL2 mutations with
      concordant structural variant juxtaposing BCL2 to
      the IgH enhancer, or mutations in chromatin modi-
      fiers KMT2D, CREBBP and EZH2; and
    Class 5: ABC-type DLBCLs characterized by the pres-
      ence of sequence variants or copy number variations
      associated with 18q gain, without sequence variants
      or copy number variations associated with increased
      transcriptional abundance of NOTCH2 or BCL6;
      and
(e)
  administering an agent to the subject, wherein:
  for a sample assigned to Class 1 in step (d), the subject
    is administered an agent selected from the group
    consisting of a NOTCH inhibitor, a BCL6 inhibitor
    and an activator of immune evasion, optionally
    wherein the NOTCH inhibitor is an oligonucleotide inhibitor of NOTCH or the BCL6 inhibitor is an oligonucleotide inhibitor of BCL6;

for a sample assigned to Class 2 in step (d), the subject is administered an agent comprising a CDK inhibitor;

for a sample assigned to Class 3 in step (d), the subject is administered an agent selected from the group consisting of a BCL2 inhibitor, a PI3K inhibitor and an epigenetic modifier, wherein the epigenetic modifier optionally is oblimersen, ABT-263, Venetoclax (ABT-199), wortmannin, L Y294002, an EZH2 inhibitor, wherein the EZH2 inhibitor is optionally 3-deazaneplanocin A (DZNep), EPZ005687, EI1, GSK126, and/or UNC1999, a CREBBP inhibitor, optionally wherein the BCL2 inhibitor is an oligonucleotide inhibitor of BCL2, optionally wherein the PI3K inhibitor is an oligonucleotide inhibitor of PI3K, and optionally wherein the inhibitor of an epigenetic modifier is an oligonucleotide inhibitor of an epigenetic modifier;

for a sample assigned to Class 4 in step (d), the subject is administered an agent selected from the group consisting of a JAK/STAT inhibitor and a BRAF/MEK1 inhibitor, optionally ruxolitinib, Vemurafenib, Cobimetinib, optionally wherein the inhibitor of JAK/STAT is an oligonucleotide inhibitor of JAK/STAT and optionally wherein the inhibitor of BRAF/MEK1 is an oligonucleotide inhibitor of BRAF/MEK1; and for a sample assigned to Class 5 in step d, the subject is administered an agent selected from the group consisting of a BCR/TLR signaling inhibitor and a BCL2 inhibitor, optionally oblimersen, ABT-263, Venetoclax (ABT-199), optionally wherein the inhibitor of BCR/TLR signaling is an antibody or oligonucleotide inhibitor of BCR/TLR signaling and optionally wherein the inhibitor of BCL2 is an oligonucleotide inhibitor of BCL2.

2. The method of claim 1, wherein identifying step (b) comprises whole exome sequencing (WES) of the sample.

3. The method of claim 1, wherein identifying step (b) comprises exome sequencing of the sample, optionally wherein identifying step (b) comprises sequencing of the five or more sequence variants or copy number variation within a selection of no more than 300,000 exome sequence regions examined for genetic variation, optionally wherein identifying step (b) comprises sequencing of the five or more sequence variants and/or sites of copy number variation within a selection of no more than 50,000 exome sequence regions examined for genetic variation, optionally wherein identifying step (b) comprises sequencing of the five or more sequence variants and/or sites of copy number variation within a selection of no more than 30,000 exome sequence regions examined for genetic variation, optionally wherein identifying step (b) comprises sequencing of the five or more sequence variants and/or sites of copy number variation within a selection of no more than 10,000 exome sequence regions examined for genetic variation, optionally wherein identifying step (b) comprises sequencing of the five or more sequence variants and/or sites of copy number variation within a selection of no more than 3,000 exome sequence regions examined for genetic variation, optionally wherein identifying step (b) comprises sequencing of the five or more sequence variants and/or sites of copy number variation within a selection of no more than 1,000 exome sequence regions examined for genetic variation, optionally wherein identifying step (b) comprises sequencing of the five or more sequence variants and/or sites of copy number variation within a selection of no more than 500 exome sequence regions examined for genetic variation, optionally wherein identifying step (b) comprises sequencing of the five or more sequence variants and/or sites of copy number variation within a selection of no more than 300 exome sequence regions examined for genetic variation, optionally wherein identifying step (b) comprises sequencing of the five or more sequence variants and/or sites of copy number variation via PCR amplification and sequencing of the sample.

4. The method of claim 1, further comprising administering a combination of agents for the assigned class to the subject.

5. The method of claim 1, wherein step (b) comprises identifying the presence or absence in the sample of ten or more of said sequence variants and/or sites of copy number variation, optionally twenty or more of said sequence variants and/or sites of copy number variation, optionally thirty or more of said sequence variants and/or sites of copy number variation, optionally forty or more of said sequence variants and/or sites of copy number variation, optionally fifty or more of said sequence variants and/or sites of copy number variation, optionally sixty or more of said sequence variants and/or sites of copy number variation and optionally seventy or more of said sequence variants and/or sites of copy number variation.

6. The method of claim 1, wherein step (b) comprises identifying the presence or absence in the sample of the seventy-five said sequence variants and/or sites of copy number variation.

7. The method of claim 1, wherein analyzing step (d) comprises use of a neural net classifier.

8. The method of claim 1, wherein identifying step (b) comprises use of a kit for identifying genetic variation in a sample, the kit comprising fewer than 500,000 oligonucleotide probes designed to detect specific forms of genetic variation, wherein the kit comprises five or more oligonucleotide probes selected from the group consisting of an oligonucleotide probe for detecting the sequence or copy number of 1P13.1:DEL;

an oligonucleotide probe for detecting the sequence or copy number of 1P31.1:DEL;

an oligonucleotide probe for detecting the sequence or copy number of 1P36.11:DEL;

an oligonucleotide probe for detecting the sequence or copy number of 2P16.1:AMP;

an oligonucleotide probe for detecting the sequence or copy number of 3P:AMP;

an oligonucleotide probe for detecting the sequence or copy number of 3P21.31:DEL;

an oligonucleotide probe for detecting the sequence or copy number of 3Q:AMP;

an oligonucleotide probe for detecting the sequence or copy number of 4Q21.22:DEL;

an oligonucleotide probe for detecting the sequence or copy number of 4Q35.1:DEL;

an oligonucleotide probe for detecting the sequence or copy number of 5P:AMP;

an oligonucleotide probe for detecting the sequence or copy number of 9P21.3:DEL;

an oligonucleotide probe for detecting the sequence or copy number of 9Q21.13:DEL;

an oligonucleotide probe for detecting the sequence or copy number of 10Q23.31:DEL;

an oligonucleotide probe for detecting the sequence or copy number of 14Q32.31:DEL;

an oligonucleotide probe for detecting the sequence or copy number of 16Q12.1:DEL;

an oligonucleotide probe for detecting the sequence or copy number of 17P:DEL;

an oligonucleotide probe for detecting the sequence or copy number of 17Q25.1:DEL;

an oligonucleotide probe for detecting the sequence or copy number of 18P:AMP;

an oligonucleotide probe for detecting the sequence or copy number of 18Q:AMP;

an oligonucleotide probe for detecting the sequence or copy number of 19P13.2:DEL;

an oligonucleotide probe for detecting the sequence or copy number of 19Q:AMP;

an oligonucleotide probe for detecting the sequence or copy number of 19Q13.42:AMP;

an oligonucleotide probe for detecting the sequence or copy number of 21Q:AMP;

an oligonucleotide probe for detecting the sequence or copy number of B2M;

an oligonucleotide probe for detecting the sequence or copy number of BCL2;

an oligonucleotide probe for detecting the sequence or copy number of BCL10;

an oligonucleotide probe for detecting the sequence or copy number of BRAF;

an oligonucleotide probe for detecting the sequence or copy number of CD58;

an oligonucleotide probe for detecting the sequence or copy number of CD70;

an oligonucleotide probe for detecting the sequence or copy number of CD79B;

an oligonucleotide probe for detecting the sequence or copy number of CD83;

an oligonucleotide probe for detecting the sequence or copy number of CREBBP;

an oligonucleotide probe for detecting the sequence or copy number of ETV6;

an oligonucleotide probe for detecting the sequence or copy number of EZH2;

an oligonucleotide probe for detecting the sequence or copy number of FAS;

oligonucleotide probes for detecting genome doubling;

an oligonucleotide probe for detecting the sequence or copy number of GNA13;

an oligonucleotide probe for detecting the sequence or copy number of GNA12;

an oligonucleotide probe for detecting the sequence or copy number of GRHPR;

an oligonucleotide probe for detecting the sequence or copy number of HIST1H1B;

an oligonucleotide probe for detecting the sequence or copy number of HIST1H1C;

an oligonucleotide probe for detecting the sequence or copy number of HIST1H1D;

an oligonucleotide probe for detecting the sequence or copy number of HIST1H1E;

an oligonucleotide probe for detecting the sequence or copy number of HIST1H2BC;

an oligonucleotide probe for detecting the sequence or copy number of HLA-B;

an oligonucleotide probe for detecting the sequence or copy number of HVCN1;

an oligonucleotide probe for detecting the sequence or copy number of IRF8;

an oligonucleotide probe for detecting the sequence or copy number of KLHL6;

an oligonucleotide probe for detecting the sequence or copy number of KMT2D;

an oligonucleotide probe for detecting the sequence or copy number of MEF2B;

an oligonucleotide probe for detecting the sequence or copy number of MYD88:L265;

an oligonucleotide probe for detecting the sequence or copy number of MYD88:OTHER;

an oligonucleotide probe for detecting the sequence or copy number of NFKBIA;

an oligonucleotide probe for detecting the sequence or copy number of NFKBIE;

an oligonucleotide probe for detecting the sequence or copy number of NOTCH2;

an oligonucleotide probe for detecting the sequence or copy number of PIM1;

an oligonucleotide probe for detecting the sequence or copy number of POU2F2;

an oligonucleotide probe for detecting the sequence or copy number of PTEN;

an oligonucleotide probe for detecting the sequence or copy number of SGK1;

an oligonucleotide probe for detecting the sequence or copy number of SPEN;

an oligonucleotide probe for detecting the sequence or copy number of STAT3;

an oligonucleotide probe for detecting the sequence or copy number of SV:BCL2;

an oligonucleotide probe for detecting the sequence or copy number of SV:BCL6;

an oligonucleotide probe for detecting the sequence or copy number of SV:CD274/PDCD1LG2;

an oligonucleotide probe for detecting the sequence or copy number of SV:MYC;

an oligonucleotide probe for detecting the sequence or copy number of SV:TP63;

an oligonucleotide probe for detecting the sequence or copy number of TBL1XR1;

an oligonucleotide probe for detecting the sequence or copy number of TMEM30A;

an oligonucleotide probe for detecting the sequence or copy number of TNFAIP3;

an oligonucleotide probe for detecting the sequence or copy number of TNFRSFI4;

an oligonucleotide probe for detecting the sequence or copy number of TP53;

an oligonucleotide probe for detecting the sequence or copy number of UBE2A;

an oligonucleotide probe for detecting the sequence or copy number of ZC3H12A;

an oligonucleotide probe for detecting the sequence or copy number of ZEB2; and an oligonucleotide probe for detecting the sequence or copy number of ZFP36L1;

and instructions for its use.

9. The method of claim 1, wherein identifying step (b) comprises use of a technology selected from the group consisting of targeted hybrid capture, an amplicon-based sequencing technology, and a non-targeted sequencing technology, optionally whole genome sequencing (WGS).

10. The method of claim 1, wherein analyzing step (d) involves comparing the sample from the subject having or at risk of DLBCL to a paired normal sample.

* * * * *